(12) United States Patent
Nabel et al.

(10) Patent No.: US 12,071,454 B2
(45) Date of Patent: Aug. 27, 2024

(54) ANTIGENIC RESPIRATORY SYNCYTIAL VIRUS POLYPEPTIDES

(71) Applicant: Sanofi, Paris (FR)

(72) Inventors: Gary J. Nabel, Bridgewater, NJ (US); Chih-Jen Wei, Bridgewater, NJ (US); Kurt Swanson, Bridgewater, NJ (US); Pradeep Dhal, Bridgewater, NJ (US); Ram Dharanipragada, Bridgewater, NJ (US); Magnus Besev, Bridgewater, NJ (US)

(73) Assignee: SANOFI, Paris (FR)

( * ) Notice: Subject to any disclaimer, the term of this patent is extended or adjusted under 35 U.S.C. 154(b) by 1001 days.

(21) Appl. No.: 17/061,065

(22) Filed: Oct. 1, 2020

(65) Prior Publication Data

US 2021/0017237 A1 Jan. 21, 2021

Related U.S. Application Data

(63) Continuation of application No. PCT/US2019/025387, filed on Apr. 2, 2019.

(60) Provisional application No. 62/652,199, filed on Apr. 3, 2018.

(51) Int. Cl.
C07K 14/195 (2006.01)

(52) U.S. Cl.
CPC ........ *C07K 14/195* (2013.01); *C07K 2319/30* (2013.01)

(58) Field of Classification Search
CPC .......................... C07K 14/195; C07K 2319/30; C07K 14/005; C07K 14/205; C07K 2319/00; C12N 2760/18534; C12N 15/62; A61P 31/14; A61K 39/12

See application file for complete search history.

(56) References Cited

U.S. PATENT DOCUMENTS

| | | | |
|---|---|---|---|
| 6,194,388 B1 | 2/2001 | Krieg et al. | |
| 6,207,646 B1 | 3/2001 | Krieg et al. | |
| 6,214,806 B1 | 4/2001 | Krieg et al. | |
| 6,218,371 B1 | 4/2001 | Krieg et al. | |
| 6,239,116 B1 | 5/2001 | Krieg et al. | |
| 6,339,068 B1 | 1/2002 | Krieg et al. | |
| 6,406,705 B1 | 6/2002 | Davis et al. | |
| 6,429,199 B1 | 8/2002 | Krieg et al. | |
| 8,562,996 B2 | 10/2013 | Spits et al. | |
| 9,703,095 B2 | 7/2017 | Pakhchyan | |
| 10,961,283 B2 | 3/2021 | Kwong et al. | |
| 2012/0267258 A1 | 10/2012 | Uraoka et al. | |
| 2014/0072958 A1 | 3/2014 | Nabel et al. | |
| 2014/0348865 A1 | 11/2014 | Kwong et al. | |
| 2016/0046675 A1* | 2/2016 | Kwong ................ | C07K 14/005 530/400 |
| 2016/0303224 A1 | 10/2016 | Kanekiyo et al. | |
| 2020/0282047 A1 | 9/2020 | Ciaramella et al. | |

FOREIGN PATENT DOCUMENTS

| | | |
|---|---|---|
| CA | 2485363 C | 10/2014 |
| EP | 2515112 B1 | 8/2015 |
| JP | 2006104216 A | 4/2006 |
| JP | 2011506565 A | 3/2011 |
| JP | 2012225885 A | 11/2012 |
| JP | 2013529078 A | 7/2013 |
| JP | 2014513678 A | 6/2014 |
| JP | 2015530369 A | 10/2015 |
| JP | 2020520674 A | 7/2020 |
| JP | 2021504445 A | 2/2021 |
| RU | 2142817 C1 | 12/1999 |
| WO | 1995004545 A1 | 2/1995 |
| WO | 9506124 A1 | 3/1995 |
| WO | 2002016421 A2 | 2/2002 |
| WO | 2009079796 A1 | 7/2009 |
| WO | 2009080719 A1 | 7/2009 |
| WO | 2009126816 A1 | 10/2009 |
| WO | 2010077717 A1 | 7/2010 |
| WO | 2011008974 A2 | 1/2011 |
| WO | 2011143623 A1 | 11/2011 |
| WO | 2012006180 A1 | 1/2012 |
| WO | 2012139069 A2 | 10/2012 |
| WO | 2013039792 A1 | 3/2013 |
| WO | 2013044203 A2 | 3/2013 |
| WO | 2014018858 A2 | 1/2014 |
| WO | 2014160463 A1 | 10/2014 |
| WO | 2015054639 A1 | 4/2015 |
| WO | 2015169271 A1 | 11/2015 |
| WO | 2015183969 A1 | 12/2015 |
| WO | 2016138160 A1 | 9/2016 |
| WO | 2017096374 A1 | 6/2017 |
| WO | 2017172890 A1 | 10/2017 |
| WO | 2017211886 A1 | 12/2017 |
| WO | 2017218819 A1 | 12/2017 |

(Continued)

OTHER PUBLICATIONS

McLellan JS. Neutralizing epitopes on the respiratory syncytial virus fusion glycoprotein. Curr Opin Virol. Apr. 2015; 11:70-5. Epub Mar. 26, 2015. (Year: 2015).*
Bowie JU, Reidhaar-Olson JF, Lim WA, Sauer RT. Deciphering the message in protein sequences: tolerance to amino acid substitutions. Science. Mar. 16, 1990;247(4948):1306-10. (Year: 1990).*
Winkler K, Kramer A, Küttner G, Seifert M, Scholz C, Wessner H, Schneider-Mergener J, Höhne W. Changing the antigen binding specificity by single point mutations of an anti-p24 (HIV-1) antibody. J Immunol. Oct. 15, 2000;165(8):4505-14. (Year: 2000).*
Kussie PH, Parhami-Seren B, Wysocki LJ, Margolies MN. A single engineered amino acid substitution changes antibody fine specificity. J Immunol. Jan. 1, 1994;152(1):146-52. (Year: 1994).*
Chen Z, Wang J, Bao L, Guo L, Zhang W, Xue Y, Zhou H, Xiao Y, Wang J, Wu F, Deng Y, Qin C, Jin Q. Human monoclonal antibodies targeting the haemagglutinin glycoprotein can neutralize H7N9 influenza virus. Nat Commun. Mar. 30, 2015;6:6714. (Year: 2015).*
Sela-Culang I, Kunik V, Ofran Y. The structural basis of antibody-antigen recognition. Front Immunol. Oct. 8, 2013;4:302. (Year: 2013).*

(Continued)

*Primary Examiner* — Rachel B Gill
(74) *Attorney, Agent, or Firm* — McNeill PLLC

(57) ABSTRACT

Antigenic respiratory syncytial virus (RSV) polypeptides for use in eliciting antibodies against RSV are provided. Also provided are antigenic polypeptides comprising an RSV polypeptide and a ferritin protein.

21 Claims, 33 Drawing Sheets

Specification includes a Sequence Listing.

(56) References Cited

FOREIGN PATENT DOCUMENTS

| | | |
|---|---|---|
| WO | 2018005558 A1 | 1/2018 |
| WO | 2018193063 A2 | 10/2018 |
| WO | 2019103993 A1 | 5/2019 |
| WO | 2019195276 A1 | 10/2019 |
| WO | 2019195284 A1 | 10/2019 |
| WO | 2019195291 A1 | 10/2019 |
| WO | 2019195314 A2 | 10/2019 |
| WO | 2019195316 A1 | 10/2019 |

OTHER PUBLICATIONS

Sirin S, Apgar JR, Bennett EM, Keating AE. AB-Bind: Antibody binding mutational database for computational affinity predictions. Protein Sci. Feb. 2016;25(2):393-409. Epub Nov. 6, 2015. (Year: 2015).*

Tsuchiya Y, Mizuguchi K. The diversity of H3 loops determines the antigen-binding tendencies of antibody CDR loops. Protein Sci. Apr. 2016;25(4):815-25. Epub Jan. 20, 2016. (Year: 2016).*

Collis AV, Brouwer AP, Martin AC. Analysis of the antigen combining site: correlations between length and sequence composition of the hypervariable loops and the nature of the antigen. J Mol Biol. Jan. 10, 2003;325(2):337-54. (Year: 2003).*

Dondelinger M, Filée P, Sauvage E, Quinting B, Muyldermans S, Galleni M, Vandevenne MS. Understanding the Significance and Implications of Antibody Numbering and Antigen-Binding Surface/Residue Definition. Front Immunol. Oct. 16, 2018;9:2278. (Year: 2018).*

Balfour Jr., Henry, "Progress, prospects, and problems in Epstein-Barr virus vaccine development", Current Opinion in Virology, 6, pp. 1-5 (2014).

Calisti et al., "Probing bulky ligand entry in engineered archaeal ferritins", Biochimica et Biophysica Acia 1861, pp. 450-455 (2017).

Khoshnejad et al., "Ferritin-based drug delivery systems; Hybrid nanocarriers for vascular immunotargeting", J. Control Release, vol. 282, p. 13-24 (Mar. 6, 2018).

Moyle et al., "Site-Specific Incorporation of Three Toll-Like Receptor 2 Targeting Adjuvants into Semisynthetic, Molecularly Defined Nanoparticles: Application to Group A Streptococcal Vaccines", Bioconjugate Chem., 25, pp. 965-978 (2014).

Sequence #206 from U.S. Appl. No. 17/061,136, accessed on Mar. 24, 2023 (1 page).

Villar et al., "Reconstituted B cell receptor signaling reveals carbohydrate-dependent mode of activation", Scientific Reports, 6:36298, 11 pages (2016).

Zhen et al., "Ferritins as nanoplatforms for imaging and drug delivery", Expert Opin. Drug Deliv, 11(12), pp. 1913-1922 (2014).

Lawson et al., "Solving the structure of human H ferritin by genetically engineering intermolecular crystal contacts", Nature, 349, pp. 541-544 (1991).

Wille-Reece et al., "HIV Gag protein conjugated to a Toll-like receptor 7/8 agonist improves the magnitude and quality of Th1 and CD8+ T cell responses in nonhuman primates", Proc Natl Acad Sci, 102(42), pp. 15190-15194 (2005).

Wilske et al., "An OspA Serotyping System for Borrelia burgdorferi Based on Reactivity with Monoclonal Antibodies and OspA Sequence Analysis", J Clin Microbio, 31(2), pp. 340-350 (1993).

Wressnigg et al., "A Novel Multivalent OspA Vaccine against Lyme Borreliosis Is Safe and Immunogenic in an Adult Population Previously Infected with Borrelia burgdorferi Sensu Lato", Clinical and Vaccine Immunology, 21(11), pp. 1490-1499 (Nov. 2014).

Written Opinion of the International Searching Authority issued in PCT Application No. PCT/US2019/025422 on Sep. 4, 2019 (13 pages).

Wu, Tom Y.-H., "Strategies for designing synthetic immune agonists", Immunology, 148(4), pp. 315-325 (Jul. 11, 2016).

Xu et al., "Trispecific broadly neutralizing HIV antibodies mediate potent SHIV protection in macaques", Science 358 (6359), pp. 85-90 (2017).

Yassine et al., "Hemagglutinin-stem nanoparticles generate heterosubtypic influenza protection", Nature Medicine 21 (9), pp. 1065-1071 (2015).

Zhang et al., "Challenges of glycosylation analysis and control: an integrated approach to producing optimal and consistent therapeutic drugs", Drug Discovery Today, 21(5), pp. 740-765 (May 2016).

Alvarez-Cienfuegos et al., "Intramolecular trimerization, a novel strategy for making multispecific antibodies with controlled orientation of the antigen binding domains", Scientific Reports 2016; 6:28643 (Jun. 2016).

Aslam et al., "The accuracy of protein structure alignment servers", Electronic Journal of Biotechnology, 20, pp. 9-13 (2016).

Bordoli et al., "Protein structure homology modeling using SWISS-MODEL workspace", Nature Protocols, 4(1), pp. 1-13 (2009).—lots of references cited within.

Bu et al., "Immunization with Components of the Viral Fusion Apparatus Elicits Antibodies That Neutralize Epstein-Barr Virus in B Cells and Epithelial Cells", Immunity, 50, pp. 1305-1316 (2019).

Carter et al., "Design and Characterization of a Computationally Optimized Broadly Reactive Hemagglutinin Vaccine for H1N1 Influenza Viruses", J Virol, 90(9), pp. 4720-4734 (May 1, 2016).

Chapter 4 of Holtzhauer, M., Basic Methods for the Biochemical Lab, Springer 2006, ISBN 978-3-540-32785-1, available from www.springer.com.

Cui et al., "Rabbits immunized with Epstein-Barr virus gH/gL or GB recombinant proteins elicit higher serum virus neutralizing activity than gp350" Vaccine, 34(34), pp. 4050-4055 (Jul. 25, 2016).

Danilchanka et al., "Cyclic Dinucleotides and the Innate Immune Response", Cell, 154, pp. 962-970 (Aug. 29, 2013).

DiLillo et al, "Broadly neutralizing hemagglutinin stalk-specific antibodies require FcγR interactions for protection against influenza virus in vivo", Nature Medicine 20(2), pp. 143-151 (2014).

Faloon et al., "An Adjuvanted, Postfusion F Protein-Based Vaccine Did Not Prevent Respiratory Syncytial Virus Illness In Older Adults", J Infect Dis., 216, pp. 1362-1370 (Dec. 1, 2017).

Gaydos et al., "Swine Influenza A Outbreak, Fort Dix, New Jersey, 1976", Emerg Infect Dis, 12(1), pp. 23-28 (1976).

GenBank Accession Nos. CEQ35765.1 (Sep. 24, 2015) (2 pages).

GenBank Accession Nos. YP_001129472.1 (Aug. 13, 2018) (2 pages).

Gomes et al., "Harnessing Nanoparticles for Immunomodulation and Vaccines", Vaccines, 5(1), p. 6, (Feb. 14, 2017).

Gross et al., "Identification of LFA-1 as a candidate autoantigen in treatment-resistant Lyme arthritis", Science, 281 (5377), pp. 703-706 (1998).

Hein et al., "Click Chemistry, a Powerful Tool for Pharmaceutical Sciences", Pharm Res, 25(10), pp. 2216-2230 (Oct. 2008).

Hu et al., "Towards the next generation of biomedicines by site-selective conjugation", Chemical Society Reviews, 45 (6), pp. 1691-1719 (Mar. 21, 2016).

Hurwitz, J., "Respiratory syncytial virus vaccine development", Expert Rev Vaccines, 10(10), pp. 1415-1433 (Oct. 2011).

International Search Report issued in PCT Application No. PCT/US2019/025422 on Sep. 4, 2019 (8 pages).

Kanekiyo et al., "Rational Design of an Epstein-Barr Virus Vaccine Targeting the Receptor-Binding Site", Cell, 162(5), pp. 1090-1100 (Aug. 27, 2015).

Kanekiyo et al., "Self-assembling influenza nanoparticle vaccines elicit broadly neutralizing H1N1 antibodies", Nature, 499(7456), pp. 102-106 (Jul. 4, 2013).

Khazina et al., "Non-LTR retrotransposons encode noncanonical RRMdomains in their first open reading frame", Proc Natl Acad Sci U S A; 106(3), pp. 731-736 (Jan. 20, 2009).

Kim et al., "Efficient Site-Specific Labeling of Proteins via Cysteines", Bioconjugate Chemistry, 19(3), pp. 786-791 (Mar. 1, 2008).

Kitahara, et al., "A Delicate Interplay of Structure, Dynamics, and Thermodynamics for Function: A High Pressure NMR Study of Outer Surface Protein A", Biophys J 102(4), pp. 916-926 (2012).

Klucker et al., "AF03, An Alternative Squalene Emulsion-Based Vaccine Adjuvant Prepared by a Phase Inversion Temperature Method", J Pharm Sci., 101(12), pp. 4490-4500 (Dec. 2012).

(56) References Cited

OTHER PUBLICATIONS

Lander, et al., "Appion: an integrated, database-driven pipeline to facilitate EM image processing", J Struct Biol, 166(1), pp. 95-102 (2009).
Li et al., "Ferritin nanoparticle technology . . . A new platform for antigen presentation and vaccine development", Industrial Biotechnology, 2(2), pp. 143-147 (Jul. 17, 2006).
Livey et al., "A New Approach to a Lyme Disease Vaccine", Clinical Infectious Diseases, vol. 52, Supplement 3, pp. S266-S270 (Feb. 1, 2011).
Lopez-Sagaseta et al., "Self-assembling protein nanoparticles in the design of vaccines", Computational and Structural Biotechnology Journal, vol. 14, pp. 58-68 (Jan. 1, 2016).
Lynn et al., "In vivo characterization of the physicochemical properties of polymer-linked TLR agonists that enhance vaccine immunogenicity", Nat Biotechnol., 33(11), pp. 1201-1210 (Nov. 2015).
McLellan et al., "Structure-Based Design of a Fusion Glycoprotein Vaccine for Respiratory Syncytial Virus", Science, 342(6158), pp. 592-598 (Nov. 1, 2013).
McLellan et al., "Structure of RSV Fusion Glycoprotein Trimer Bound to a Prefusion-Specific Neutralizing Antibody", Science, 340(6136), pp. 1113-1117 (2013).
McLellan, et al., "Structure of Respiratory Syncytial Virus Fusion Glycoprotein in the Postfusion Conformation Reveals Preservation of Neutralizing Epitopes", J Virol 85(15), pp. 7788-7796 (2011).
Notification of Transmittal of The International Search Report and The Written Opinion of The International Searching Authority, or the Declaration, issued in PCT Application No. PCT/US2019/025377 on Jul. 10, 2019 (16 pages).
Notification of Transmittal of The International Search Report and The Written Opinion of The International Searching Authority, or the Declaration, issued in PCT Application No. PCT/US2019/025387 on Jul. 9, 2019 (20 pages).
Notification of Transmittal of The International Search Report and The Written Opinion of The International Searching Authority, or the Declaration, issued in PCT Application No. PCT/US2019/025419 on Oct. 18, 2019 (21 pages).
Notification of Transmittal of The International Search Report and The Written Opinion of The International Searching Authority, or the Declaration, issued in PCT Application No. PCT/US2019/025367 on Jul. 9, 2019 (17 pages).
Perez et al., "Novel Epstein-Barr virus-like particles incorporating gH/gL-EBNA1 or gB-LMP2 induce high neutralizing antibody titers and EBV-specific T-cell responses in immunized mice", Oncotarget, 8(12), (Mar. 21, 2017).
Ra et al., "Lumazine synthase protein cage nanoparticles as antigen delivery nanoplatforms for dendritic cell-based vaccine development", Clin Exp Vaccine Res, 3, pp. 227-234 (2014).
Rosa et al. "The burgeoning molecular genetics of the Lyme disease spirochaete", Nat Rev Microbiol 3(2), pp. 129-143 (2005).
Sashihara et al., "Human Antibody Titers to Epstein-Barr Virus (EBV) gp350 Correlate with Neutralization of Infectivity Better than Antibody Titers to EBV gp42 Using a Rapid Flow Cytometry-Based EBV Neutralization Assay", Virology, 391(2), pp. 249-256 (Sep. 1, 2009).
Sliepen et al., "Presenting native-like HIV-1 envelope trimers on ferritin nanoparticles improves their immunogenicity", Retrovirology, 11(1), p. e1004767 (Sep. 26, 2015).
Sorzano et al., XMIPP: a new generation of an open-source image processing package for electron microscopy, J Struct Biol, 148(2), pp. 194-204 (2004).
Steff et al., "Pre-fusion RSV F strongly boosts pre-fusion specific neutralizing responses in cattle pre-exposed to povine RSV", Nature Communications, 8(1) (Oct. 20, 2017) (abstract).
Swanson et al., "Structural basis for immunization with postfusion respiratory syncytial virus fusion F glycoprotein (RSV F) to elicit high neutralizing antibody titers", Proc Natl Acad Sci, 108(23), pp. 9619-9624 (2011).
Trikha, J., et al. "High Resolution Crystal Structures of Amphibian Red-Cell L Ferritin: Potential Roles for Structural Plasticity and Solvation in Function", J Mol Biol, 248(5), pp. 949-967 (1995).
Tripp et al., "Respiratory Syncytial Virus: Targeting the G Protein Provides a New Approach for an Old Problem", Journal of Virology, 92(3), pp. 1-8 (Nov. 8, 2017).
Uchida et al., "Targeting of Cancer Cells with Ferrimagnetic Ferritin Cage Nanoparticles", Journal of the American Chemical Society, 128(51), pp. 16626-16633 (Dec. 1, 2006).
Van Geel et al., "Chemoenzymatic Conjugation of Toxic Payloads to the Globally Conserved N-Glycan of Native mAbs Provides Homogeneous and Highly Efficacious Antibody-Drug Conjugates", Bioconjugate Chem., 26, pp. 2233-2242 (2015).
Wang et al., "Functional ferritin nanoparticles for biomedical applications", Frontiers of Chemical Science and Engineering, 11(4), pp. 633-646 (Feb. 15, 2017).

* cited by examiner

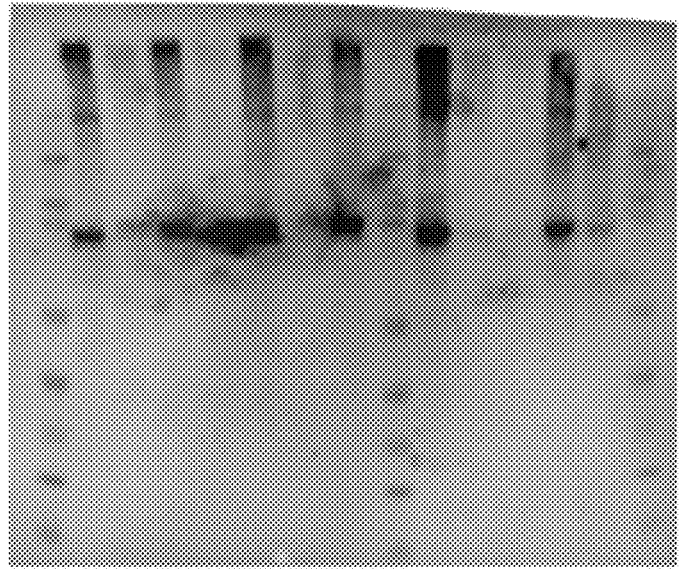

Lane #  Expression level in media
1. Ladder
2. RF8090: NIH DS-CAV1 scF-bf-pFerr   Yes (Benchmark)
3. RF8100: Glycan addition T324N   Poor, reduced expression
4. RF8101 : Glycan addition E328N   Yes, improved expression
5. RF8102: Glycan addition K390T   Poor, reduced expression
6. RF8103: Glycan addition S348N   Yes, improved expression
7. RF8104: Glycan addition Y478S   No, reduced expression
8. RF8105: Glycan addition R507N   Yes, improved expression
9. Ladder
10. RF8108: Proline addition I217P   Yes, improved expression
11. RF8109: Cavity filling Q224L   Poor, reduce expression
12. RF8110 : Cavity filling Q224L and Q225V   Poor, reduced expression
13. RF8111 : Cavity filling N228L   Yes, equal or increased expression
14. RF8112 : Cavity filling N228F   Poor, reduced expression
15. Ladder

*Figure 2*

Anti-*Pre-fusion* F Antibody Response

Figure 12A

Anti-*Post-fusion* F Antibody Response

Structural model of RSV G Peptide conjugated to Ferritin

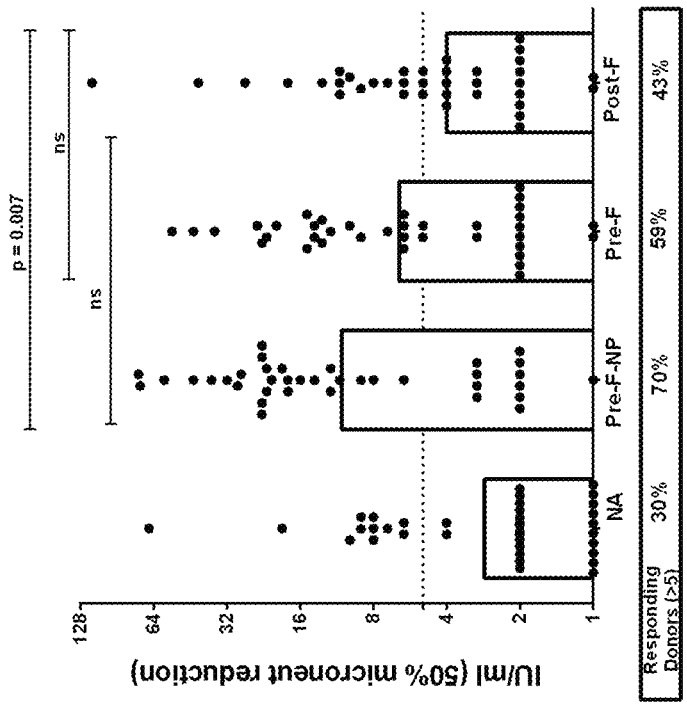
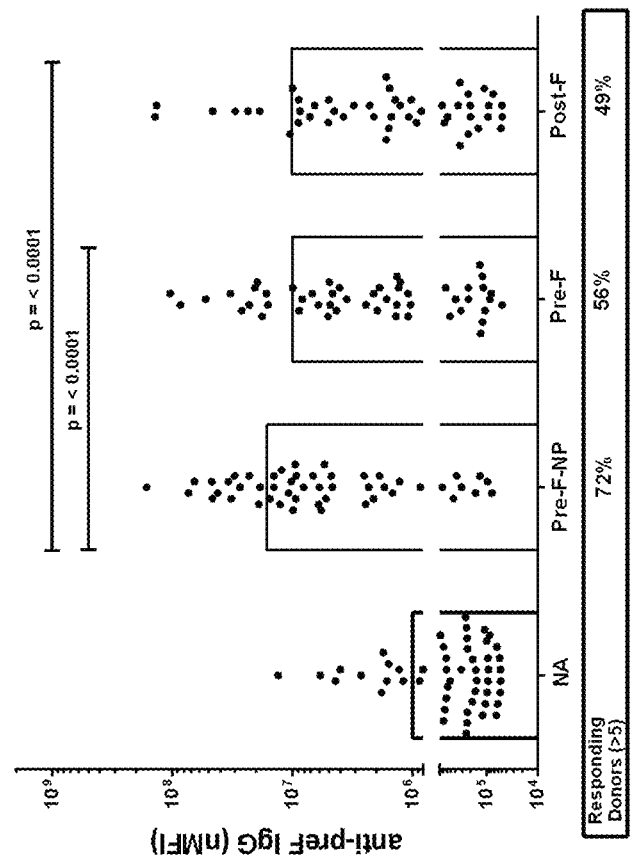
*Figure 20B*
*Figure 20A*

SEQUENCE LISTING

```
<160> NUMBER OF SEQ ID NOS: 230

<210> SEQ ID NO 1
<211> LENGTH: 651
<212> TYPE: PRT
<213> ORGANISM: Artificial Sequence
<220> FEATURE:
<223> OTHER INFORMATION: Synthetic polypeptide

<400> SEQUENCE: 1

Met Glu Leu Leu Ile Leu Lys Ala Asn Ala Ile Thr Thr Ile Leu Thr
1               5                   10                  15
```

```
Ala Val Thr Phe Cys Phe Ala Ser Gly Gln Asn Ile Thr Glu Glu Phe
             20                  25                  30

Tyr Gln Ser Thr Cys Ser Ala Val Ser Lys Gly Tyr Leu Ser Ala Leu
         35                  40                  45

Arg Thr Gly Trp Tyr Thr Ser Val Ile Thr Ile Glu Leu Ser Asn Ile
 50                  55                  60

Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
             85                  90                  95

Met Gly Ser Gly Asn Val Gly Leu Gly Gly Ala Ile Ala Ser Gly Val
            100                 105                 110

Ala Val Cys Lys Val Leu His Leu Glu Gly Glu Val Asn Lys Ile Lys
            115                 120                 125

Ser Ala Leu Leu Ser Thr Asn Lys Ala Val Val Ser Leu Ser Asn Gly
130                 135                 140

Val Ser Val Leu Thr Phe Lys Val Leu Asp Leu Lys Asn Tyr Ile Asp
145                 150                 155                 160

Lys Gln Leu Leu Pro Ile Leu Asn Lys Gln Ser Cys Ser Ile Ser Asn
            165                 170                 175

Ile Glu Thr Val Ile Glu Phe Gln Gln Lys Asn Asn Arg Leu Leu Glu
            180                 185                 190

Ile Thr Arg Glu Phe Ser Val Asn Ala Gly Val Thr Thr Pro Val Ser
        195                 200                 205

Thr Tyr Met Leu Thr Asn Ser Glu Leu Leu Ser Leu Ile Asn Asp Met
210                 215                 220

Pro Ile Thr Asn Asp Gln Lys Lys Leu Met Ser Asn Asn Val Gln Ile
225                 230                 235                 240

Val Arg Gln Gln Ser Tyr Ser Ile Met Cys Ile Ile Lys Glu Glu Val
            245                 250                 255

Leu Ala Tyr Val Val Gln Leu Pro Leu Tyr Gly Val Ile Asp Thr Pro
            260                 265                 270

Cys Trp Lys Leu His Thr Ser Pro Leu Cys Thr Thr Asn Thr Lys Glu
            275                 280                 285

Gly Ser Asn Ile Cys Leu Thr Arg Thr Asp Arg Gly Trp Tyr Cys Asp
290                 295                 300

Asn Ala Gly Ser Val Ser Phe Phe Pro Gln Ala Glu Thr Cys Lys Val
305                 310                 315                 320

Gln Ser Asn Arg Val Phe Cys Asp Thr Met Asn Ser Arg Thr Leu Pro
            325                 330                 335

Ser Glu Val Asn Leu Cys Asn Val Asp Ile Phe Asn Pro Lys Tyr Asp
            340                 345                 350

Cys Lys Ile Met Thr Ser Lys Thr Asp Val Ser Ser Ser Val Ile Thr
            355                 360                 365

Ser Leu Gly Ala Ile Val Ser Cys Tyr Gly Lys Thr Lys Cys Thr Ala
370                 375                 380

Ser Asn Lys Asn Arg Gly Ile Ile Lys Thr Phe Ser Asn Gly Cys Asp
385                 390                 395                 400

Tyr Val Ser Asn Lys Gly Val Asp Thr Val Ser Val Gly Asn Thr Leu
            405                 410                 415

Tyr Tyr Val Asn Lys Gln Glu Gly Lys Ser Leu Tyr Val Lys Gly Glu
            420                 425                 430
```

```
Pro Ile Ile Asn Phe Tyr Asp Pro Leu Val Phe Pro Ser Asp Glu Phe
            435                 440                 445

Asp Ala Ser Ile Ser Gln Val Asn Glu Lys Ile Asn Gln Ser Leu Ala
450                 455                 460

Phe Ile Arg Lys Ser Asp Glu Leu Leu Ser Gly Ser Gly Ser Glu Ser
465                 470                 475                 480

Gln Val Arg Gln Gln Phe Ser Lys Asp Ile Glu Lys Leu Leu Asn Glu
                485                 490                 495

Gln Val Asn Lys Glu Met Gln Ser Ser Asn Leu Tyr Met Ser Met Ser
            500                 505                 510

Ser Trp Ser Tyr Thr His Ser Leu Asp Gly Ala Gly Leu Phe Leu Phe
            515                 520                 525

Asp His Ala Ala Glu Glu Tyr Glu His Ala Lys Lys Leu Ile Ile Phe
530                 535                 540

Leu Asn Glu Asn Asn Val Pro Val Gln Leu Thr Ser Ile Ser Ala Pro
545                 550                 555                 560

Glu His Lys Phe Glu Gly Leu Thr Gln Ile Phe Gln Lys Ala Tyr Glu
                565                 570                 575

His Glu Gln His Ile Ser Glu Ser Ile Asn Asn Ile Val Asp His Ala
            580                 585                 590

Ile Lys Cys Lys Asp His Ala Thr Phe Asn Phe Leu Gln Trp Tyr Val
            595                 600                 605

Ala Glu Gln His Glu Glu Val Leu Phe Lys Asp Ile Leu Asp Lys
            610                 615                 620

Ile Glu Leu Ile Gly Asn Glu Asn His Gly Leu Tyr Leu Ala Asp Gln
625                 630                 635                 640

Tyr Val Lys Gly Ile Ala Lys Ser Arg Lys Ser
                645                 650

<210> SEQ ID NO 2
<211> LENGTH: 651
<212> TYPE: PRT
<213> ORGANISM: Artificial Sequence
<220> FEATURE:
<223> OTHER INFORMATION: Synthetic polypeptide

<400> SEQUENCE: 2

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Ser Gly Asn Val Gly Leu Gly Gly Ala Ile Ala Ser Gly Val
            100                 105                 110

Ala Val Cys Lys Val Leu His Leu Glu Gly Glu Val Asn Lys Ile Lys
        115                 120                 125

Ser Ala Leu Leu Ser Thr Asn Lys Ala Val Val Ser Leu Ser Asn Gly
    130                 135                 140
```

```
Val Ser Val Leu Thr Phe Lys Val Leu Asp Leu Lys Asn Tyr Ile Asp
145                 150                 155                 160

Lys Gln Leu Leu Pro Ile Leu Asn Lys Gln Ser Cys Ser Ile Ser Asn
                165                 170                 175

Ile Glu Thr Val Ile Glu Phe Gln Gln Lys Asn Asn Arg Leu Leu Glu
            180                 185                 190

Ile Thr Arg Glu Phe Ser Val Asn Ala Gly Val Thr Thr Pro Val Ser
        195                 200                 205

Thr Tyr Met Leu Thr Asn Ser Glu Leu Leu Ser Leu Ile Asn Asp Met
    210                 215                 220

Pro Ile Thr Asn Asp Gln Lys Lys Leu Met Ser Asn Asn Val Gln Ile
225                 230                 235                 240

Val Arg Gln Gln Ser Tyr Ser Ile Met Cys Ile Ile Lys Glu Glu Val
                245                 250                 255

Leu Ala Tyr Val Val Gln Leu Pro Leu Tyr Gly Val Ile Asp Thr Pro
                260                 265                 270

Cys Trp Lys Leu His Thr Ser Pro Leu Cys Thr Thr Asn Thr Lys Glu
            275                 280                 285

Gly Ser Asn Ile Cys Leu Thr Arg Thr Asp Arg Gly Trp Tyr Cys Asp
290                 295                 300

Asn Ala Gly Ser Val Ser Phe Phe Pro Gln Ala Glu Thr Cys Lys Val
305                 310                 315                 320

Gln Ser Asn Arg Val Phe Cys Asp Thr Met Asn Ser Arg Thr Leu Pro
                325                 330                 335

Ser Glu Val Asn Leu Cys Asn Val Asp Ile Phe Asn Pro Lys Tyr Asp
                340                 345                 350

Cys Lys Ile Met Thr Ser Lys Thr Asp Val Ser Ser Ser Val Ile Thr
                355                 360                 365

Ser Leu Gly Ala Ile Val Ser Cys Tyr Gly Lys Thr Lys Cys Thr Ala
            370                 375                 380

Ser Asn Lys Asn Arg Gly Ile Ile Lys Thr Phe Ser Asn Gly Cys Asp
385                 390                 395                 400

Tyr Val Ser Asn Lys Gly Val Asp Thr Val Ser Val Gly Asn Thr Leu
                405                 410                 415

Tyr Tyr Val Asn Lys Gln Glu Gly Lys Ser Leu Tyr Val Lys Gly Glu
                420                 425                 430

Pro Ile Ile Asn Phe Tyr Asp Pro Leu Val Phe Pro Ser Asp Glu Phe
            435                 440                 445

Asp Ala Ser Ile Ser Gln Val Asn Glu Lys Ile Asn Gln Ser Leu Ala
450                 455                 460

Phe Ile Arg Lys Ser Asp Glu Leu Leu Ser Gly Ser Gly Ser Glu Ser
465                 470                 475                 480

Gln Val Arg Gln Gln Phe Ser Lys Asp Ile Glu Lys Leu Leu Asn Glu
                485                 490                 495

Gln Val Asn Lys Glu Met Gln Ser Ser Asn Leu Tyr Met Ser Met Ser
                500                 505                 510

Ser Trp Ser Tyr Thr His Ser Leu Asp Gly Ala Gly Leu Phe Leu Phe
            515                 520                 525

Asp His Ala Ala Glu Glu Tyr Glu His Ala Lys Lys Leu Ile Ile Phe
                530                 535                 540

Leu Asn Glu Asn Asn Val Pro Val Gln Leu Thr Ser Ile Ser Ala Pro
545                 550                 555                 560

Glu His Lys Phe Glu Gly Leu Thr Gln Ile Phe Gln Lys Ala Tyr Glu
```

His Glu Gln His Ile Ser Glu Ser Ile Asn Asn Ile Val Asp His Ala
565                 570                 575
                580                585                590

Ile Lys Cys Lys Asp His Ala Thr Phe Asn Phe Leu Gln Trp Tyr Val
            595             600             605

Ala Glu Gln His Glu Glu Val Leu Phe Lys Asp Ile Leu Asp Lys
        610             615             620

Ile Glu Leu Ile Gly Asn Glu Asn His Gly Leu Tyr Leu Ala Asp Gln
625             630             635             640

Tyr Val Lys Gly Ile Ala Lys Ser Arg Lys Ser
                645                 650

<210> SEQ ID NO 3
<211> LENGTH: 651
<212> TYPE: PRT
<213> ORGANISM: Artificial Sequence
<220> FEATURE:
<223> OTHER INFORMATION: Synthetic polypeptide

<400> SEQUENCE: 3

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Ser Gly Asn Val Gly Leu Gly Gly Ala Ile Ala Ser Gly Val
            100                 105                 110

Ala Val Cys Lys Val Leu His Leu Glu Gly Glu Val Asn Lys Ile Lys
        115                 120                 125

Ser Ala Leu Leu Ser Thr Asn Lys Ala Val Val Ser Leu Ser Asn Gly
    130                 135                 140

Val Ser Val Leu Thr Phe Lys Val Leu Asp Leu Lys Asn Tyr Ile Asp
145                 150                 155                 160

Lys Gln Leu Leu Pro Ile Leu Asn Lys Gln Ser Cys Ser Ile Ser Asn
                165                 170                 175

Ile Glu Thr Val Ile Glu Phe Gln Gln Lys Asn Asn Arg Leu Leu Glu
            180                 185                 190

Ile Thr Arg Glu Phe Ser Val Asn Ala Gly Val Thr Thr Pro Val Ser
        195                 200                 205

Thr Tyr Met Leu Thr Asn Ser Glu Leu Leu Ser Leu Ile Asn Asp Met
    210                 215                 220

Pro Ile Thr Asn Asp Gln Lys Lys Leu Met Ser Asn Asn Val Gln Ile
225                 230                 235                 240

Val Arg Gln Gln Ser Tyr Ser Ile Met Cys Ile Ile Lys Glu Glu Val
                245                 250                 255

Leu Ala Tyr Val Val Gln Leu Pro Leu Tyr Gly Val Ile Asp Thr Pro
            260                 265                 270

Cys Trp Lys Leu His Thr Ser Pro Leu Cys Thr Asn Asn Thr Lys Glu

```
                    275                 280                 285
Gly Ser Asn Ile Cys Leu Thr Arg Thr Asp Arg Gly Trp Tyr Cys Asp
290                 295                 300

Asn Ala Gly Ser Val Ser Phe Phe Pro Gln Ala Glu Thr Cys Lys Val
305                 310                 315                 320

Gln Ser Asn Arg Val Phe Cys Asp Thr Met Asn Ser Arg Thr Leu Pro
                325                 330                 335

Ser Glu Val Asn Leu Cys Asn Val Asp Ile Phe Asn Pro Lys Tyr Asp
                340                 345                 350

Cys Lys Ile Met Thr Ser Lys Thr Asp Val Ser Ser Val Ile Thr
                355                 360                 365

Ser Leu Gly Ala Ile Val Ser Cys Tyr Gly Lys Thr Lys Cys Thr Ala
370                 375                 380

Ser Asn Lys Asn Arg Gly Ile Ile Lys Thr Phe Ser Asn Gly Cys Asp
385                 390                 395                 400

Tyr Val Ser Asn Lys Gly Val Asp Thr Val Ser Val Gly Asn Thr Leu
                405                 410                 415

Tyr Tyr Val Asn Lys Gln Glu Gly Lys Ser Leu Tyr Val Lys Gly Glu
                420                 425                 430

Pro Ile Ile Asn Phe Tyr Asp Pro Leu Val Phe Pro Ser Asp Glu Phe
                435                 440                 445

Asp Ala Ser Ile Ser Gln Val Asn Glu Lys Ile Asn Gln Ser Leu Ala
450                 455                 460

Phe Ile Arg Lys Ser Asp Glu Leu Leu Ser Gly Ser Gly Ser Glu Ser
465                 470                 475                 480

Gln Val Arg Gln Gln Phe Ser Lys Asp Ile Glu Lys Leu Leu Asn Glu
                485                 490                 495

Gln Val Asn Lys Glu Met Gln Ser Ser Asn Leu Tyr Met Ser Met Ser
                500                 505                 510

Ser Trp Ser Tyr Thr His Ser Leu Asp Gly Ala Gly Leu Phe Leu Phe
                515                 520                 525

Asp His Ala Ala Glu Glu Tyr Glu His Ala Lys Lys Leu Ile Ile Phe
                530                 535                 540

Leu Asn Glu Asn Asn Val Pro Val Gln Leu Thr Ser Ile Ser Ala Pro
545                 550                 555                 560

Glu His Lys Phe Glu Gly Leu Thr Gln Ile Phe Gln Lys Ala Tyr Glu
                565                 570                 575

His Glu Gln His Ile Ser Glu Ser Ile Asn Asn Ile Val Asp His Ala
                580                 585                 590

Ile Lys Cys Lys Asp His Ala Thr Phe Asn Phe Leu Gln Trp Tyr Val
                595                 600                 605

Ala Glu Gln His Glu Glu Val Leu Phe Lys Asp Ile Leu Asp Lys
                610                 615                 620

Ile Glu Leu Ile Gly Asn Glu Asn His Gly Leu Tyr Leu Ala Asp Gln
625                 630                 635                 640

Tyr Val Lys Gly Ile Ala Lys Ser Arg Lys Ser
                645                 650
```

<210> SEQ ID NO 4
<211> LENGTH: 651
<212> TYPE: PRT
<213> ORGANISM: Artificial Sequence
<220> FEATURE:
<223> OTHER INFORMATION: Synthetic polypeptide

<400> SEQUENCE: 4

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Ser Gly Asn Val Gly Leu Gly Gly Ala Ile Ala Ser Gly Val
            100                 105                 110

Ala Val Cys Lys Val Leu His Leu Glu Gly Glu Val Asn Lys Ile Lys
        115                 120                 125

Ser Ala Leu Leu Ser Thr Asn Lys Ala Val Val Ser Leu Ser Asn Gly
    130                 135                 140

Val Ser Val Leu Thr Phe Lys Val Leu Asp Leu Lys Asn Tyr Ile Asp
145                 150                 155                 160

Lys Gln Leu Leu Pro Ile Leu Asn Lys Gln Ser Cys Ser Ile Ser Asn
                165                 170                 175

Ile Glu Thr Val Ile Glu Phe Gln Gln Lys Asn Asn Arg Leu Leu Glu
            180                 185                 190

Ile Thr Arg Glu Phe Ser Val Asn Ala Gly Val Thr Thr Pro Val Ser
        195                 200                 205

Thr Tyr Met Leu Thr Asn Ser Glu Leu Leu Ser Leu Ile Asn Asp Met
210                 215                 220

Pro Ile Thr Asn Asp Gln Lys Lys Leu Met Ser Asn Asn Val Gln Ile
225                 230                 235                 240

Val Arg Gln Gln Ser Tyr Ser Ile Met Cys Ile Ile Lys Glu Glu Val
                245                 250                 255

Leu Ala Tyr Val Val Gln Leu Pro Leu Tyr Gly Val Ile Asp Thr Pro
            260                 265                 270

Cys Trp Lys Leu His Thr Ser Pro Leu Cys Thr Thr Asn Thr Lys Asn
        275                 280                 285

Gly Ser Asn Ile Cys Leu Thr Arg Thr Asp Arg Gly Trp Tyr Cys Asp
    290                 295                 300

Asn Ala Gly Ser Val Ser Phe Phe Pro Gln Ala Glu Thr Cys Lys Val
305                 310                 315                 320

Gln Ser Asn Arg Val Phe Cys Asp Thr Met Asn Ser Arg Thr Leu Pro
                325                 330                 335

Ser Glu Val Asn Leu Cys Asn Val Asp Ile Phe Asn Pro Lys Tyr Asp
            340                 345                 350

Cys Lys Ile Met Thr Ser Lys Thr Asp Val Ser Ser Ser Val Ile Thr
        355                 360                 365

Ser Leu Gly Ala Ile Val Ser Cys Tyr Gly Lys Thr Lys Cys Thr Ala
    370                 375                 380

Ser Asn Lys Asn Arg Gly Ile Ile Lys Thr Phe Ser Asn Gly Cys Asp
385                 390                 395                 400

Tyr Val Ser Asn Lys Gly Val Asp Thr Val Ser Val Gly Asn Thr Leu
                405                 410                 415
```

Tyr Tyr Val Asn Lys Gln Glu Gly Lys Ser Leu Tyr Val Lys Gly Glu
            420                 425                 430

Pro Ile Ile Asn Phe Tyr Asp Pro Leu Val Phe Pro Ser Asp Glu Phe
            435                 440                 445

Asp Ala Ser Ile Ser Gln Val Asn Glu Lys Ile Asn Gln Ser Leu Ala
450                 455                 460

Phe Ile Arg Lys Ser Asp Glu Leu Leu Ser Gly Ser Gly Ser Glu Ser
465                 470                 475                 480

Gln Val Arg Gln Gln Phe Ser Lys Asp Ile Glu Lys Leu Leu Asn Glu
                485                 490                 495

Gln Val Asn Lys Glu Met Gln Ser Ser Asn Leu Tyr Met Ser Met Ser
            500                 505                 510

Ser Trp Ser Tyr Thr His Ser Leu Asp Gly Ala Gly Leu Phe Leu Phe
            515                 520                 525

Asp His Ala Ala Glu Glu Tyr Glu His Ala Lys Lys Leu Ile Ile Phe
            530                 535                 540

Leu Asn Glu Asn Asn Val Pro Val Gln Leu Thr Ser Ile Ser Ala Pro
545                 550                 555                 560

Glu His Lys Phe Glu Gly Leu Thr Gln Ile Phe Gln Lys Ala Tyr Glu
                565                 570                 575

His Glu Gln His Ile Ser Glu Ser Ile Asn Asn Ile Val Asp His Ala
            580                 585                 590

Ile Lys Cys Lys Asp His Ala Thr Phe Asn Phe Leu Gln Trp Tyr Val
            595                 600                 605

Ala Glu Gln His Glu Glu Val Leu Phe Lys Asp Ile Leu Asp Lys
            610                 615                 620

Ile Glu Leu Ile Gly Asn Glu Asn His Gly Leu Tyr Leu Ala Asp Gln
625                 630                 635                 640

Tyr Val Lys Gly Ile Ala Lys Ser Arg Lys Ser
                645                 650

<210> SEQ ID NO 5
<211> LENGTH: 651
<212> TYPE: PRT
<213> ORGANISM: Artificial Sequence
<220> FEATURE:
<223> OTHER INFORMATION: Synthetic polypeptide

<400> SEQUENCE: 5

Met Glu Leu Leu Ile Leu Lys Ala Asn Ala Ile Thr Thr Ile Leu Thr
1                   5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Ser Gly Asn Val Gly Leu Gly Gly Ala Ile Ala Ser Gly Val
            100                 105                 110

Ala Val Cys Lys Val Leu His Leu Glu Gly Glu Val Asn Lys Ile Lys
        115                 120                 125

```
Ser Ala Leu Leu Ser Thr Asn Lys Ala Val Ser Leu Ser Asn Gly
130                 135                 140

Val Ser Val Leu Thr Phe Lys Val Leu Asp Leu Lys Asn Tyr Ile Asp
145                 150                 155                 160

Lys Gln Leu Leu Pro Ile Leu Asn Lys Gln Ser Cys Ser Ile Ser Asn
            165                 170                 175

Ile Glu Thr Val Ile Glu Phe Gln Gln Lys Asn Asn Arg Leu Leu Glu
            180                 185                 190

Ile Thr Arg Glu Phe Ser Val Asn Ala Gly Val Thr Thr Pro Val Ser
        195                 200                 205

Thr Tyr Met Leu Thr Asn Ser Glu Leu Leu Ser Leu Ile Asn Asp Met
210                 215                 220

Pro Ile Thr Asn Asp Gln Lys Lys Leu Met Ser Asn Asn Val Gln Ile
225                 230                 235                 240

Val Arg Gln Gln Ser Tyr Ser Ile Met Cys Ile Ile Lys Glu Glu Val
                245                 250                 255

Leu Ala Tyr Val Val Gln Leu Pro Leu Tyr Gly Val Ile Asp Thr Pro
                260                 265                 270

Cys Trp Lys Leu His Thr Ser Pro Leu Cys Thr Thr Asn Thr Lys Glu
            275                 280                 285

Gly Ser Asn Ile Cys Leu Thr Arg Thr Asp Arg Gly Trp Tyr Cys Asp
290                 295                 300

Asn Ala Gly Ser Val Ser Phe Phe Pro Gln Ala Glu Thr Cys Lys Val
305                 310                 315                 320

Gln Ser Asn Arg Val Phe Cys Asp Thr Met Asn Ser Arg Thr Leu Pro
                325                 330                 335

Ser Glu Val Asn Leu Cys Asn Val Asp Ile Phe Asn Pro Thr Tyr Asp
                340                 345                 350

Cys Lys Ile Met Thr Ser Lys Thr Asp Val Ser Ser Ser Val Ile Thr
            355                 360                 365

Ser Leu Gly Ala Ile Val Ser Cys Tyr Gly Lys Thr Lys Cys Thr Ala
370                 375                 380

Ser Asn Lys Asn Arg Gly Ile Ile Lys Thr Phe Ser Asn Gly Cys Asp
385                 390                 395                 400

Tyr Val Ser Asn Lys Gly Val Asp Thr Val Ser Val Gly Asn Thr Leu
                405                 410                 415

Tyr Tyr Val Asn Lys Gln Glu Gly Lys Ser Leu Tyr Val Lys Gly Glu
                420                 425                 430

Pro Ile Ile Asn Phe Tyr Asp Pro Leu Val Phe Pro Ser Asp Glu Phe
            435                 440                 445

Asp Ala Ser Ile Ser Gln Val Asn Glu Lys Ile Asn Gln Ser Leu Ala
450                 455                 460

Phe Ile Arg Lys Ser Asp Glu Leu Leu Ser Gly Ser Gly Ser Glu Ser
465                 470                 475                 480

Gln Val Arg Gln Gln Phe Ser Lys Asp Ile Glu Lys Leu Leu Asn Glu
                485                 490                 495

Gln Val Asn Lys Glu Met Gln Ser Ser Asn Leu Tyr Met Ser Met Ser
            500                 505                 510

Ser Trp Ser Tyr Thr His Ser Leu Asp Gly Ala Gly Leu Phe Leu Phe
            515                 520                 525

Asp His Ala Ala Glu Glu Tyr Glu His Ala Lys Lys Leu Ile Ile Phe
530                 535                 540
```

```
Leu Asn Glu Asn Asn Val Pro Val Gln Leu Thr Ser Ile Ser Ala Pro
545                 550                 555                 560

Glu His Lys Phe Glu Gly Leu Thr Gln Ile Phe Gln Lys Ala Tyr Glu
                565                 570                 575

His Glu Gln His Ile Ser Glu Ser Ile Asn Asn Ile Val Asp His Ala
            580                 585                 590

Ile Lys Cys Lys Asp His Ala Thr Phe Asn Phe Leu Gln Trp Tyr Val
        595                 600                 605

Ala Glu Gln His Glu Glu Val Leu Phe Lys Asp Ile Leu Asp Lys
    610                 615                 620

Ile Glu Leu Ile Gly Asn Glu Asn His Gly Leu Tyr Leu Ala Asp Gln
625                 630                 635                 640

Tyr Val Lys Gly Ile Ala Lys Ser Arg Lys Ser
                645                 650

<210> SEQ ID NO 6
<211> LENGTH: 651
<212> TYPE: PRT
<213> ORGANISM: Artificial Sequence
<220> FEATURE:
<223> OTHER INFORMATION: Synthetic polypeptide

<400> SEQUENCE: 6

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Ser Gly Asn Val Gly Leu Gly Gly Ala Ile Ala Ser Gly Val
            100                 105                 110

Ala Val Cys Lys Val Leu His Leu Glu Gly Glu Val Asn Lys Ile Lys
        115                 120                 125

Ser Ala Leu Leu Ser Thr Asn Lys Ala Val Val Ser Leu Ser Asn Gly
130                 135                 140

Val Ser Val Leu Thr Phe Lys Val Leu Asp Leu Lys Asn Tyr Ile Asp
145                 150                 155                 160

Lys Gln Leu Leu Pro Ile Leu Asn Lys Gln Ser Cys Ser Ile Ser Asn
                165                 170                 175

Ile Glu Thr Val Ile Glu Phe Gln Gln Lys Asn Asn Arg Leu Leu Glu
            180                 185                 190

Ile Thr Arg Glu Phe Ser Val Asn Ala Gly Val Thr Thr Pro Val Ser
        195                 200                 205

Thr Tyr Met Leu Thr Asn Ser Glu Leu Leu Ser Leu Ile Asn Asp Met
210                 215                 220

Pro Ile Thr Asn Asp Gln Lys Lys Leu Met Ser Asn Asn Val Gln Ile
225                 230                 235                 240

Val Arg Gln Gln Ser Tyr Ser Ile Met Cys Ile Ile Lys Glu Glu Val
                245                 250                 255
```

Leu Ala Tyr Val Val Gln Leu Pro Tyr Gly Val Ile Asp Thr Pro
                260                 265                 270

Cys Trp Lys Leu His Thr Ser Pro Leu Cys Thr Thr Asn Thr Lys Glu
            275                 280                 285

Gly Ser Asn Ile Cys Leu Thr Arg Thr Asp Arg Gly Trp Tyr Cys Asp
        290                 295                 300

Asn Ala Gly Asn Val Ser Phe Phe Pro Gln Ala Glu Thr Cys Lys Val
305                 310                 315                 320

Gln Ser Asn Arg Val Phe Cys Asp Thr Met Asn Ser Arg Thr Leu Pro
                325                 330                 335

Ser Glu Val Asn Leu Cys Asn Val Asp Ile Phe Asn Pro Lys Tyr Asp
            340                 345                 350

Cys Lys Ile Met Thr Ser Lys Thr Asp Val Ser Ser Val Ile Thr
            355                 360                 365

Ser Leu Gly Ala Ile Val Ser Cys Tyr Gly Lys Thr Lys Cys Thr Ala
        370                 375                 380

Ser Asn Lys Asn Arg Gly Ile Ile Lys Thr Phe Ser Asn Gly Cys Asp
385                 390                 395                 400

Tyr Val Ser Asn Lys Gly Val Asp Thr Val Ser Val Gly Asn Thr Leu
                405                 410                 415

Tyr Tyr Val Asn Lys Gln Glu Gly Lys Ser Leu Tyr Val Lys Gly Glu
            420                 425                 430

Pro Ile Ile Asn Phe Tyr Asp Pro Leu Val Phe Pro Ser Asp Glu Phe
        435                 440                 445

Asp Ala Ser Ile Ser Gln Val Asn Glu Lys Ile Asn Gln Ser Leu Ala
450                 455                 460

Phe Ile Arg Lys Ser Asp Glu Leu Leu Ser Gly Ser Gly Ser Glu Ser
465                 470                 475                 480

Gln Val Arg Gln Gln Phe Ser Lys Asp Ile Glu Lys Leu Leu Asn Glu
                485                 490                 495

Gln Val Asn Lys Glu Met Gln Ser Ser Asn Leu Tyr Met Ser Met Ser
            500                 505                 510

Ser Trp Ser Tyr Thr His Ser Leu Asp Gly Ala Gly Leu Phe Leu Phe
        515                 520                 525

Asp His Ala Ala Glu Glu Tyr Glu His Ala Lys Lys Leu Ile Ile Phe
530                 535                 540

Leu Asn Glu Asn Asn Val Pro Val Gln Leu Thr Ser Ile Ser Ala Pro
545                 550                 555                 560

Glu His Lys Phe Glu Gly Leu Thr Gln Ile Phe Gln Lys Ala Tyr Glu
                565                 570                 575

His Glu Gln His Ile Ser Glu Ser Ile Asn Asn Ile Val Asp His Ala
            580                 585                 590

Ile Lys Cys Lys Asp His Ala Thr Phe Asn Phe Leu Gln Trp Tyr Val
        595                 600                 605

Ala Glu Gln His Glu Glu Val Leu Phe Lys Asp Ile Leu Asp Lys
610                 615                 620

Ile Glu Leu Ile Gly Asn Glu Asn His Gly Leu Tyr Leu Ala Asp Gln
625                 630                 635                 640

Tyr Val Lys Gly Ile Ala Lys Ser Arg Lys Ser
                645                 650

<210> SEQ ID NO 7
<211> LENGTH: 651
<212> TYPE: PRT

<213> ORGANISM: Artificial Sequence
<220> FEATURE:
<223> OTHER INFORMATION: Synthetic polypeptide

<400> SEQUENCE: 7

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Ser Gly Asn Val Gly Leu Gly Gly Ala Ile Ala Ser Gly Val
            100                 105                 110

Ala Val Cys Lys Val Leu His Leu Glu Gly Glu Val Asn Lys Ile Lys
        115                 120                 125

Ser Ala Leu Leu Ser Thr Asn Lys Ala Val Val Ser Leu Ser Asn Gly
    130                 135                 140

Val Ser Val Leu Thr Phe Lys Val Leu Asp Leu Lys Asn Tyr Ile Asp
145                 150                 155                 160

Lys Gln Leu Leu Pro Ile Leu Asn Lys Gln Ser Cys Ser Ile Ser Asn
                165                 170                 175

Ile Glu Thr Val Ile Glu Phe Gln Gln Lys Asn Asn Arg Leu Leu Glu
            180                 185                 190

Ile Thr Arg Glu Phe Ser Val Asn Ala Gly Val Thr Thr Pro Val Ser
        195                 200                 205

Thr Tyr Met Leu Thr Asn Ser Glu Leu Leu Ser Leu Ile Asn Asp Met
    210                 215                 220

Pro Ile Thr Asn Asp Gln Lys Lys Leu Met Ser Asn Asn Val Gln Ile
225                 230                 235                 240

Val Arg Gln Gln Ser Tyr Ser Ile Met Cys Ile Ile Lys Glu Glu Val
                245                 250                 255

Leu Ala Tyr Val Val Gln Leu Pro Leu Tyr Gly Val Ile Asp Thr Pro
            260                 265                 270

Cys Trp Lys Leu His Thr Ser Pro Leu Cys Thr Thr Asn Thr Lys Glu
        275                 280                 285

Gly Ser Asn Ile Cys Leu Thr Arg Thr Asp Arg Gly Trp Tyr Cys Asp
    290                 295                 300

Asn Ala Gly Ser Val Ser Phe Phe Pro Gln Ala Glu Thr Cys Lys Val
305                 310                 315                 320

Gln Ser Asn Arg Val Phe Cys Asp Thr Met Asn Ser Arg Thr Leu Pro
                325                 330                 335

Ser Glu Val Asn Leu Cys Asn Val Asp Ile Phe Asn Pro Lys Tyr Asp
            340                 345                 350

Cys Lys Ile Met Thr Ser Lys Thr Asp Val Ser Ser Val Ile Thr
        355                 360                 365

Ser Leu Gly Ala Ile Val Ser Cys Tyr Gly Lys Thr Lys Cys Thr Ala
    370                 375                 380

Ser Asn Lys Asn Arg Gly Ile Ile Lys Thr Phe Ser Asn Gly Cys Asp

```
                385                 390                 395                 400
Tyr Val Ser Asn Lys Gly Val Asp Thr Val Ser Val Gly Asn Thr Leu
            405                 410                 415

Tyr Tyr Val Asn Lys Gln Glu Gly Lys Ser Leu Tyr Val Lys Gly Glu
            420                 425                 430

Pro Ile Ile Asn Phe Ser Asp Pro Leu Val Phe Pro Ser Asp Glu Phe
            435                 440                 445

Asp Ala Ser Ile Ser Gln Val Asn Glu Lys Ile Asn Gln Ser Leu Ala
            450                 455                 460

Phe Ile Arg Lys Ser Asp Glu Leu Leu Ser Gly Ser Gly Ser Glu Ser
465                 470                 475                 480

Gln Val Arg Gln Gln Phe Ser Lys Asp Ile Glu Lys Leu Leu Asn Glu
                485                 490                 495

Gln Val Asn Lys Glu Met Gln Ser Ser Asn Leu Tyr Met Ser Met Ser
            500                 505                 510

Ser Trp Ser Tyr Thr His Ser Leu Asp Gly Ala Gly Leu Phe Leu Phe
            515                 520                 525

Asp His Ala Ala Glu Glu Tyr Glu His Ala Lys Lys Leu Ile Ile Phe
            530                 535                 540

Leu Asn Glu Asn Asn Val Pro Val Gln Leu Thr Ser Ile Ser Ala Pro
545                 550                 555                 560

Glu His Lys Phe Glu Gly Leu Thr Gln Ile Phe Gln Lys Ala Tyr Glu
                565                 570                 575

His Glu Gln His Ile Ser Glu Ser Ile Asn Asn Ile Val Asp His Ala
            580                 585                 590

Ile Lys Cys Lys Asp His Ala Thr Phe Asn Phe Leu Gln Trp Tyr Val
            595                 600                 605

Ala Glu Gln His Glu Glu Val Leu Phe Lys Asp Ile Leu Asp Lys
            610                 615                 620

Ile Glu Leu Ile Gly Asn Glu Asn His Gly Leu Tyr Leu Ala Asp Gln
625                 630                 635                 640

Tyr Val Lys Gly Ile Ala Lys Ser Arg Lys Ser
                645                 650

<210> SEQ ID NO 8
<211> LENGTH: 651
<212> TYPE: PRT
<213> ORGANISM: Artificial Sequence
<220> FEATURE:
<223> OTHER INFORMATION: Synthetic polypeptide

<400> SEQUENCE: 8

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Ser Gly Asn Val Gly Leu Gly Gly Ala Ile Ala Ser Gly Val
```

```
            100                 105                 110
Ala Val Cys Lys Val Leu His Leu Glu Gly Glu Val Asn Lys Ile Lys
            115                 120                 125
Ser Ala Leu Leu Ser Thr Asn Lys Ala Val Val Ser Leu Ser Asn Gly
            130                 135                 140
Val Ser Val Leu Thr Phe Lys Val Leu Asp Leu Lys Asn Tyr Ile Asp
145                 150                 155                 160
Lys Gln Leu Leu Pro Ile Leu Asn Lys Gln Ser Cys Ser Ile Ser Asn
            165                 170                 175
Ile Glu Thr Val Ile Glu Phe Gln Gln Lys Asn Asn Arg Leu Leu Glu
            180                 185                 190
Ile Thr Arg Glu Phe Ser Val Asn Ala Gly Val Thr Thr Pro Val Ser
            195                 200                 205
Thr Tyr Met Leu Thr Asn Ser Glu Leu Leu Ser Leu Ile Asn Asp Met
            210                 215                 220
Pro Ile Thr Asn Asp Gln Lys Lys Leu Met Ser Asn Asn Val Gln Ile
225                 230                 235                 240
Val Arg Gln Gln Ser Tyr Ser Ile Met Cys Ile Ile Lys Glu Glu Val
            245                 250                 255
Leu Ala Tyr Val Val Gln Leu Pro Leu Tyr Gly Val Ile Asp Thr Pro
            260                 265                 270
Cys Trp Lys Leu His Thr Ser Pro Leu Cys Thr Thr Asn Thr Lys Glu
            275                 280                 285
Gly Ser Asn Ile Cys Leu Thr Arg Thr Asp Arg Gly Trp Tyr Cys Asp
            290                 295                 300
Asn Ala Gly Ser Val Ser Phe Phe Pro Gln Ala Glu Thr Cys Lys Val
305                 310                 315                 320
Gln Ser Asn Arg Val Phe Cys Asp Thr Met Asn Ser Arg Thr Leu Pro
            325                 330                 335
Ser Glu Val Asn Leu Cys Asn Val Asp Ile Phe Asn Pro Lys Tyr Asp
            340                 345                 350
Cys Lys Ile Met Thr Ser Lys Thr Asp Val Ser Ser Ser Val Ile Thr
            355                 360                 365
Ser Leu Gly Ala Ile Val Ser Cys Tyr Gly Lys Thr Lys Cys Thr Ala
            370                 375                 380
Ser Asn Lys Asn Arg Gly Ile Ile Lys Thr Phe Ser Asn Gly Cys Asp
385                 390                 395                 400
Tyr Val Ser Asn Lys Gly Val Asp Thr Val Ser Val Gly Asn Thr Leu
            405                 410                 415
Tyr Tyr Val Asn Lys Gln Glu Gly Lys Ser Leu Tyr Val Lys Gly Glu
            420                 425                 430
Pro Ile Ile Asn Phe Tyr Asp Pro Leu Val Phe Pro Ser Asp Glu Phe
            435                 440                 445
Asp Ala Ser Ile Ser Gln Val Asn Glu Lys Ile Asn Gln Ser Leu Ala
450                 455                 460
Phe Ile Asn Lys Ser Asp Glu Leu Leu Ser Gly Ser Gly Ser Glu Ser
465                 470                 475                 480
Gln Val Arg Gln Gln Phe Ser Lys Asp Ile Glu Lys Leu Leu Asn Glu
            485                 490                 495
Gln Val Asn Lys Glu Met Gln Ser Ser Asn Leu Tyr Met Ser Met Ser
            500                 505                 510
Ser Trp Ser Tyr Thr His Ser Leu Asp Gly Ala Gly Leu Phe Leu Phe
            515                 520                 525
```

```
Asp His Ala Ala Glu Glu Tyr Glu His Ala Lys Lys Leu Ile Ile Phe
        530                 535                 540

Leu Asn Glu Asn Asn Val Pro Val Gln Leu Thr Ser Ile Ser Ala Pro
545                 550                 555                 560

Glu His Lys Phe Glu Gly Leu Thr Gln Ile Phe Gln Lys Ala Tyr Glu
                565                 570                 575

His Glu Gln His Ile Ser Glu Ser Ile Asn Asn Ile Val Asp His Ala
                580                 585                 590

Ile Lys Cys Lys Asp His Ala Thr Phe Asn Phe Leu Gln Trp Tyr Val
        595                 600                 605

Ala Glu Gln His Glu Glu Val Leu Phe Lys Asp Ile Leu Asp Lys
        610                 615                 620

Ile Glu Leu Ile Gly Asn Glu Asn His Gly Leu Tyr Leu Ala Asp Gln
625                 630                 635                 640

Tyr Val Lys Gly Ile Ala Lys Ser Arg Lys Ser
                645                 650

<210> SEQ ID NO 9
<211> LENGTH: 651
<212> TYPE: PRT
<213> ORGANISM: Artificial Sequence
<220> FEATURE:
<223> OTHER INFORMATION: Synthetic polypeptide

<400> SEQUENCE: 9

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
                35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Ser Gly Asn Val Gly Leu Gly Gly Ala Ile Ala Ser Gly Val
                100                 105                 110

Ala Val Ser Lys Val Leu His Leu Glu Gly Glu Val Asn Lys Ile Lys
            115                 120                 125

Ser Ala Leu Leu Ser Thr Asn Lys Ala Val Val Ser Leu Ser Asn Gly
        130                 135                 140

Val Ser Val Leu Thr Phe Lys Val Leu Asp Leu Lys Asn Tyr Ile Asp
145                 150                 155                 160

Lys Gln Leu Leu Pro Ile Leu Asn Lys Gln Ser Cys Ser Ile Ser Asn
                165                 170                 175

Pro Glu Thr Val Ile Glu Phe Gln Gln Lys Asn Asn Arg Leu Leu Glu
            180                 185                 190

Ile Thr Arg Glu Phe Ser Val Asn Ala Gly Val Thr Thr Pro Val Ser
        195                 200                 205

Thr Tyr Met Leu Thr Asn Ser Glu Leu Leu Ser Leu Ile Asn Asp Met
        210                 215                 220

Pro Ile Thr Asn Asp Gln Lys Lys Leu Met Ser Asn Asn Val Gln Ile
225                 230                 235                 240
```

```
Val Arg Gln Gln Ser Tyr Ser Ile Met Ser Ile Ile Lys Glu Glu Val
                245                 250                 255

Leu Ala Tyr Val Val Gln Leu Pro Leu Tyr Gly Val Ile Asp Thr Pro
                260                 265                 270

Cys Trp Lys Leu His Thr Ser Pro Leu Cys Thr Thr Asn Thr Lys Glu
                275                 280                 285

Gly Ser Asn Ile Cys Leu Thr Arg Thr Asp Arg Gly Trp Tyr Cys Asp
                290                 295                 300

Asn Ala Gly Ser Val Ser Phe Phe Pro Gln Ala Glu Thr Cys Lys Val
305                 310                 315                 320

Gln Ser Asn Arg Val Phe Cys Asp Thr Met Asn Ser Arg Thr Leu Pro
                325                 330                 335

Ser Glu Val Asn Leu Cys Asn Val Asp Ile Phe Asn Pro Lys Tyr Asp
                340                 345                 350

Cys Lys Ile Met Thr Ser Lys Thr Asp Val Ser Ser Ser Val Ile Thr
                355                 360                 365

Ser Leu Gly Ala Ile Val Ser Cys Tyr Gly Lys Thr Lys Cys Thr Ala
                370                 375                 380

Ser Asn Lys Asn Arg Gly Ile Ile Lys Thr Phe Ser Asn Gly Cys Asp
385                 390                 395                 400

Tyr Val Ser Asn Lys Gly Val Asp Thr Val Ser Val Gly Asn Thr Leu
                405                 410                 415

Tyr Tyr Val Asn Lys Gln Glu Gly Lys Ser Leu Tyr Val Lys Gly Glu
                420                 425                 430

Pro Ile Ile Asn Phe Tyr Asp Pro Leu Val Phe Pro Ser Asp Glu Phe
                435                 440                 445

Asp Ala Ser Ile Ser Gln Val Asn Glu Lys Ile Asn Gln Ser Leu Ala
450                 455                 460

Phe Ile Arg Lys Ser Asp Glu Leu Leu Ser Gly Ser Gly Ser Glu Ser
465                 470                 475                 480

Gln Val Arg Gln Gln Phe Ser Lys Asp Ile Glu Lys Leu Leu Asn Glu
                485                 490                 495

Gln Val Asn Lys Glu Met Gln Ser Ser Asn Leu Tyr Met Ser Met Ser
                500                 505                 510

Ser Trp Ser Tyr Thr His Ser Leu Asp Gly Ala Gly Leu Phe Leu Phe
                515                 520                 525

Asp His Ala Ala Glu Glu Tyr Glu His Ala Lys Lys Leu Ile Ile Phe
                530                 535                 540

Leu Asn Glu Asn Asn Val Pro Val Gln Leu Thr Ser Ile Ser Ala Pro
545                 550                 555                 560

Glu His Lys Phe Glu Gly Leu Thr Gln Ile Phe Gln Lys Ala Tyr Glu
                565                 570                 575

His Glu Gln His Ile Ser Glu Ser Ile Asn Asn Ile Val Asp His Ala
                580                 585                 590

Ile Lys Cys Lys Asp His Ala Thr Phe Asn Phe Leu Gln Trp Tyr Val
                595                 600                 605

Ala Glu Gln His Glu Glu Val Leu Phe Lys Asp Ile Leu Asp Lys
                610                 615                 620

Ile Glu Leu Ile Gly Asn Glu Asn His Gly Leu Tyr Leu Ala Asp Gln
625                 630                 635                 640

Tyr Val Lys Gly Ile Ala Lys Ser Arg Lys Ser
                645                 650
```

```
<210> SEQ ID NO 10
<211> LENGTH: 651
<212> TYPE: PRT
<213> ORGANISM: Artificial Sequence
<220> FEATURE:
<223> OTHER INFORMATION: Synthetic polypeptide

<400> SEQUENCE: 10

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Ser Gly Asn Val Gly Leu Gly Gly Ala Ile Ala Ser Gly Val
            100                 105                 110

Ala Val Ser Lys Val Leu His Leu Glu Gly Glu Val Asn Lys Ile Lys
        115                 120                 125

Ser Ala Leu Leu Ser Thr Asn Lys Ala Val Val Ser Leu Ser Asn Gly
    130                 135                 140

Val Ser Val Leu Thr Phe Lys Val Leu Asp Leu Lys Asn Tyr Ile Asp
145                 150                 155                 160

Lys Gln Leu Leu Pro Ile Leu Asn Lys Gln Ser Cys Ser Ile Ser Asn
                165                 170                 175

Pro Glu Thr Val Ile Glu Phe Gln Gln Lys Asn Leu Arg Leu Leu Glu
            180                 185                 190

Ile Thr Arg Glu Phe Ser Val Asn Ala Gly Val Thr Thr Pro Val Ser
        195                 200                 205

Thr Tyr Met Leu Thr Asn Ser Glu Leu Leu Ser Leu Ile Asn Asp Met
    210                 215                 220

Pro Ile Thr Asn Asp Gln Lys Lys Leu Met Ser Asn Asn Val Gln Ile
225                 230                 235                 240

Val Arg Gln Gln Ser Tyr Ser Ile Met Ser Ile Ile Lys Glu Glu Val
                245                 250                 255

Leu Ala Tyr Val Val Gln Leu Pro Leu Tyr Gly Val Ile Asp Thr Pro
            260                 265                 270

Cys Trp Lys Leu His Thr Ser Pro Leu Cys Thr Thr Asn Thr Lys Glu
        275                 280                 285

Gly Ser Asn Ile Cys Leu Thr Arg Thr Asp Arg Gly Trp Tyr Cys Asp
    290                 295                 300

Asn Ala Gly Ser Val Ser Phe Phe Pro Gln Ala Glu Thr Cys Lys Val
305                 310                 315                 320

Gln Ser Asn Arg Val Phe Cys Asp Thr Met Asn Ser Arg Thr Leu Pro
                325                 330                 335

Ser Glu Val Asn Leu Cys Asn Val Asp Ile Phe Asn Pro Lys Tyr Asp
            340                 345                 350

Cys Lys Ile Met Thr Ser Lys Thr Asp Val Ser Ser Ser Val Ile Thr
        355                 360                 365
```

```
Ser Leu Gly Ala Ile Val Ser Cys Tyr Gly Lys Thr Lys Cys Thr Ala
    370                 375                 380

Ser Asn Lys Asn Arg Gly Ile Ile Lys Thr Phe Ser Asn Gly Cys Asp
385                 390                 395                 400

Tyr Val Ser Asn Lys Gly Val Asp Thr Val Ser Val Gly Asn Thr Leu
                405                 410                 415

Tyr Tyr Val Asn Lys Gln Glu Gly Lys Ser Leu Tyr Val Lys Gly Glu
                420                 425                 430

Pro Ile Ile Asn Phe Tyr Asp Pro Leu Val Phe Pro Ser Asp Glu Phe
                435                 440                 445

Asp Ala Ser Ile Ser Gln Val Asn Glu Lys Ile Asn Gln Ser Leu Ala
450                 455                 460

Phe Ile Arg Lys Ser Asp Glu Leu Leu Ser Gly Ser Gly Ser Glu Ser
465                 470                 475                 480

Gln Val Arg Gln Gln Phe Ser Lys Asp Ile Glu Lys Leu Leu Asn Glu
                485                 490                 495

Gln Val Asn Lys Glu Met Gln Ser Ser Asn Leu Tyr Met Ser Met Ser
                500                 505                 510

Ser Trp Ser Tyr Thr His Ser Leu Asp Gly Ala Gly Leu Phe Leu Phe
                515                 520                 525

Asp His Ala Ala Glu Glu Tyr Glu His Ala Lys Lys Leu Ile Ile Phe
530                 535                 540

Leu Asn Glu Asn Asn Val Pro Val Gln Leu Thr Ser Ile Ser Ala Pro
545                 550                 555                 560

Glu His Lys Phe Glu Gly Leu Thr Gln Ile Phe Gln Lys Ala Tyr Glu
                565                 570                 575

His Glu Gln His Ile Ser Glu Ser Ile Asn Asn Ile Val Asp His Ala
                580                 585                 590

Ile Lys Cys Lys Asp His Ala Thr Phe Asn Phe Leu Gln Trp Tyr Val
                595                 600                 605

Ala Glu Gln His Glu Glu Val Leu Phe Lys Asp Ile Leu Asp Lys
                610                 615                 620

Ile Glu Leu Ile Gly Asn Glu Asn His Gly Leu Tyr Leu Ala Asp Gln
625                 630                 635                 640

Tyr Val Lys Gly Ile Ala Lys Ser Arg Lys Ser
                645                 650

<210> SEQ ID NO 11
<211> LENGTH: 651
<212> TYPE: PRT
<213> ORGANISM: Artificial Sequence
<220> FEATURE:
<223> OTHER INFORMATION: Synthetic polypeptide

<400> SEQUENCE: 11

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
                35                  40                  45

Arg Thr Gly Trp Tyr Thr Ser Val Ile Thr Ile Glu Leu Ser Asn Ile
                50                  55                  60

Lys Glu Asn Lys Cys Asn Gly Thr Asp Ala Lys Val Lys Leu Ile Lys
65                  70                  75                  80
```

-continued

```
Gln Glu Leu Asp Lys Tyr Lys Asn Ala Val Thr Glu Leu Gln Leu Leu
                85                  90                  95

Met Gly Ser Gly Asn Val Gly Leu Gly Gly Ala Ile Ala Ser Gly Val
            100                 105                 110

Ala Val Cys Lys Val Leu His Leu Glu Gly Glu Val Asn Lys Ile Lys
            115                 120                 125

Ser Ala Leu Leu Ser Thr Asn Lys Ala Val Val Ser Leu Ser Asn Gly
        130                 135                 140

Val Ser Val Leu Thr Phe Lys Val Leu Asp Leu Lys Asn Tyr Ile Asp
145                 150                 155                 160

Lys Gln Leu Leu Pro Ile Leu Asn Lys Gln Ser Cys Ser Ile Ser Asn
                165                 170                 175

Pro Glu Thr Val Ile Glu Phe Gln Gln Lys Asn Asn Arg Leu Leu Glu
            180                 185                 190

Ile Thr Arg Glu Phe Ser Val Asn Ala Gly Val Thr Thr Pro Val Ser
        195                 200                 205

Thr Tyr Met Leu Thr Asn Ser Glu Leu Leu Ser Leu Ile Asn Asp Met
    210                 215                 220

Pro Ile Thr Asn Asp Gln Lys Lys Leu Met Ser Asn Asn Val Gln Ile
225                 230                 235                 240

Val Arg Gln Gln Ser Tyr Ser Ile Met Cys Ile Ile Lys Glu Glu Val
                245                 250                 255

Leu Ala Tyr Val Val Gln Leu Pro Leu Tyr Gly Val Ile Asp Thr Pro
            260                 265                 270

Cys Trp Lys Leu His Thr Ser Pro Leu Cys Thr Thr Asn Thr Lys Glu
        275                 280                 285

Gly Ser Asn Ile Cys Leu Thr Arg Thr Asp Arg Gly Trp Tyr Cys Asp
    290                 295                 300

Asn Ala Gly Ser Val Ser Phe Phe Pro Gln Ala Glu Thr Cys Lys Val
305                 310                 315                 320

Gln Ser Asn Arg Val Phe Cys Asp Thr Met Asn Ser Arg Thr Leu Pro
                325                 330                 335

Ser Glu Val Asn Leu Cys Asn Val Asp Ile Phe Asn Pro Lys Tyr Asp
            340                 345                 350

Cys Lys Ile Met Thr Ser Lys Thr Asp Val Ser Ser Ser Val Ile Thr
        355                 360                 365

Ser Leu Gly Ala Ile Val Ser Cys Tyr Gly Lys Thr Lys Cys Thr Ala
    370                 375                 380

Ser Asn Lys Asn Arg Gly Ile Ile Lys Thr Phe Ser Asn Gly Cys Asp
385                 390                 395                 400

Tyr Val Ser Asn Lys Gly Val Asp Thr Val Ser Val Gly Asn Thr Leu
                405                 410                 415

Tyr Tyr Val Asn Lys Gln Glu Gly Lys Ser Leu Tyr Val Lys Gly Glu
            420                 425                 430

Pro Ile Ile Asn Phe Tyr Asp Pro Leu Val Phe Pro Ser Asp Glu Phe
        435                 440                 445

Asp Ala Ser Ile Ser Gln Val Asn Glu Lys Ile Asn Gln Ser Leu Ala
    450                 455                 460

Phe Ile Arg Lys Ser Asp Glu Leu Leu Ser Gly Ser Gly Ser Glu Ser
465                 470                 475                 480

Gln Val Arg Gln Gln Phe Ser Lys Asp Ile Glu Lys Leu Leu Asn Glu
                485                 490                 495

Gln Val Asn Lys Glu Met Gln Ser Ser Asn Leu Tyr Met Ser Met Ser
```

```
                    500                 505                 510
Ser Trp Ser Tyr Thr His Ser Leu Asp Gly Ala Gly Leu Phe Leu Phe
            515                 520                 525

Asp His Ala Ala Glu Tyr Glu His Ala Lys Lys Leu Ile Ile Phe
        530                 535                 540

Leu Asn Glu Asn Asn Val Pro Val Gln Leu Thr Ser Ile Ser Ala Pro
545                 550                 555                 560

Glu His Lys Phe Glu Gly Leu Thr Gln Ile Phe Gln Lys Ala Tyr Glu
                565                 570                 575

His Glu Gln His Ile Ser Glu Ser Ile Asn Asn Ile Val Asp His Ala
            580                 585                 590

Ile Lys Cys Lys Asp His Ala Thr Phe Asn Phe Leu Gln Trp Tyr Val
        595                 600                 605

Ala Glu Gln His Glu Glu Val Leu Phe Lys Asp Ile Leu Asp Lys
    610                 615                 620

Ile Glu Leu Ile Gly Asn Glu Asn His Gly Leu Tyr Leu Ala Asp Gln
625                 630                 635                 640

Tyr Val Lys Gly Ile Ala Lys Ser Arg Lys Ser
                645                 650

<210> SEQ ID NO 12
<211> LENGTH: 651
<212> TYPE: PRT
<213> ORGANISM: Artificial Sequence
<220> FEATURE:
<223> OTHER INFORMATION: Synthetic polypeptide

<400> SEQUENCE: 12

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Ser Gly Asn Val Gly Leu Gly Gly Ala Ile Ala Ser Gly Val
            100                 105                 110

Ala Val Cys Lys Val Leu His Leu Glu Gly Glu Val Asn Lys Ile Lys
        115                 120                 125

Ser Ala Leu Leu Ser Thr Asn Lys Ala Val Val Ser Leu Ser Asn Gly
    130                 135                 140

Val Ser Val Leu Thr Phe Lys Val Leu Asp Leu Lys Asn Tyr Ile Asp
145                 150                 155                 160

Lys Gln Leu Leu Pro Ile Leu Asn Lys Gln Ser Cys Ser Ile Ser Asn
                165                 170                 175

Ile Glu Thr Val Ile Glu Phe Leu Gln Lys Asn Asn Arg Leu Leu Glu
            180                 185                 190

Ile Thr Arg Glu Phe Ser Val Asn Ala Gly Val Thr Thr Pro Val Ser
        195                 200                 205

Thr Tyr Met Leu Thr Asn Ser Glu Leu Leu Ser Leu Ile Asn Asp Met
```

```
            210                 215                 220
Pro Ile Thr Asn Asp Gln Lys Lys Leu Met Ser Asn Asn Val Gln Ile
225                 230                 235                 240

Val Arg Gln Gln Ser Tyr Ser Ile Met Cys Ile Ile Lys Glu Glu Val
                    245                 250                 255

Leu Ala Tyr Val Val Gln Leu Pro Leu Tyr Gly Val Ile Asp Thr Pro
                260                 265                 270

Cys Trp Lys Leu His Thr Ser Pro Leu Cys Thr Thr Asn Thr Lys Glu
            275                 280                 285

Gly Ser Asn Ile Cys Leu Thr Arg Thr Asp Arg Gly Trp Tyr Cys Asp
        290                 295                 300

Asn Ala Gly Ser Val Ser Phe Phe Pro Gln Ala Glu Thr Cys Lys Val
305                 310                 315                 320

Gln Ser Asn Arg Val Phe Cys Asp Thr Met Asn Ser Arg Thr Leu Pro
                    325                 330                 335

Ser Glu Val Asn Leu Cys Asn Val Asp Ile Phe Asn Pro Lys Tyr Asp
                340                 345                 350

Cys Lys Ile Met Thr Ser Lys Thr Asp Val Ser Ser Ser Val Ile Thr
            355                 360                 365

Ser Leu Gly Ala Ile Val Ser Cys Tyr Gly Lys Thr Lys Cys Thr Ala
        370                 375                 380

Ser Asn Lys Asn Arg Gly Ile Ile Lys Thr Phe Ser Asn Gly Cys Asp
385                 390                 395                 400

Tyr Val Ser Asn Lys Gly Val Asp Thr Val Ser Val Gly Asn Thr Leu
                    405                 410                 415

Tyr Tyr Val Asn Lys Gln Glu Gly Lys Ser Leu Tyr Val Lys Gly Glu
                420                 425                 430

Pro Ile Ile Asn Phe Tyr Asp Pro Leu Val Phe Pro Ser Asp Glu Phe
            435                 440                 445

Asp Ala Ser Ile Ser Gln Val Asn Glu Lys Ile Asn Gln Ser Leu Ala
        450                 455                 460

Phe Ile Arg Lys Ser Asp Glu Leu Leu Ser Gly Ser Gly Ser Glu Ser
465                 470                 475                 480

Gln Val Arg Gln Gln Phe Ser Lys Asp Ile Glu Lys Leu Leu Asn Glu
                    485                 490                 495

Gln Val Asn Lys Glu Met Gln Ser Ser Asn Leu Tyr Met Ser Met Ser
                500                 505                 510

Ser Trp Ser Tyr Thr His Ser Leu Asp Gly Ala Gly Leu Phe Leu Phe
            515                 520                 525

Asp His Ala Ala Glu Glu Tyr Glu His Ala Lys Lys Leu Ile Ile Phe
        530                 535                 540

Leu Asn Glu Asn Asn Val Pro Val Gln Leu Thr Ser Ile Ser Ala Pro
545                 550                 555                 560

Glu His Lys Phe Glu Gly Leu Thr Gln Ile Phe Gln Lys Ala Tyr Glu
                    565                 570                 575

His Glu Gln His Ile Ser Glu Ser Ile Asn Asn Ile Val Asp His Ala
                580                 585                 590

Ile Lys Cys Lys Asp His Ala Thr Phe Asn Phe Leu Gln Trp Tyr Val
            595                 600                 605

Ala Glu Gln His Glu Glu Val Leu Phe Lys Asp Ile Leu Asp Lys
        610                 615                 620

Ile Glu Leu Ile Gly Asn Glu Asn His Gly Leu Tyr Leu Ala Asp Gln
625                 630                 635                 640
```

```
Tyr Val Lys Gly Ile Ala Lys Ser Arg Lys Ser
            645                 650
```

<210> SEQ ID NO 13
<211> LENGTH: 651
<212> TYPE: PRT
<213> ORGANISM: Artificial Sequence
<220> FEATURE:
<223> OTHER INFORMATION: Synthetic polypeptide

<400> SEQUENCE: 13

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Ser Gly Asn Val Gly Leu Gly Gly Ala Ile Ala Ser Gly Val
            100                 105                 110

Ala Val Cys Lys Val Leu His Leu Glu Gly Glu Val Asn Lys Ile Lys
        115                 120                 125

Ser Ala Leu Leu Ser Thr Asn Lys Ala Val Val Ser Leu Ser Asn Gly
    130                 135                 140

Val Ser Val Leu Thr Phe Lys Val Leu Asp Leu Lys Asn Tyr Ile Asp
145                 150                 155                 160

Lys Gln Leu Leu Pro Ile Leu Asn Lys Gln Ser Cys Ser Ile Ser Asn
                165                 170                 175

Ile Glu Thr Val Ile Glu Phe Leu Val Lys Asn Asn Arg Leu Leu Glu
            180                 185                 190

Ile Thr Arg Glu Phe Ser Val Asn Ala Gly Val Thr Thr Pro Val Ser
        195                 200                 205

Thr Tyr Met Leu Thr Asn Ser Glu Leu Leu Ser Leu Ile Asn Asp Met
    210                 215                 220

Pro Ile Thr Asn Asp Gln Lys Lys Leu Met Ser Asn Asn Val Gln Ile
225                 230                 235                 240

Val Arg Gln Gln Ser Tyr Ser Ile Met Cys Ile Ile Lys Glu Glu Val
                245                 250                 255

Leu Ala Tyr Val Val Gln Leu Pro Leu Tyr Gly Val Ile Asp Thr Pro
            260                 265                 270

Cys Trp Lys Leu His Thr Ser Pro Leu Cys Thr Thr Asn Thr Lys Glu
        275                 280                 285

Gly Ser Asn Ile Cys Leu Thr Arg Thr Asp Arg Gly Trp Tyr Cys Asp
    290                 295                 300

Asn Ala Gly Ser Val Ser Phe Phe Pro Gln Ala Glu Thr Cys Lys Val
305                 310                 315                 320

Gln Ser Asn Arg Val Phe Cys Asp Thr Met Asn Ser Arg Thr Leu Pro
                325                 330                 335

Ser Glu Val Asn Leu Cys Asn Val Asp Ile Phe Asn Pro Lys Tyr Asp
            340                 345                 350
```

```
Cys Lys Ile Met Thr Ser Lys Thr Asp Val Ser Ser Val Ile Thr
            355                 360                 365
Ser Leu Gly Ala Ile Val Ser Cys Tyr Gly Lys Thr Lys Cys Thr Ala
        370                 375                 380
Ser Asn Lys Asn Arg Gly Ile Ile Lys Thr Phe Ser Asn Gly Cys Asp
385                 390                 395                 400
Tyr Val Ser Asn Lys Gly Val Asp Thr Val Ser Val Gly Asn Thr Leu
                405                 410                 415
Tyr Tyr Val Asn Lys Gln Glu Gly Lys Ser Leu Tyr Val Lys Gly Glu
            420                 425                 430
Pro Ile Ile Asn Phe Tyr Asp Pro Leu Val Phe Pro Ser Asp Glu Phe
            435                 440                 445
Asp Ala Ser Ile Ser Gln Val Asn Glu Lys Ile Asn Gln Ser Leu Ala
        450                 455                 460
Phe Ile Arg Lys Ser Asp Glu Leu Leu Ser Gly Ser Gly Ser Glu Ser
465                 470                 475                 480
Gln Val Arg Gln Gln Phe Ser Lys Asp Ile Glu Lys Leu Leu Asn Glu
                485                 490                 495
Gln Val Asn Lys Glu Met Gln Ser Ser Asn Leu Tyr Met Ser Met Ser
            500                 505                 510
Ser Trp Ser Tyr Thr His Ser Leu Asp Gly Ala Gly Leu Phe Leu Phe
        515                 520                 525
Asp His Ala Ala Glu Glu Tyr Glu His Ala Lys Lys Leu Ile Ile Phe
        530                 535                 540
Leu Asn Glu Asn Asn Val Pro Val Gln Leu Thr Ser Ile Ser Ala Pro
545                 550                 555                 560
Glu His Lys Phe Glu Gly Leu Thr Gln Ile Phe Gln Lys Ala Tyr Glu
                565                 570                 575
His Glu Gln His Ile Ser Glu Ser Ile Asn Asn Ile Val Asp His Ala
            580                 585                 590
Ile Lys Cys Lys Asp His Ala Thr Phe Asn Phe Leu Gln Trp Tyr Val
        595                 600                 605
Ala Glu Gln His Glu Glu Val Leu Phe Lys Asp Ile Leu Asp Lys
        610                 615                 620
Ile Glu Leu Ile Gly Asn Glu Asn His Gly Leu Tyr Leu Ala Asp Gln
625                 630                 635                 640
Tyr Val Lys Gly Ile Ala Lys Ser Arg Lys Ser
                645                 650

<210> SEQ ID NO 14
<211> LENGTH: 651
<212> TYPE: PRT
<213> ORGANISM: Artificial Sequence
<220> FEATURE:
<223> OTHER INFORMATION: Synthetic polypeptide

<400> SEQUENCE: 14

Met Glu Leu Leu Ile Leu Lys Ala Asn Ala Ile Thr Thr Ile Leu Thr
1               5                   10                  15
Ala Val Thr Phe Cys Phe Ala Ser Gly Gln Asn Ile Thr Glu Glu Phe
            20                  25                  30
Tyr Gln Ser Thr Cys Ser Ala Val Ser Lys Gly Tyr Leu Ser Ala Leu
        35                  40                  45
Arg Thr Gly Trp Tyr Thr Ser Val Ile Thr Ile Glu Leu Ser Asn Ile
    50                  55                  60
```

```
Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
             85                  90                  95

Met Gly Ser Gly Asn Val Gly Leu Gly Gly Ala Ile Ala Ser Gly Val
            100                 105                 110

Ala Val Cys Lys Val Leu His Leu Glu Gly Glu Val Asn Lys Ile Lys
        115                 120                 125

Ser Ala Leu Leu Ser Thr Asn Lys Ala Val Val Ser Leu Ser Asn Gly
130                 135                 140

Val Ser Val Leu Thr Phe Lys Val Leu Asp Leu Lys Asn Tyr Ile Asp
145                 150                 155                 160

Lys Gln Leu Leu Pro Ile Leu Asn Lys Gln Ser Cys Ser Ile Ser Asn
                165                 170                 175

Ile Glu Thr Val Ile Glu Phe Gln Gln Lys Asn Leu Arg Leu Leu Glu
            180                 185                 190

Ile Thr Arg Glu Phe Ser Val Asn Ala Gly Val Thr Thr Pro Val Ser
        195                 200                 205

Thr Tyr Met Leu Thr Asn Ser Glu Leu Leu Ser Leu Ile Asn Asp Met
210                 215                 220

Pro Ile Thr Asn Asp Gln Lys Lys Leu Met Ser Asn Asn Val Gln Ile
225                 230                 235                 240

Val Arg Gln Gln Ser Tyr Ser Ile Met Cys Ile Ile Lys Glu Glu Val
                245                 250                 255

Leu Ala Tyr Val Val Gln Leu Pro Leu Tyr Gly Val Ile Asp Thr Pro
            260                 265                 270

Cys Trp Lys Leu His Thr Ser Pro Leu Cys Thr Thr Asn Thr Lys Glu
        275                 280                 285

Gly Ser Asn Ile Cys Leu Thr Arg Thr Asp Arg Gly Trp Tyr Cys Asp
290                 295                 300

Asn Ala Gly Ser Val Ser Phe Phe Pro Gln Ala Glu Thr Cys Lys Val
305                 310                 315                 320

Gln Ser Asn Arg Val Phe Cys Asp Thr Met Asn Ser Arg Thr Leu Pro
                325                 330                 335

Ser Glu Val Asn Leu Cys Asn Val Asp Ile Phe Asn Pro Lys Tyr Asp
            340                 345                 350

Cys Lys Ile Met Thr Ser Lys Thr Asp Val Ser Ser Ser Val Ile Thr
        355                 360                 365

Ser Leu Gly Ala Ile Val Ser Cys Tyr Gly Lys Thr Lys Cys Thr Ala
370                 375                 380

Ser Asn Lys Asn Arg Gly Ile Ile Lys Thr Phe Ser Asn Gly Cys Asp
385                 390                 395                 400

Tyr Val Ser Asn Lys Gly Val Asp Thr Val Ser Val Gly Asn Thr Leu
                405                 410                 415

Tyr Tyr Val Asn Lys Gln Glu Gly Lys Ser Leu Tyr Val Lys Gly Glu
            420                 425                 430

Pro Ile Ile Asn Phe Tyr Asp Pro Leu Val Phe Pro Ser Asp Glu Phe
        435                 440                 445

Asp Ala Ser Ile Ser Gln Val Asn Glu Lys Ile Asn Gln Ser Leu Ala
450                 455                 460

Phe Ile Arg Lys Ser Asp Glu Leu Leu Ser Gly Ser Gly Ser Glu Ser
465                 470                 475                 480
```

```
Gln Val Arg Gln Gln Phe Ser Lys Asp Ile Glu Lys Leu Leu Asn Glu
                485                 490                 495

Gln Val Asn Lys Glu Met Gln Ser Ser Asn Leu Tyr Met Ser Met Ser
            500                 505                 510

Ser Trp Ser Tyr Thr His Ser Leu Asp Gly Ala Gly Leu Phe Leu Phe
        515                 520                 525

Asp His Ala Ala Glu Tyr Glu His Ala Lys Lys Leu Ile Ile Phe
    530                 535                 540

Leu Asn Glu Asn Asn Val Pro Val Gln Leu Thr Ser Ile Ser Ala Pro
545                 550                 555                 560

Glu His Lys Phe Glu Gly Leu Thr Gln Ile Phe Gln Lys Ala Tyr Glu
                565                 570                 575

His Glu Gln His Ile Ser Glu Ser Ile Asn Asn Ile Val Asp His Ala
            580                 585                 590

Ile Lys Cys Lys Asp His Ala Thr Phe Asn Phe Leu Gln Trp Tyr Val
        595                 600                 605

Ala Glu Gln His Glu Glu Val Leu Phe Lys Asp Ile Leu Asp Lys
    610                 615                 620

Ile Glu Leu Ile Gly Asn Glu Asn His Gly Leu Tyr Leu Ala Asp Gln
625                 630                 635                 640

Tyr Val Lys Gly Ile Ala Lys Ser Arg Lys Ser
                645                 650

<210> SEQ ID NO 15
<211> LENGTH: 651
<212> TYPE: PRT
<213> ORGANISM: Artificial Sequence
<220> FEATURE:
<223> OTHER INFORMATION: Synthetic polypeptide

<400> SEQUENCE: 15

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Ser Gly Asn Val Gly Leu Gly Gly Ala Ile Ala Ser Gly Val
            100                 105                 110

Ala Val Cys Lys Val Leu His Leu Glu Gly Glu Val Asn Lys Ile Lys
        115                 120                 125

Ser Ala Leu Leu Ser Thr Asn Lys Ala Val Val Ser Leu Ser Asn Gly
    130                 135                 140

Val Ser Val Leu Thr Phe Lys Val Leu Asp Leu Lys Asn Tyr Ile Asp
145                 150                 155                 160

Lys Gln Leu Leu Pro Ile Leu Asn Lys Gln Ser Cys Ser Ile Ser Asn
                165                 170                 175

Ile Glu Thr Val Ile Glu Phe Gln Gln Lys Asn Phe Arg Leu Leu Glu
            180                 185                 190
```

-continued

```
Ile Thr Arg Glu Phe Ser Val Asn Ala Gly Val Thr Pro Val Ser
        195                 200                 205
Thr Tyr Met Leu Thr Asn Ser Glu Leu Leu Ser Leu Ile Asn Asp Met
210                 215                 220
Pro Ile Thr Asn Asp Gln Lys Lys Leu Met Ser Asn Asn Val Gln Ile
225                 230                 235                 240
Val Arg Gln Gln Ser Tyr Ser Ile Met Cys Ile Ile Lys Glu Glu Val
                245                 250                 255
Leu Ala Tyr Val Val Gln Leu Pro Leu Tyr Gly Val Ile Asp Thr Pro
                260                 265                 270
Cys Trp Lys Leu His Thr Ser Pro Leu Cys Thr Thr Asn Thr Lys Glu
            275                 280                 285
Gly Ser Asn Ile Cys Leu Thr Arg Thr Asp Arg Gly Trp Tyr Cys Asp
        290                 295                 300
Asn Ala Gly Ser Val Ser Phe Phe Pro Gln Ala Glu Thr Cys Lys Val
305                 310                 315                 320
Gln Ser Asn Arg Val Phe Cys Asp Thr Met Asn Ser Arg Thr Leu Pro
                325                 330                 335
Ser Glu Val Asn Leu Cys Asn Val Asp Ile Phe Asn Pro Lys Tyr Asp
                340                 345                 350
Cys Lys Ile Met Thr Ser Lys Thr Asp Val Ser Ser Ser Val Ile Thr
            355                 360                 365
Ser Leu Gly Ala Ile Val Ser Cys Tyr Gly Lys Thr Lys Cys Thr Ala
        370                 375                 380
Ser Asn Lys Asn Arg Gly Ile Ile Lys Thr Phe Ser Asn Gly Cys Asp
385                 390                 395                 400
Tyr Val Ser Asn Lys Gly Val Asp Thr Val Ser Val Gly Asn Thr Leu
                405                 410                 415
Tyr Tyr Val Asn Lys Gln Glu Gly Lys Ser Leu Tyr Val Lys Gly Glu
                420                 425                 430
Pro Ile Ile Asn Phe Tyr Asp Pro Leu Val Phe Pro Ser Asp Glu Phe
            435                 440                 445
Asp Ala Ser Ile Ser Gln Val Asn Glu Lys Ile Asn Gln Ser Leu Ala
450                 455                 460
Phe Ile Arg Lys Ser Asp Glu Leu Leu Ser Gly Ser Gly Ser Glu Ser
465                 470                 475                 480
Gln Val Arg Gln Gln Phe Ser Lys Asp Ile Glu Lys Leu Leu Asn Glu
                485                 490                 495
Gln Val Asn Lys Glu Met Gln Ser Ser Asn Leu Tyr Met Ser Met Ser
            500                 505                 510
Ser Trp Ser Tyr Thr His Ser Leu Asp Gly Ala Gly Leu Phe Leu Phe
        515                 520                 525
Asp His Ala Ala Glu Glu Tyr Glu His Ala Lys Lys Leu Ile Ile Phe
    530                 535                 540
Leu Asn Glu Asn Asn Val Pro Val Gln Leu Thr Ser Ile Ser Ala Pro
545                 550                 555                 560
Glu His Lys Phe Glu Gly Leu Thr Gln Ile Phe Gln Lys Ala Tyr Glu
                565                 570                 575
His Glu Gln His Ile Ser Glu Ser Ile Asn Asn Ile Val Asp His Ala
            580                 585                 590
Ile Lys Cys Lys Asp His Ala Thr Phe Asn Phe Leu Gln Trp Tyr Val
        595                 600                 605
Ala Glu Gln His Glu Glu Glu Val Leu Phe Lys Asp Ile Leu Asp Lys
```

```
            610                 615                 620
Ile Glu Leu Ile Gly Asn Glu Asn His Gly Leu Tyr Leu Ala Asp Gln
625                 630                 635                 640

Tyr Val Lys Gly Ile Ala Lys Ser Arg Lys Ser
                645                 650

<210> SEQ ID NO 16
<211> LENGTH: 651
<212> TYPE: PRT
<213> ORGANISM: Artificial Sequence
<220> FEATURE:
<223> OTHER INFORMATION: Synthetic polypeptide

<400> SEQUENCE: 16

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Ser Gly Asn Val Gly Leu Gly Gly Ala Ile Ala Ser Gly Val
                100                 105                 110

Ala Val Ser Lys Val Leu His Leu Glu Gly Glu Val Asn Lys Ile Lys
            115                 120                 125

Ser Ala Leu Leu Ser Thr Asn Lys Ala Val Val Ser Leu Ser Asn Gly
130                 135                 140

Val Ser Val Leu Thr Phe Lys Val Leu Asp Leu Lys Asn Tyr Ile Asp
145                 150                 155                 160

Lys Gln Leu Leu Pro Ile Leu Asn Lys Gln Ser Cys Ser Ile Ser Asn
                165                 170                 175

Pro Glu Thr Val Ile Glu Phe Gln Gln Lys Asn Asn Arg Leu Leu Glu
                180                 185                 190

Ile Thr Arg Glu Phe Ser Val Asn Ala Gly Val Thr Thr Pro Val Ser
            195                 200                 205

Thr Tyr Met Leu Thr Asn Ser Glu Leu Leu Ser Leu Ile Asn Asp Met
210                 215                 220

Pro Ile Thr Asn Asp Gln Lys Lys Leu Met Ser Asn Asn Val Gln Ile
225                 230                 235                 240

Val Arg Gln Gln Ser Tyr Ser Ile Met Ser Ile Ile Lys Glu Glu Val
                245                 250                 255

Leu Ala Tyr Val Val Gln Leu Pro Leu Tyr Gly Val Ile Asp Thr Pro
                260                 265                 270

Cys Trp Lys Leu His Thr Ser Pro Leu Cys Thr Thr Asn Thr Lys Glu
            275                 280                 285

Gly Ser Asn Ile Cys Leu Thr Arg Thr Asp Arg Gly Trp Tyr Cys Asp
            290                 295                 300

Asn Ala Gly Ser Val Ser Phe Phe Pro Gln Ala Glu Thr Cys Lys Val
305                 310                 315                 320

Gln Ser Asn Arg Val Phe Cys Asp Thr Met Asn Ser Arg Thr Leu Pro
```

```
                    325                 330                 335
    Ser Glu Val Asn Leu Cys Asn Val Asp Ile Phe Asn Pro Lys Tyr Asp
                340                 345                 350
    Cys Lys Ile Met Thr Ser Lys Thr Asp Val Ser Ser Val Ile Thr
                355                 360                 365
    Ser Leu Gly Ala Ile Val Ser Cys Tyr Gly Lys Thr Lys Cys Thr Ala
                370                 375                 380
    Ser Asn Lys Asn Arg Gly Ile Ile Lys Thr Phe Ser Asn Gly Cys Asp
    385                 390                 395                 400
    Tyr Val Ser Asn Lys Gly Val Asp Thr Val Ser Val Gly Asn Thr Leu
                    405                 410                 415
    Tyr Tyr Val Asn Lys Gln Glu Gly Lys Ser Leu Tyr Val Lys Gly Glu
                420                 425                 430
    Pro Ile Ile Asn Phe Tyr Asp Pro Leu Val Phe Pro Ser Asp Glu Phe
                435                 440                 445
    Asp Ala Ser Ile Ser Gln Val Asn Glu Lys Ile Asn Gln Ser Leu Ala
                450                 455                 460
    Phe Ile Arg Lys Ser Asp Glu Leu Leu Ser Gly Ser Gly Ser Glu Ser
    465                 470                 475                 480
    Gln Val Arg Gln Gln Phe Ser Lys Asp Ile Glu Lys Leu Leu Asn Glu
                    485                 490                 495
    Gln Val Asn Lys Glu Met Gln Ser Ser Asn Leu Tyr Met Ser Met Ser
                500                 505                 510
    Ser Trp Ser Tyr Thr His Ser Leu Asp Gly Ala Gly Leu Phe Leu Phe
                515                 520                 525
    Asp His Ala Ala Glu Glu Tyr Glu His Ala Lys Lys Leu Ile Ile Phe
                530                 535                 540
    Leu Asn Glu Asn Asn Val Pro Val Gln Leu Thr Ser Ile Ser Ala Pro
    545                 550                 555                 560
    Glu His Cys Phe Glu Gly Leu Thr Gln Ile Phe Gln Lys Ala Tyr Glu
                    565                 570                 575
    His Glu Gln His Ile Ser Glu Ser Ile Asn Asn Ile Val Asp His Ala
                580                 585                 590
    Ile Lys Ser Lys Asp His Ala Thr Phe Asn Phe Leu Gln Trp Tyr Val
                595                 600                 605
    Ala Glu Gln His Glu Glu Val Leu Phe Lys Asp Ile Leu Asp Lys
                610                 615                 620
    Ile Glu Leu Ile Gly Asn Glu Asn His Gly Leu Tyr Leu Ala Asp Gln
    625                 630                 635                 640
    Tyr Val Lys Gly Ile Ala Lys Ser Arg Lys Ser
                    645                 650

<210> SEQ ID NO 17
<211> LENGTH: 651
<212> TYPE: PRT
<213> ORGANISM: Artificial Sequence
<220> FEATURE:
<223> OTHER INFORMATION: Synthetic polypeptide

<400> SEQUENCE: 17

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
```

```
            35                  40                  45
Arg Thr Gly Trp Tyr Thr Ser Val Ile Thr Ile Glu Leu Ser Asn Ile
 50                  55                  60
Lys Glu Asn Lys Cys Asn Gly Thr Asp Ala Lys Val Lys Leu Ile Lys
 65                  70                  75                  80
Gln Glu Leu Asp Lys Tyr Lys Asn Ala Val Thr Glu Leu Gln Leu Leu
                 85                  90                  95
Met Gly Ser Gly Asn Val Gly Leu Gly Gly Ala Ile Ala Ser Gly Val
                100                 105                 110
Ala Val Ser Lys Val Leu His Leu Glu Gly Glu Val Asn Lys Ile Lys
                115                 120                 125
Ser Ala Leu Leu Ser Thr Asn Lys Ala Val Val Ser Leu Ser Asn Gly
130                 135                 140
Val Ser Val Leu Thr Phe Lys Val Leu Asp Leu Lys Asn Tyr Ile Asp
145                 150                 155                 160
Lys Gln Leu Leu Pro Ile Leu Asn Lys Gln Ser Cys Ser Ile Ser Asn
                165                 170                 175
Pro Glu Thr Val Ile Glu Phe Gln Gln Lys Asn Asn Arg Leu Leu Glu
                180                 185                 190
Ile Thr Arg Glu Phe Ser Val Asn Ala Gly Val Thr Thr Pro Val Ser
                195                 200                 205
Thr Tyr Met Leu Thr Asn Ser Glu Leu Leu Ser Leu Ile Asn Asp Met
210                 215                 220
Pro Ile Thr Asn Asp Gln Lys Lys Leu Met Ser Asn Asn Val Gln Ile
225                 230                 235                 240
Val Arg Gln Gln Ser Tyr Ser Ile Met Ser Ile Ile Lys Glu Glu Val
                245                 250                 255
Leu Ala Tyr Val Val Gln Leu Pro Leu Tyr Gly Val Ile Asp Thr Pro
                260                 265                 270
Cys Trp Lys Leu His Thr Ser Pro Leu Cys Thr Thr Asn Thr Lys Asn
                275                 280                 285
Gly Ser Asn Ile Cys Leu Thr Arg Thr Asp Arg Gly Trp Tyr Cys Asp
290                 295                 300
Asn Ala Gly Asn Val Ser Phe Phe Pro Gln Ala Glu Thr Cys Lys Val
305                 310                 315                 320
Gln Ser Asn Arg Val Phe Cys Asp Thr Met Asn Ser Arg Thr Leu Pro
                325                 330                 335
Ser Glu Val Asn Leu Cys Asn Val Asp Ile Phe Asn Pro Lys Tyr Asp
                340                 345                 350
Cys Lys Ile Met Thr Ser Lys Thr Asp Val Ser Ser Ser Val Ile Thr
                355                 360                 365
Ser Leu Gly Ala Ile Val Ser Cys Tyr Gly Lys Thr Lys Cys Thr Ala
                370                 375                 380
Ser Asn Lys Asn Arg Gly Ile Ile Lys Thr Phe Ser Asn Gly Cys Asp
385                 390                 395                 400
Tyr Val Ser Asn Lys Gly Val Asp Thr Val Ser Val Gly Asn Thr Leu
                405                 410                 415
Tyr Tyr Val Asn Lys Gln Glu Gly Lys Ser Leu Tyr Val Lys Gly Glu
                420                 425                 430
Pro Ile Ile Asn Phe Tyr Asp Pro Leu Val Phe Pro Ser Asp Glu Phe
                435                 440                 445
Asp Ala Ser Ile Ser Gln Val Asn Glu Lys Ile Asn Gln Ser Leu Ala
450                 455                 460
```

Phe Ile Asn Lys Ser Asp Glu Leu Leu Ser Gly Ser Glu Ser
465                 470                 475                 480

Gln Val Arg Gln Gln Phe Ser Lys Asp Ile Glu Lys Leu Leu Asn Glu
            485                 490                 495

Gln Val Asn Lys Glu Met Gln Ser Ser Asn Leu Tyr Met Ser Met Ser
                500                 505                 510

Ser Trp Ser Tyr Thr His Ser Leu Asp Gly Ala Gly Leu Phe Leu Phe
            515                 520                 525

Asp His Ala Ala Glu Glu Tyr Glu His Ala Lys Lys Leu Ile Ile Phe
530                 535                 540

Leu Asn Glu Asn Asn Val Pro Val Gln Leu Thr Ser Ile Ser Ala Pro
545                 550                 555                 560

Glu His Cys Phe Glu Gly Leu Thr Gln Ile Phe Gln Lys Ala Tyr Glu
                565                 570                 575

His Glu Gln His Ile Ser Glu Ser Ile Asn Asn Ile Val Asp His Ala
            580                 585                 590

Ile Lys Ser Lys Asp His Ala Thr Phe Asn Phe Leu Gln Trp Tyr Val
595                 600                 605

Ala Glu Gln His Glu Glu Val Leu Phe Lys Asp Ile Leu Asp Lys
610                 615                 620

Ile Glu Leu Ile Gly Asn Glu Asn His Gly Leu Tyr Leu Ala Asp Gln
625                 630                 635                 640

Tyr Val Lys Gly Ile Ala Lys Ser Arg Lys Ser
                645                 650

<210> SEQ ID NO 18
<211> LENGTH: 651
<212> TYPE: PRT
<213> ORGANISM: Artificial Sequence
<220> FEATURE:
<223> OTHER INFORMATION: Synthetic polypeptide

<400> SEQUENCE: 18

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Ser Gly Asn Val Gly Leu Gly Gly Ala Ile Ala Ser Gly Val
            100                 105                 110

Ala Val Ser Lys Val Leu His Leu Glu Gly Glu Val Asn Lys Ile Lys
        115                 120                 125

Ser Ala Leu Leu Ser Thr Asn Lys Ala Val Val Ser Leu Ser Asn Gly
    130                 135                 140

Val Ser Val Leu Thr Phe Lys Val Leu Asp Leu Lys Asn Tyr Ile Asp
145                 150                 155                 160

Lys Gln Leu Leu Pro Ile Leu Asn Lys Gln Ser Cys Ser Ile Ser Asn
                165                 170                 175

```
Pro Glu Thr Val Ile Glu Phe Gln Gln Lys Asn Asn Arg Leu Leu Glu
            180                 185                 190

Ile Thr Arg Glu Phe Ser Val Asn Ala Gly Val Thr Thr Pro Val Ser
            195                 200                 205

Thr Tyr Met Leu Thr Asn Ser Glu Leu Leu Ser Leu Ile Asn Asp Met
    210                 215                 220

Pro Ile Thr Asn Asp Gln Lys Lys Leu Met Ser Asn Asn Val Gln Ile
225                 230                 235                 240

Val Arg Gln Gln Ser Tyr Ser Ile Met Ser Ile Ile Lys Glu Glu Val
                245                 250                 255

Leu Ala Tyr Val Val Gln Leu Pro Leu Tyr Gly Val Ile Asp Thr Pro
            260                 265                 270

Cys Trp Lys Leu His Thr Ser Pro Leu Cys Thr Thr Asn Thr Lys Asn
            275                 280                 285

Gly Ser Asn Ile Cys Leu Thr Arg Thr Asp Arg Gly Trp Tyr Cys Asp
    290                 295                 300

Asn Ala Gly Asn Val Ser Phe Phe Pro Gln Ala Glu Thr Cys Lys Val
305                 310                 315                 320

Gln Ser Asn Arg Val Phe Cys Asp Thr Met Asn Ser Arg Thr Leu Pro
                325                 330                 335

Ser Glu Val Asn Leu Cys Asn Val Asp Ile Phe Asn Pro Lys Tyr Asp
            340                 345                 350

Cys Lys Ile Met Thr Ser Lys Thr Asp Val Ser Ser Ser Val Ile Thr
            355                 360                 365

Ser Leu Gly Ala Ile Val Ser Cys Tyr Gly Lys Thr Lys Cys Thr Ala
    370                 375                 380

Ser Asn Lys Asn Arg Gly Ile Ile Lys Thr Phe Ser Asn Gly Cys Asp
385                 390                 395                 400

Tyr Val Ser Asn Lys Gly Val Asp Thr Val Ser Val Gly Asn Thr Leu
                405                 410                 415

Tyr Tyr Val Asn Lys Gln Glu Gly Lys Ser Leu Tyr Val Lys Gly Glu
            420                 425                 430

Pro Ile Ile Asn Phe Tyr Asp Pro Leu Val Phe Pro Ser Asp Glu Phe
            435                 440                 445

Asp Ala Ser Ile Ser Gln Val Asn Glu Leu Ile Asn Gln Ser Leu Ala
450                 455                 460

Phe Ile Asn Gln Ser Asp Glu Leu Leu Ser Gly Ser Gly Ser Glu Ser
465                 470                 475                 480

Gln Val Arg Gln Gln Phe Ser Lys Asp Ile Glu Lys Leu Leu Asn Glu
                485                 490                 495

Gln Val Asn Lys Glu Met Gln Ser Ser Asn Leu Tyr Met Ser Met Ser
            500                 505                 510

Ser Trp Ser Tyr Thr His Ser Leu Asp Gly Ala Gly Leu Phe Leu Phe
    515                 520                 525

Asp His Ala Ala Glu Glu Tyr Glu His Ala Lys Lys Leu Ile Ile Phe
    530                 535                 540

Leu Asn Glu Asn Asn Val Pro Val Gln Leu Thr Ser Ile Ser Ala Pro
545                 550                 555                 560

Glu His Cys Phe Glu Gly Leu Thr Gln Ile Phe Gln Lys Ala Tyr Glu
                565                 570                 575

His Glu Gln His Ile Ser Glu Ser Ile Asn Asn Ile Val Asp His Ala
            580                 585                 590
```

```
Ile Lys Ser Lys Asp His Ala Thr Phe Asn Phe Leu Gln Trp Tyr Val
            595                 600                 605

Ala Glu Gln His Glu Glu Val Leu Phe Lys Asp Ile Leu Asp Lys
610                 615                 620

Ile Glu Leu Ile Gly Asn Glu Asn His Gly Leu Tyr Leu Ala Asp Gln
625                 630                 635                 640

Tyr Val Lys Gly Ile Ala Lys Ser Arg Lys Ser
                645                 650

<210> SEQ ID NO 19
<211> LENGTH: 651
<212> TYPE: PRT
<213> ORGANISM: Artificial Sequence
<220> FEATURE:
<223> OTHER INFORMATION: Synthetic polypeptide

<400> SEQUENCE: 19

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
50                  55                  60

Lys Glu Asn Lys Val Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Ser Gly Asn Val Gly Leu Gly Gly Ala Ile Ala Ser Gly Val
            100                 105                 110

Ala Val Ser Lys Val Leu His Leu Glu Gly Glu Val Asn Lys Ile Lys
        115                 120                 125

Ser Ala Leu Leu Ser Thr Asn Lys Ala Val Val Ser Leu Ser Asn Gly
130                 135                 140

Val Ser Val Leu Thr Phe Lys Val Leu Asp Leu Lys Asn Tyr Ile Asp
145                 150                 155                 160

Lys Gln Leu Leu Pro Ile Leu Asn Lys Gln Ser Val Ser Ile Ser Asn
                165                 170                 175

Pro Glu Thr Val Ile Glu Phe Gln Gln Lys Asn Asn Arg Leu Leu Glu
            180                 185                 190

Ile Thr Arg Glu Phe Ser Val Asn Ala Gly Val Thr Thr Pro Val Ser
        195                 200                 205

Thr Tyr Met Leu Thr Asn Ser Glu Leu Leu Ser Leu Ile Asn Asp Met
210                 215                 220

Pro Ile Thr Asn Asp Gln Lys Lys Leu Met Ser Asn Asn Val Gln Ile
225                 230                 235                 240

Val Arg Gln Gln Ser Tyr Ser Ile Met Ser Ile Ile Lys Glu Glu Val
                245                 250                 255

Leu Ala Tyr Val Val Gln Leu Pro Leu Tyr Gly Val Ile Asp Thr Pro
            260                 265                 270

Cys Trp Lys Leu His Thr Ser Pro Leu Cys Thr Thr Asn Thr Lys Asn
        275                 280                 285

Gly Ser Asn Ile Cys Leu Thr Arg Thr Asp Arg Gly Trp Tyr Cys Asp
290                 295                 300
```

```
Asn Ala Gly Asn Val Ser Phe Phe Pro Gln Ala Glu Thr Cys Lys Val
305                 310                 315                 320

Gln Ser Asn Arg Val Phe Cys Asp Thr Met Asn Ser Arg Thr Leu Pro
            325                 330                 335

Ser Glu Val Asn Leu Cys Asn Val Asp Ile Phe Asn Pro Lys Tyr Asp
            340                 345                 350

Cys Lys Ile Met Thr Ser Lys Thr Asp Val Ser Ser Val Ile Thr
            355                 360                 365

Ser Leu Gly Ala Ile Val Ser Cys Tyr Gly Lys Thr Lys Cys Thr Ala
        370                 375                 380

Ser Asn Lys Asn Arg Gly Ile Ile Lys Thr Phe Ser Asn Gly Cys Asp
385                 390                 395                 400

Tyr Val Ser Asn Lys Gly Val Asp Thr Val Ser Val Gly Asn Thr Leu
            405                 410                 415

Tyr Tyr Val Asn Lys Gln Glu Gly Lys Ser Leu Tyr Val Lys Gly Glu
            420                 425                 430

Pro Ile Ile Asn Phe Tyr Asp Pro Leu Val Phe Pro Ser Asp Glu Phe
            435                 440                 445

Asp Ala Ser Ile Ser Gln Val Asn Glu Lys Ile Asn Gln Ser Leu Ala
450                 455                 460

Phe Ile Asn Lys Ser Asp Glu Leu Leu Ser Gly Ser Gly Ser Glu Ser
465                 470                 475                 480

Gln Val Arg Gln Gln Phe Ser Lys Asp Ile Glu Lys Leu Leu Asn Glu
            485                 490                 495

Gln Val Asn Lys Glu Met Gln Ser Ser Asn Leu Tyr Met Ser Met Ser
            500                 505                 510

Ser Trp Ser Tyr Thr His Ser Leu Asp Gly Ala Gly Leu Phe Leu Phe
            515                 520                 525

Asp His Ala Ala Glu Glu Tyr Glu His Ala Lys Lys Leu Ile Ile Phe
530                 535                 540

Leu Asn Glu Asn Asn Val Pro Val Gln Leu Thr Ser Ile Ser Ala Pro
545                 550                 555                 560

Glu His Cys Phe Glu Gly Leu Thr Gln Ile Phe Gln Lys Ala Tyr Glu
            565                 570                 575

His Glu Gln His Ile Ser Glu Ser Ile Asn Asn Ile Val Asp His Ala
            580                 585                 590

Ile Lys Ser Lys Asp His Ala Thr Phe Asn Phe Leu Gln Trp Tyr Val
            595                 600                 605

Ala Glu Gln His Glu Glu Val Leu Phe Lys Asp Ile Leu Asp Lys
            610                 615                 620

Ile Glu Leu Ile Gly Asn Glu Asn His Gly Leu Tyr Leu Ala Asp Gln
625                 630                 635                 640

Tyr Val Lys Gly Ile Ala Lys Ser Arg Lys Ser
            645                 650

<210> SEQ ID NO 20
<211> LENGTH: 651
<212> TYPE: PRT
<213> ORGANISM: Artificial Sequence
<220> FEATURE:
<223> OTHER INFORMATION: Synthetic polypeptide

<400> SEQUENCE: 20

Met Glu Leu Leu Ile Leu Lys Ala Asn Ala Ile Thr Thr Ile Leu Thr
1               5                   10                  15
```

-continued

```
Ala Val Thr Phe Cys Phe Ala Ser Gly Gln Asn Ile Thr Glu Phe
             20                  25                  30
Tyr Gln Ser Thr Cys Ser Ala Val Ser Lys Gly Tyr Leu Ser Ala Leu
         35                  40                  45
Arg Thr Gly Trp Tyr Thr Ser Val Ile Thr Ile Glu Leu Ser Asn Ile
 50                  55                  60
Lys Glu Asn Lys Cys Asn Gly Thr Asp Ala Lys Val Lys Leu Ile Lys
 65                  70                  75                  80
Gln Glu Leu Asp Lys Tyr Lys Asn Ala Val Thr Glu Leu Gln Leu Leu
                 85                  90                  95
Met Gly Ser Gly Asn Val Gly Leu Gly Gly Ala Ile Ala Ser Gly Val
                100                 105                 110
Ala Val Ser Lys Val Leu His Leu Glu Gly Glu Val Asn Lys Ile Lys
             115                 120                 125
Ser Ala Leu Leu Ser Thr Asn Lys Ala Val Val Ser Leu Ser Asn Gly
 130                 135                 140
Val Ser Val Leu Thr Phe Lys Val Leu Asp Leu Lys Asn Tyr Ile Asp
145                 150                 155                 160
Lys Gln Leu Leu Pro Ile Leu Asn Lys Gln Ser Cys Ser Ile Ser Asn
                165                 170                 175
Pro Glu Thr Val Ile Glu Phe Gln Gln Lys Asn Asn Arg Leu Leu Glu
             180                 185                 190
Ile Thr Arg Glu Phe Ser Val Asn Ala Gly Val Thr Thr Pro Val Ser
         195                 200                 205
Thr Tyr Met Leu Thr Asn Ser Glu Leu Leu Ser Leu Ile Asn Asp Met
210                 215                 220
Pro Ile Thr Asn Asp Gln Lys Lys Leu Met Ser Asn Asn Val Gln Ile
225                 230                 235                 240
Val Arg Gln Gln Ser Tyr Ser Ile Met Ser Ile Ile Lys Glu Glu Val
                245                 250                 255
Leu Ala Tyr Val Val Gln Leu Pro Leu Tyr Gly Val Ile Asp Thr Pro
             260                 265                 270
Cys Trp Lys Leu His Thr Ser Pro Leu Cys Thr Thr Asn Thr Lys Asn
         275                 280                 285
Gly Ser Asn Ile Cys Leu Thr Arg Thr Asp Arg Gly Trp Tyr Cys Asp
290                 295                 300
Asn Ala Gly Asn Val Ser Phe Phe Pro Gln Ala Glu Thr Cys Lys Val
305                 310                 315                 320
Gln Ser Asn Arg Val Phe Cys Asp Thr Met Asn Ser Arg Thr Leu Pro
                325                 330                 335
Ser Glu Val Asn Leu Cys Asn Val Asp Ile Phe Asn Pro Lys Tyr Asp
             340                 345                 350
Cys Lys Ile Met Thr Ser Lys Thr Asp Val Ser Ser Ser Val Ile Thr
         355                 360                 365
Ser Leu Gly Ala Ile Val Ser Cys Tyr Gly Lys Thr Lys Cys Thr Ala
 370                 375                 380
Ser Asn Lys Asn Arg Gly Ile Ile Lys Thr Phe Ser Asn Gly Cys Asp
385                 390                 395                 400
Tyr Val Ser Asn Lys Gly Val Asp Thr Val Ser Val Gly Asn Thr Leu
                405                 410                 415
Tyr Tyr Val Asn Lys Gln Glu Gly Lys Ser Leu Tyr Val Lys Gly Glu
             420                 425                 430
Pro Ile Ile Asn Phe Tyr Asp Pro Leu Val Phe Pro Ser Asp Glu Phe
```

```
            435                 440                 445
Asp Ala Ser Ile Ser Gln Val Asn Glu Leu Ile Asn Gln Ser Leu Ala
450                 455                 460

Phe Ile Asn Gln Ser Asp Glu Leu Leu Ser Gly Ser Gly Ser Glu Ser
465                 470                 475                 480

Gln Val Arg Gln Gln Phe Ser Asn Asp Ile Glu Asn Leu Leu Asn Glu
                485                 490                 495

Gln Val Asn Lys Glu Met Gln Ser Ser Asn Leu Tyr Met Ser Met Ser
            500                 505                 510

Ser Trp Ser Tyr Thr His Ser Leu Asp Gly Ala Gly Leu Phe Leu Phe
        515                 520                 525

Asp His Ala Ala Glu Glu Tyr Glu His Ala Lys Lys Leu Ile Ile Phe
    530                 535                 540

Leu Asn Glu Asn Asn Val Pro Val Gln Leu Thr Ser Ile Ser Ala Pro
545                 550                 555                 560

Glu His Cys Phe Glu Gly Leu Thr Gln Ile Phe Gln Lys Ala Tyr Glu
                565                 570                 575

His Glu Gln His Ile Ser Glu Ser Ile Asn Asn Ile Val Asp His Ala
            580                 585                 590

Ile Lys Ser Lys Asp His Ala Thr Phe Asn Phe Leu Gln Trp Tyr Val
        595                 600                 605

Ala Glu Gln His Glu Glu Val Leu Phe Lys Asp Ile Leu Asp Lys
    610                 615                 620

Ile Glu Leu Ile Gly Asn Glu Asn His Gly Leu Tyr Leu Ala Asp Gln
625                 630                 635                 640

Tyr Val Lys Gly Ile Ala Lys Ser Arg Lys Ser
                645                 650

<210> SEQ ID NO 21
<211> LENGTH: 651
<212> TYPE: PRT
<213> ORGANISM: Artificial Sequence
<220> FEATURE:
<223> OTHER INFORMATION: Synthetic polypeptide

<400> SEQUENCE: 21

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Ser Gly Asn Val Gly Leu Gly Gly Ala Ile Ala Ser Gly Val
            100                 105                 110

Ala Val Ser Lys Val Leu His Leu Glu Gly Glu Val Asn Lys Ile Lys
        115                 120                 125

Ser Ala Leu Leu Ser Thr Asn Lys Ala Val Val Ser Leu Ser Asn Gly
130                 135                 140

Val Ser Val Leu Thr Phe Lys Val Leu Asp Leu Lys Asn Tyr Ile Asp
```

-continued

```
            145                 150                 155                 160
Lys Gln Leu Leu Pro Ile Leu Asn Lys Gln Ser Cys Ser Ile Ser Asn
                    165                 170                 175
Pro Glu Thr Val Ile Glu Phe Gln Gln Lys Asn Asn Arg Leu Leu Glu
                    180                 185                 190
Ile Thr Arg Glu Phe Ser Val Asn Ala Gly Val Thr Thr Pro Val Ser
                    195                 200                 205
Thr Tyr Met Leu Thr Asn Ser Glu Leu Leu Ser Leu Ile Asn Asp Met
            210                 215                 220
Pro Ile Thr Asn Asp Gln Lys Lys Leu Met Ser Asn Asn Val Gln Ile
225                 230                 235                 240
Val Arg Gln Gln Ser Tyr Ser Ile Met Ser Ile Ile Lys Glu Glu Val
                    245                 250                 255
Leu Ala Tyr Val Val Gln Leu Pro Leu Tyr Gly Val Ile Asp Thr Pro
                    260                 265                 270
Cys Trp Lys Leu His Thr Ser Pro Leu Cys Thr Thr Asn Thr Lys Asn
                    275                 280                 285
Gly Ser Asn Ile Cys Leu Thr Arg Thr Asp Arg Gly Trp Tyr Cys Asp
            290                 295                 300
Asn Ala Gly Asn Val Ser Phe Phe Pro Gln Ala Glu Thr Cys Lys Val
305                 310                 315                 320
Gln Ser Asn Arg Val Phe Cys Asp Thr Met Asn Ser Arg Thr Leu Pro
                    325                 330                 335
Ser Glu Val Asn Leu Cys Asn Val Asp Ile Phe Asn Pro Lys Tyr Asp
                    340                 345                 350
Cys Lys Ile Met Thr Ser Lys Thr Asp Val Ser Ser Ser Val Ile Thr
                    355                 360                 365
Ser Leu Gly Ala Ile Val Ser Cys Tyr Gly Lys Thr Lys Cys Thr Ala
            370                 375                 380
Ser Asn Lys Asn Arg Gly Ile Ile Lys Thr Phe Ser Asn Gly Cys Asp
385                 390                 395                 400
Tyr Val Ser Asn Lys Gly Val Asp Thr Val Ser Val Gly Asn Thr Leu
                    405                 410                 415
Tyr Tyr Val Asn Lys Gln Glu Gly Asn Ser Leu Tyr Val Asn Gly Glu
                    420                 425                 430
Pro Ile Ile Asn Phe Tyr Asp Pro Leu Val Phe Pro Ser Asp Glu Phe
                    435                 440                 445
Asp Ala Ser Ile Ser Gln Val Asn Glu Leu Ile Asn Gln Ser Leu Ala
450                 455                 460
Phe Ile Asn Gln Ser Asp Glu Leu Leu Ser Gly Ser Gly Ser Glu Ser
465                 470                 475                 480
Gln Val Arg Gln Gln Phe Ser Lys Asp Ile Glu Lys Leu Leu Asn Glu
                    485                 490                 495
Gln Val Asn Lys Glu Met Gln Ser Ser Asn Leu Tyr Met Ser Met Ser
                    500                 505                 510
Ser Trp Ser Tyr Thr His Ser Leu Asp Gly Ala Gly Leu Phe Leu Phe
            515                 520                 525
Asp His Ala Ala Glu Glu Tyr Glu His Ala Lys Lys Leu Ile Ile Phe
            530                 535                 540
Leu Asn Glu Asn Asn Val Pro Val Gln Leu Thr Ser Ile Ser Ala Pro
545                 550                 555                 560
Glu His Cys Phe Glu Gly Leu Thr Gln Ile Phe Gln Lys Ala Tyr Glu
                    565                 570                 575
```

```
His Glu Gln His Ile Ser Glu Ser Ile Asn Asn Ile Val Asp His Ala
                585                 585                 590

Ile Lys Ser Lys Asp His Ala Thr Phe Asn Phe Leu Gln Trp Tyr Val
        595                 600                 605

Ala Glu Gln His Glu Glu Val Leu Phe Lys Asp Ile Leu Asp Lys
        610                 615                 620

Ile Glu Leu Ile Gly Asn Glu Asn His Gly Leu Tyr Leu Ala Asp Gln
625                 630                 635                 640

Tyr Val Lys Gly Ile Ala Lys Ser Arg Lys Ser
                645                 650
```

<210> SEQ ID NO 22
<211> LENGTH: 651
<212> TYPE: PRT
<213> ORGANISM: Artificial Sequence
<220> FEATURE:
<223> OTHER INFORMATION: Synthetic polypeptide

<400> SEQUENCE: 22

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Ser Gly Asn Val Gly Leu Gly Gly Ala Ile Ala Ser Gly Val
                100                 105                 110

Ala Val Ser Lys Val Leu His Leu Glu Gly Glu Val Asn Lys Ile Lys
            115                 120                 125

Ser Ala Leu Leu Ser Thr Asn Lys Ala Val Val Ser Leu Ser Asn Gly
        130                 135                 140

Val Ser Val Leu Thr Phe Lys Val Leu Asp Leu Lys Asn Tyr Ile Asp
145                 150                 155                 160

Lys Gln Leu Leu Pro Ile Leu Asn Lys Gln Ser Cys Ser Ile Ser Asn
                165                 170                 175

Pro Glu Thr Val Ile Glu Phe Gln Gln Lys Asn Asn Arg Leu Leu Glu
            180                 185                 190

Ile Thr Arg Glu Phe Ser Val Asn Ala Gly Val Thr Thr Pro Val Ser
        195                 200                 205

Thr Tyr Met Leu Thr Asn Ser Glu Leu Leu Ser Leu Ile Asn Asp Met
    210                 215                 220

Pro Ile Thr Asn Asp Gln Lys Lys Leu Met Ser Asn Asn Val Gln Ile
225                 230                 235                 240

Val Arg Gln Gln Ser Tyr Ser Ile Met Ser Ile Ile Lys Glu Glu Val
                245                 250                 255

Leu Ala Tyr Val Val Gln Leu Pro Leu Tyr Gly Val Ile Asp Thr Pro
            260                 265                 270

Cys Trp Lys Leu His Thr Ser Pro Leu Cys Thr Thr Asn Thr Lys Asn
        275                 280                 285
```

Gly Ser Asn Ile Cys Leu Thr Arg Thr Asp Arg Gly Trp Tyr Cys Asp
            290                 295                 300

Asn Ala Gly Asn Val Ser Phe Phe Pro Gln Ala Glu Thr Cys Lys Val
305                 310                 315                 320

Gln Ser Asn Arg Val Phe Cys Asp Thr Met Asn Ser Arg Thr Leu Pro
                325                 330                 335

Ser Glu Val Asn Leu Cys Asn Val Asp Ile Phe Asn Pro Lys Tyr Asp
            340                 345                 350

Cys Lys Ile Met Thr Ser Lys Thr Asp Val Ser Ser Val Ile Thr
            355                 360                 365

Ser Leu Gly Ala Ile Val Ser Cys Tyr Gly Lys Thr Lys Cys Thr Ala
370                 375                 380

Ser Asn Lys Asn Arg Gly Ile Ile Lys Thr Phe Ser Asn Gly Cys Asp
385                 390                 395                 400

Tyr Val Ser Asn Lys Gly Val Asp Thr Val Ser Val Gly Asn Thr Leu
                405                 410                 415

Tyr Tyr Val Asn Lys Gln Glu Gly Asn Ser Leu Tyr Val Asn Gly Glu
            420                 425                 430

Pro Ile Ile Asn Phe Tyr Asp Pro Leu Val Phe Pro Ser Asp Glu Phe
                435                 440                 445

Asp Ala Ser Ile Ser Gln Val Asn Glu Leu Ile Asn Gln Ser Leu Ala
450                 455                 460

Phe Ile Asn Gln Ser Asp Glu Leu Leu Ser Gly Ser Gly Ser Glu Ser
465                 470                 475                 480

Gln Val Arg Gln Gln Phe Ser Asn Asp Ile Glu Asn Leu Leu Asn Glu
                485                 490                 495

Gln Val Asn Lys Glu Met Gln Ser Ser Asn Leu Tyr Met Ser Met Ser
            500                 505                 510

Ser Trp Ser Tyr Thr His Ser Leu Asp Gly Ala Gly Leu Phe Leu Phe
            515                 520                 525

Asp His Ala Ala Glu Glu Tyr Glu His Ala Lys Lys Leu Ile Ile Phe
530                 535                 540

Leu Asn Glu Asn Asn Val Pro Val Gln Leu Thr Ser Ile Ser Ala Pro
545                 550                 555                 560

Glu His Cys Phe Glu Gly Leu Thr Gln Ile Phe Gln Lys Ala Tyr Glu
                565                 570                 575

His Glu Gln His Ile Ser Glu Ser Ile Asn Asn Ile Val Asp His Ala
            580                 585                 590

Ile Lys Ser Lys Asp His Ala Thr Phe Asn Phe Leu Gln Trp Tyr Val
            595                 600                 605

Ala Glu Gln His Glu Glu Val Leu Phe Lys Asp Ile Leu Asp Lys
610                 615                 620

Ile Glu Leu Ile Gly Asn Glu Asn His Gly Leu Tyr Leu Ala Asp Gln
625                 630                 635                 640

Tyr Val Lys Gly Ile Ala Lys Ser Arg Lys Ser
                645                 650

<210> SEQ ID NO 23
<211> LENGTH: 651
<212> TYPE: PRT
<213> ORGANISM: Artificial Sequence
<220> FEATURE:
<223> OTHER INFORMATION: Synthetic polypeptide

<400> SEQUENCE: 23

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Ser Gly Asn Val Gly Leu Gly Gly Ala Ile Ala Ser Gly Val
            100                 105                 110

Ala Val Ser Lys Val Leu His Leu Glu Gly Glu Val Asn Lys Ile Lys
        115                 120                 125

Ser Ala Leu Leu Ser Thr Asn Lys Ala Val Val Ser Leu Ser Asn Gly
    130                 135                 140

Val Ser Val Leu Thr Phe Lys Val Leu Asp Leu Lys Asn Tyr Ile Asp
145                 150                 155                 160

Lys Gln Leu Leu Pro Ile Leu Asn Lys Gln Ser Cys Ser Ile Ser Asn
                165                 170                 175

Pro Glu Thr Val Ile Glu Phe Gln Gln Lys Asn Asn Arg Leu Leu Glu
            180                 185                 190

Ile Thr Arg Glu Phe Ser Val Asn Ala Gly Val Thr Thr Pro Val Ser
        195                 200                 205

Thr Tyr Met Leu Thr Asn Ser Glu Leu Leu Ser Leu Ile Asn Asp Met
    210                 215                 220

Pro Ile Thr Asn Asp Gln Lys Lys Leu Met Ser Asn Asn Val Gln Ile
225                 230                 235                 240

Val Arg Gln Gln Ser Tyr Ser Ile Met Ser Ile Ile Lys Glu Glu Val
                245                 250                 255

Leu Ala Tyr Val Val Gln Leu Pro Leu Tyr Gly Val Ile Asp Thr Pro
            260                 265                 270

Cys Trp Lys Leu His Thr Ser Pro Leu Cys Thr Thr Asn Thr Lys Asn
        275                 280                 285

Gly Ser Asn Ile Cys Leu Thr Arg Thr Asp Arg Gly Trp Tyr Cys Asp
    290                 295                 300

Asn Ala Gly Asn Val Ser Phe Phe Pro Gln Ala Glu Thr Cys Lys Val
305                 310                 315                 320

Gln Ser Asn Arg Val Phe Cys Asp Thr Met Asn Ser Arg Thr Leu Pro
                325                 330                 335

Ser Glu Val Asn Leu Cys Asn Val Asp Ile Phe Asn Pro Lys Tyr Asp
            340                 345                 350

Cys Lys Ile Met Thr Ser Lys Thr Asp Val Ser Ser Ser Val Ile Thr
        355                 360                 365

Ser Leu Gly Ala Ile Val Ser Cys Tyr Gly Lys Thr Lys Cys Thr Ala
    370                 375                 380

Ser Asn Lys Asn Arg Gly Ile Ile Lys Thr Phe Ser Asn Gly Cys Asp
385                 390                 395                 400

Tyr Val Ser Asn Lys Gly Val Asp Thr Val Ser Val Gly Asn Thr Leu
                405                 410                 415
```

```
Tyr Tyr Val Asn Lys Gln Glu Gly Lys Ser Leu Tyr Val Lys Gly Glu
            420                 425                 430

Pro Ile Ile Asn Phe Tyr Asp Pro Leu Val Phe Pro Ser Asp Glu Phe
        435                 440                 445

Asp Ala Ser Ile Ser Gln Val Asn Glu Leu Ile Asn Gln Ser Leu Ala
    450                 455                 460

Phe Ile Asn Gln Ser Asp Glu Leu Leu Ser Gly Ser Gly Ser Glu Ser
465                 470                 475                 480

Gln Val Gln Gln Gln Phe Ser Lys Asp Ile Glu Lys Leu Leu Asn Glu
                485                 490                 495

Gln Val Asn Lys Glu Met Gln Ser Ser Asn Leu Tyr Met Ser Met Ser
            500                 505                 510

Ser Trp Ser Tyr Thr His Ser Leu Asp Gly Ala Gly Leu Phe Leu Phe
        515                 520                 525

Asp His Ala Ala Glu Glu Tyr Glu His Ala Lys Lys Leu Ile Ile Phe
    530                 535                 540

Leu Asn Glu Asn Asn Val Pro Val Gln Leu Thr Ser Ile Ser Ala Pro
545                 550                 555                 560

Glu His Cys Phe Glu Gly Leu Thr Gln Ile Phe Gln Lys Ala Tyr Glu
                565                 570                 575

His Glu Gln His Ile Ser Glu Ser Ile Asn Asn Ile Val Asp His Ala
            580                 585                 590

Ile Lys Ser Lys Asp His Ala Thr Phe Asn Phe Leu Gln Trp Tyr Val
        595                 600                 605

Ala Glu Gln His Glu Glu Val Leu Phe Lys Asp Ile Leu Asp Lys
    610                 615                 620

Ile Glu Leu Ile Gly Asn Glu Asn His Gly Leu Tyr Leu Ala Asp Gln
625                 630                 635                 640

Tyr Val Lys Gly Ile Ala Lys Ser Arg Lys Ser
                645                 650

<210> SEQ ID NO 24
<211> LENGTH: 530
<212> TYPE: PRT
<213> ORGANISM: Artificial Sequence
<220> FEATURE:
<223> OTHER INFORMATION: Synthetic polypeptide

<400> SEQUENCE: 24

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125
```

-continued

```
Leu Ser Lys Lys Arg Lys Arg Arg Ala Ile Ala Ser Gly Val Ala Val
130                 135                 140

Ser Lys Val Leu His Leu Glu Gly Glu Val Asn Lys Ile Lys Ser Ala
145                 150                 155                 160

Leu Leu Ser Thr Asn Lys Ala Val Val Ser Leu Ser Asn Gly Val Ser
                165                 170                 175

Val Leu Thr Ser Lys Val Leu Asp Leu Lys Asn Tyr Ile Asp Lys Gln
            180                 185                 190

Leu Leu Pro Ile Val Asn Lys Gln Ser Cys Ser Ile Ser Asn Ile Glu
        195                 200                 205

Thr Val Ile Glu Phe Gln Gln Lys Asn Asn Arg Leu Leu Glu Ile Thr
210                 215                 220

Arg Glu Phe Ser Val Asn Ala Gly Val Thr Thr Pro Val Ser Thr Tyr
225                 230                 235                 240

Met Leu Thr Asn Ser Glu Leu Leu Ser Leu Ile Asn Asp Met Pro Ile
                245                 250                 255

Thr Asn Asp Gln Lys Lys Leu Met Ser Asn Asn Val Gln Ile Val Arg
            260                 265                 270

Gln Gln Ser Tyr Ser Ile Met Ser Ile Ile Lys Glu Glu Val Leu Ala
        275                 280                 285

Tyr Val Val Gln Leu Pro Leu Tyr Gly Val Ile Asp Thr Pro Cys Trp
290                 295                 300

Lys Leu His Thr Ser Pro Leu Cys Thr Thr Asn Thr Lys Glu Gly Ser
305                 310                 315                 320

Asn Ile Cys Leu Thr Arg Thr Asp Arg Gly Trp Tyr Cys Asp Asn Ala
                325                 330                 335

Gly Ser Val Ser Phe Phe Pro Gln Ala Glu Thr Cys Lys Val Gln Ser
            340                 345                 350

Asn Arg Val Phe Cys Asp Thr Met Asn Ser Leu Thr Leu Pro Ser Glu
        355                 360                 365

Val Asn Leu Cys Asn Val Asp Ile Phe Asn Pro Lys Tyr Asp Cys Lys
370                 375                 380

Ile Met Thr Ser Lys Thr Asp Val Ser Ser Val Ile Thr Ser Leu
385                 390                 395                 400

Gly Ala Ile Val Ser Cys Tyr Gly Lys Thr Lys Cys Thr Ala Ser Asn
                405                 410                 415

Lys Asn Arg Gly Ile Ile Lys Thr Phe Ser Asn Gly Cys Asp Tyr Val
            420                 425                 430

Ser Asn Lys Gly Val Asp Thr Val Ser Val Gly Asn Thr Leu Tyr Tyr
        435                 440                 445

Val Asn Lys Gln Glu Gly Lys Ser Leu Tyr Val Lys Gly Glu Pro Ile
450                 455                 460

Ile Asn Phe Tyr Asp Pro Leu Val Phe Pro Ser Asp Glu Phe Asp Ala
465                 470                 475                 480

Ser Ile Ser Gln Val Asn Glu Lys Ile Asn Gln Ser Leu Ala Phe Ile
                485                 490                 495

Arg Lys Ser Asp Glu Leu Leu Gly Leu Glu Val Leu Phe Gln Gly Pro
            500                 505                 510

His His His His His His His Ser Ala Trp Ser His Pro Gln Phe
        515                 520                 525

Glu Lys
530
```

<210> SEQ ID NO 25
<211> LENGTH: 689
<212> TYPE: PRT
<213> ORGANISM: Artificial Sequence
<220> FEATURE:
<223> OTHER INFORMATION: Synthetic polypeptide

<400> SEQUENCE: 25

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
```

```
                      370                 375                 380
Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
                435                 440                 445

Thr Val Ser Val Gly Asn Thr Leu Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu Ser Gly Gly Ser Ser Gly Ser Gly Gly Ser Asp Ile Ile Lys
            515                 520                 525

Leu Leu Asn Glu Gln Val Asn Lys Glu Met Gln Ser Ser Asn Leu Tyr
                530                 535                 540

Met Ser Met Ser Ser Trp Cys Tyr Thr His Ser Leu Asp Gly Ala Gly
545                 550                 555                 560

Leu Phe Leu Phe Asp His Ala Ala Glu Glu Tyr Glu His Ala Lys Lys
                565                 570                 575

Leu Ile Ile Phe Leu Asn Glu Asn Asn Val Pro Val Gln Leu Thr Ser
                580                 585                 590

Ile Ser Ala Pro Glu His Lys Phe Glu Gly Leu Thr Gln Ile Phe Gln
                595                 600                 605

Lys Ala Tyr Glu His Glu Gln His Ile Ser Glu Ser Ile Asn Asn Ile
                610                 615                 620

Val Asp His Ala Ile Lys Ser Lys Asp His Ala Thr Phe Asn Phe Leu
625                 630                 635                 640

Gln Trp Tyr Val Ala Glu Gln His Glu Glu Val Leu Phe Lys Asp
                645                 650                 655

Ile Leu Asp Lys Ile Glu Leu Ile Gly Asn Glu Asn His Gly Leu Tyr
                660                 665                 670

Leu Ala Asp Gln Tyr Val Lys Gly Ile Ala Lys Ser Arg Lys Ser Gly
                675                 680                 685

Ser

<210> SEQ ID NO 26
<211> LENGTH: 574
<212> TYPE: PRT
<213> ORGANISM: Human respiratory syncytial virus

<400> SEQUENCE: 26

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
```

-continued

```
                 50                  55                  60
Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Pro Thr Asn Asn Arg Ala Arg Arg Glu Leu Pro
                100                 105                 110

Arg Phe Met Asn Tyr Thr Leu Asn Asn Ala Lys Lys Thr Asn Val Thr
                115                 120                 125

Leu Ser Lys Lys Arg Lys Arg Arg Phe Leu Gly Phe Leu Leu Gly Val
                130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
                180                 185                 190

Leu Asp Leu Lys Asn Tyr Ile Asp Lys Gln Leu Leu Pro Ile Val Asn
                195                 200                 205

Lys Gln Ser Cys Ser Ile Ser Asn Ile Glu Thr Val Ile Glu Phe Gln
                210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
                260                 265                 270

Leu Met Ser Asn Asn Val Gln Ile Val Arg Gln Gln Ser Tyr Ser Ile
                275                 280                 285

Met Ser Ile Ile Lys Glu Glu Val Leu Ala Tyr Val Val Gln Leu Pro
                290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
                340                 345                 350

Pro Gln Ala Glu Thr Cys Lys Val Gln Ser Asn Arg Val Phe Cys Asp
                355                 360                 365

Thr Met Asn Ser Leu Thr Leu Pro Ser Glu Ile Asn Leu Cys Asn Val
                370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Met Asp
                435                 440                 445

Thr Val Ser Val Gly Asn Thr Leu Tyr Val Asn Lys Gln Glu Gly
                450                 455                 460

Lys Ser Leu Tyr Val Lys Gly Glu Pro Ile Ile Asn Phe Tyr Asp Pro
465                 470                 475                 480
```

```
Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 27
<211> LENGTH: 297
<212> TYPE: PRT
<213> ORGANISM: Human respiratory syncytial virus

<400> SEQUENCE: 27

Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Val Ala Gln Ile Thr Leu Ser Ile Leu Ala Met
        35                  40                  45

Ile Ile Ser Thr Ser Leu Ile Ile Val Ala Ile Ile Phe Ile Ala Ser
    50                  55                  60

Ala Asn His Lys Ile Thr Ser Thr Thr Thr Ile Ile Gln Asp Ala Thr
65                  70                  75                  80

Asn Gln Ile Lys Asn Thr Thr Pro Thr Tyr Leu Thr Gln Asn Pro Gln
                85                  90                  95

Leu Gly Ile Ser Pro Ser Asn Pro Ser Asp Ile Thr Ser Leu Ile Thr
            100                 105                 110

Thr Ile Leu Asp Ser Thr Thr Pro Gly Val Lys Ser Thr Leu Gln Ser
        115                 120                 125

Thr Thr Val Gly Thr Lys Asn Thr Thr Thr Thr Gln Ala Gln Pro Asn
    130                 135                 140

Lys Pro Thr Thr Lys Gln Arg Gln Asn Lys Pro Ser Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Arg Thr Thr Thr Lys Pro Thr Lys Lys Pro Thr Pro
        195                 200                 205

Lys Thr Thr Lys Lys Gly Pro Lys Pro Gln Thr Thr Lys Ser Lys Glu
    210                 215                 220

Ala Pro Thr Thr Lys Pro Thr Glu Glu Pro Thr Ile Asn Thr Thr Lys
225                 230                 235                 240

Thr Asn Ile Ile Thr Thr Leu Leu Thr Ser Asn Thr Thr Arg Asn Pro
                245                 250                 255

Glu Leu Thr Ser Gln Met Glu Thr Phe His Ser Thr Ser Ser Glu Gly
            260                 265                 270

Asn Pro Ser Pro Ser Gln Val Ser Ile Thr Ser Glu Tyr Pro Ser Gln
```

```
                    275                 280                 285
Pro Ser Ser Pro Pro Asn Thr Pro Arg
    290                 295

<210> SEQ ID NO 28
<211> LENGTH: 233
<212> TYPE: PRT
<213> ORGANISM: Human respiratory syncytial virus

<400> SEQUENCE: 28

Asn His Lys Val Thr Leu Thr Thr Ala Ile Ile Gln Asp Ala Thr Ser
1               5                   10                  15

Gln Ile Lys Asn Thr Thr Pro Thr Tyr Leu Thr Gln Asp Pro Gln Leu
            20                  25                  30

Gly Ile Ser Phe Ser Asn Leu Ser Glu Ile Thr Ser Gln Thr Thr Thr
        35                  40                  45

Ile Leu Ala Ser Thr Thr Pro Gly Val Lys Ser Asn Leu Gln Pro Thr
    50                  55                  60

Thr Val Lys Thr Lys Asn Thr Thr Thr Thr Gln Thr Gln Pro Ser Lys
65                  70                  75                  80

Pro Thr Thr Lys Gln Arg Gln Asn Lys Pro Pro Asn Lys Pro Asn Asn
                85                  90                  95

Asp Phe His Phe Glu Val Phe Asn Phe Val Pro Cys Ser Ile Cys Ser
            100                 105                 110

Asn Asn Pro Thr Cys Trp Ala Ile Cys Lys Arg Ile Pro Asn Lys Lys
        115                 120                 125

Pro Gly Lys Lys Thr Thr Thr Lys Pro Thr Lys Lys Pro Thr Phe Lys
    130                 135                 140

Thr Thr Lys Lys Asp His Lys Pro Gln Thr Thr Lys Pro Lys Glu Val
145                 150                 155                 160

Pro Thr Thr Lys Pro Thr Glu Glu Pro Thr Ile Asn Thr Thr Lys Thr
                165                 170                 175

Asn Ile Ile Thr Thr Leu Leu Thr Asn Asn Thr Thr Gly Asn Pro Lys
            180                 185                 190

Leu Thr Ser Gln Met Glu Thr Phe His Ser Thr Ser Ser Glu Gly Asn
        195                 200                 205

Leu Ser Pro Ser Gln Val Ser Thr Thr Ser Glu His Pro Ser Gln Pro
    210                 215                 220

Ser Ser Pro Pro Asn Thr Thr Arg Gln
225                 230

<210> SEQ ID NO 29
<211> LENGTH: 56
<212> TYPE: PRT
<213> ORGANISM: Artificial Sequence
<220> FEATURE:
<223> OTHER INFORMATION: Synthetic polypeptide

<400> SEQUENCE: 29

Ser Gly Gly Ser Ser Gly Ser Ser Glu Glu Glu Gly Gly Ser Arg Gln
1               5                   10                  15

Asn Lys Pro Asn Asn Asp Phe His Phe Glu Val Phe Asn Phe Val Pro
            20                  25                  30

Cys Ser Ile Cys Ser Asn Asn Pro Thr Cys Trp Ala Ile Cys Lys Arg
        35                  40                  45

Ile Pro Asn Lys Lys Glu Glu Glu
    50                  55
```

<210> SEQ ID NO 30
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 30
tgactgtgaa cgttcgagat ga                                           22

<210> SEQ ID NO 31
<211> LENGTH: 7
<212> TYPE: PRT
<213> ORGANISM: Artificial Sequence
<220> FEATURE:
<223> OTHER INFORMATION: Synthetic peptide

<400> SEQUENCE: 31

Gly Ser Gly Asn Val Gly Leu
1               5

<210> SEQ ID NO 32
<211> LENGTH: 43
<212> TYPE: PRT
<213> ORGANISM: Artificial Sequence
<220> FEATURE:
<223> OTHER INFORMATION: Synthetic peptide

<400> SEQUENCE: 32

Arg Gln Asn Lys Pro Pro Asn Lys Pro Asn Asn Asp Phe His Phe Glu
1               5                   10                  15

Val Phe Asn Phe Val Pro Cys Ser Ile Cys Ser Asn Asn Pro Thr Cys
                20                  25                  30

Trp Ala Ile Cys Lys Arg Ile Pro Asn Lys Lys
            35                  40

<210> SEQ ID NO 33
<211> LENGTH: 42
<212> TYPE: PRT
<213> ORGANISM: Artificial Sequence
<220> FEATURE:
<223> OTHER INFORMATION: Synthetic peptide

<400> SEQUENCE: 33

Arg Lys Asn Pro Pro Lys Lys Pro Lys Asp Asp Tyr His Phe Glu Val
1               5                   10                  15

Phe Asn Phe Val Pro Cys Ser Ile Cys Gly Asn Asn Gln Leu Cys Lys
                20                  25                  30

Ser Ile Cys Lys Thr Ile Pro Asn Lys Lys
            35                  40

<210> SEQ ID NO 34

<400> SEQUENCE: 34

000

<210> SEQ ID NO 35

<400> SEQUENCE: 35

000

-continued

<210> SEQ ID NO 36
<400> SEQUENCE: 36
000

<210> SEQ ID NO 37
<400> SEQUENCE: 37
000

<210> SEQ ID NO 38
<400> SEQUENCE: 38
000

<210> SEQ ID NO 39
<400> SEQUENCE: 39
000

<210> SEQ ID NO 40
<400> SEQUENCE: 40
000

<210> SEQ ID NO 41
<400> SEQUENCE: 41
000

<210> SEQ ID NO 42
<400> SEQUENCE: 42
000

<210> SEQ ID NO 43
<400> SEQUENCE: 43
000

<210> SEQ ID NO 44
<400> SEQUENCE: 44
000

<210> SEQ ID NO 45
<400> SEQUENCE: 45
000

<210> SEQ ID NO 46
<400> SEQUENCE: 46
000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70
<400> SEQUENCE: 70
000

<210> SEQ ID NO 71
<400> SEQUENCE: 71
000

<210> SEQ ID NO 72
<400> SEQUENCE: 72
000

<210> SEQ ID NO 73
<400> SEQUENCE: 73
000

<210> SEQ ID NO 74
<400> SEQUENCE: 74
000

<210> SEQ ID NO 75
<400> SEQUENCE: 75
000

<210> SEQ ID NO 76
<400> SEQUENCE: 76
000

<210> SEQ ID NO 77
<400> SEQUENCE: 77
000

<210> SEQ ID NO 78
<400> SEQUENCE: 78
000

<210> SEQ ID NO 79
<400> SEQUENCE: 79
000

<210> SEQ ID NO 80
<400> SEQUENCE: 80
000

<210> SEQ ID NO 81

```
<400> SEQUENCE: 81
000

<210> SEQ ID NO 82
<400> SEQUENCE: 82
000

<210> SEQ ID NO 83
<400> SEQUENCE: 83
000

<210> SEQ ID NO 84
<400> SEQUENCE: 84
000

<210> SEQ ID NO 85
<400> SEQUENCE: 85
000

<210> SEQ ID NO 86
<400> SEQUENCE: 86
000

<210> SEQ ID NO 87
<400> SEQUENCE: 87
000

<210> SEQ ID NO 88
<400> SEQUENCE: 88
000

<210> SEQ ID NO 89
<400> SEQUENCE: 89
000

<210> SEQ ID NO 90
<400> SEQUENCE: 90
000

<210> SEQ ID NO 91
<400> SEQUENCE: 91
000

<210> SEQ ID NO 92
<400> SEQUENCE: 92
```

-continued

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101

<400> SEQUENCE: 101

000

<210> SEQ ID NO 102

<400> SEQUENCE: 102

000

<210> SEQ ID NO 103

<400> SEQUENCE: 103

000

-continued

<210> SEQ ID NO 104

<400> SEQUENCE: 104

000

<210> SEQ ID NO 105

<400> SEQUENCE: 105

000

<210> SEQ ID NO 106

<400> SEQUENCE: 106

000

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

<210> SEQ ID NO 111

<400> SEQUENCE: 111

000

<210> SEQ ID NO 112

<400> SEQUENCE: 112

000

<210> SEQ ID NO 113

<400> SEQUENCE: 113

000

<210> SEQ ID NO 114

<400> SEQUENCE: 114

000

```
<210> SEQ ID NO 115
<400> SEQUENCE: 115
000

<210> SEQ ID NO 116
<400> SEQUENCE: 116
000

<210> SEQ ID NO 117
<400> SEQUENCE: 117
000

<210> SEQ ID NO 118
<400> SEQUENCE: 118
000

<210> SEQ ID NO 119
<400> SEQUENCE: 119
000

<210> SEQ ID NO 120
<400> SEQUENCE: 120
000

<210> SEQ ID NO 121
<400> SEQUENCE: 121
000

<210> SEQ ID NO 122
<400> SEQUENCE: 122
000

<210> SEQ ID NO 123
<400> SEQUENCE: 123
000

<210> SEQ ID NO 124
<400> SEQUENCE: 124
000

<210> SEQ ID NO 125
<400> SEQUENCE: 125
000

<210> SEQ ID NO 126
```

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135

<400> SEQUENCE: 135

000

<210> SEQ ID NO 136

<400> SEQUENCE: 136

000

<210> SEQ ID NO 137

<400> SEQUENCE: 137

000

<210> SEQ ID NO 138

<400> SEQUENCE: 138

000

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

-continued

```
<210> SEQ ID NO 149
<400> SEQUENCE: 149
000

<210> SEQ ID NO 150
<400> SEQUENCE: 150
000

<210> SEQ ID NO 151
<400> SEQUENCE: 151
000

<210> SEQ ID NO 152
<400> SEQUENCE: 152
000

<210> SEQ ID NO 153
<400> SEQUENCE: 153
000

<210> SEQ ID NO 154
<400> SEQUENCE: 154
000

<210> SEQ ID NO 155
<400> SEQUENCE: 155
000

<210> SEQ ID NO 156
<400> SEQUENCE: 156
000

<210> SEQ ID NO 157
<400> SEQUENCE: 157
000

<210> SEQ ID NO 158
<400> SEQUENCE: 158
000

<210> SEQ ID NO 159
<400> SEQUENCE: 159
000

<210> SEQ ID NO 160
```

```
<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166

<400> SEQUENCE: 166

000

<210> SEQ ID NO 167

<400> SEQUENCE: 167

000

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171

<400> SEQUENCE: 171
```

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

```
<210> SEQ ID NO 194
<400> SEQUENCE: 194
000

<210> SEQ ID NO 195
<400> SEQUENCE: 195
000

<210> SEQ ID NO 196
<400> SEQUENCE: 196
000

<210> SEQ ID NO 197
<400> SEQUENCE: 197
000

<210> SEQ ID NO 198
<400> SEQUENCE: 198
000

<210> SEQ ID NO 199
<400> SEQUENCE: 199
000

<210> SEQ ID NO 200
<400> SEQUENCE: 200
000

<210> SEQ ID NO 201
<211> LENGTH: 173
<212> TYPE: PRT
<213> ORGANISM: Artificial Sequence
<220> FEATURE:
<223> OTHER INFORMATION: Synthetic polypeptide

<400> SEQUENCE: 201

Glu Ser Gln Val Arg Gln Gln Phe Ser Lys Asp Ile Glu Lys Leu Leu
1               5                   10                  15

Asn Glu Gln Val Asn Lys Glu Met Gln Ser Ser Asn Leu Tyr Met Cys
            20                  25                  30

Met Ser Ser Trp Ser Tyr Thr His Ser Leu Asp Gly Ala Gly Leu Phe
        35                  40                  45

Leu Phe Asp His Ala Ala Glu Glu Tyr Glu His Ala Lys Lys Leu Ile
    50                  55                  60

Ile Phe Leu Asn Glu Asn Asn Val Pro Val Gln Leu Thr Ser Ile Ser
65                  70                  75                  80

Ala Pro Glu His Lys Phe Glu Gly Leu Thr Gln Ile Phe Gln Lys Ala
                85                  90                  95

Tyr Glu His Glu Gln His Ile Ser Glu Ser Ile Asn Asn Ile Val Asp
            100                 105                 110
```

His Ala Ile Lys Ser Lys Asp His Ala Thr Phe Asn Phe Leu Gln Trp
            115                 120                 125

Tyr Val Ala Glu Gln His Glu Glu Val Leu Phe Lys Asp Ile Leu
        130                 135                 140

Asp Lys Ile Glu Leu Ile Gly Asn Glu Asn His Gly Leu Tyr Leu Ala
145                 150                 155                 160

Asp Gln Tyr Val Lys Gly Ile Ala Lys Ser Arg Lys Ser
                165                 170

<210> SEQ ID NO 202
<211> LENGTH: 173
<212> TYPE: PRT
<213> ORGANISM: Artificial Sequence
<220> FEATURE:
<223> OTHER INFORMATION: Synthetic polypeptide

<400> SEQUENCE: 202

Glu Ser Gln Val Arg Gln Gln Phe Ser Lys Asp Ile Glu Lys Leu Leu
1               5                   10                  15

Asn Glu Gln Val Asn Lys Glu Met Gln Ser Ser Asn Leu Tyr Met Ser
                20                  25                  30

Met Ser Ser Trp Ser Tyr Thr His Ser Leu Asp Gly Ala Gly Leu Phe
            35                  40                  45

Leu Phe Asp His Ala Ala Glu Glu Tyr Glu His Ala Lys Lys Leu Ile
50                  55                  60

Ile Phe Leu Asn Glu Asn Asn Val Pro Val Gln Leu Thr Cys Ile Ser
65                  70                  75                  80

Ala Pro Glu His Lys Phe Glu Gly Leu Thr Gln Ile Phe Gln Lys Ala
                85                  90                  95

Tyr Glu His Glu Gln His Ile Ser Glu Ser Ile Asn Asn Ile Val Asp
            100                 105                 110

His Ala Ile Lys Ser Lys Asp His Ala Thr Phe Asn Phe Leu Gln Trp
            115                 120                 125

Tyr Val Ala Glu Gln His Glu Glu Val Leu Phe Lys Asp Ile Leu
        130                 135                 140

Asp Lys Ile Glu Leu Ile Gly Asn Glu Asn His Gly Leu Tyr Leu Ala
145                 150                 155                 160

Asp Gln Tyr Val Lys Gly Ile Ala Lys Ser Arg Lys Ser
                165                 170

<210> SEQ ID NO 203
<211> LENGTH: 173
<212> TYPE: PRT
<213> ORGANISM: Artificial Sequence
<220> FEATURE:
<223> OTHER INFORMATION: Synthetic polypeptide

<400> SEQUENCE: 203

Glu Ser Gln Val Arg Gln Gln Phe Ser Lys Asp Ile Glu Lys Leu Leu
1               5                   10                  15

Asn Glu Gln Val Asn Lys Glu Met Gln Ser Ser Asn Leu Tyr Met Ser
                20                  25                  30

Met Ser Ser Trp Ser Tyr Thr His Ser Leu Asp Gly Ala Gly Leu Phe
            35                  40                  45

Leu Phe Asp His Ala Ala Glu Glu Tyr Glu His Ala Lys Lys Leu Ile
50                  55                  60

Ile Phe Leu Asn Glu Asn Asn Val Pro Val Gln Leu Thr Ser Ile Ser
65                  70                  75                  80

Cys Pro Glu His Lys Phe Glu Gly Leu Thr Gln Ile Phe Gln Lys Ala
                85                  90                  95

Tyr Glu His Glu Gln His Ile Ser Glu Ser Ile Asn Asn Ile Val Asp
            100                 105                 110

His Ala Ile Lys Ser Lys Asp His Ala Thr Phe Asn Phe Leu Gln Trp
        115                 120                 125

Tyr Val Ala Glu Gln His Glu Glu Val Leu Phe Lys Asp Ile Leu
    130                 135                 140

Asp Lys Ile Glu Leu Ile Gly Asn Glu Asn His Gly Leu Tyr Leu Ala
145                 150                 155                 160

Asp Gln Tyr Val Lys Gly Ile Ala Lys Ser Arg Lys Ser
            165                 170

<210> SEQ ID NO 204
<211> LENGTH: 173
<212> TYPE: PRT
<213> ORGANISM: Artificial Sequence
<220> FEATURE:
<223> OTHER INFORMATION: Synthetic polypeptide

<400> SEQUENCE: 204

Glu Ser Gln Val Arg Gln Gln Phe Ser Lys Asp Ile Glu Lys Leu Leu
1               5                   10                  15

Asn Glu Gln Val Asn Lys Glu Met Gln Ser Ser Asn Leu Tyr Met Ser
            20                  25                  30

Met Ser Ser Trp Ser Tyr Thr His Ser Leu Asp Gly Ala Gly Leu Phe
        35                  40                  45

Leu Phe Asp His Ala Ala Glu Glu Tyr Glu His Ala Lys Lys Leu Ile
    50                  55                  60

Ile Phe Leu Asn Glu Asn Asn Val Pro Val Gln Leu Thr Ser Ile Ser
65                  70                  75                  80

Ala Pro Glu His Cys Phe Glu Gly Leu Thr Gln Ile Phe Gln Lys Ala
                85                  90                  95

Tyr Glu His Glu Gln His Ile Ser Glu Ser Ile Asn Asn Ile Val Asp
            100                 105                 110

His Ala Ile Lys Ser Lys Asp His Ala Thr Phe Asn Phe Leu Gln Trp
        115                 120                 125

Tyr Val Ala Glu Gln His Glu Glu Val Leu Phe Lys Asp Ile Leu
    130                 135                 140

Asp Lys Ile Glu Leu Ile Gly Asn Glu Asn His Gly Leu Tyr Leu Ala
145                 150                 155                 160

Asp Gln Tyr Val Lys Gly Ile Ala Lys Ser Arg Lys Ser
            165                 170

<210> SEQ ID NO 205
<211> LENGTH: 173
<212> TYPE: PRT
<213> ORGANISM: Artificial Sequence
<220> FEATURE:
<223> OTHER INFORMATION: Synthetic polypeptide

<400> SEQUENCE: 205

Glu Ser Gln Val Arg Gln Gln Phe Ser Lys Asp Ile Glu Lys Leu Leu
1               5                   10                  15

Asn Glu Gln Val Asn Lys Glu Met Gln Ser Ser Asn Leu Tyr Met Ser
            20                  25                  30

Met Ser Ser Trp Ser Tyr Thr His Ser Leu Asp Gly Ala Gly Leu Phe

```
                    35                  40                  45

Leu Phe Asp His Ala Ala Glu Glu Tyr Glu His Ala Lys Lys Leu Ile
         50                  55                  60

Ile Phe Leu Asn Glu Asn Asn Val Pro Val Gln Leu Thr Ser Ile Ser
 65                  70                  75                  80

Ala Pro Glu His Lys Phe Glu Gly Leu Thr Gln Ile Phe Gln Lys Ala
                 85                  90                  95

Tyr Glu His Glu Gln His Ile Ser Glu Cys Ile Asn Asn Ile Val Asp
                100                 105                 110

His Ala Ile Lys Ser Lys Asp His Ala Thr Phe Asn Phe Leu Gln Trp
            115                 120                 125

Tyr Val Ala Glu Gln His Glu Glu Val Leu Phe Lys Asp Ile Leu
        130                 135                 140

Asp Lys Ile Glu Leu Ile Gly Asn Glu Asn His Gly Leu Tyr Leu Ala
145                 150                 155                 160

Asp Gln Tyr Val Lys Gly Ile Ala Lys Ser Arg Lys Ser
                165                 170
```

<210> SEQ ID NO 206
<211> LENGTH: 173
<212> TYPE: PRT
<213> ORGANISM: Artificial Sequence
<220> FEATURE:
<223> OTHER INFORMATION: Synthetic polypeptide

<400> SEQUENCE: 206

```
Glu Ser Gln Val Arg Gln Gln Phe Ser Lys Asp Ile Glu Lys Leu Leu
  1               5                  10                  15

Asn Glu Gln Val Asn Lys Glu Met Gln Ser Ser Asn Leu Tyr Met Ser
                 20                  25                  30

Met Ser Ser Trp Ser Tyr Thr His Ser Leu Asp Gly Ala Gly Leu Phe
             35                  40                  45

Leu Phe Asp His Ala Ala Glu Glu Tyr Glu His Ala Lys Lys Leu Ile
         50                  55                  60

Ile Phe Leu Asn Glu Asn Asn Val Pro Val Gln Leu Thr Ser Ile Ser
 65                  70                  75                  80

Ala Pro Glu His Lys Phe Glu Gly Leu Thr Gln Ile Phe Gln Lys Ala
                 85                  90                  95

Tyr Glu His Glu Gln His Ile Ser Glu Ser Ile Asn Asn Ile Val Asp
                100                 105                 110

His Ala Ile Lys Cys Lys Asp His Ala Thr Phe Asn Phe Leu Gln Trp
            115                 120                 125

Tyr Val Ala Glu Gln His Glu Glu Val Leu Phe Lys Asp Ile Leu
        130                 135                 140

Asp Lys Ile Glu Leu Ile Gly Asn Glu Asn His Gly Leu Tyr Leu Ala
145                 150                 155                 160

Asp Gln Tyr Val Lys Gly Ile Ala Lys Ser Arg Lys Ser
                165                 170
```

<210> SEQ ID NO 207
<211> LENGTH: 173
<212> TYPE: PRT
<213> ORGANISM: Artificial Sequence
<220> FEATURE:
<223> OTHER INFORMATION: Synthetic polypeptide

<400> SEQUENCE: 207

-continued

Glu Ser Gln Val Arg Gln Gln Phe Ser Lys Asp Ile Glu Lys Leu Leu
1               5                   10                  15

Asn Cys Gln Val Asn Lys Glu Met Gln Ser Ser Asn Leu Tyr Met Ser
                20                  25                  30

Met Ser Ser Trp Ser Tyr Thr His Ser Leu Asp Gly Ala Gly Leu Phe
            35                  40                  45

Leu Phe Asp His Ala Ala Glu Glu Tyr Glu His Ala Lys Lys Leu Ile
        50                  55                  60

Ile Phe Leu Asn Glu Asn Asn Val Pro Val Gln Leu Thr Ser Ile Ser
65                  70                  75                  80

Ala Pro Glu His Lys Phe Glu Gly Leu Thr Gln Ile Phe Gln Lys Ala
                85                  90                  95

Tyr Glu His Glu Gln His Ile Ser Glu Ser Ile Asn Asn Ile Val Asp
                100                 105                 110

His Ala Ile Lys Ser Lys Asp His Ala Thr Phe Asn Phe Leu Gln Trp
                115                 120                 125

Tyr Val Ala Glu Gln His Glu Glu Val Leu Phe Lys Asp Ile Leu
        130                 135                 140

Asp Lys Ile Glu Leu Ile Gly Asn Glu Asn His Gly Leu Tyr Leu Ala
145                 150                 155                 160

Asp Gln Tyr Val Lys Gly Ile Ala Lys Ser Arg Lys Ser
                165                 170

<210> SEQ ID NO 208
<211> LENGTH: 173
<212> TYPE: PRT
<213> ORGANISM: Artificial Sequence
<220> FEATURE:
<223> OTHER INFORMATION: Synthetic polypeptide

<400> SEQUENCE: 208

Glu Ser Gln Val Arg Gln Gln Phe Ser Lys Asp Ile Glu Lys Leu Leu
1               5                   10                  15

Asn Glu Gln Val Asn Lys Glu Met Asn Ser Ser Asn Leu Tyr Met Ser
                20                  25                  30

Met Ser Ser Trp Cys Tyr Thr His Ser Leu Asp Gly Ala Gly Leu Phe
            35                  40                  45

Leu Phe Asp His Ala Ala Glu Glu Tyr Glu His Ala Lys Lys Leu Ile
        50                  55                  60

Ile Phe Leu Asn Glu Asn Asn Val Pro Val Gln Leu Thr Ser Ile Ser
65                  70                  75                  80

Ala Pro Glu His Lys Phe Glu Gly Leu Thr Gln Ile Phe Gln Lys Ala
                85                  90                  95

Tyr Glu His Glu Gln His Ile Ser Glu Ser Ile Asn Asn Ile Val Asp
                100                 105                 110

His Ala Ile Lys Ser Lys Asp His Ala Thr Phe Asn Phe Leu Gln Trp
                115                 120                 125

Tyr Val Ala Glu Gln His Glu Glu Val Leu Phe Lys Asp Ile Leu
        130                 135                 140

Asp Lys Ile Glu Leu Ile Gly Asn Glu Asn His Gly Leu Tyr Leu Ala
145                 150                 155                 160

Asp Gln Tyr Val Lys Gly Ile Ala Lys Ser Arg Lys Ser
                165                 170

<210> SEQ ID NO 209
<211> LENGTH: 166

<212> TYPE: PRT
<213> ORGANISM: Helicobacter pylori

<400> SEQUENCE: 209

```
Leu Ser Lys Asp Ile Ile Lys Leu Leu Asn Glu Gln Val Asn Lys Glu
1               5                   10                  15

Met Asn Ser Ser Asn Leu Tyr Met Ser Met Ser Ser Trp Cys Tyr Thr
            20                  25                  30

His Ser Leu Asp Gly Ala Gly Leu Phe Leu Phe Asp His Ala Ala Glu
        35                  40                  45

Glu Tyr Glu His Ala Lys Lys Leu Ile Ile Phe Leu Asn Glu Asn Asn
    50                  55                  60

Val Pro Val Gln Leu Thr Ser Ile Ser Ala Pro Glu His Lys Phe Glu
65                  70                  75                  80

Gly Leu Thr Gln Ile Phe Gln Lys Ala Tyr Glu His Glu Gln His Ile
                85                  90                  95

Ser Glu Ser Ile Asn Asn Ile Val Asp His Ala Ile Lys Ser Lys Asp
            100                 105                 110

His Ala Thr Phe Asn Phe Leu Gln Trp Tyr Val Ala Glu Gln His Glu
        115                 120                 125

Glu Val Leu Phe Lys Asp Ile Leu Asp Lys Ile Glu Leu Ile Gly
    130                 135                 140

Asn Glu Asn His Gly Leu Tyr Leu Ala Asp Gln Tyr Val Lys Gly Ile
145                 150                 155                 160

Ala Lys Ser Arg Lys Ser
                165
```

<210> SEQ ID NO 210
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 210
tgactgtgaa cgttcgagat ga                                             22

<210> SEQ ID NO 211
<211> LENGTH: 191
<212> TYPE: PRT
<213> ORGANISM: Trichoplusia ni

<400> SEQUENCE: 211

```
Thr Gln Cys Asn Val Asn Pro Val Gln Ile Pro Lys Asp Trp Ile Thr
1               5                   10                  15

Met His Arg Ser Cys Arg Asn Ser Met Arg Gln Gln Ile Gln Met Glu
            20                  25                  30

Val Gly Ala Ser Leu Gln Tyr Leu Ala Met Gly Ala His Phe Ser Lys
        35                  40                  45

Asp Val Val Asn Arg Pro Gly Phe Ala Gln Leu Phe Phe Asp Ala Ala
    50                  55                  60

Ser Glu Glu Arg Glu His Ala Met Lys Leu Ile Glu Tyr Leu Leu Met
65                  70                  75                  80

Arg Gly Glu Leu Thr Asn Asp Val Ser Leu Leu Gln Val Arg Pro
                85                  90                  95

Pro Thr Arg Ser Ser Trp Lys Gly Gly Val Glu Ala Leu Glu His Ala
            100                 105                 110
```

```
Leu Ser Met Glu Ser Asp Val Thr Lys Ser Ile Arg Asn Val Ile Lys
            115                 120                 125

Ala Cys Glu Asp Asp Ser Glu Phe Asn Asp Tyr His Leu Val Asp Tyr
        130                 135                 140

Leu Thr Gly Asp Phe Leu Glu Glu Gln Tyr Lys Gly Gln Arg Asp Leu
145                 150                 155                 160

Ala Gly Lys Ala Ser Thr Leu Lys Lys Leu Met Asp Arg His Glu Ala
                165                 170                 175

Leu Gly Glu Phe Ile Phe Asp Lys Leu Leu Gly Ile Asp Val
            180                 185                 190

<210> SEQ ID NO 212
<211> LENGTH: 212
<212> TYPE: PRT
<213> ORGANISM: Trichoplusia ni

<400> SEQUENCE: 212

Ala Asp Thr Cys Tyr Asn Asp Val Ala Leu Asp Cys Gly Ile Thr Ser
1               5                   10                  15

Asn Ser Leu Ala Leu Pro Arg Cys Asn Ala Val Tyr Gly Glu Tyr Gly
            20                  25                  30

Ser His Gly Asn Val Ala Thr Glu Leu Gln Ala Tyr Ala Lys Leu His
        35                  40                  45

Leu Glu Arg Ser Tyr Asp Tyr Leu Leu Ser Ala Tyr Phe Asn Asn
50                  55                  60

Tyr Gln Thr Asn Arg Ala Gly Phe Ser Lys Leu Phe Lys Lys Leu Ser
65                  70                  75                  80

Asp Glu Ala Trp Ser Lys Thr Ile Asp Ile Ile Lys His Val Thr Lys
                85                  90                  95

Arg Gly Asp Lys Met Asn Phe Asp Gln His Ser Thr Met Lys Thr Glu
            100                 105                 110

Arg Lys Asn Tyr Thr Ala Glu Asn His Glu Leu Glu Ala Leu Ala Lys
        115                 120                 125

Ala Leu Asp Thr Gln Lys Glu Leu Ala Glu Arg Ala Phe Tyr Ile His
    130                 135                 140

Arg Glu Ala Thr Arg Asn Ser Gln His Leu His Asp Pro Glu Ile Ala
145                 150                 155                 160

Gln Tyr Leu Glu Glu Phe Ile Glu Asp His Ala Glu Lys Ile Arg
                165                 170                 175

Thr Leu Ala Gly His Thr Ser Asp Leu Lys Lys Phe Ile Thr Ala Asn
            180                 185                 190

Asn Gly His Asp Leu Ser Leu Ala Leu Tyr Val Phe Asp Glu Tyr Leu
        195                 200                 205

Gln Lys Thr Val
    210

<210> SEQ ID NO 213
<211> LENGTH: 174
<212> TYPE: PRT
<213> ORGANISM: Pyrococcus furiosus

<400> SEQUENCE: 213

Met Leu Ser Glu Arg Met Leu Lys Ala Leu Asn Asp Gln Leu Asn Arg
1               5                   10                  15

Glu Leu Tyr Ser Ala Tyr Leu Tyr Phe Ala Met Ala Ala Tyr Phe Glu
            20                  25                  30
```

Asp Leu Gly Leu Glu Gly Phe Ala Asn Trp Met Lys Ala Gln Ala Glu
            35                  40                  45

Glu Glu Ile Gly His Ala Leu Arg Phe Tyr Asn Tyr Ile Tyr Asp Arg
 50                  55                  60

Asn Gly Arg Val Glu Leu Asp Glu Ile Pro Lys Pro Lys Glu Trp
 65                  70                  75                  80

Glu Ser Pro Leu Lys Ala Phe Glu Ala Ala Tyr His Glu Lys Phe
                85                  90                  95

Ile Ser Lys Ser Ile Tyr Glu Leu Ala Leu Ala Glu Glu Lys
                100                 105                 110

Asp Tyr Ser Thr Arg Ala Phe Leu Glu Trp Phe Ile Asn Gln Val
                115                 120                 125

Glu Glu Glu Ala Ser Val Lys Lys Ile Leu Asp Lys Leu Lys Phe Ala
130                 135                 140

Lys Asp Ser Pro Gln Ile Leu Phe Met Leu Asp Lys Glu Leu Ser Ala
145                 150                 155                 160

Arg Ala Pro Lys Leu Pro Gly Leu Leu Met Gln Gly Gly Glu
                165                 170

<210> SEQ ID NO 214
<211> LENGTH: 183
<212> TYPE: PRT
<213> ORGANISM: Homo sapiens

<400> SEQUENCE: 214

Met Thr Thr Ala Ser Thr Ser Gln Val Arg Gln Asn Tyr His Gln Asp
 1               5                  10                  15

Ser Glu Ala Ala Ile Asn Arg Gln Ile Asn Leu Glu Leu Tyr Ala Ser
                20                  25                  30

Tyr Val Tyr Leu Ser Met Ser Tyr Tyr Phe Asp Arg Asp Asp Val Ala
                35                  40                  45

Leu Lys Asn Phe Ala Lys Tyr Phe Leu His Gln Ser His Glu Glu Arg
                50                  55                  60

Glu His Ala Glu Lys Leu Met Lys Leu Gln Asn Gln Arg Gly Gly Arg
 65                  70                  75                  80

Ile Phe Leu Gln Asp Ile Lys Lys Pro Asp Cys Asp Asp Trp Glu Ser
                85                  90                  95

Gly Leu Asn Ala Met Glu Cys Ala Leu His Leu Glu Lys Asn Val Gln
                100                 105                 110

Gln Ser Leu Leu Glu Leu His Lys Leu Ala Thr Asp Lys Asn Asp Pro
                115                 120                 125

His Leu Cys Asp Phe Ile Glu Thr His Tyr Leu Asn Glu Gln Val Lys
130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
                165                 170                 175

Gly Asp Ser Asp Gln Glu Ser
            180

<210> SEQ ID NO 215
<211> LENGTH: 204
<212> TYPE: PRT
<213> ORGANISM: Homo sapiens

<400> SEQUENCE: 215

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Ser Ser
            20                  25                  30

Gln Ile Arg Gln Asn Tyr Ser Thr Asp Val Glu Ala Ala Val Asn Ser
        35                  40                  45

Leu Val Asn Leu Tyr Leu Gln Ala Ser Tyr Thr Tyr Leu Ser Leu Gly
    50                  55                  60

Phe Tyr Phe Asp Arg Asp Asp Val Ala Leu Glu Gly Val Ser His Phe
65                  70                  75                  80

Phe Arg Glu Leu Ala Glu Glu Lys Arg Glu Gly Tyr Glu Arg Leu Leu
                85                  90                  95

Lys Met Gln Asn Gln Arg Gly Gly Arg Ala Leu Phe Gln Asp Ile Lys
            100                 105                 110

Lys Pro Ala Glu Asp Glu Trp Gly Lys Thr Pro Asp Ala Met Lys Ala
        115                 120                 125

Ala Met Ala Leu Glu Lys Lys Leu Asn Gln Ala Leu Leu Asp Leu His
    130                 135                 140

Ala Leu Gly Ser Ala Arg Thr Asp Pro His Leu Cys Asp Phe Leu Glu
145                 150                 155                 160

Thr His Phe Leu Asp Glu Val Lys Leu Ile Lys Lys Met Gly Asp
                165                 170                 175

His Leu Thr Asn Leu His Arg Leu Gly Gly Pro Glu Ala Gly Leu Gly
            180                 185                 190

Glu Tyr Leu Phe Glu Arg Leu Thr Leu Lys His Asp
        195                 200

<210> SEQ ID NO 216
<211> LENGTH: 154
<212> TYPE: PRT
<213> ORGANISM: Aquifex aeolicus

<400> SEQUENCE: 216

Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Cys Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Ile Arg Gly Ala Thr Pro His Phe Asp Tyr Ile Ala Ser Glu Val
                85                  90                  95

Ser Lys Gly Leu Ala Asn Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Lys His Gly Asn Lys Gly Trp Glu Ala Ala Leu Ser Ala Ile
    130                 135                 140

Glu Met Ala Asn Leu Phe Lys Ser Leu Arg
145                 150

<210> SEQ ID NO 217

```
<211> LENGTH: 8
<212> TYPE: PRT
<213> ORGANISM: Unknown
<220> FEATURE:
<223> OTHER INFORMATION: Bullfrog linker sequence

<400> SEQUENCE: 217

Glu Ser Gln Val Arg Gln Gln Phe
1               5

<210> SEQ ID NO 218
<211> LENGTH: 15
<212> TYPE: PRT
<213> ORGANISM: Artificial Sequence
<220> FEATURE:
<223> OTHER INFORMATION: Synthetic peptide

<400> SEQUENCE: 218

Cys Leu Val Pro Arg Gly Ser Leu Glu His His His His His
1               5                   10                  15

<210> SEQ ID NO 219
<211> LENGTH: 156
<212> TYPE: PRT
<213> ORGANISM: Escherichia coli

<400> SEQUENCE: 219

Met Asn Ile Ile Glu Ala Asn Val Ala Thr Pro Asp Ala Arg Val Ala
1               5                   10                  15

Ile Thr Ile Ala Arg Phe Asn Asn Phe Ile Asn Asp Ser Leu Leu Glu
            20                  25                  30

Gly Ala Ile Asp Ala Leu Lys Arg Ile Gly Gln Val Lys Asp Glu Asn
        35                  40                  45

Ile Thr Val Val Trp Val Pro Gly Ala Tyr Glu Leu Pro Leu Ala Ala
    50                  55                  60

Gly Ala Leu Ala Lys Thr Gly Lys Tyr Asp Ala Val Ile Ala Leu Gly
65                  70                  75                  80

Thr Val Ile Arg Gly Gly Thr Ala His Phe Glu Tyr Val Ala Gly Gly
                85                  90                  95

Ala Ser Asn Gly Leu Ala His Val Ala Gln Asp Ser Glu Ile Pro Val
            100                 105                 110

Ala Phe Gly Val Leu Thr Thr Glu Ser Ile Glu Gln Ala Ile Glu Arg
        115                 120                 125

Ala Gly Thr Lys Ala Gly Asn Lys Gly Ala Glu Ala Ala Leu Thr Ala
    130                 135                 140

Leu Glu Met Ile Asn Val Leu Lys Ala Ile Lys Ala
145                 150                 155

<210> SEQ ID NO 220
<211> LENGTH: 16
<212> TYPE: PRT
<213> ORGANISM: Artificial Sequence
<220> FEATURE:
<223> OTHER INFORMATION: Synthetic peptide

<400> SEQUENCE: 220

Gly Gly Gly Gly Ser Gly Gly Gly Ser Gly Gly Gly Gly Ser Gly
1               5                   10                  15

<210> SEQ ID NO 221
<211> LENGTH: 28
<212> TYPE: PRT
```

<213> ORGANISM: Artificial Sequence
<220> FEATURE:
<223> OTHER INFORMATION: Synthetic peptide

<400> SEQUENCE: 221

Gly Gly Ser Gly Ser Gly Ser Asn Ser Ser Ala Ser Ser Gly Ala Ser
1               5                   10                  15

Ser Gly Gly Ala Ser Gly Gly Ser Gly Gly Ser Gly
            20                  25

<210> SEQ ID NO 222
<211> LENGTH: 46
<212> TYPE: PRT
<213> ORGANISM: Artificial Sequence
<220> FEATURE:
<223> OTHER INFORMATION: Synthetic polypeptide

<400> SEQUENCE: 222

Gly Gly Ser Gly Ser Ala Ser Ser Gly Ala Ser Ala Ser Gly Ser Ser
1               5                   10                  15

Asn Gly Ser Gly Ser Gly Ser Gly Ser Asn Ser Ser Ala Ser Ser Gly
            20                  25                  30

Ala Ser Ser Gly Gly Ala Ser Gly Gly Ser Gly Gly Ser Gly
        35                  40                  45

<210> SEQ ID NO 223
<211> LENGTH: 26
<212> TYPE: PRT
<213> ORGANISM: Artificial Sequence
<220> FEATURE:
<223> OTHER INFORMATION: Synthetic peptide

<400> SEQUENCE: 223

Gly Gly Ser Gly Ser Ala Ser Ala Glu Ala Ala Ala Lys Glu Ala Ala
1               5                   10                  15

Ala Lys Ala Gly Gly Ser Gly Gly Ser Gly
            20                  25

<210> SEQ ID NO 224
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 224

Gly Gly Ser Gly Ser Ala Ser Ala Glu Ala Ala Ala Lys Glu Ala Ala
1               5                   10                  15

Ala Lys Glu Ala Ala Ala Lys Ala Ser Gly Gly Ser Gly Gly Ser Gly
            20                  25                  30

<210> SEQ ID NO 225
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 225

Ser Gly Gly Gly Ser Gly Ser Ala Ser Ser Gly Ala Ser Ala Ser Gly
1               5                   10                  15

Ser Ser Cys Ser Gly Ser Gly Ser Gly Ser Ser Ala Ser Ser Gly
            20                  25                  30

```
<210> SEQ ID NO 226
<211> LENGTH: 4
<212> TYPE: PRT
<213> ORGANISM: Artificial Sequence
<220> FEATURE:
<223> OTHER INFORMATION: Synthetic peptide

<400> SEQUENCE: 226

Gly Gly Gly Ser
1

<210> SEQ ID NO 227
<211> LENGTH: 8
<212> TYPE: PRT
<213> ORGANISM: Artificial Sequence
<220> FEATURE:
<223> OTHER INFORMATION: Synthetic peptide

<400> SEQUENCE: 227

Gly Gly Gly Ser Gly Gly Gly Ser
1               5

<210> SEQ ID NO 228
<211> LENGTH: 20
<212> TYPE: PRT
<213> ORGANISM: Artificial Sequence
<220> FEATURE:
<223> OTHER INFORMATION: Synthetic peptide

<400> SEQUENCE: 228

Gly Gly Gly Ser Gly Gly Gly Ser Gly Gly Gly Ser Gly Gly Gly Ser
1               5                   10                  15

Gly Gly Gly Ser
            20

<210> SEQ ID NO 229
<211> LENGTH: 5
<212> TYPE: PRT
<213> ORGANISM: Artificial Sequence
<220> FEATURE:
<223> OTHER INFORMATION: Synthetic peptide

<400> SEQUENCE: 229

Ser Gly Ser Gly Ser
1               5

<210> SEQ ID NO 230
<211> LENGTH: 6
<212> TYPE: PRT
<213> ORGANISM: Artificial Sequence
<220> FEATURE:
<223> OTHER INFORMATION: 6xHis tag

<400> SEQUENCE: 230

His His His His His His
1               5
```

ANTIGENIC RESPIRATORY SYNCYTIAL VIRUS POLYPEPTIDES

This application is a continuation of International Application No. PCT/US2019/025387, filed Apr. 2, 2019, which claims the benefit of priority of U.S. Provisional Patent Application No. 62/652,199, filed Apr. 3, 2018, the entire contents of which are incorporated herein by reference.

The instant application contains a Sequence Listing which has been submitted electronically in ASCII format and is hereby incorporated by reference in its entirety. Said ASCII copy, created on Sep. 30, 2020, is named 2020-09-30_01121-0031-00US_SL_ST25.txt and is 187,403 bytes in size.

Even with many successes in the field of vaccinology, new breakthroughs are needed to protect humans against many life-threatening infectious diseases. Many currently licensed vaccines rely on decade-old technologies to produce live-attenuated or inactivated killed pathogens, which carry inherent safety concerns and in many cases, stimulate only short-lived, weak immune responses that require the administration of multiple doses. While advances in genetic and biochemical engineering have made it possible to develop therapeutic agents to challenging disease targets, these applications to the field of vaccinology have not been fully realized. Recombinant protein technologies now allow the design of optimal antigens. Additionally, nanoparticles have increasingly demonstrated the potential for optimal antigen presentation and targeted drug delivery. Nanoparticles with multiple attached antigens have been shown to have increased binding avidity afforded by the multivalent display of their molecular cargos, and an ability to cross biological barriers more efficiently due to their nanoscopic size. *Helicobacter pylori* (*H. pylori*) ferritin nanoparticles fused to influenza virus haemagglutinin (HA) protein has allowed improved antigen stability and increased immunogenicity in mouse influenza models (see Kanekiyo et al., Nature 499:102-106 (2013)). This fusion protein self-assembled into an octahedrally-symmetric nanoparticle and presented 8 trimeric HA spikes to give a robust immune response in various pre-clinical models when used with an adjuvant.

Respiratory syncytial virus (RSV) is a leading cause of severe respiratory disease in infants and a major cause of respiratory illness in the elderly. It remains an unmet vaccine need despite decades of research. While the need for a vaccine is clear, development of an RSV vaccine was stymied in the 1960s when a clinical trial using a formalin inactivated RSV virus made disease, following RSV infection, more severe in infants. See, Hurwitz (2011) Expert Rev Vaccines 10(10): 1415-1433. More recently, clinical programs using an RSV F antigen in its post-fusion conformation failed to elicit sufficient efficacy in adults. See, Faloon et al. (2017) JID 216:1362-1370. However, RSV F antigens stabilized in the pre-fusion conformation may elicit a neutralizing response superior to that of the post-fusion antigens that have failed in the clinic.

Here, a set of new polypeptides, nanoparticles, compositions, methods, and uses involving RSV polypeptides is presented. Novel RSV F polypeptides were generated, including polypeptides in which an epitope of the RSV polypeptide that is shared between pre-fusion RSV F and post-fusion RSV F is blocked, e.g., by an N-glycan at a glycosylation site added by a mutation. Also generated were antigenic polypeptides and nanoparticles comprising these novel RSV polypeptides and ferritin. Antigenic ferritin polypeptides comprising RSV G polypeptides were also generated. Furthermore, self-adjuvanting antigenic polypeptides comprising RSV polypeptides and ferritin were developed wherein immune-stimulatory moieties, such as adjuvants, were directly, chemically attached to the antigenic polypeptide. The direct conjugation of an immune-stimulatory moiety to the antigenic polypeptide allows for targeted co-delivery of the immune-stimulatory moiety and RSV polypeptide in a single macromolecular entity, which can greatly decrease the potential for systemic toxicity that is feared with traditional vaccines that comprise antigens and immune-stimulatory molecules such as adjuvants as separate molecules. The co-delivery of immune-stimulatory moieties together with RSV polypeptides in a macromolecular entity and their multivalent presentation may also reduce the overall dose needed to elicit protection, reducing manufacturing burdens and costs.

SUMMARY

It is an object of this disclosure to provide compositions, kits, methods, and uses that can provide one or more of the advantages discussed above, or at least provide the public with a useful choice. Accordingly, the following embodiments are disclosed herein.

Embodiment 1 is an antigenic RSV polypeptide comprising an RSV F polypeptide, wherein an epitope of the RSV polypeptide that is shared between pre-fusion RSV F and post-fusion RSV F is blocked.

Embodiment 2 is an antigenic RSV polypeptide comprising an RSV F polypeptide, wherein the RSV F polypeptide comprises amino acid residues 62-69 and 196-209 of SEQ ID NO: 26 and an asparagine corresponding to position 328, 348, or 507 of SEQ ID NO: 26.

Embodiment 3 is the antigenic RSV polypeptide of embodiment 2, wherein an epitope of the RSV polypeptide that is shared between pre-fusion RSV F and post-fusion RSV F is blocked.

Embodiment 3b is the antigenic RSV polypeptide of embodiment 1 or 3, wherein the blocked epitope is an epitope of antigenic site 1 of RSV F.

Embodiment 3c is the antigenic RSV polypeptide of embodiment 1 or 3-3b, wherein two or more epitopes shared between pre-fusion RSV F and post-fusion RSV F are blocked.

Embodiment 3d is the antigenic RSV polypeptide of embodiment 1 or 3-3c, wherein two or more epitopes of antigenic site 1 of RSV F are blocked.

Embodiment 3e is the antigenic RSV polypeptide of embodiment 1 or 3-3d, wherein one or more, or all, epitopes that topologically overlap with the blocked epitope are also blocked.

Embodiment 3f is the antigenic RSV polypeptide of embodiment 3e, wherein the blocked epitope is an epitope of antigenic site 1 of RSV F.

Embodiment 4 is the antigenic RSV polypeptide of any one of the preceding embodiments, comprising a pre-fusion RSV F.

Embodiment 5 is the antigenic RSV polypeptide of any one of the preceding embodiments, which is recognized by a pre-fusion RSV F-specific antibody selected from D25 or AM14.

Embodiment 6 is the antigenic RSV polypeptide of embodiment 4 or 5, wherein the pre-fusion RSV F comprises an epitope not found on post-fusion RSV F.

Embodiment 7 is the antigenic RSV polypeptide of any one of embodiments 1-3, comprising a post-fusion RSV F.

Embodiment 8 is the antigenic RSV polypeptide of any one of embodiments 1 or 3-6, wherein the epitope is blocked with an N-glycan attached to asparagine.

Embodiment 9 is the antigenic RSV polypeptide of embodiment 7, wherein the asparagine corresponds to a non-asparagine residue in a wild-type RSV F sequence (SEQ ID NO: 26), optionally wherein the non-asparagine residue corresponds to position 328, 348, or 507 of SEQ ID NO: 26.

Embodiment 10 is the antigenic RSV polypeptide of any one of the preceding embodiments, further comprising a ferritin protein.

Embodiment 11 is the antigenic RSV polypeptide of embodiment 11, wherein the ferritin comprises a mutation replacing a surface-exposed amino acid with a cysteine.

Embodiment 12 is an antigenic RSV polypeptide comprising an RSV F polypeptide and a ferritin protein, wherein the ferritin protein comprises a mutation replacing a surface exposed amino acid with a cysteine.

Embodiment 13 is the antigenic RSV polypeptide of any one of embodiments 11-12, wherein the ferritin comprises one or more of E12C, S26C, S72C, A75C, K79C, S100C, and S111C mutations of *H. pylori* ferritin or one or more corresponding mutations in a non-*H. pylori* ferritin as determined by pairwise or structural alignment.

Embodiment 14 is the antigenic RSV polypeptide of any one of embodiments 10-13, comprising one or more immune-stimulatory moieties linked to the ferritin via a surface-exposed amino acid, optionally wherein the surface-exposed amino acid is a cysteine resulting from a mutation.

Embodiment 15 is the antigenic RSV polypeptide of any one of embodiments 10-14, wherein the ferritin comprises a mutation replacing a surface-exposed asparagine with a non-asparagine amino acid, optionally wherein the asparagine is at position 19 of *H. pylori* ferritin, or an analogous position in a non-*H. pylori* ferritin as determined by pairwise or structural alignment.

Embodiment 16 is the antigenic RSV polypeptide of any one of embodiments 10-15, wherein the ferritin comprises a mutation replacing an internal cysteine with a non-cysteine amino acid, optionally wherein the internal cysteine is at position 31 of *H. pylori* ferritin, or a position that corresponds to position 31 of *H. pylori* ferritin as determined by pair-wise or structural alignment.

Embodiment 17 is the antigenic RSV polypeptide of any one of embodiments 12-16, wherein the RSV F polypeptide comprises an epitope not found on post-fusion RSV F which is a site 0 epitope, optionally wherein the site 0 epitope comprises amino acid residues 62-69 and 196-209 of SEQ ID NO: 26.

Embodiment 18 is the antigenic RSV polypeptide of any one of the preceding embodiments, wherein the RSV F polypeptide comprises an asparagine at a position corresponding to position 328 of SEQ ID NO: 26.

Embodiment 19 is the antigenic RSV polypeptide of any one of the preceding embodiments, wherein the RSV F polypeptide comprises an asparagine at a position corresponding to position 348 of SEQ ID NO: 26.

Embodiment 20 is the antigenic RSV polypeptide of any one of the preceding embodiments, wherein the RSV F polypeptide comprises an asparagine at a position corresponding to position 507 of SEQ ID NO: 26.

Embodiment 21 is the antigenic RSV polypeptide of any one of the preceding embodiments, wherein RSV F polypeptide comprises a leucine at a position corresponding to position lysine 498 of SEQ ID NO: 26.

Embodiment 22 is the antigenic RSV polypeptide of any one of the preceding embodiments, wherein the RSV F polypeptide comprises a proline at a position corresponding to position isoleucine 217 of SEQ ID NO: 26.

Embodiment 23 is the antigenic RSV polypeptide of any one of the preceding embodiments, wherein the RSV F polypeptide comprises an amino acid other than cysteine at a position corresponding to position 155 of SEQ ID NO: 26 and/or an amino acid other than cysteine at position corresponding to position 290 of SEQ ID NO: 26.

Embodiment 24 is the antigenic RSV polypeptide of any one of the preceding embodiments, comprising a serine at a position corresponding to position 155 of SEQ ID NO: 26 and/or a serine at a position corresponding to position 290 of SEQ ID NO: 26.

Embodiment 25 is the antigenic RSV polypeptide of any one of the preceding embodiments, wherein the RSV F polypeptide lacks a furin cleavage site, optionally wherein a linker is present in place of the furin cleavage site.

Embodiment 26 is the antigenic RSV polypeptide of any one of the preceding embodiments, wherein the RSV F polypeptide comprises a sequence having at least 85%, 90%, 95%, 97%, 98%, 99%, or 99.5% identity to amino acids 1-478 of SEQ ID NO: 17.

Embodiment 27 is the antigenic RSV polypeptide of any one of the preceding embodiments, wherein the RSV F polypeptide comprises a sequence having at least 85%, 90%, 95%, 97%, 98%, 99%, or 99.5% identity to the sequence of SEQ ID NO: 17.

Embodiment 28 is the antigenic RSV polypeptide of embodiment 20 or 21, comprising amino acids 1-478 of SEQ ID NO: 17.

Embodiment 29 is the antigenic RSV polypeptide of any one of embodiments 1-19, wherein the RSV F polypeptide comprises a sequence having at least 85%, 90%, 95%, 97%, 98%, 99%, or 99.5% identity to amino acids 1-478 of SEQ ID NO: 23.

Embodiment 30 is the antigenic RSV polypeptide of any one of embodiments 1-19 or 23, wherein the RSV F polypeptide comprises a sequence having at least 85%, 90%, 95%, 97%, 98%, 99%, or 99.5% identity to the sequence of SEQ ID NO: 23.

Embodiment 31 is the antigenic RSV polypeptide of embodiment 23 or 24, comprising amino acids 1-478 of SEQ ID NO: 23.

Embodiment 32 is the antigenic RSV polypeptide of any one of the preceding embodiments, comprising the sequence of any one of SEQ ID NOs: 3-23.

Embodiment 32a is the antigenic RSV polypeptide of claim 32, comprising the sequence of SEQ ID NO: 17.

Embodiment 32b is the antigenic RSV polypeptide of claim 32, comprising the sequence of SEQ ID NO: 23.

Embodiment 33 is a ferritin particle comprising the antigenic RSV polypeptide of any one of embodiments 10-32b.

Embodiment 34 is a composition comprising the antigenic RSV polypeptide or ferritin particle of any one of the preceding embodiments and an RSV G polypeptide.

Embodiment 34b is the composition of embodiment 34, wherein the composition comprises the ferritin particle, and the ferritin particle comprises the RSV G polypeptide, optionally wherein the RSV G polypeptide is chemically conjugated to the ferritin particle.

Embodiment 34c is the composition of embodiment 34 or 34b, wherein the RSV G polypeptide is not glycosylated.

Embodiment 35 is a composition comprising the antigenic RSV polypeptide or ferritin particle of any one of embodiments 1-33, or the composition of any one of embodiments 34-34c, further comprising a pharmaceutically acceptable carrier.

Embodiment 36 is the antigenic RSV polypeptide, ferritin particle, or composition of any one of embodiments 1-35 for use in a method of eliciting an immune response to RSV or in protecting a subject against RSV infection.

Embodiment 37 is a method of eliciting an immune response to RSV or protecting a subject against RSV infection comprising administering any one or more of the antigenic RSV polypeptide, ferritin particle, or composition of any one of embodiments 1-36 to a subject.

Embodiment 38 is the antigenic RSV polypeptide, ferritin particle, composition, or method of any one of embodiments 36-37, wherein the subject is human.

Embodiment 39 is a nucleic acid encoding the antigenic RSV polypeptide of any one of embodiments 1-32b, optionally wherein the nucleic acid is an mRNA.

Embodiment 39b is a composition or kit comprising the nucleic acid of embodiment 39 and a nucleic acid encoding an RSV G polypeptide, optionally wherein one or both nucleic acids are mRNAs.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate several embodiments and together with the description, serve to explain the principles described herein.

BRIEF DESCRIPTION OF THE DRAWINGS

(FIG. 1A) Linear diagram listing residue numbers corresponding to the N terminus of each segment. Numbering is according to SEQ ID NO: 26. Domains 1-3 are indicated with DI, DII and DIII, respectively, and heptad repeat region A (HRA) and heptad repeat region B (HRB) are also labeled. The C-terminal ferritin is labeled (Ferritin Nanoparticle). The F1 and F2 fragments of the RSV F moiety are labeled below the cartoon. The region between the F1 and F2 fragment, where the peptide 27 fragment (p27) fusion peptide (FP) and furin cleavage sites (furin sites) were deleted and replaced with a flexible linker to form single chain F constructs, is depicted as a line and labeled above the cartoon. Stars above the diagram indicate approximate locations of engineered glycosylation sites E328N, S348N and R507N. (FIG. 1B) Structural model of pre-fusion RSV F moiety indicating key neutralizing (Nab) epitopes for D25, AM14, 101F, and Palivizumab antibodies. The approximate region of shared pre-fusion and post-fusion structural epitopes is indicated with a white triangle. The locations of exemplary engineered glycosylation sites E328N, S348N and R507N are labeled. The engineered glycosylation sites map to regions structurally shared between pre-fusion and post-fusion conformations and away from key neutralizing epitopes recognized by antibodies such as D25, AM14, 101F and Palivizumab. As such, constructs containing these engineered glycan sites still bind to the above neutralizing antibodies (data not shown). (FIG. 1C) Structural model of RSV pre-fusion F protein nanoparticle (Pre-F-NP) with HRA and HRB regions shaded darker. The resulting folded Pre-F-NP constructs can form 24-mers that display the key epitopes listed in FIG. 1B. (FIG. 1D) 2D class averages of electron micrographs of RSV Pre-F-NP construct RF8085 (SEQ ID NO: 1) showing symmetry of RSV F trimer moieties on the 24-mer ferritin nanoparticle.

FIG. 2 shows small-scale expression of several Pre-F-NP constructs expressed in 293 cell conditioned media as measured by D25 antibody Western blot. RF8090 is SEQ ID NO: 2, which is a cloning variant used in CHO expression having the same sequence as RF8085, i.e., SEQ ID NO:1. RF8085 and RF8090 are Pre-F-NP constructs harboring the disulfide and cavity filling mutations of DS-CAV with the deletions and single chain linker described in FIG. 1A fused N-terminally to ferritin. RF8100-RF8105 and RF8108-RF8112 have the sequences of SEQ ID NOs: 3-8 and 11-14, respectively. scF-pFerr=fusion protein of RSV F polypeptide and ferritin. Mutations that appear to improve expression of the construct relative to the RF8090 benchmark are indicated below the Western blot. Notable mutations include the addition of glycan sites via the E328N, S348N and R507N mutations and the central helix capping mutation I327P, which increased expression and secretion of the RSV F nanoparticle into the conditioned media as measured by Western blot.

(FIG. 9A) Expression of RF8117 and RF8140 from three and four pools of CHO cells, respectively, into CHO conditioned media was compared to yields of RF8090 in CHO conditioned media by D25-Western blot analysis. All three CHO pools for RF8117 and all four CHO pools for RF8140 express to higher yields than RF8090. (FIG. 9B) Expression of RF8117 into CHO conditioned media as measured by D25 pre-fusion F-specific antibody by Octet. The left panel shows response of RF8140 purified from 293 media of known concentrations plotted against response of binding to D25 on a Protein A tip providing a standard curve. Individual dots represent responses to D25 binding from RF8117 CHO conditioned media. The right panel shows calculated yield of RF8117 or RF8140 in CHO pool conditioned media based on D25 binding response. Both RF8117 and RF8140 were expressed in the media as measured by D25 and AM14 binding, demonstrating that like 293 cells, CHO cells are able to express the Pre-F-NPs in a folded manner which retains the pre-fusion F trimer structure.

(FIG. 10A) Comparison of RSV neutralizing titers elicited by High Dose (1 µg) and Low Dose (0.1 µg) immunization of DS-CAV1 (Pre-F Trimer, SEQ ID NO: 25), Post-fusion F Trimer (Post-F Trimer; SEQ ID NO: 24) or Pre-F-NP with engineered glycosylation (Pre-F-NP; RF8117, SEQ ID NO: 17) was measured by VERO cell assay. All RSV polypeptides were administered with adjuvant AF03 as described herein. Throughout, unless states otherwise, AF03 was administered with the RSV polypeptide or nanoparticle, but not conjugated to it. RSV polypeptides and doses are labeled below the x-axis. Statistical analysis of high dose responses relative to Pre-F-NP immunization is indicated. (FIG. 10B) Comparison of RSV neutralizing titers elicited by High Dose (1 µg) and Low Dose (0.1 µg) immunization with DS-CAV1 (Pre-F Trimer), Pre-F-NP without engineered glycosylation (RF8113, SEQ ID NO: 16) or Pre-F-NP with engineered glycosylation (RF8117, SEQ ID NO: 17) as measured by VERO cell assay. All RSV polypeptides were administered with adjuvant AF03 (not conjugated to any polypeptide or nanoparticle) as described herein. RSV polypeptides and doses are labeled below the x-axis.

(FIG. 11A) Pre-fusion F trimer binding antibody responses elicited in mice from immunization between post-fusion F and Pre-F-NP (RF8140, SEQ ID NO: 23) are compared. (FIG. 11B) Neutralizing antibody responses elicited in mice from immunization with post-fusion F and Pre-F-NP (RF8140, SEQ ID NO: 23) are shown. (FIG. 11C) Pre-fusion F trimer binding antibody responses elicited in non-human primates by Pre-F-NP with or without adjuvant (AF03, indicated in parentheses below) are compared. (FIG. 11D) RSV neutralizing titers elicited by immunization with Pre-F-NP (RF8140, SEQ ID NO: 23) with and without AF03 adjuvant are compared. In mice, Pre-F-NP elicits a higher pre-fusion F binding response and RSV neutralizing response compared to post-fusion trimer. In non-human primates, Pre-F-NP elicits a potent neutralizing response.

FIGS. 12A-12B show that engineered glycosylation sites block post-fusion epitopes. (FIG. 12A) Antibody response to pre-fusion F (DS-CAV1) elicited by immunization with Pre-F-NP without engineered glycosylation (RF8113) or Pre-F-NP with engineered glycosylation (Engineered Gly Particle) at high (1 µg) and low (0.1 µg) dose as measured by Octet is shown. (FIG. 12B) Antibody response to post-fusion trimer elicited by immunization with Pre-F-NP without engineered glycosylation (RF8113) or Pre-F-NP with engineered glycosylation (RF8117) at high (1 µg) and low (0.1 µg) dose as measured by Octet is shown. As above, all RSV polypeptides were mixed with AF03 during immunization. While both RF8113 and RF8117 elicit robust antibody responses to pre-fusion F, the post-fusion F antibody response elicited by RF8117 is greatly reduced. This is due to the engineered glycans mapping to the shared pre-fusion and post-fusion epitopes (FIG. 2B).

FIGS. 13A-C show blocking of non-neutralizing epitopes by engineered glycosylation sites. (FIG. 13A) Comparison of RSV neutralizing titers elicited by immunization with Pre-F NP with wild-type glycosylation sites ("Wt Glycan Particle"; RF8113, SEQ ID NO: 16) versus Pre-F NP with additional engineered glycosylation sites ("+Glycan Particle"; RF8117, SEQ ID NO: 17) at 0.1 µg dose in mouse studies as measured by VERO cell assay. (FIG. 13B) Comparison of RSV Post-fusion F trimer-binding antibody responses elicited by immunization with Wt Glycan Particle (RF8113, SEQ ID NO: 16) versus+Glycan Particle (RF8117, SEQ ID NO: 17) at 0.1 µg dose in mouse studies. (FIG. 13C) Ratio of measured neutralization titers to binding titers from panels A and B demonstrating that the engineered glycans did not reduce the functional, neutralizing antibody response but did decrease the non-neutralizing antibodies elicited to the shared pre-fusion/post-fusion epitopes (FIG. 1B), thus improving the Neutralizing/Binding antibody ratio.

FIG. 14A-D. Characterization of RSV G central domain peptide (Gcc) conjugated to ferritin nanoparticle. (FIG. 14A) Coomassie-stained SDS-PAGE gel showing the click-conjugation of RSV G central domain (SEQ ID NO. 29) to ferritin nanoparticle, forming the Gcc-NP antigen. (FIG. 14B) Structural model of Gcc-NP. (FIG. 14C) Comparison of Gcc-binding antibody responses elicited by immunization with Gcc peptide alone (Gcc peptide, SEQ ID NO. 29) versus Gcc peptide conjugated to nanoparticle (Gcc-NP) in mouse studies. A representative response from naïve sera is shown in white box, while responses from post-second immunization are shown in light grey boxes and responses from post-third immunizations are shown in dark grey boxes. (FIG. 14D) Comparison of RSV neutralizing titers elicited by immunization with Gcc peptide (SEQ ID NO. 29) versus Gcc-NP in mouse studies post-third injection as measured by HAE cell assay. Sera from naïve animals and sera from animals immunized with Gcc peptide were pooled and titers are shown as bars.

(FIG. 15A) Immunization of mice with RF8140 alone (Pre-F-NP) or RF8140 and Gcc-NP (Pre-F-NP+Gcc-NP) elicited antibodies that bind pre-fusion F trimer. (FIG. 15B) Immunization of mice with Gcc-NP alone (Gcc-NP) or RF8140 and Gcc-NP (Pre-F-NO+Gcc-NP) elicited antibodies that bind Gcc peptide. (FIG. 15C) Animals immunized with either Pre-F-NP alone, Gcc-NP alone, or the co-administration of Pre-F-NP and Gcc-NP elicit a neutralizing response post-second and post-third immunization as measured by HAE neutralizing assay. Co-administration of Pre-F-NP+Gcc-NP elicited a neutralizing response superior to that elicited by immunization with only Pre-F-NP.

(FIG. 16A) Neutralizing titers were observed in VERO cell assays for sera from RF8140 immunization and RF8140+Gcc-NP co-administration, but not naïve sera or sera from Gcc-NP immunization alone. Depletion of sera from RF8140 or RF8140+Gcc-NP groups with pre-fusion F trimer reduced the measurable neutralizing titers. (FIG. 16B) Neutralizing titers were observed in HAE cell assays for sera from animals immunized with RF8140, Gcc-NP, or RF8140 co-administered with Gcc-NP. Sera from naïve animals did not have a neutralizing response. Sera from animals immunized with RF8140 that is depleted with pre-fusion F trimer has a reduction in measurable neutralizing titer. Sera from animals immunized with Gcc-NP that is depleted with G ectodomain has a reduction in measurable neutralizing titer. Sera from animals immunized with a co-administration of RF8140 and Gcc-NP does not have a reduced measurable neutralizing titer when depleted with pre-fusion F trimer alone, but does have a reduced measurable neutralizing titer when depleted with both pre-fusion F trimer and G ectodomain. Together, these data suggest co-administration with the Pre-F-NP and Gcc-NP does not interfere with the antigens' respective abilities to elicit neutralizing antibodies to pre-fusion F or G.

(FIG. 17A) Neutralizing titers for sera from mice immunized with RF8117 either unadjuvanted (No Adj), adjuvanted with Alum, or adjuvanted with AF03 are shown as measured by VERO cell assay. (FIG. 17B) Neutralizing titers for sera from mice immunized with RF8117 either unadjuvanted (No Adj), RF8117 adjuvanted with SPA09, or RF8140 adjuvanted with AF03 are shown as measured by VERO cell assay. In all cases for either RF8117 or RF8140, in naïve mice adjuvanted groups elicited a higher neutralizing titer than non-adjuvanted groups.

(FIG. 18A) Pre-fusion F trimer responses measured in NHP sera after immunization with RF8140 either unadjuvanted (No Adj), adjuvanted with AF03 or adjuvanted with SPA09 (two doses of SPA09 were used, as indicated below) as measured by ELISA. At all timepoints, adjuvanting with AF03 or SPA09 elicits a superior neutralizing response. (FIG. 18B) Neutralizing titers for sera from NHPs immunized with RF8140 either unadjuvanted (No Adj), adjuvanted with AF03 or adjuvanted with SPA09 (two doses of SPA09 were used, as indicated below) as measured by VERO cell assay. In all cases immunization with RF8140 with adjuvant elicits a higher neutralizing titer than non-adjuvanted groups at all timepoints.

FIGS. 19A-B. Conjugation of RF8140 to TLR7/8 agonist SM7/8 or TLR9 agonist CpG elicits a superior pre-fusion F-binding titer relative to unadjuvanted RF8140 alone. (FIG. 19A) Pre-fusion F trimer-binding response measured in sera from either naïve mice, mice immunized with unadjuvanted RF8140, mice immunized with RF8140 conjugated with SM7/8 adjuvant, RF8140 adjuvanted with 130 ng of SM7/8 or RF8140 adjuvanted with 20 µg SM7/8 are shown. RF8140 conjugated to SM7/8 elicits a higher pre-fusion F trimer-binding titer than unadjuvanted or SM7/8 adjuvanted groups. (FIG. 19B) Pre-fusion F trimer-binding response measured in sera from either naïve mice, mice immunized with unadjuvanted RF8140, mice immunized with RF8140 conjugated with CpG adjuvant, RF8140 adjuvanted with 680 ng of CpG or RF8140 adjuvanted with 20 µg SM7/8 are shown. RF8140 conjugated to SM7/8 elicits a higher pre-fusion F trimer-binding titer than unadjuvanted or SM7/8 adjuvanted groups.

FIGS. 20A-G. F-subunit vaccine candidates elicit pre-F directed neutralizing antibodies and a Th1 $CD4^+$ T cell response in the MIMIC system. (FIG. 20A) Anti-pre-F titers in MIMIC system were measured by AF after priming with each Ag at molar equivalent concentration of F with 10 ng/ml of pre-F NP (n=48-49 donors per group). (FIG. 20B) Microneutralization titers were measured and are represented in International units/ml (IU/ml). (FIG. 20C) A ratio between anti-pre-F and post-F >1 represents a higher level of pre-F-binding antibody versus post-F-binding antibody while a ratio value <1 represents a greater Ab response to post-F. (FIG. 20D) The production of TNFα in activated $CD154^+/CD4^+$ T cells re-stimulated with F protein loaded target cells was measured using flow cytometry, n=48. Statistical significance was determined via Tukey-Kramer-HSD multiple comparison (FIG. 20E) Pre-existing antibody titer in humans subjects (serostatus) is strongly correlated with the magnitude of the RSV immune response in MIMIC system. Linear regression plot showing anti-pre-F IgG in sera from each donor versus total anti-pre-F IgG response was generated by software or algorithm and the p value for the common slope was analyzed by statistics method (n=50). Y-axis represents anti-pre-F IgG levels obtained following priming with RSV. (FIG. 20F) As in FIG. 20E, linear regression plot showing anti-pre-F IgG in sera from each donor versus total anti-pre-F IgG after priming with F subunit vaccine candidates (post-F in squares, pre-F-NP in circles and DC-Cav1 in diamonds). The anti-pre-F IgG pre-existing circulating titers ranged from 199,800 to 3,037,600,000. Each dot represents the IgG value of each individual donor. (FIG. 20G) Comparison of Gcc-binding antibody responses elicited by treatment with Gcc peptide alone (Gcc peptide) versus Gcc peptide conjugated to nanoparticle (Gcc-NP) in human B-cells. A no treatment group is shown for comparison as above.

(FIG. 22A) Gcc-binding antibody responses elicited to the Gcc A2 strain measured at two weeks post the second injection (light grey boxes) and two weeks post the third injection (dark grey boxes) elicited by the high dose (5 µg) of RSV Gcc-NP. Naïve mouse sera response is shown as a negative control. (FIG. 22B) Gcc-binding antibody responses elicited to the Gcc A2 strain measured at two weeks post the second injection (light grey boxes) and two weeks post the third injection (dark grey boxes) elicited by the low dose (0.5 µg) of RSV Gcc-NP.

(FIG. 23A) Gcc-binding antibody responses elicited to the Gcc B1 strain measured at two weeks post the second injection (light grey boxes) and two weeks post the third injection (dark grey boxes) elicited by a high dose (5 µg) of RSV Gcc-NP. Naïve mouse sera response is shown as a negative control. (FIG. 23B) Gcc-binding antibody responses elicited to the Gcc B1 strain measured at two weeks post the second injection (light grey boxes) and two weeks post the third injection (dark grey boxes) elicited by a low dose (0.5 µg) of RSV Gcc-NP.

DETAILED DESCRIPTION

Figure 1A:
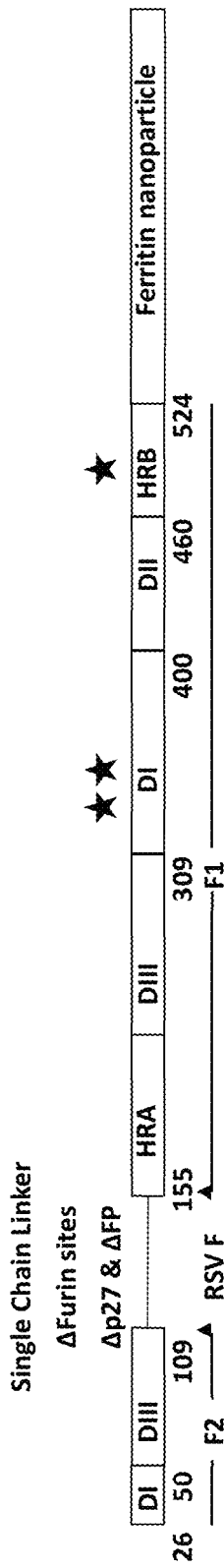
FIGS. 1A-1D show an exemplary RSV Pre-F-NP polypeptide structure.

RSV polypeptides are provided, which can be antigenic when administered alone, with adjuvant as a separate molecule, and/or as part of a nanoparticle (e.g., ferritin particle or lumazine synthase particle), which can be self-adjuvanting. In some embodiments, the antigenic RSV polypeptides comprise an RSV F polypeptide and a ferritin, and/or an RSV F polypeptide in which an epitope of the RSV polypeptide that is shared between pre-fusion RSV F and post-fusion RSV F is blocked. RSV F polypeptides that direct production of antibodies against the pre-fusion conformation of RSV F induced higher in vivo antibody response to pre-fusion RSV F in comparison to post-fusion RSV F. Also described herein are RSV G polypeptides comprising all or part of RSV G, and can further comprise a ferritin. The RSV G and RSV F proteins are essential for attachment and fusion of RSV to host cells.

RSV F exists in two conformational states, the pre-fusion and post-fusion conformations. In its native pre-fusion state, RSV F is a trimer comprised of 3 protomers. Thus, immunization with RSV F polypeptides in the pre-fusion conformation may have improved properties. In some embodiments, the RSV F polypeptide is designed to induce immunity against RSV F in the pre-fusion conformation. RSV G is an attachment protein responsible for associating RSV with human airway epithelial cells.

A. Definitions

"Antigenic site 0" or "site 0 epitope," as used herein, refer to a site located at the apex of the pre-fusion RSV F trimer, comprising amino acid residues 62-69 and 196-209 of wild-type RSV F (SEQ ID NO: 26). The site 0 epitope is a binding site for antibodies that have specificity for pre-fusion RSV F, such as D25 and AM14, and binding of antibodies to the site 0 epitope blocks cell-surface attachment of RSV (see McLellan et al., Science 340(6136):1113-1117 (2013)).

"Antigen stability," as used herein, refers to stability of the antigen over time or in solution.

"Cavity filling substitutions," as used herein, refers to engineered hydrophobic substitutions to fill cavities present in the pre-fusion RSV F trimer.

"F protein," or "RSV F protein" refers to the protein of RSV responsible for driving fusion of the viral envelope with host cell membrane during viral entry.

"RSV F polypeptide" or "F polypeptide" refers to a polypeptide comprising at least one epitope of F protein.

"Glycan addition," as used herein, refers to the addition of mutations which introduce glycosylation sites not present in wild-type RSV F, which can be engineered to increase construct expression, increase construct stability, or block epitopes shared between the pre-fusion and post-fusion confirmation. A modified protein comprising glycan additions would have more glycosylation and therefore a higher molecular weight. Glycan addition of can reduce the extent to which an RSV F polypeptide elicits antibodies to the post-fusion conformation of RSV F.

"G protein" or "RSV G protein" as used herein, refers to the attachment protein responsible for associating RSV with human airway epithelial cells. An exemplary wild-type RSV G amino acid sequence is provided as SEQ ID NO: 27. RSV G protein comprises an ectodomain (approximately amino acids 66-297 of RSV G (SEQ ID NO: 27)) that resides extracellularly. Within the ectodomain of RSV G is a central conserved region (Gcc or CCR, approximately amino acids 151-193 of SEQ ID NO: 27). The CCR of RSV G comprises a CX3C motif. The CX3C motif mediates binding of G protein to the CX3CR1 receptor.

"Helix PRO capping" or "helix proline capping," as used herein, refer to when a helix cap comprises a proline, which can stabilize helix formation.

"Intra-protomer stabilizing substitutions," as used herein, describe amino acid substitutions in RSV F that stabilize the pre-fusion conformation by stabilizing the interaction within a protomer of the RSV F trimer.

"Inter-protomer stabilizing substitutions," as used herein, describe amino acid substitutions in RSV F that stabilize the pre-fusion conformation by stabilizing the interaction of the protomers of the RSV F trimer with each other.

"Protease cleavage" as used herein, refers to proteolysis (sometimes also referred to as "clipping" in the art) of susceptible residues (e.g., lysine or arginine) in a polypeptide sequence.

"Post-fusion," as used herein with respect to RSV F, refers to a stable conformation of RSV F that occurs after merging of the virus and cell membranes.

"Pre-fusion," as used herein with respect to RSV F, refers to a conformation of RSV F that is adopted before virus-cell interaction.

"Protomer," as used herein, refers to a structural unit of an oligomeric protein. In the case of RSV F, an individual unit of the RSV F trimer is a protomer.

"Ferritin" or "ferritin protein," as used herein, refers to a protein with detectable sequence identity to *H. pylori* ferritin (SEQ ID NO: 208 or 209) or another ferritin discussed herein, such as *P. furiosus* ferritin, *Trichoplusia ni* ferritin, or human ferritin, that serves to store iron, e.g., intracellularly or in tissues or to carry iron in the bloodstream. Such exemplary ferritins, including those that occur as two polypeptide chains, known as the heavy and light chains (e.g., *T. ni* and human ferritin), are discussed in detail below. In some embodiments, a ferritin comprises a sequence with at least 15%, 20%, 30%, 40%, 50%, 60%, 70%, 75%, 80%, 85%, 90%, 95%, 97%, 98%, 99%, or 99.5% identity to a ferritin sequence disclosed herein, e.g., in Table 1 (Sequence Table). A ferritin may be a fragment of a full-length naturally-occurring sequence.

"Wild-type ferritin," as used herein, refers to a ferritin whose sequence consists of a naturally-occurring sequence. Ferritins also include full-length ferritin or a fragment of ferritin with one or more differences in its amino acid sequence from a wild-type ferritin.

As used herein, a "ferritin monomer" refers to a single ferritin molecule (or, where applicable, a single ferritin heavy or light chain) that has not assembled with other ferritin molecules. A "ferritin multimer" comprises multiple associated ferritin monomers. A "ferritin protein" includes monomeric ferritin and multimeric ferritin.

As used herein, "ferritin particle," refers to ferritin that has self-assembled into a globular form. Ferritin particles are sometimes referred to as "ferritin nanoparticles" or simply "nanoparticles". In some embodiments, a ferritin particle comprises 24 ferritin monomers (or, where applicable, 24 total heavy and light chains).

"Hybrid ferritin," as used herein, refers to ferritin comprising *H. pylori* ferritin with an amino terminal extension of bullfrog ferritin. An exemplary sequence used as an amino terminal extension of bullfrog ferritin appears as SEQ ID NO: 217. In hybrid ferritin, the amino terminal extension of bullfrog ferritin can be fused to *H. pylori* ferritin such that immune-stimulatory moiety attachment sites are distributed evenly on the ferritin particle surface. "Bullfrog linker" as used herein is a linker comprising the sequence of SEQ ID NO: 217. Hybrid ferritin is also sometimes referred to as "bfpFerr" or "bfp ferritin." Any of the constructs comprising a bullfrog sequence can be provided without the bullfrog sequence, such as, for example, without a linker or with an alternative linker. Exemplary bullfrog linker sequences are provided in Table 1. Where Table 1 shows a bullfrog linker, the same construct may be made without a linker or with an alternative linker.

"N-glycan," as used herein, refers to a saccharide chain attached to a protein at the amide nitrogen of an N (asparagine) residue of the protein. As such, an N-glycan is formed by the process of N-glycosylation. This glycan may be a polysaccharide.

"Glycosylation," as used herein, refers to the addition of a saccharide unit to a protein.

"Immune response," as used herein, refers to a response of a cell of the immune system, such as a B cell, T cell, dendritic cell, macrophage or polymorphonucleocyte, to a stimulus such as an antigen or vaccine. An immune response can include any cell of the body involved in a host defense response, including for example, an epithelial cell that secretes an interferon or a cytokine. An immune response includes, but is not limited to, an innate and/or adaptive immune response. As used herein, a "protective immune response" refers to an immune response that protects a subject from infection (e.g., prevents infection or prevents the development of disease associated with infection). Methods of measuring immune responses are well known in the art and include, for example, by measuring proliferation and/or activity of lymphocytes (such as B or T cells), secretion of cytokines or chemokines, inflammation, antibody production and the like. An "antibody response" is an immune response in which antibodies are produced.

As used herein, an "antigen" refers to an agent that elicits an immune response, and/or an agent that is bound by a T cell receptor (e.g., when presented by an MHC molecule) or to an antibody (e.g., produced by a B cell) when exposed or administered to an organism. In some embodiments, an antigen elicits a humoral response (e.g., including production of antigen-specific antibodies) in an organism. Alternatively, or additionally, in some embodiments, an antigen elicits a cellular response (e.g., involving T-cells whose receptors specifically interact with the antigen) in an organism. A particular antigen may elicit an immune response in one or several members of a target organism (e.g., mice, rabbits, primates, humans), but not in all members of the target organism species. In some embodiments, an antigen elicits an immune response in at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the members of a target organism species. In some embodiments, an antigen binds to an antibody and/or T cell receptor, and may or may not induce a particular physiological response in an organism. In some embodiments, for example, an antigen may bind to an antibody and/or to a T cell receptor in vitro, whether or not such an interaction occurs in vivo. In some embodiments, an antigen reacts with the products of specific humoral or cellular immunity, including those induced by heterologous immunogens. Antigens include antigenic ferritin proteins comprising ferritin (e.g., comprising one or more mutations) and a non-ferritin polypeptide (e.g., RSV polypeptide) as described herein.

An "immune-stimulatory moiety," as used herein, refers to a moiety that is covalently attached to a ferritin or antigenic ferritin polypeptide and that can activate a component of the immune system (either alone or when attached to ferritin or antigenic ferritin polypeptide). Exemplary immune-stimulatory moieties include agonists of toll-like receptors (TLRs), e.g., TLR 4, 7, 8, or 9. In some embodiments, an immune-stimulatory moiety is an adjuvant.

"Adjuvant," as used herein, refers to a substance or vehicle that non-specifically enhances the immune response to an antigen. Adjuvants can include, without limitation, a suspension of minerals (e.g., alum, aluminum hydroxide, or phosphate) on which antigen is adsorbed; a water-in-oil or oil-in-water emulsion in which antigen solution is emulsified in mineral oil or in water (e.g., Freund's incomplete adjuvant). Sometimes killed mycobacteria is included (e.g., Freund's complete adjuvant) to further enhance antigenicity. Immuno-stimulatory oligonucleotides (e.g., a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants can also include biological molecules, such as Toll-Like Receptor (TLR) agonists and costimulatory molecules. An adjuvant may be administered as a separate molecule in a composition or covalently bound (conjugated) to ferritin or an antigenic ferritin polypeptide.

An "antigenic RSV polypeptide" is used herein to refer to a polypeptide comprising all or part of an RSV amino acid sequence of sufficient length that the molecule is antigenic with respect to RSV. Antigenicity may be a feature of the RSV sequence as part of a construct further comprising a heterologous sequence, such as a ferritin and/or immune-stimulatory moiety. That is, if an RSV sequence is part of a construct further comprising a heterologous sequence, then it is sufficient that the construct can serve as an antigen that generates anti-RSV antibodies, regardless of whether the RSV sequence without the heterologous sequence could do so.

"Antigenic ferritin polypeptide" and "antigenic ferritin protein" are used interchangeably herein to refer to a polypeptide comprising a ferritin and a non-ferritin polypeptide (e.g., an RSV polypeptide) of sufficient length that the molecule is antigenic with respect to the non-ferritin polypeptide. The antigenic ferritin polypeptide may further comprise an immune-stimulatory moiety. Antigenicity may be a feature of the non-ferritin sequence as part of the larger construct. That is, it is sufficient that the construct can serve as an antigen against the non-ferritin polypeptide, regardless of whether the non-ferritin polypeptide without the ferritin (and immune-stimulatory moiety if applicable) could do so. In some embodiments, the non-ferritin polypeptide is an RSV polypeptide, in which case the antigenic ferritin polypeptide is also an "antigenic RSV polypeptide." To be clear, however, an antigenic RSV polypeptide does not need to comprise ferritin. "Antigenic polypeptide" is used herein to refer to a polypeptide which is either or both of an antigenic ferritin polypeptide and an antigenic RSV polypeptide.

"Self-adjuvanting," as used herein, refers to a composition or polypeptide comprising a ferritin and an immune-stimulatory moiety directly conjugated to the ferritin so that the ferritin and immune-stimulatory moiety are in the same molecular entity. An antigenic ferritin polypeptide comprising a non-ferritin polypeptide may be conjugated to an immune-stimulatory moiety to generate a self-adjuvanting polypeptide.

A "surface-exposed" amino acid, as used herein, refers to an amino acid residue in a protein (e.g., a ferritin) with a side chain that can be contacted by solvent molecules when the protein is in its native three-dimensional conformation after multimerization, if applicable. Thus, for example, in the case of ferritin that forms a 24-mer, a surface-exposed amino acid residue is one whose side chain can be contacted by solvent when the ferritin is assembled as a 24-mer, e.g., as a ferritin multimer or ferritin particle.

As used herein, a "subject" refers to any member of the animal kingdom. In some embodiments, "subject" refers to humans. In some embodiments, "subject" refers to non-human animals. In some embodiments, subjects include, but are not limited to, mammals, birds, reptiles, amphibians, fish, insects, and/or worms. In certain embodiments, the non-human subject is a mammal (e.g., a rodent, a mouse, a rat, a rabbit, a monkey, a dog, a cat, a sheep, cattle, a primate, and/or a pig). In some embodiments, a subject may be a transgenic animal, genetically-engineered animal, and/or a clone. In certain embodiments of the present invention the subject is an adult, an adolescent or an infant. In some embodiments, terms "individual" or "patient" are used and are intended to be interchangeable with "subject".

As used herein, the term "vaccination" or "vaccinate" refers to the administration of a composition intended to generate an immune response, for example to a disease-causing agent. Vaccination can be administered before, during, and/or after exposure to a disease-causing agent, and/or to the development of one or more symptoms, and in some embodiments, before, during, and/or shortly after exposure to the agent. In some embodiments, vaccination includes multiple administrations, appropriately spaced in time, of a vaccinating composition.

The disclosure describes nucleic acid sequences and amino acid sequences having a certain degree of identity to a given nucleic acid sequence or amino acid sequence, respectively (a references sequence).

"Sequence identity" between two nucleic acid sequences indicates the percentage of nucleotides that are identical between the sequences. "Sequence identity" between two amino acid sequences indicates the percentage of amino acids that are identical between the sequences.

The terms "% identical", "% identity" or similar terms are intended to refer, in particular, to the percentage of nucleotides or amino acids which are identical in an optimal alignment between the sequences to be compared. Said percentage is purely statistical, and the differences between the two sequences may be but are not necessarily randomly distributed over the entire length of the sequences to be compared. Comparisons of two sequences are usually carried out by comparing said sequences, after optimal alignment, with respect to a segment or "window of comparison", in order to identify local regions of corresponding sequences. The optimal alignment for a comparison may be carried out manually or with the aid of the local homology algorithm by Smith and Waterman, 1981, Ads App. Math. 2, 482, with the aid of the local homology algorithm by Needleman and Wunsch, 1970, J. Mol. Biol. 48, 443, with the aid of the similarity search algorithm by Pearson and Lipman, 1988, Proc. Natl Acad. Sci. USA 88, 2444, or with the aid of computer programs using said algorithms (GAP, BESTFIT, FASTA, BLAST P, BLAST N and TFASTA in Wisconsin Genetics Software Package, Genetics Computer Group, 575 Science Drive, Madison, Wis.).

Percentage identity is obtained by determining the number of identical positions at which the sequences to be compared correspond, dividing this number by the number of positions compared (e.g., the number of positions in the reference sequence) and multiplying this result by 100.

In some embodiments, the degree of identity is given for a region which is at least about 50%, at least about 60%, at least about 70%, at least about 80%, at least about 90% or about 100% of the entire length of the reference sequence. For example, if the reference nucleic acid sequence consists of 200 nucleotides, the degree of identity is given for at least about 100, at least about 120, at least about 140, at least about 160, at least about 180, or about 200 nucleotides, in some embodiments in continuous nucleotides. In some embodiments, the degree of identity is given for the entire length of the reference sequence.

Nucleic acid sequences or amino acid sequences having a particular degree of identity to a given nucleic acid sequence or amino acid sequence, respectively, may have at least one functional property of said given sequence, e.g., and in some instances, are functionally equivalent to said given sequence. One important property includes the ability to act as a cytokine, in particular when administered to a subject. In some embodiments, a nucleic acid sequence or amino acid sequence having a particular degree of identity to a given nucleic acid sequence or amino acid sequence is functionally equivalent to said given sequence.

As used herein, the term "kit" refers to a packaged set of related components, such as one or more compounds or compositions and one or more related materials such as solvents, solutions, buffers, instructions, or desiccants.

B. Antigenic RSV Polypeptides Comprising an RSV F Polypeptide Comprising One or More Asparagines at Certain Positions Provided herein are antigenic RSV polypeptides comprising an RSV F polypeptide. The RSV F polypeptide may comprise the whole sequence of RSV F or a portion of RSV F. In some embodiments, an epitope of the RSV polypeptide that is shared between pre-fusion RSV F and post-fusion RSV F is blocked. Blocking an epitope reduces or eliminates the generation of antibodies against the epitope when the antigenic RSV polypeptide is administered to a subject. This can increase the proportion of antibodies that target an epitope specific to a particular conformation of F, such as the pre-fusion conformation. Because F has the pre-fusion conformation in viruses that have not yet entered cells, an increased proportion of antibodies that target pre-fusion F can provide a greater degree of neutralization (e.g., expressed as a neutralizing to binding ratio, as described herein). Blocking can be achieved by engineering a bulky moiety such as an N-glycan in the vicinity of the shared epitope. For example, an N-glycosylation site not present in wild-type F can be added, e.g., by mutating an appropriate residue to asparagine. In some embodiments, the blocked epitope is an epitope of antigenic site 1 of RSV F. In some embodiments, two or more epitopes shared between pre-fusion RSV F and post-fusion RSV F are blocked. In some embodiments, two or more epitopes of antigenic site 1 of RSV F are blocked. In some embodiments, one or more, or all, epitopes that topologically overlap with the blocked epitope are also blocked, optionally wherein the blocked epitope is an epitope of antigenic site 1 of RSV F.

In some embodiments, the RSV F polypeptide comprises an asparagine corresponding to position 328, 348, or 507 of SEQ ID NO: 26. In some embodiments, the polypeptide comprises asparagines that correspond to at least two of positions 328, 348, or 507 of SEQ ID NO: 26. In some embodiments, the polypeptide comprises asparagines that correspond to positions 328, 348, or 507 of SEQ ID NO: 26. As described in the examples, it has been found that such asparagines can function as glycosylation sites. Furthermore, without wishing to be bound by any particular theory, glycans at these sites may inhibit development of antibodies to nearby epitopes, which include epitopes common to pre- and post-fusion RSV F protein, when the polypeptide is administered to a subject. In some embodiments, glycosylation of the asparagine corresponding to position 328, 348, or 507 of SEQ ID NO: 26 blocks at least one epitope shared between pre-fusion RSV F and post-fusion RSV F, such as an epitope of antigenic site 1. Inhibiting the development of antibodies to epitopes common to pre- and post-fusion RSV F protein can be beneficial because it can direct antibody development against epitopes specific to pre-fusion RSV F protein, such as the site 0 epitope, which may have more effective neutralizing activity than antibodies to other RSV F epitopes. The site 0 epitope involves amino acid residues 62-69 and 196-209 of SEQ ID NO: 26. Accordingly, in some embodiments, the RSV F polypeptide comprises amino acid residues 62-69 and 196-209 of SEQ ID NO: 26.

It should be noted that constructs described herein may have deletions or substitutions of different length relative to wild type RSV F. For example, in the construct of SEQ ID NO: 23 and others, positions 98-144 of the wild-type sequence (SEQ ID NO: 26) are replaced with GSGNVGL (positions 98-104 of SEQ ID NO: 23; also SEQ ID NO: 31), resulting in a net removal of 40 amino acids, such that positions 328, 348, or 507 of SEQ ID NO: 26 correspond to positions 288, 308, and 467 of SEQ ID NO: 23. In general, positions in constructs described herein can be mapped onto the wild-type sequence of SEQ ID NO: 26 by pairwise alignment, e.g., using the Needleman-Wunsch algorithm with standard parameters (EBLOSUM62 matrix, Gap penalty 10, gap extension penalty 0.5). See also the discussion of structural alignment provided herein as an alternative approach for identifying corresponding positions.

In some embodiments, the RSV F polypeptide comprises mutations that add glycans to block epitopes on the pre-fusion antigen that are structurally similar to those on the surface of the post-fusion RSV F. In some embodiments, glycans are added to specifically block epitopes that may be present in the post-fusion conformation of RSV F. In some embodiments, glycans are added that block epitopes that may be present in the post-fusion confirmation of RSV F but do not affect one or more epitopes present on the pre-fusion confirmation of RSV F, such as the site 0 epitope.

In some embodiments, the glycans added at the one or more glycosylation sites discussed above increase secretion in expression systems, such as mammalian cells, compared to other constructs.

In some embodiments, the RSV F polypeptide comprises a sequence having at least 85%, 90%, 95%, 97%, 98%, 99%, or 99.5% identity to amino acids 1-478 of SEQ ID NO: 17. In some embodiments, the RSV F polypeptide comprises a sequence having at least 85%, 90%, 95%, 97%, 98%, 99%, or 99.5% identity to the sequence of SEQ ID NO: 17. In some embodiments, the RSV F polypeptide comprises amino acids 1-478 of SEQ ID NO: 17. In some embodiments, the RSV F polypeptide comprises the sequence of SEQ ID NO: 17.

In some embodiments, the RSV F polypeptide comprises a sequence having at least 85%, 90%, 95%, 97%, 98%, 99%, or 99.5% identity to amino acids 1-478 of SEQ ID NO: 23. In some embodiments, the RSV F polypeptide comprises a sequence having at least 85%, 90%, 95%, 97%, 98%, 99%, or 99.5% identity to the sequence of SEQ ID NO: 23. In some embodiments, the RSV F polypeptide comprises amino acids 1-478 of SEQ ID NO: 23. In some embodiments, the RSV F polypeptide comprises the sequence of SEQ ID NO: 23.

In some embodiments, the RSV F polypeptide comprises the DS-CAV1 sequence (as described, for example, in McLellan, J. S., et al., *Science* 342(6158):592-598 (2013)) (SEQ ID NO: 25) in which further modifications are made including at least one, two, or three of the asparagines described above.

In some embodiments, the polypeptide further comprises a ferritin protein. The ferritin protein can further comprise any of the features described below in the section concerning ferritin, or a combination thereof.

The RSV F polypeptide can further comprise any of the additional features set forth in the following discussion, or any feasible combination of such features.

Single Chain Constructs

In some embodiments, the RSV polypeptide is a single chain construct, e.g., an RSV polypeptide that lacks furin cleavage sites. In some embodiments, an RSV F lacks one or more furin cleavage sites. Constructs that lack furin cleavage sites are expressed as single polypeptides that are not cleaved into the biological F1/F2 fragments of the native F protein.

Amino Acid Substitutions

In some embodiments, an RSV F comprises a single amino acid substitution relative to a wild-type sequence. In some embodiments, an RSV F comprises more than one single amino acid substitution, e.g., 2, 3, 4, 5, 6, 7, 8, 9, 10, 11, 12, 13, 14, or 15 substitutions relative to a wild-type sequence. An exemplary wild-type sequence is SEQ ID NO: 26.

In some embodiments, an amino acid substitution or pair of amino acid substitutions are inter-protomer stabilizing substitution(s). Exemplary substitutions that can be inter-protomer stabilizing are V207L; N228F; I217V and E218F; I221L and E222M; or Q224A and Q225L, using the position numbering of SEQ ID NO: 26.

In some embodiments, an amino acid substitution or pair of amino acid substitutions are intra-protomer stabilizing. Exemplary substitutions that can be intra-protomer stabilizing are V220I; and A74L and Q81L, using the position numbering of SEQ ID NO: 26.

In some embodiments, an amino acid substitution is helix stabilizing, i.e., predicted to stabilize the helical domain of RSV F. Stabilization of the helical domain can contribute to the stability of the site 0 epitope and of the pre-fusion conformation of RSV F generally. Exemplary substitutions that can be helix stabilizing are N216P or I217P, using the position numbering of SEQ ID NO: 26.

In some embodiments, an amino acid substitution is helix capping. In some embodiments, an amino acid substitution is helix PRO capping. Helix capping is based on the biophysical observation that, while a proline residue mutation place in an alpha helix may disrupt the helix formation, a proline at the N-terminus of a helical region may help induce helical formation by stabilizing the PHI/PSI bond angles. Exemplary substitutions that can be helix capping are N216P or I217P, using the position numbering of SEQ ID NO: 26

In some embodiments, an amino acid substitution replaces a disulfide mutation of DS-CAV1. In some embodiments, the engineered disulfide of DS-CAV1 is reverted to wild-type (C69S and/or C212S mutations of DS-CAV1, using the position numbering of SEQ ID NO: 26. In some embodiments, one or more C residue of DS-CAV1 is replaced with a S residue to eliminate a disulfide bond. In some embodiments, C69S or C212S substitution using the position numbering of SEQ ID NO: 26 eliminates a disulfide bond. In some embodiments, an RSV F polypeptide comprises both C69S and C212S using the position numbering of SEQ ID NO: 26. In some embodiments, replacing such cysteines and thereby eliminating a disulfide bond blocks reduction (i.e. acceptance of electrons from a reducing agent) of the RSV F polypeptide. In some embodiments, an I217P substitution using the position numbering of SEQ ID NO: 26 is comprised in an antigen instead of substitution at C69 and/or C212. Position 217 in SEQ ID NO: 26 corresponds to position 177 in SEQ ID NO: 23.

In some embodiments, an amino acid substitution prevents proteolysis by trypsin or trypsin-like proteases. In some embodiments, the amino acid substitution that prevents such proteolysis is in the heptad repeat region B (HRB) region of RSV F. Appearance of fragments consistent with proteolysis of an RSV F-ferritin construct that comprised a wild-type HRB region suggested a lysine or arginine in this region was being targeted for proteolysis. An amino acid substitution to remove a K or R residue may be termed a knockout (KO). In some embodiments, a K or R is substituted for L or Q. In some embodiments, a K is substituted for L or Q. In some embodiments, the RSV F polypeptide comprises K498L and/or K508Q, using the position numbering of SEQ ID NO: 26. The corresponding positions in SEQ ID NO: 23 are 458 and 468, respectively. In some embodiments, the RSV F polypeptide comprises both K498L and K508Q.

In some embodiments, an amino acid substitution adds glycans. In some embodiments, an amino acid substitution increases glycosylation by adding glycans to RSV F polypeptides. Substitutions to add glycans may also be referred to as engineered glycosylation, as compared to native glycosylation (without additional glycans).

In some embodiments, the amino acid substitution to add glycans was substitution with an N. In some embodiments, amino acid substitution with an N allows N-linked glycosylation. In some embodiments, substitution with an N is accompanied by substitution with a T or S at the second amino acid position C-terminal to the N, which forms an N×T/S glycosylation motif. In some embodiments, the N is surface-exposed. As shown in the examples below, mutations that increased glycosylation could provide increased expression of a polypeptide comprising an RSV F polypeptide.

Changes to the Properties of the RSV F Polypeptide Based on Modifications

Modifications to the amino sequence of RSV F can change the properties of an RSV F polypeptide. A property of an RSV F polypeptide can include any structural or functional characteristic of the RSV F polypeptide.

In some embodiments, a single modification to the amino acid sequence changes multiple properties of the RSV F polypeptide. In some embodiments, an RSV F polypeptide can comprise multiple modifications that change different properties of an RSV F polypeptide. In some embodiments, multiple modifications produce a greater change in the properties of an RSV F polypeptide.

In some embodiments, multiple modifications can have an additive effect on a particular property. For example, two amino acid substitutions to add glycans can produce a greater increase in glycosylation of the RSV F polypeptide compared to either single amino acid substitution.

In some embodiments, multiple modifications affect different properties of an RSV F polypeptide. For example, one or more amino acid substitutions to increase glycosylation can be made together with one or more amino acid substitutions to block reduction.

In some embodiments, modifications to an RSV F polypeptide stabilize the pre-fusion confirmation.

In some embodiments, modifications stabilize the site 0 epitope (also known as antigenic site 0) of pre-fusion RSV F, as described, for example, in McLellan et al., Science 340(6136):1113-1117 (2013). In some embodiments, a modification that stabilizes the site 0 epitope is inter-protomer stabilizing. In some embodiments, a modification that stabilizes the site 0 epitope stabilizes pre-fusion F, as measured by Site 0 and Site V binding as measured by binding to antibodies D25 or AM14, respectively.

In some embodiments, modifications increase expression of RSV F in expression systems. In some embodiments, modifications increase secretion of RSV F in expression systems. In some embodiments, modifications increase stability of the recombinant RSV F after expression. This change can be in any type of expression system, such as bacterial, fungal, insect, or mammalian.

In some embodiments, amino acid substitutions that introduce a proline increase expression compared to other constructs. In some embodiments, amino acid substitutions that add glycans increase expression compared to other constructs. In some embodiments, amino acid substitutions that substitute K or R for other amino acids increase expression compared to other constructs. An observable increase in expression can result from any mechanism that increases the yield of a fermentation run or other production process, including relative inhibition of protease cleavage or degradation and/or increase in stability in the host cell or in the extracellular milieu. In some embodiments, amino acid substitutions that substitute one or more K residues in the HRB region of RSV F for other amino acids increase expression compared to other constructs.

In some embodiments, amino acid substitutions that substitute K for other amino acids increase stability of RSV F polypeptides. In some embodiments, amino acid substitutions that substitute one or more K residues in the HRB region of RSV F for other amino acids increase stability of RSV F polypeptides. In some embodiments, this increased stability is due to a reduction in protease cleavage.

In some embodiments, an RSV F comprises mutation(s) that remove a disulfide, e.g., to prevent conjugation after reduction. In some embodiments, the I217P substitution blocks reduction of the RSV F polypeptide. In some embodiments, amino acid substitutions that substitute K for other amino acids block reduction of the RSV F polypeptide in the presence of a reducing agent.

In some embodiments, single chain constructs increase expression compared to other constructs.

In some embodiments, the RSV F polypeptide comprises the DS-CAV1 sequence (SEQ ID NO: 25) (as described in McLellan, J. S., et al., *Science* 342(6158):592-598 (2013)). In some embodiments, the RSV F polypeptide comprises the sequence of DS-CAV1 in which further modifications are made, e.g., including at least one, two, or three of the asparagines described above.

C. RSV G Polypeptides

As used herein, an RSV G polypeptide may comprise the whole sequence of RSV G or a portion of RSV G. An RSV G polypeptide may comprise modifications compared to a wildtype sequence. In some embodiments, the RSV G polypeptide is an RSV G modified as compared to wild-type RSV G (SEQ ID NO: 27).

In some embodiments, these modifications are changes to the amino acid of the RSV G polypeptide as compared to wild-type RSV G.

In some embodiments, the RSV G polypeptide comprises all or part of the ectodomain of RSV G (SEQ ID NO: 28 or positions corresponding thereto). In some embodiments, the RSV G polypeptide comprises all or part of the Gcc region (amino acids 151-193 of RSV G (SEQ ID NO: 27)). In some embodiments, the RSV G polypeptide comprises a CX3C motif. In some embodiments, the RSV G polypeptide binds to the CX3CR1 receptor. The Gcc region is both conserved and immunogenic, and thus can be used to elicit antibodies with broad activity against RSV strains. In some embodiments, an RSV Gcc strain A is provided as shown in SEQ ID NO: 32. In some embodiments, an RSV Gcc strain B is provided as shown in SEQ ID NO: 33.

In some embodiments, the RSV G polypeptide is not glycosylated. For example, an RSV G polypeptide can lack NXS/TX glycosylation sites, either due to truncation or mutation of N or S/T residues (e.g., to Q or A, respectively), or a combination thereof.

In some embodiments, the RSV G polypeptide is part of an antigenic ferritin polypeptide. For example, the RSV G polypeptide can be conjugated to a ferritin as described herein, such as via a surface-exposed cysteine on the ferritin. In some embodiments, this ferritin nanoparticle is a fusion protein also comprising an RSV F polypeptide, such as any of the polypeptides comprising an RSV F polypeptide and a ferritin protein described above.

D. Antigenic RSV Polypeptides Comprising Ferritin

Also provided herein is an antigenic RSV polypeptide comprising a ferritin and an RSV polypeptide. The RSV polypeptide can be an RSV F polypeptide, such as any of the RSV F polypeptides described herein. The RSV F polypeptide may comprise the whole sequence of RSV F or a portion of RSV F. The RSV F polypeptide may comprise one or more modification (e.g., amino acid substitution) compared to a wildtype sequence. The RSV polypeptide can be an RSV G polypeptide, such as any of the RSV G polypeptides described herein.

In some embodiments, the ferritin in the polypeptide is a wild-type ferritin. In some embodiments, the ferritin is bacterial, insect, fungal, bird, or mammalian. In some embodiments, the ferritin is human. In some embodiments, the ferritin is bacterial.

In some embodiments, the ferritin is a light chain and/or heavy chain ferritin. In some embodiments, the ferritin is an insect ferritin, such as *Trichoplusia ni* heavy chain ferritin (SEQ ID NO: 211) or *Trichoplusia ni* light chain ferritin (SEQ ID NO: 212). In some embodiments, the ferritin is a human ferritin, such as human heavy chain ferritin (SEQ ID NO: 214 or FTH1, GENE ID No: 2495) or human light chain ferritin (SEQ ID NO: 215 or FTL, GENE ID No: 2512). In some embodiments, a ferritin nanoparticle comprises 24 total subunits of heavy chain ferritin and light chain ferritin, such as in human or *Trichoplusia ni* ferritin nanoparticles. *T. ni* ferritin nanoparticles can comprise 12 subunits of heavy chain ferritin and 12 subunits of light chain ferritin.

In some embodiments, an antigenic RSV polypeptide comprises a light chain ferritin and an RSV polypeptide. In some embodiments, an antigenic RSV polypeptide comprises a heavy chain ferritin and an RSV polypeptide. In some embodiments, an antigenic RSV polypeptide comprising a light chain ferritin and an RSV polypeptide can assemble with a heavy chain ferritin that is not linked to an RSV polypeptide. In some embodiments, an antigenic RSV polypeptide comprising a heavy chain ferritin and an RSV polypeptide can assemble with a light chain ferritin that is not linked to an RSV polypeptide. A ferritin not linked to an RSV polypeptide (or, more generally, a non-ferritin polypeptide) may be referred as a "naked ferritin."

In some embodiments, an antigenic polypeptide comprising a heavy chain ferritin and a polypeptide can assemble with an antigenic polypeptide comprising a light chain ferritin and an RSV polypeptide to allow presentation of two of the same or different non-ferritin polypeptides on a single ferritin nanoparticle. In some embodiments, the two different non-ferritin polypeptides are RSV polypeptides. In some embodiments, the two different non-ferritin polypeptides are encoded by RSV and a different infectious agent. In some embodiments, the different non-ferritin polypeptide from a different infectious agent is from a virus or bacterium.

In some embodiments, an antigenic polypeptide comprising a heavy chain ferritin and a non-ferritin polypeptide can assemble with a polypeptide comprising a light chain ferritin and a non-ferritin polypeptide to produce a bivalent composition, wherein one or both of the non-ferritin polypeptides are RSV polypeptides, such as RSV F or G polypeptides, e.g., an RSV F or G polypeptide described herein.

In some embodiments, the ferritin is *H. pylori* ferritin (see SEQ ID NO: 208 or 209 for an exemplary *H. pylori* ferritin sequence), optionally with one or more mutations such as those described herein. In some embodiments, the lower sequence homology between *H. pylori* ferritin (or other bacterial ferritins) and human ferritin may decrease the potential for autoimmunity when used as a vaccine platform (see Kanekiyo et al., Cell 162, 1090-1100 (2015)).

In some embodiments, the ferritin is *Pyrococcus furiosus* ferritin (NCBI seq WP_011011871.1) with one or more mutations described herein.

In some embodiments, the ferritin comprises a sequence having greater than 70%, greater than 75%, greater than 80%, greater than 85%, greater than 90%, greater than 95%, greater than 97%, greater than 98%, or greater than 99% identity to a wild-type ferritin.

In some embodiments, a nanoparticle is provided comprising an antigenic RSV polypeptide as disclosed herein comprising an RSV polypeptide and a ferritin.

In some embodiments, a different protein capable of forming a nanoparticle is substituted for ferritin. In some embodiments, this protein is lumazine synthase (see Ra et al., Clin Exp Vaccine Res 3:227-234 (2014)). In some embodiments, this protein is lumazine synthase serotype 1, 2, 3, 4, 5, 6, or 7. Exemplary lumazine synthase sequences are provided as SEQ ID NO: 216 and 219. In some embodiments, the lumazine synthase comprises a sequence with 80%, 85%, 90%, 95%, 98%, or 99% identity to SEQ ID NO: 216 or 219.

1. Cysteine for Conjugation

In some embodiments, ferritin is mutated to provide a chemical handle for conjugation of an immune-stimulatory moiety and/or RSV polypeptide. This can be achieved with a mutation replacing a surface-exposed non-cysteine amino acid with a cysteine. For the avoidance of doubt, language such as "replacing a surface-exposed amino acid with a cysteine" necessarily implies that the surface-exposed amino acid in the wild-type or pre-mutation sequence is not cysteine. Another approach for providing a chemical handle for conjugation of an immune-stimulatory moiety or RSV polypeptide is to include a segment of amino acids, such as a linker, N- or C-terminal to the ferritin, wherein the segment of amino acids comprises a cysteine. In some embodiments, this cysteine (whether replacing a surface-exposed amino acid or in an N- or C-terminal linker) is unpaired, which means that it does not have an appropriate partner cysteine to form a disulfide bond. In some embodiments, this cysteine does not change the secondary structure of ferritin. In some embodiments, this cysteine does not change the tertiary structure of ferritin.

In some embodiments, this cysteine can be used to conjugate agents, such as immune-stimulatory moieties, to ferritin. In some embodiments, this cysteine provides a free thiol group that is reactive. In some embodiments, agents conjugated to this cysteine on ferritin are exposed on the surface of an assembled ferritin particle. In some embodiments, this cysteine can interact with molecules and cells of the subject after administration while the ferritin particle is assembled.

In some embodiments, the presence of this cysteine allows conjugation of one or more immune-stimulatory moieties, e.g., adjuvants. In some embodiments, conjugation of the immune-stimulatory moiety would not occur in the absence of this cysteine.

In some embodiments, the non-cysteine amino acid that is replaced with a cysteine is selected from E12, S72, A75, K79, S100, and S111 of *H. pylori* ferritin. Thus, in some embodiments, the surface-exposed amino acid that is replaced in favor of cysteine is an amino acid residue that corresponds to E12, S26, S72, A75, K79, S100, or S111 of *H. pylori* ferritin. Analogous amino acids can be found in non-*H. pylori* ferritin by pair-wise or structural alignment. In some embodiments, the non-cysteine amino acid that is replaced with a cysteine can be selected from an amino acid that corresponds to S3, S19, S33, 182, A86, A102, and A120 of human light chain ferritin. In some embodiments, the surface-exposed amino acid to be replaced with a cysteine is selected based on the understanding that if the native amino acid were replaced with cysteine, it would be reactive in an assembled ferritin multimer or particle and/or that this cysteine does not disrupt the stability of the ferritin multimer or particle and/or that this cysteine does not lead to reduction in expression levels of ferritin.

In some embodiments, the ferritin comprises an E12C mutation. In some embodiments, the E12C residue can be used to conjugate agents (e.g., immune-stimulatory moieties and/or RSV polypeptides) to ferritin. In some embodiments, the E12C residue provides a free thiol group that is reactive. In some embodiments, agents conjugated to the E12C residue on ferritin monomers are expressed on the surface on an assembled ferritin multimer or particle. In some embodiments, twenty-four E12C residues (one from each monomer) are present on the surface of a ferritin multimer or particle.

In some embodiments, the ferritin comprises an S26C mutation. In some embodiments, the S26C residue can be used to conjugate agents (e.g., immune-stimulatory moieties and/or RSV polypeptides) to ferritin. In some embodiments, the S26C residue provides a free thiol group that is reactive. In some embodiments, agents conjugated to the S26C residue on ferritin monomers are expressed on the surface on an assembled ferritin multimer or particle. In some embodiments, twenty-four S26C residues (one from each monomer) are present on the surface of a ferritin multimer or particle.

In some embodiments, the ferritin comprises an S72C mutation. In some embodiments, the S72C residue can be used to conjugate agents (e.g., immune-stimulatory moieties and/or RSV polypeptides) to ferritin. In some embodiments, the S72C residue provides a free thiol group that is reactive. In some embodiments, agents conjugated to the S72C residue on ferritin monomers are expressed on the surface on an assembled ferritin multimer or particle. In some embodiments, twenty-four S72C residues (one from each monomer) are present on the surface of a ferritin multimer or particle.

In some embodiments, the ferritin comprises an A75C mutation. In some embodiments, the A75C residue can be used to conjugate agents (e.g., immune-stimulatory moieties and/or RSV polypeptides) to ferritin. In some embodiments, the A75C residue provides a free thiol group that is reactive. In some embodiments, agents conjugated to the A75C residue on ferritin monomers are expressed on the surface on an assembled ferritin multimer or particle. In some embodiments, twenty-four A75C residues (one from each monomer) are present on the surface of a ferritin multimer or particle.

In some embodiments, the ferritin comprises an K79C mutation. In some embodiments, the K79C residue can be used to conjugate agents (e.g., immune-stimulatory moieties and/or RSV polypeptides) to ferritin. In some embodiments, the K79C residue provides a free thiol group that is reactive. In some embodiments, agents conjugated to the K79C residue on ferritin monomers are expressed on the surface on an assembled ferritin multimer or particle. In some embodiments, twenty-four K79C residues (one from each monomer) are present on the surface of a ferritin multimer or particle.

In some embodiments, the ferritin comprises an S100C mutation. In some embodiments, the S100C residue can be used to conjugate agents (e.g., immune-stimulatory moieties and/or RSV polypeptides) to ferritin. In some embodiments, the S100C residue provides a free thiol group that is reactive. In some embodiments, agents conjugated to the S100C residue on ferritin monomers are expressed on the surface on an assembled ferritin multimer or particle. In some embodiments, twenty-four S100C residues (one from each monomer) are present on the surface of a ferritin multimer or particle.

In some embodiments, the ferritin comprises an S111C mutation. In some embodiments, the S111C residue can be used to conjugate agents (e.g., immune-stimulatory moieties and/or RSV polypeptides) to ferritin. In some embodiments, the S111C residue provides a free thiol group that is reactive. In some embodiments, agents conjugated to the S111C residue on ferritin monomers are expressed on the surface on an assembled ferritin multimer or particle. In some embodiments, twenty-four S111C residues (one from each monomer) are present on the surface of a ferritin multimer or particle.

2. Removal of Internal Cysteine

In some embodiments, the ferritin comprises a mutation replacing an internal cysteine with a non-cysteine amino acid. Removal of a native internal cysteine residue can ensure that there is only one unpaired cysteine per ferritin monomer and avoid undesired reactions such as disulfide formation and may result in a more stable and efficient result (e.g., adjuvant presentation). In some embodiments, C31 of *H. pylori* ferritin is replaced with a non-cysteine amino acid. In some embodiments, C31 of *H. pylori* ferritin is replaced with a serine (C31S), although any non-cysteine residue may be used, e.g., alanine, glycine, threonine, or asparagine. Analogous amino acids can be found in non-*H. pylori* ferritin by pair-wise or structural alignment. Thus, in some embodiments, the internal cysteine that is replaced in favor of non-cysteine is an amino acid residue that aligns with C31 of *H. pylori* ferritin. Exemplary ferritin sequences showing a C31S mutation are shown in SEQ ID NOS: 201-207. In some embodiments, when more than one internal cysteine is present in ferritin, two or more (e.g., each) internal cysteine is replaced with a non-cysteine amino acid, such as serine or an amino acid selected from serine, alanine, glycine, threonine, or asparagine.

3. Glycosylation

Human-compatible glycosylation can contribute to safety and efficacy in recombinant drug products. Regulatory approval may be contingent on demonstrating appropriate glycosylation as a critical quality attribute (see Zhang et al., Drug Discovery Today 21(5):740-765 (2016)). N-glycans can result from glycosylation of asparagine side chains and can differ in structure between humans and other organisms such as bacteria and yeast. Thus, it may be desirable to reduce or eliminate non-human glycosylation and/or N-glycan formation in ferritin according to the disclosure. In some embodiments, controlling glycosylation of ferritin improves the efficacy and/or safety of the composition, especially when used for human vaccination.

In some embodiments, ferritin is mutated to inhibit formation of an N-glycan. In some embodiments, a mutated ferritin has reduced glycosylation as compared to its corresponding wild type ferritin.

In some embodiments, the ferritin comprises a mutation replacing a surface-exposed asparagine with a non-asparagine amino acid. In some embodiments, the surface-exposed asparagine is N19 of *H. pylori* ferritin or a position that corresponds to position 31 of *H. pylori* ferritin as determined by pair-wise or structural alignment In some embodiments, mutating such an asparagine, e.g., N19 of *H. pylori* ferritin, decreases glycosylation of ferritin. In some embodiments, the mutation replaces the asparagine with a glutamine. In some embodiments, the ferritin is an *H. pylori* ferritin comprising an N19Q mutation. SEQ ID NOS: 201-207 are exemplary ferritin sequences comprising N19Q mutations.

A mammal exposed to a glycosylated protein produced in bacteria or yeast may generate an immune response to the glycosylated protein, because the pattern of glycosylation of a given protein in bacterial or yeast could be different from the pattern of glycosylation of the same protein in a mammal. Thus, some glycosylated therapeutic proteins may not be appropriate for production in bacteria or yeast.

In some embodiments, decreased glycosylation of ferritin by amino acid mutation facilitates protein production in bacteria or yeast. In some embodiments, decreased glycosylation of ferritin reduces the potential for adverse effects in mammals upon administration of mutated ferritin that is expressed in bacteria or yeast. In some embodiments, the reactogenicity in a human subject of a mutated ferritin produced in bacteria or yeast is lower because glycosylation is decreased. In some embodiments, the incidence of hypersensitivity responses in human subjects is lower following treatment with a mutated ferritin with reduced glycosylation compared to wildtype ferritin.

In some embodiments, degradation in a subject of a composition comprising a mutated ferritin with reduced glycosylation is slower compared with a composition comprising a wild-type ferritin, or a composition comprising a corresponding ferritin with wild-type glycosylation. In some embodiments, a composition comprising a mutated ferritin with reduced glycosylation has reduced clearance in a subject compared with a composition comprising a wild-type ferritin, or a composition comprising a corresponding ferritin with wild-type glycosylation. In some embodiments, a composition comprising a mutated ferritin with reduced glycosylation has a longer-serum half-life compared to wild-type ferritin, or a composition comprising a corresponding ferritin with wild-type glycosylation.

4. Combinations of Mutations

In some embodiments, a ferritin comprises more than one type of mutation described herein. In some embodiments, the ferritin comprises one or more mutations independently selected from: a mutation to decrease glycosylation, a mutation to remove an internal cysteine, and a mutation to generate a surface-exposed cysteine. In some embodiments, the ferritin comprises a mutation to decrease glycosylation, a mutation to remove an internal cysteine, and a mutation to generate a surface-exposed cysteine.

In some embodiments, the ferritin comprises an N19Q mutation, a C31S mutation, and a mutation to generate a surface-exposed cysteine. In some embodiments, the ferritin comprises an N19Q mutation, a C31S mutation, and an E12C mutation. In some embodiments, the ferritin comprises an N19Q mutation, a C31S mutation, and an S72C mutation. In some embodiments, the ferritin comprises an N19Q mutation, a C31S mutation, and an A75C mutation. In some embodiments, the ferritin comprises an N19Q mutation, a C31S mutation, and an K79C mutation. In some embodiments, the ferritin comprises an N19Q mutation, a C31S mutation, and an S100C mutation. In some embodiments, the ferritin comprises an N19Q mutation, a C31S mutation, and an S111C mutation. In some embodiments, the ferritin comprises mutations corresponding to any of the foregoing sets of mutations, wherein the corresponding mutations change an N to a Q, a C to an S, and a non-cysteine surface-exposed amino acid to a cysteine at positions determined by pair-wise alignment of the ferritin amino acid sequence to an H. pylori ferritin amino acid sequence (SEQ ID NO: 208 or 209).

Exemplary ferritins comprising more than one type of mutation are provided in SEQ ID NOS: 201-207.

5. Structural Alignment

As discussed herein, positions of mutations corresponding to those described with respect to a given polypeptide (e.g., H. pylori ferritin) can be identified by pairwise or structural alignment. Structural alignment is relevant to large protein families such as ferritin where the proteins share similar structures despite considerable sequence variation and many members of the family have been structurally characterized, and can also be used to identify corresponding positions in different versions of other polypeptides described herein, such as RSV polypeptides (e.g., RSV F or G). The protein databank (PDB) comprises 3D structures for many ferritins, including those listed below with their accession numbers.

2jd6, 2jd7—PfFR—*Pyrococcus furiosus*. 2jd8—PfFR+ Zn. 3a68—soFR from gene SferH4—soybean. 3a9q—soFR from gene SferH4 (mutant). 3egm, 3bvf, 3bvi, 3bvk, 3bv1—HpFR—*Heliobacter pylori*. 5c6f—HpFR (mutant)+Fe. 1z4a, 1vlg—FR—*Thermotoga maritime*. 1s3q, 1sq3, 3kx9—FR—*Archaeoglubus fulgidus*. 1krq—FR—*Campylobacter jejuni*. 1eum—EcFR—*Escherichia coli*. 4reu—EcFR+Fe. 4xgs—EcFR (mutant)+Fe202. 4ztt—EcFR (mutant)+Fe20+ Fe2+Fe+02. 1qgh—LiFR—*Listeria innocua*. 3qz3—VcFR—*Vibrio cholerae*. 3vnx—FR—*Ulva pertusa*. 4ism, 4isp, 4itt, 4itw, 4iwj, 4iwk, 4ixk, 3e6s—PnmFR—Pseudo-nitschia multiseries. 4zkh, 4zkw, 4zkx, 4z15, 4z16, 4z1w, 4zmc—PnmFR (mutant)+Fe. 1z6o—FR—*Trichoplusia ni*. 4cmy—FR+Fe—*Chlorobaculum tepidum*. Ferritin light chain (FTL). 1lb3, 1h96—mFTL—mouse. 1rcc, 1rcd, 1rci—bFTL+tartrate+Mg. 1rce, 1rcg—bFTL+tartrate+Mn. 3noz, 3np0, 3np2, 3o7r—hoFTL (mutant)—horse. 3o7s, 3u90—hoFTL. 4vlw—hoFTL—cryo EM. 3rav, 3rd0—hoFTL+barbiturate. Ferritin light+heavy chains: 5gn8—hFTH+Ca.

Structural alignment involves identifying corresponding residues across two (or more) polypeptide sequences by (i) modeling the structure of a first sequence using the known structure of the second sequence or (ii) comparing the structures of the first and second sequences where both are known, and identifying the residue in the first sequence most similarly positioned to a residue of interest in the second sequence. Corresponding residues are identified in some algorithms based on alpha-carbon distance minimization in the overlaid structures (e.g., what set of paired alpha carbons provides a minimized root-mean-square deviation for the alignment). When identifying positions in a non-*H. pylori* ferritin corresponding to positions described with respect to *H. pylori* ferritin, *H. pylori* ferritin can be the "second" sequence. Where a non-*H. pylori* ferritin of interest does not have an available known structure, but is more closely related to another non-*H. pylori* ferritin that does have a known structure than to *H. pylori* ferritin, it may be most effective to model the non-*H. pylori* ferritin of interest using the known structure of the closely related non-*H. pylori* ferritin, and then compare that model to the *H. pylori* ferritin structure to identify the desired corresponding residue in the ferritin of interest. There is an extensive literature on structural modeling and alignment; representative disclosures include U.S. Pat. No. 6,859,736; 8,738,343; and those cited in Aslam et al., Electronic Journal of Biotechnology 20 (2016) 9-13. For discussion of modeling a structure based on a known related structure or structures, see, e.g., Bordoli et al., Nature Protocols 4 (2009) 1-13, and references cited therein.

6. Immune-Stimulatory Moieties; Adjuvants; Conjugated RSV Polypeptides

In some embodiments, an RSV polypeptide and/or an immune-stimulatory moiety, such as an adjuvant, is attached to a surface-exposed amino acid. In some embodiments, the surface-exposed amino acid is a cysteine, e.g., resulting from a mutation discussed above. In some embodiments, the surface-exposed amino acid is a lysine, aspartate, or glutamate. Conjugation procedures using glutaraldehyde (for conjugation of a lysine with an amino-bearing linker or moiety) or a carbodiimide (e.g., 1-Cyclohexyl-3-(2-morpholin-4-yl-ethyl) carbodiimide or 1-Ethyl-3-(3-dimethyl-aminopropyl) carbodiimide (EDC; EDAC) for conjugating an aspartate or glutamate to an amino-bearing linker or moiety, or a lysine to a carboxyl-bearing linker or moiety) are described in, e.g., Chapter 4 of Holtzhauer, M., Basic Methods for the Biochemical Lab, Springer 2006, ISBN 978-3-540-32785-1, available from springer.com.

In some embodiments, an immune-stimulatory moiety, such as an adjuvant, is attached to a surface-exposed amino acid of ferritin. In some embodiments, more than one immune-stimulatory moiety, such as an adjuvant, is attached to a surface-exposed amino acid of ferritin. In some embodiments, twenty-four immune-stimulatory moieties are attached to a ferritin multimer or particle (e.g., one moiety for each monomer in the *H. pylori* ferritin particle). In some embodiments with multiple immune-stimulatory moieties attached to a ferritin nanoparticle, all of the immune-stimulatory moieties are identical. In some embodiments with multiple immune-stimulatory moieties attached to a ferritin nanoparticle, all of the immune-stimulatory moieties are not identical.

a) Types of Immune-Stimulatory Moieties; Adjuvants

Any immune-stimulatory moiety that can be attached to a surface-exposed amino acid (e.g., cysteine) can be used in ferritins according to this disclosure. In some embodiments, the immune-stimulatory moiety is a B cell agonist.

In some embodiments, the immune-stimulatory moiety is not hydrophobic. In some embodiments, the immune-stimulatory moiety is hydrophilic. In some embodiments, the immune-stimulatory moiety is polar. In some embodiments, the immune-stimulatory moiety is capable of hydrogen bonding or ionic bonding, e.g., comprises a hydrogen bond donor, hydrogen bond acceptor, cationic moiety, or anionic moiety. A moiety is considered cationic or anionic if it would be ionized in aqueous solution at a physiologically relevant pH, such as pH 6, 7, 7.4, or 8.

In some embodiments, the immune-stimulatory moiety is an adjuvant. In some embodiments, the adjuvant comprises a pathogen associated molecular pattern (PAMP). In some embodiments, the adjuvant is a toll-like receptor (TLR)

agonist or stimulator of interferon genes (STING) agonist. In some embodiments, the adjuvant activates TLR signaling in B and/or T cells. In some embodiments, the adjuvant regulates the adaptive immune response.

(1) TLR2 Agonists

In some embodiments, the immune-stimulatory moiety is a TLR2 agonist. In some embodiments, the immune-stimulatory moiety stimulates TLR2 signaling. In some embodiments, the immune-stimulatory moiety is a synthetic small molecule ligand of TLR2. In some embodiments, the immune-stimulatory moiety is a synthetic small molecule agonist of TLR2 signaling.

In some embodiments, the TLR2 agonist is PAM2CSK4, FSL-1, or PAM3CSK4.

(2) TLR7/8 Agonists

In some embodiments, the immune-stimulatory moiety is a TLR7 and/or TLR8 agonist (i.e., an agonist of at least one of TLR7 and TLR8). In some embodiments, the immune-stimulatory moiety stimulates TLR7 and/or TLR8 signaling. In some embodiments, the immune-stimulatory moiety is a synthetic small molecule ligand of TLR7 and/or TLR8. In some embodiments, the immune-stimulatory moiety is a synthetic small molecule agonist of TLR7 and/or TLR8 signaling.

In some embodiments, the TLR7 and/or TLR8 agonist is single-stranded (ssRNA). In some embodiments, the TLR7 and/or TLR8 agonist is an imidazoquinoline. In some embodiments, the TLR7 and/or TLR8 agonist is a nucleoside analog.

In some embodiments, the TLR7 and/or TLR8 agonist is an imidazoquinolinamine Toll-like receptor (TLR) agonist, such as 3M-012 (3M Pharmaceuticals). The structure of free 3M-012 is:

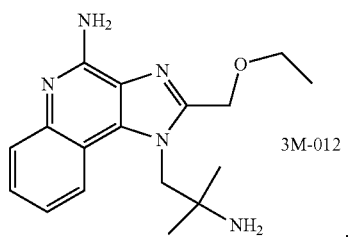 [SMILES: CCOCc1nc2c(N)nc3ccccc3c2n1CC(C)(C)N]

3M-012

It is understood that an immune-stimulatory moiety such as 3M-012 or any moiety discussed herein can be conjugated to a ferritin by substituting an appropriate peripheral atom of the moiety (e.g., a hydrogen) with a bond to a ferritin described herein, e.g., at the sulfur of a surface-exposed cysteine or a linker attached to such a sulfur. Thus, when conjugated to a ferritin, the structure of the immune-stimulatory moiety will differ slightly from the structure of the free molecule.

In some embodiments the TLR7 and/or TLR8 agonist is SM 7/8a. The structure of free SM 7/8a is:

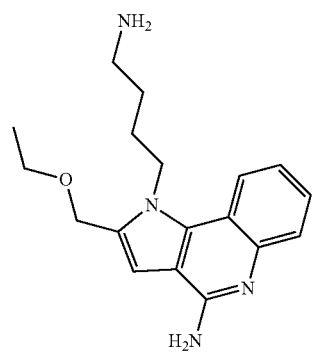

See, e.g., Nat Biotechnol. 2015 November; 33(11):1201-10. doi: 10.1038/nbt.3371.

(3) TLR9 Agonists

In some embodiments, the immune-stimulatory moiety is a TLR9 agonist. In some embodiments, the immune-stimulatory moiety stimulates TLR9 signaling. In some embodiments, the immune-stimulatory moiety is a synthetic small molecule ligand of TLR9. In some embodiments, the immune-stimulatory moiety is a synthetic small molecule agonist of TLR9 signaling.

In some embodiments, the TLR9 agonist is a CpG oligodeoxynucleotide (ODN). In some embodiments, the TLR9 agonist is an unmethylated CpG ODN. In some embodiments, the CpG ODN comprises a partial or complete phosphorothioate (PS) backbone instead of the natural phosphodiester (PO) backbone found in ordinary DNA.

In some embodiments, the CpG ODN is a Class B ODN, which comprises one or more 6mer CpG motif comprising 5' Purine (Pu)-Pyrimidine (Py)-C-G-Py-Pu 3'; has a fully phosphorothioated (i.e., PS-modified) backbone; and has a length of 18-28 nucleotides. In some embodiments, the CpG ODN comprises the sequence of SEQ ID NO: 210, optionally comprising phosphorothioate linkages in the backbone.

In some embodiments, the TLR9 agonist comprises an immune-stimulatory sequence (ISS). In some embodiments the TLR9 agonist is ISS-1018 (Dynavax) (SEQ ID NO: 210).

(4) STING Agonists

In some embodiments, the immune-stimulatory moiety is a STING (Stimulator of Interferon Genes Protein, also known as Endoplasmic Reticulum IFN Stimulator) agonist. In some embodiments, the immune-stimulatory moiety stimulates STING signaling. In some embodiments, the immune-stimulatory moiety is a synthetic small molecule ligand of STING. In some embodiments, the immune-stimulatory moiety is a synthetic small molecule agonist of STING signaling.

In some embodiments the STING agonist is a cyclic dinucleotide (CDN). See, e.g., Danilchanka et al., Cell 154:962-970 (2013). Exemplary CDNs include cdA, cdG, cAMP-cGMP, and 2'-5',3'-5' cGAMP (see Danilchanka et al. for structures). STING agonists also include synthetic agonists such as DMXAA

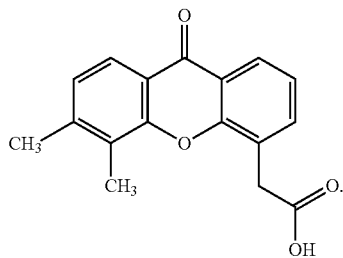 [SMILES: Cc1ccc2c(=O)c3cccc(CC(=O)O)c3oc2c1C]

b) Conjugated RSV Polypeptides

In some embodiments, an RSV polypeptide is conjugated to a surface-exposed amino acid of ferritin. In some embodiments, the RSV polypeptide renders the ferritin protein antigenic. In some embodiments, the RSV polypeptide is antigenic alone, whereas in some embodiments, the RSV polypeptide is antigenic because of its association with ferritin. In some embodiments, the RSV polypeptide is any one of the RSV F or G polypeptides described herein.

c) Conjugation

In some embodiments, a surface-exposed cysteine (e.g., resulting from a mutation described herein) or a cysteine in a peptide linker attached to ferritin (e.g., N-terminally to ferritin) is used to conjugate an immune-stimulatory moiety, such as an adjuvant, or an RSV polypeptide to a ferritin. In some embodiments, a linker is conjugated to such a cysteine, which linker can be subsequently conjugated to an immune-stimulatory moiety, such as an adjuvant, or an RSV polypeptide. In some embodiments, such a cysteine creates a chemical handle for conjugation reactions to attach an adjuvant, linker, or an RSV polypeptide. In some embodiments, bioconjugates are produced, wherein an immune-stimulatory moiety, such as an adjuvant, or an RSV polypeptide is linked to a ferritin after reduction of such a cysteine. In some embodiments, the cysteine is an unpaired surface-exposed cysteine, i.e., that lacks a partner cysteine in an appropriate position to form a disulfide bond. In some embodiments, the cysteine is an unpaired cysteine that comprises a free thiol side chain.

(1) Types of Conjugation Chemistries

Any type chemistry can be used to conjugate the immune-stimulatory moiety, such as an adjuvant, or an RSV polypeptide to the ferritin, e.g., via reaction a surface-exposed amino acid such as cysteine or another amino acid such as Lys, Glu, or Asp.

In some embodiments, the conjugation is performed using click chemistry. As used herein, "click chemistry" refers to a reaction between a pair of functional groups that rapidly and selective react (i.e., "click") with each other. In some embodiments, the click chemistry can be performed under mild, aqueous conditions. In some embodiments, a click chemistry reaction takes advantage of a cysteine on the surface of the ferritin, such as a cysteine resulting from mutation of a surface-exposed amino acid, to perform click chemistry using a functional group that can react with the cysteine.

A variety of reactions that fulfill the criteria for click chemistry are known in the field, and one skilled in the art could use any one of a number of published methodologies (see, e.g., Hein et al., Pharm Res 25(10):2216-2230 (2008)). A wide range of commercially available reagents for click chemistry could be used, such as those from Sigma Aldrich, Jena Bioscience, or Lumiprobe. In some embodiments, conjugation is performed using click chemistry as described in the Examples below.

In some embodiments, the click chemistry reaction occurs after reduction of the ferritin.

In some embodiments, the click chemistry may be a 1-step click reaction. In some embodiments, the click chemistry may be a 2-step click reaction.

In some embodiments, the reaction(s) comprises metal-free click chemistry. In some embodiments, the reaction(s) comprise thiol-maleimide and/or disulfide exchange.

Metal Free Click Chemistry

Metal-free click chemistry can be used for conjugation reactions to avoid potential oxidation of proteins. Metal-free click chemistry has been used to form antibody conjugates (see van Geel et al., Bioconjugate Chem. 2015, 26, 2233-2242).

In some embodiments, metal-free click chemistry is used in reactions to attach adjuvant to ferritin. In some embodiments, copper-free conjugation is used in reactions to attach adjuvant to ferritin. In some embodiments, the metal-free click chemistry uses bicyclo[6.1.0]nonyne (BCN). In some embodiments, the metal-free click chemistry uses dibenzoazacyclooctyne (DBCO). In some embodiments BCN or DBCO reacts with an azide group.

DBCO has high specificity for azide groups via a strain-promoted click reaction in the absence of a catalyst, resulting in high yield of a stable triazole. In some embodiments, DBCO reacts with azide in the absence of copper catalyst.

In some embodiments, metal-free click chemistry is used in a 1-step click reaction. In some embodiments, metal-free click chemistry is used in a 2-step click reaction.

Thiol-Maleimide and Disulfide Exchange

Ferritins described herein can comprise a cysteine comprising a thiol, also known as a sulfhydryl, which is available for reaction with sulfhydryl-reactive chemical groups (or which can be made available through reduction). Thus, the cysteine allows chemoselective modification to add an immune-stimulatory moiety, such as an adjuvant, to the ferritin. Under basic conditions, the cysteine will be deprotonated to generate a thiolate nucleophile, which can react with soft electrophiles, such as maleimides and iodoacetamides. The reaction of the cysteine with a maleimide or iodoacetamide results in a carbon-sulfur bond.

In some embodiments, a sulfhydryl-reactive chemical group reacts with the surface-exposed cysteine or cysteine in the linker of the ferritin. In some embodiments, the sulfhydryl-reactive chemical group is a haloacetyl, maleimide, aziridine, acryloyl, arylating agent, vinylsulfone, pyridyl disulfide, or TNB-thiol.

In some embodiments, the sulfhydryl-reactive chemical group conjugates to the sulfhydryl of the cysteine by alkylation (i.e., formation of a thioether bond)). In some embodiments, the sulfhydryl-reactive chemical group conjugates to the sulfhydryl of the cysteine by disulfide exchange (i.e., formation of a disulfide bond).

In some embodiments, the reaction to conjugate an immune-stimulatory moiety, such as an adjuvant, to the ferritin is a thiol-maleimide reaction.

In some embodiments, the sulfhydryl-reactive chemical group is a maleimide. In some embodiments, reaction of a maleimide with the cysteine results in formation of a stable thioester linkage, e.g., that is not reversible. In some embodiments, the maleimide does not react with tyrosines, histidines, or methionines in the ferritin. In some embodiments, unreacted maleimides are quenched at the end of the reaction by adding a free thiol, e.g., in excess.

In some embodiments, the reaction to conjugate an immune-stimulatory moiety, such as an adjuvant, to the ferritin is a thiol-disulfide exchange, also known as a disulfide interchange. In some embodiments, the reaction involves formation of a mixed disulfide comprising a portion of the original disulfide. In some embodiments, the original disulfide is the cysteine introduced in the ferritin by mutation of a surface-exposed amino acid or addition of an N-terminal linker.

In some embodiments, the sulfhydryl-reactive chemical group is a pyridyl dithiol. In some embodiments, the sulfhydryl-reactive chemical group is a TNB-thiol group.

(2) Conjugated Linkers

In some embodiments, an immune-stimulatory moiety, such as an adjuvant, or an RSV polypeptide is attached to the ferritin via a linker that is covalently bound to a surface-exposed amino acid such as a cysteine. In some embodiments, the linker comprises a polyethylene glycol, e.g., a PEG linker. In some embodiments, the polyethylene glycol (e.g., PEG) linker increases water solubility and ligation efficiency of the ferritin linked to the immune-stimulatory moiety, such as an adjuvant. The PEG linker is between 2 and 18 PEGs long, e.g., PEG4, PEG5, PEG6, PEG7, PEG5, PEG5, PEG10, PEG11, PEG12, PEG13, PEG14, PEG15, PEG16, PEG17, and PEG18.

In some embodiments of the 2-step click chemistry protocol, the amine-reactive group is DBCO. In some embodiments of the 2-step click chemistry protocol, the DBCO reacts with an azide group attached to an ISM.

In some embodiments, a maleimide-linker-DBCO is used. In some embodiments, the maleimide-linker-DBCO is conjugated to ferritin after the ferritin is reduced. In some embodiments, the maleimide-linker-reagent is conjugated to ferritin by reaction of the maleimide with the cysteine of the ferritin in a first step. In some embodiments, the DBCO is used to link to an ISM attached to azide. In some embodiments, the ISM coupled to azide is ISS-1018. In some embodiments, the adjuvant coupled to azide is 3M-012 or CpG.

In some embodiments, a linker with a reactive group is added to the ISM. In some embodiments, the linker is a PEG4-azide linker or a PEG4-maleimide linker.

In some embodiments, a PEG4-azide linker is conjugated to 3M-012. An exemplary structure of 3M-012 conjugated to a PEG4-azide linker is:

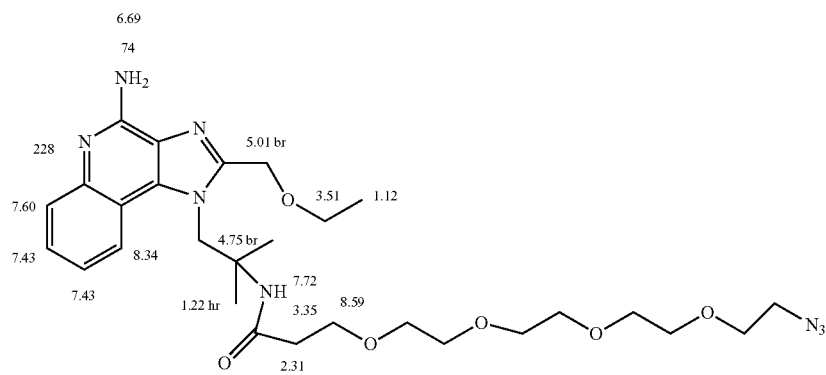 [SMILES: CCOCc1nc2c(N)nc3ccccc3c2n1CC(C)(C)NC(=O)CCOCCOCCOCCOCCN=[N+]=[N-]]

In some embodiments, the linker comprises a maleimide. In some embodiments, the linker comprises the components of immune-stimulatory moiety (ISM)-linker-maleimide. In some embodiments, the ISM-linker-maleimide is conjugated to ferritin in a 1-step click chemistry reaction by reaction of the maleimide with a cysteine of the ferritin. In some embodiments, the ISM of the adjuvant-linker-maleimide is SM7/8a. In some embodiments, the linker of the ISM-linker-maleimide is PEG4. In some embodiments, the ISM-linker-maleimide is SM7/8a-PEG4-maleimide.

In some embodiments, a 2-step click chemistry protocol is used with a linker comprising a sulfhydryl-reactive chemical group at one end and an amine-reactive group at the other end. In such a 2-step click chemistry protocol, a sulfhydryl-reactive chemical group reacts with a cysteine of the ferritin, while the amine-reactive group reacts with a reagent attached to the ISM. In this way, the ISM is conjugated to the ferritin via a set of 2 click chemistry reagents.

In some embodiments of the 2-step click chemistry protocol, the sulfhydryl-reactive chemical group is maleimide. In some embodiments of the 2-step click chemistry protocol, the maleimide reacts with the cysteine introduced in the ferritin by mutation of a surface-exposed amino acid or addition of an N-terminal linker.

In some embodiments, a PEG4-azide linker is conjugated to SM7/8a. An exemplary structure of SM7/8a conjugated to a PEG4-azide linker is:

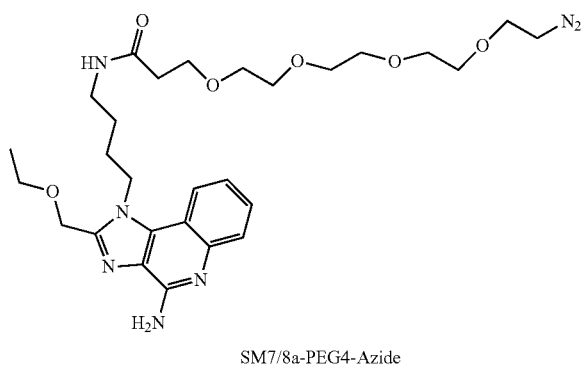

SM7/8a-PEG4-Azide

In some embodiments, a PEG4-maleimide linker is conjugated to SM7/8a. An exemplary structure of SM7/8a conjugated to a PEG4-maleimide linker is:

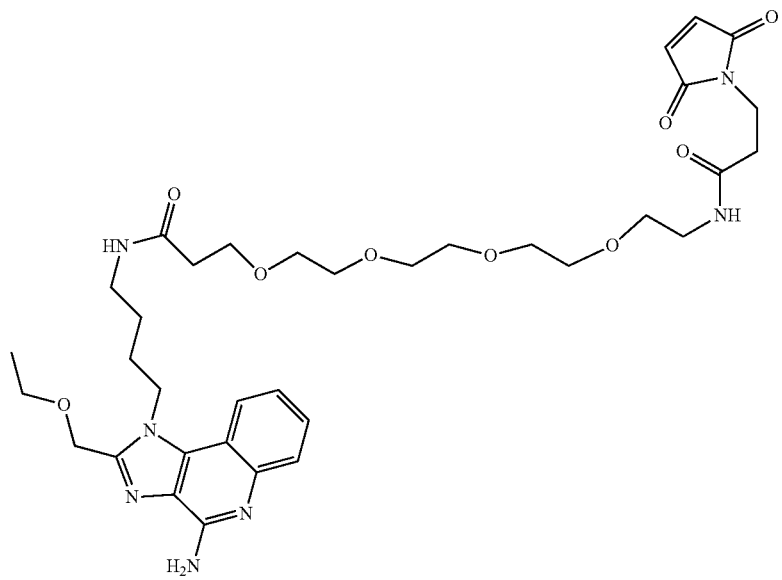

SM7/8 a-PEG4-Maleimide

In some embodiments, an azide group is conjugated to ISS-1018. An exemplary structure of ISS-1018 conjugated to an NHS ester-azide linker is:

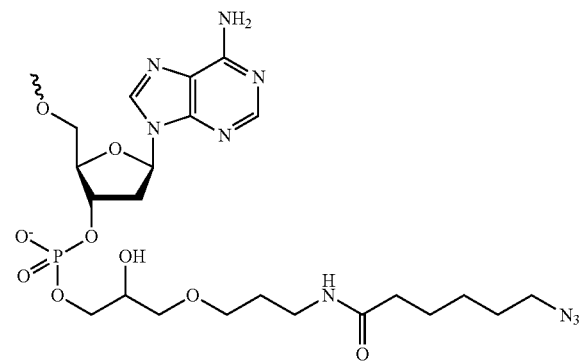

E. Linkers

In some embodiments, a linker separates the amino acid sequence of the RSV polypeptide from the amino acid sequence of ferritin. Any linker may be used. In some embodiments, the linker is a peptide linker, which can facilitate expression of the antigenic ferritin polypeptide as a fusion protein (e.g., from a single open reading frame). In some embodiments, the linker is a glycine-serine linker. In some embodiments, the glycine-serine linker is GS, GGGS (SEQ ID NO: 226), 2XGGGS (SEQ ID NO: 227) (i.e., GGGSGGGS (SEQ ID NO: 227)), or 5XGGGS (SEQ ID NO: 228). The linker may be N- or C-terminal to ferritin.

In some embodiments, the linker is 2, 3, 4, 5, 6, 7, 8, 9, or 10 amino acids in length. In some embodiments, the linker is about 2-4, 2-6, 2-8, 2-10, 2-12, or 2-14 amino acids in length. In some embodiments, the linker is at least 15 amino acids in length. In some embodiments, the linker is at least 25 amino acids in length. In some embodiments, the linker is at least 30 amino acids in length. In some embodiments, the linker is at least 35 amino acids in length. In some embodiments, the linker is at least 40 amino acids in length. In some embodiments, the linker is less than or equal to 60 amino acids in length. In some embodiments, the linker is less than or equal to 50 amino acids in length. In some embodiments, the linker is about 16, 28, 40, 46, or 47 amino acids in length. In some embodiments, the linker is flexible. In some embodiments, the linker comprises a cysteine, e.g., for use as a site for conjugation of an immune-stimulatory moiety (e.g., adjuvant); an exemplary linker comprising a cysteine is provided as SEQ ID NO: 225. In some embodiments, the linker comprises a sequence with at least 75%, 80%, 85%, 90%, or 95% identity to SEQ ID NO: 225, and further comprises a cysteine corresponding to the cysteine in SEQ ID NO: 225. In some embodiments, the linker comprises at least 25 amino acids (e.g., 25 to 60 amino acids), wherein a cysteine is located at a position ranging from the $8^{th}$ amino acid from the N-terminus to the $8^{th}$ amino acid from the C-terminus, or within 10 amino acids of the central residue or bond of the linker.

In some embodiments, the linker comprises glycine (G) and/or serine (S) amino acids. In some embodiments, the linker comprises or consists of glycine (G), serine (S), asparagine (N), and/or alanine (A) amino acids, and optionally a cysteine as discussed above. In some embodiments, the linker comprises an amino acid sequence with at least 80%, 85%, 90%, 95%, 97%, 98%, 99%, or 100% identity to SEQ ID NO: 222. In some embodiments, the linker comprises GGGGSGGGGSGGGGSG (SEQ ID NO: 220), GGSGSGSNSSASSGASSGGASGGSGGSG (SEQ ID NO: 221), GGSGSASSGASASGSSNGSGSGSGSNSSASS-GASSGGASGGSGGSG (SEQ ID NO: 222), or GS. In some embodiments, the linker comprises FR1 (SEQ ID NO: 223) or FR2 (SEQ ID NO: 224).

In some embodiments, the ferritin comprises H. pylori ferritin with the amino terminal extension of bullfrog ferritin (which will be referred to as hybrid ferritin). In some embodiments, this hybrid ferritin forms multimers with RSV polypeptide-attachment sites distributed evenly on the surface (see Kanekiyo 2015). In some embodiments, N-terminal fusion proteins with hybrid ferritin allow presentation of an RSV polypeptide on the ferritin nanoparticle surface. In some embodiments, a ferritin comprises a glutamate at a position corresponding to position 13 of SEQ ID NO: 208 (hybrid ferritin, which comprises this glutamate) or position 6 in SEQ ID NO: 209 (wild-type *H. pylori* ferritin, in which position 6 is isoleucine). In combination with a bullfrog linker, this glutamate is thought to preserve the conserved salt bridge found in human and bullfrog ferritins (6R and 14E in both human light chain and bullfrog lower-subunit ferritins). See Kanekiyo et al., Cell 162, 1090-1100 (2015)).

In some embodiments, an RSV polypeptide is linked to ferritin via a cysteine-thrombin-histidine linker. In some embodiments, this linker is used to directly conjugate a moiety (e.g., immune-stimulatory moiety or RSV polypeptide) to ferritin via click chemistry. An exemplary sequence comprising a cysteine-thrombin-histidine linker is SEQ ID NO: 218. Click chemistry suitable for conjugation reactions involving the cysteine-thrombin-histidine linker is discussed above.

In some embodiments, a linker comprising a cysteine as a conjugation site for an immune-stimulatory moiety such as an adjuvant is used in a construct comprising a ferritin molecule lacking an unpaired, surface-exposed cysteine, or in a construct comprising a ferritin molecule comprising an unpaired, surface-exposed cysteine.

In some embodiments, a construct does not comprise a linker. In some embodiments, a construct comprises one linker. In some embodiments, a construct comprises two or more than two linkers.

F. Compositions; Uses and Methods for Vaccination

In some embodiments, the present invention provides methods of immunizing a subject against infection with RSV. The present invention further provides methods of eliciting an immune response against RSV in a subject. In some embodiments, the present methods comprise administering to the subject an effective amount of a pharmaceutical composition described herein to a subject. In some embodiments, the present methods comprises administering to the subject an effective amount of an antigenic RSV polypeptide, antigenic ferritin polypeptide, or nanoparticle described herein to a subject.

In some embodiments, a composition comprising any one or more of the polypeptides, nanoparticles, or fusion proteins described herein and a pharmaceutically acceptable vehicle, adjuvant, or excipient is provided.

In some embodiments, a polypeptide, nanoparticle, or composition described herein is administered to a subject, such as a human, to immunize against infection caused by RSV. In some embodiments, a polypeptide or fusion protein described herein is administered to a subject, such as a human, to produce a protective immune response to future infection with RSV. In some embodiments, any one or more of the polypeptides, nanoparticles, or compositions described herein are provided for use in immunizing against infection caused by RSV. In some embodiments, any one or more of the polypeptides, nanoparticles, or compositions described herein are provided for use in producing a protective immune response to future infection with RSV. In some embodiments, the protective immune response decreases the incidence of infection with RSV, pneumonia, bronchiolitis, or asthma In some embodiments, a composition comprises an RSV F polypeptide described herein. In some embodiments, a composition comprises an RSV G polypeptide described herein. In some embodiments, a composition comprises an RSV F polypeptide described herein and an RSV G polypeptide. In some embodiments, a composition comprises an RSV G polypeptide described herein and an RSV F polypeptide. In some embodiments, a composition comprises an RSV F polypeptide described herein and an RSV G polypeptide described herein.

In some embodiments, a composition comprising an RSV F polypeptide described herein elicits a superior neutralizing response to RSV compared to immunization with a post-fusion RSV F polypeptide. In some embodiments, immunization with an RSV F polypeptide described herein (e.g., a polypeptide or nanoparticle comprising an RSV F polypeptide described herein) elicits a higher titer of antibodies directed against pre-fusion RSV F compared to immunization with a post-fusion RSV F. In some embodiments, immunization with an RSV F polypeptide described herein elicits a lower titer of antibodies directed against post-fusion RSV F compared to immunization with a post-fusion RSV F. In some embodiments, immunization with an RSV F polypeptide described herein elicits a higher ratio of total antibody being directed against pre-fusion RSV F compared to immunization with a post-fusion RSV F. Immunization with an RSV antigen described herein may provide better protection against RSV compared to immunization with a post-fusion RSV F. Epitopes present in post-fusion RSV F, and shared with pre-fusion F, may be non-neutralizing and in some instances have been suggested to elicit antibodies which increase RSV infection. In some embodiments, a composition comprising an RSV F polypeptide described herein elicits a higher neutralizing response to RSV while lessening the antibodies directed against post-fusion RSV F. Thus, in some embodiments, a composition comprising an RSV F polypeptide described herein elicits a higher RSV neutralizing titer to post-fusion F binding response.

In some embodiments, immunization with an RSV antigen described herein yields an improved safety profile compared to immunization with a post-fusion RSV F. This improved safety profile may be related to blocking non-neutralizing epitopes or poorly neutralizing epitopes present on the post-fusion conformation. It has been reported that antibodies which bind the post-fusion conformation may increase RSV infection through antibody mediated viral infection. Thus, post-fusion antibodies that do not significantly neutralize the RSV virus may increase RSV infection, such as those that recognize both the pre-fusion and post-fusion conformation.

In some embodiments, a composition comprising an RSV G polypeptide described herein elicits a neutralizing response to RSV.

In some embodiments, a composition comprising an RSV F and RSV G polypeptide described herein elicits a neutralizing response to RSV. In some embodiments, a composition comprising an RSV F and RSV G polypeptide described herein provides improved protection against RSV, e.g., a higher neutralizing titer than a composition that does not comprise both antigens.

1. Subjects

In some embodiments, the subject is a mammal. In some embodiments, the subject is a human.

In some embodiments, the subject is an adult (greater than or equal to 18 years of age). In some embodiments, the subject is a child or adolescent (less than 18 years of age). In some embodiments, the subject is elderly (greater than 60 years of age). In some embodiments, the subject is a non-elderly adult (greater than or equal to 18 years of age and less than or equal to 60 years of age).

In some embodiments, more than one administration of the composition is administered to the subject. In some embodiments, a booster administration improves the immune response.

In some embodiments, any one or more of the antigenic polypeptides, or compositions described herein are for use in a mammal, such as a primate (e.g., non-human primate, such as a monkey (e.g., a macaque, such as rhesus or cynomolgus) or ape), rodent (e.g., mouse or rat), or domesticated mammal (e.g., dog, rabbit, cat, horse, sheep, cow, goat, camel, or donkey). In some embodiments, any one or more of the antigenic polypeptides, or compositions described herein are for use in a bird, such as a fowl (e.g., chicken, turkey, duck, goose, guineafowl, or swan).

2. Adjuvants

As described herein, adjuvants may be conjugated to ferritin via a surface exposed amino acid, e.g., a cysteine. Non-conjugated adjuvant may also be administered together with the antigenic ferritin polypeptides described herein to a subject. In some embodiments, administration of adjuvant together with the antigenic ferritin polypeptide produces a higher titer of antibodies against the RSV polypeptide in the subject as compared to administration of the RSV polypeptide alone, or antigenic ferritin polypeptide alone, without the adjuvant. An adjuvant may promote earlier, more potent, or more persistent immune response to the antigenic polypeptide.

In some embodiments, a composition comprises one adjuvant. In some embodiments, a composition comprises more than one adjuvant. In some embodiments, a composition does not comprise an adjuvant.

In some embodiments, an adjuvant comprises aluminum. In some embodiments, an adjuvant is aluminum phosphate. In some embodiments, an adjuvant is Alum (Alyhydrogel '85 2%; Brenntag—Cat #21645-51-2).

In some embodiments, an adjuvant is an organic adjuvant. In some embodiments, an adjuvant is an oil-based adjuvant. In some embodiments, an adjuvant comprises an oil-in-water nanoemulsion.

In some embodiments, an adjuvant comprises squalene. In some embodiments, the adjuvant comprising squalene is Ribi (Sigma adjuvant system Cat #S6322-1v1), Addavax™ MF59, AS03, or AF03 (see U.S. Pat. No. 9,703,095). In some embodiments, the adjuvant comprising squalene is a nanoemulsion.

In some embodiments, an adjuvant comprises a polyacrylic acid polymer (PAA). In some embodiments, the adjuvant comprising PAA is SPA09 (see WO 2017218819).

In some embodiments, an adjuvant comprises non-metabolizable oils. In some embodiments, the adjuvant is Incomplete Freund's Adjuvant (IFA).

In some embodiments, an adjuvant comprises non-metabolizable oils and killed Mycobacterium tuberculosis. In some embodiments, the adjuvant is Complete Freund's Adjuvant (CFA).

In some embodiments, an adjuvant is a lipopolysaccharide. In some embodiments, an adjuvant is monophosphoryl A (MPL or MPLA).

3. Pharmaceutical Compositions

In various embodiments, a pharmaceutical composition comprising an antigenic ferritin polypeptide described herein and/or related entities is provided. In some embodiments, the pharmaceutical composition is an immunogenic composition (e.g., a vaccine) capable of eliciting an immune response such as a protective immune response against a pathogen.

For example, in some embodiments, the pharmaceutical compositions may comprise one or more of the following: (1) an antigenic ferritin protein comprising (i) a mutation replacing a surface-exposed amino acid with a cysteine and (ii) an RSV polypeptide; (2) an antigenic ferritin protein comprising (i) a mutation replacing a surface exposed amino acid with a cysteine and an immune-stimulatory moiety linked to the cysteine; and (ii) an RSV polypeptide; (3) antigenic ferritin protein comprising (i) a surface-exposed cysteine, (ii) a peptide linker N-terminal to the ferritin protein, and (iii) an RSV polypeptide N-terminal to the peptide linker; (4) an antigenic ferritin protein comprising: (i) a mutation replacing a surface exposed amino acid with a cysteine and an immune-stimulatory moiety linked to the cysteine, (ii) a mutation replacing the internal cysteine at position 31 of *H. pylori* ferritin, or a mutation of an internal cysteine at a position that is analogous to position 31 of a non-*H. pylori* ferritin as determined by pair-wise or structural alignment, with a non-cysteine amino acid, (iii) a mutation replacing a surface-exposed asparagine with a non-asparagine amino acid, and (iv) an RSV polypeptide; or (5) a ferritin particle comprising any of the foregoing ferritin proteins. In some embodiments, the pharmaceutical composition comprises an antigenic RSV polypeptide comprising an RSV F polypeptide, wherein an epitope of the RSV polypeptide that is shared between pre-fusion RSV F and post-fusion RSV F is blocked, and/or an antigenic RSV polypeptide comprising an RSV F polypeptide, wherein the RSV F polypeptide comprises amino acid residues 62-69 and 196-209 of SEQ ID NO: 26 and an asparagine corresponding to position 328, 348, or 507 of SEQ ID NO: 26, optionally wherein the antigenic RSV polypeptide further comprises ferritin.

In some embodiments, the present invention provides pharmaceutical compositions comprising antibodies or other agents related to the antigenic polypeptides described herein. In an embodiment, the pharmaceutical composition comprises antibodies that bind to and/or compete with an antigenic polypeptide described herein. Alternatively, the antibodies may recognize viral particles comprising the RSV polypeptide component of an antigenic polypeptide described herein.

In some embodiments, the pharmaceutical compositions as described herein are administered alone or in combination with one or more agents to enhance an immune response, e.g., an adjuvant described above. In some embodiments, a pharmaceutical composition further comprises an adjuvant described above.

In some embodiments, the pharmaceutical composition further comprises a pharmaceutically acceptable carrier or excipient. As used herein, the term "carrier" refers to a diluent, adjuvant, excipient, or vehicle with which a pharmaceutical composition is administered. In exemplary embodiments, carriers can include sterile liquids, such as, for example, water and oils, including oils of petroleum, animal, vegetable, or synthetic origin, such as, for example, peanut oil, soybean oil, mineral oil, sesame oil and the like. In some embodiments, carriers are or include one or more solid components. Pharmaceutically acceptable carriers can also include, but are not limited to, saline, buffered saline, dextrose, glycerol, ethanol, and combinations thereof. As used herein, an excipient is any non-therapeutic agent that may be included in a pharmaceutical composition, for example to provide or contribute to a desired consistency or stabilizing effect. Suitable pharmaceutical excipients include, but are not limited to, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. In various embodiments, the pharmaceutical composition is sterile.

In some embodiments, the pharmaceutical composition contains minor amounts of wetting or emulsifying agents, or pH buffering agents. In some embodiments, the pharmaceutical compositions of may include any of a variety of additives, such as stabilizers, buffers, or preservatives. In addition, auxiliary, stabilizing, thickening, lubricating, and coloring agents can be included.

In various embodiments, the pharmaceutical composition may be formulated to suit any desired mode of administration. For example, the pharmaceutical composition can take the form of solutions, suspensions, emulsion, drops, tablets, pills, pellets, capsules, capsules containing liquids, gelatin capsules, powders, sustained-release formulations, suppositories, emulsions, aerosols, sprays, suspensions, lyophilized powder, frozen suspension, desiccated powder, or any other form suitable for use. General considerations in the formulation and manufacture of pharmaceutical agents may be found, for example, in Remington's Pharmaceutical Sciences, 19th ed., Mack Publishing Co., Easton, PA, 1995; incorporated herein by reference.

The pharmaceutical composition can be administered via any route of administration. Routes of administration include, for example, oral, intradermal, intramuscular, intraperitoneal, intravenous, subcutaneous, intranasal, mucosal, epidural, sublingual, intranasal, intracerebral, intravaginal, transdermal, rectally, by intratracheal instillation, bronchial instillation, inhalation, or topically. Administration can be local or systemic. In some embodiments, administration is carried out orally. In another embodiment, the administration is by parenteral injection. In some instances, administration results in the release of the antigenic ferritin polypeptide described herein into the bloodstream. The mode of administration can be left to the discretion of the practitioner.

In some embodiments, the pharmaceutical composition is suitable for parenteral administration (e.g. intravenous, intramuscular, intraperitoneal, and subcutaneous). Such compositions can be formulated as, for example, solutions, suspensions, dispersions, emulsions, and the like. They may also be manufactured in the form of sterile solid compositions (e.g. lyophilized composition), which can be dissolved or suspended in sterile injectable medium immediately before use. For example, parenteral administration can be achieved by injection. In such embodiments, injectables are prepared in conventional forms, i.e., either as liquid solutions or suspensions, solid forms suitable for solution or suspension in liquid prior to injection, or as emulsions. In some embodiments, injection solutions and suspensions are prepared from sterile powders, lyophilized powders, or granules.

In a further embodiment, the pharmaceutical composition is formulated for delivery by inhalation (e.g., for direct delivery to the lungs and the respiratory system). For example, the composition may take the form of a nasal spray or any other known aerosol formulation. In some embodiments, preparations for inhaled or aerosol delivery comprise a plurality of particles. In some embodiments, such preparations can have a mean particle size of about 1, about 2, about 3, about 4, about 5, about 6, about 7, about 8, about 9, about 10, about 11, about 12, or about 13 microns. In some embodiments, preparations for inhaled or aerosol delivery are formulated as a dry powder. In some embodiments, preparations for inhaled or aerosol delivery are formulated as a wet powder, for example through inclusion of a wetting agent. In some embodiments, the wetting agent is selected from the group consisting of water, saline, or other liquid of physiological pH.

In some embodiments, the pharmaceutical composition in accordance with the invention are administered as drops to the nasal or buccal cavity. In some embodiments, a dose may comprise a plurality of drops (e.g., 1-100, 1-50, 1-20, 1-10, 1-5, etc.).

The present pharmaceutical composition may be administered in any dose appropriate to achieve a desired outcome. In some embodiments, the desired outcome is the induction of a long-lasting adaptive immune response against the source of an RSV polypeptide present in an antigenic ferritin polypeptide present in the composition. In some embodiments, the desired outcome is a reduction in the intensity, severity, frequency, and/or delay of onset of one or more symptoms of infection. In some embodiments, the desired outcome is the inhibition or prevention of infection. The dose required will vary from subject to subject depending on the species, age, weight, and general condition of the subject, the severity of the infection being prevented or treated, the particular composition being used, and its mode of administration.

In some embodiments, pharmaceutical compositions in accordance with the invention are administered in single or multiple doses. In some embodiments, the pharmaceutical compositions are administered in multiple doses administered on different days (e.g., prime-boost vaccination strategies). In some embodiments, the pharmaceutical composition is administered as part of a booster regimen.

In various embodiments, the pharmaceutical composition is co-administered with one or more additional therapeutic agents. Co-administration does not require the therapeutic agents to be administered simultaneously, if the timing of their administration is such that the pharmacological activities of the additional therapeutic agent and the active ingredient(s) in the pharmaceutical composition overlap in time, thereby exerting a combined therapeutic effect. In general, each agent will be administered at a dose and on a time schedule determined for that agent.

4. Nucleic Acid/mRNA

Also provided is a nucleic acid encoding an antigenic polypeptide described herein. In some embodiments, the nucleic acid is an mRNA. Any nucleic acid capable of undergoing translation resulting in a polypeptide is considered an mRNA for purposes of this disclosure.

5. Kits

Also provided herein are kits comprising one or more antigenic polypeptides, nucleic acids, antigenic ferritin particles, antigenic lumazine synthase particles, compositions, or pharmaceutical compositions described herein. In some embodiments, a kit further comprises one or more of a solvent, solution, buffer, instructions, or desiccant.

TABLE 1

(Sequence Table): Description of the Sequences

| Description | Sequence | SEQ ID NO |
|---|---|---|
| RF8085 NIH DS-CAV1 with single chain linker SGSGS (SEQ ID NO: 229) on bullfrog (bf) hp ferritin N19Q_C31S_S111C (control)(same protein sequence as 2, expressed with transient transfection cloning vector) | MELLILKANAITTILTAVTFCFASGQNITEEFYQSTCSAVSKGYLSALRTGWYTSVITIELSNIKEN KCNGTDAKVKLIKQELDKYKNAVTELQLLMGSGNVGLGGAIASGVAVCKVLHLEGEVNKIKSALLST NKAVVSLSNGVSVLTFKVLDLKNYIDKQLLPILNKQSCSISNIETVIEFQQKNNRLLEITREFSVNA GVTTPVSTYMLTNSELLSLINDMPITNDQKKLMSNNVQIVRQQSYSIMCIIKEEVLAYVVQLPLYGV IDTPCWKLHTSPLCTTNTKEGSNICLTRTDRGWYCDNAGSVSFFPQAETCKVQSNRVFCDTMNSRTL PSEVNLCNVDIFNPKYDCKIMTSKTDVSSSVITSLGAIVSCYGKTKCTASNKNRGIIKTFSNGCDYV SNKGVDTVSVGNTLYYVNKQEGKSLYVKGEPIINFYDPLVFPSDEFDASISQVNEKINQSLAFIRKS DELLSGSGSESQVRQQFSKDIEKLLNEQVNKEMQSSNLYMSMSSWSYTHSLDGAGLFLFDHAAEEYE HAKKLIIFLNENNVPVQLTSISAPEHKFEGLTQIFQKAYEHEQHISESINNIVDHAIKCKDHATFNF LQWYVAEQHEEEVLFKDILDKIELIGNENHGLYLADQYVKGIAKSRKS | 1 |
| RF8090: NIH DS-CAV1 with single chain linker SGSGS (SEQ ID NO: 229) on bullfrog (bf) hp ferritin N19Q_C31S_S111C (control)(same protein sequence as 1, expressed with cloning vector used for CHO cell line generation | MELLILKANAITTILTAVTFCFASGQNITEEFYQSTCSAVSKGYLSALRTGWYTSVITIELSNIKEN KCNGTDAKVKLIKQELDKYKNAVTELQLLMGSGNVGLGGAIASGVAVCKVLHLEGEVNKIKSALLST NKAVVSLSNGVSVLTFKVLDLKNYIDKQLLPILNKQSCSISNIETVIEFQQKNNRLLEITREFSVNA GVTTPVSTYMLTNSELLSLINDMPITNDQKKLMSNNVQIVRQQSYSIMCIIKEEVLAYVVQLPLYGV IDTPCWKLHTSPLCTTNTKEGSNICLTRTDRGWYCDNAGSVSFFPQAETCKVQSNRVFCDTMNSRTL PSEVNLCNVDIFNPKYDCKIMTSKTDVSSSVITSLGAIVSCYGKTKCTASNKNRGIIKTFSNGCDYV SNKGVDTVSVGNTLYYVNKQEGKSLYVKGEPIINFYDPLVFPSDEFDASISQVNEKINQSLAFIRKS DELLSGSGSESQVRQQFSKDIEKLLNEQVNKEMQSSNLYMSMSSWSYTHSLDGAGLFLFDHAAEEYE HAKKLIIFLNENNVPVQLTSISAPEHKFEGLTQIFQKAYEHEQHISESINNIVDHAIKCKDHATFNF LQWYVAEQHEEEVLFKDILDKIELIGNENHGLYLADQYVKGIAKSRKS | 2 |
| RF8100: Add a single T324N glycan site to RSV scF_SGSGS-bf-pFerr_N19Q_C31S S111C] | MELLILKANAITTILTAVTFCFASGQNITEEFYQSTCSAVSKGYLSALRTGWYTSVITIELSNIKEN KCNGTDAKVKLIKQELDKYKNAVTELQLLMGSGNVGLGGAIASGVAVCKVLHLEGEVNKIKSALLST NKAVVSLSNGVSVLTFKVLDLKNYIDKQLLPILNKQSCSISNIETVIEFQQKNNRLLEITREFSVNA GVTTPVSTYMLTNSELLSLINDMPITNDQKKLMSNNVQIVRQQSYSIMCIIKEEVLAYVVQLPLYGV IDTPCWKLHTSPLCTTNTKEGSNICLTRTDRGWYCDNAGSVSFFPQAETCKVQSNRVFCDTMNSRTL PSEVNLCNVDIFNPKYDCKIMTSKTDVSSSVITSLGAIVSCYGKTKCTASNKNRGIIKTFSNGCDYV SNKGVDTVSVGNTLYYVNKQEGKSLYVKGEPIINFYDPLVFPSDEFDASISQVNEKINQSLAFIRKS DELLSGSGSESQVRQQFSKDIEKLLNEQVNKEMQSSNLYMSMSSWSYTHSLDGAGLFLFDHAAEEYE HAKKLIIFLNENNVPVQLTSISAPEHKFEGLTQIFQKAYEHEQHISESINNIVDHAIKCKDHATFNF LQWYVAEQHEEEVLFKDILDKIELIGNENHGLYLADQYVKGIAKSRKS | 3 |
| RF8101: Add a single glycan site E328N to RSV scF_SGSGS-bf-pFerr_N19Q_C31S | MELLILKANAITTILTAVTFCFASGQNITEEFYQSTCSAVSKGYLSALRTGWYTSVITIELSNIKEN KCNGTDAKVKLIKQELDKYKNAVTELQLLMGSGNVGLGGAIASGVAVCKVLHLEGEVNKIKSALLST NKAVVSLSNGVSVLTFKVLDLKNYIDKQLLPILNKQSCSISNIETVIEFQQKNNRLLEITREFSVNA GVTTPVSTYMLTNSELLSLINDMPITNDQKKLMSNNVQIVRQQSYSIMCIIKEEVLAYVVQLPLYGV IDTPCWKLHTSPLCTTNTKNGSNICLTRTDRGWYCDNAGSVSFFPQAETCKVQSNRVFCDTMNSRTL PSEVNLCNVDIFNPKYDCKIMTSKTDVSSSVITSLGAIVSCYGKTKCTASNKNRGIIKTFSNGCDYV SNKGVDTVSVGNTLYYVNKQEGKSLYVKGEPIINFYDPLVFPSDEFDASISQVNEKINQSLAFIRKS DELLSGSGSESQVRQQFSKDIEKLLNEQVNKEMQSSNLYMSMSSWSYTHSLDGAGLFLFDHAAEEYE HAKKLIIFLNENNVPVQLTSISAPEHKFEGLTQIFQKAYEHEQHISESINNIVDHAIKCKDHATFNF LQWYVAEQHEEEVLFKDILDKIELIGNENHGLYLADQYVKGIAKSRKS | 4 |
| RF8102: Add a single glycan site K390I to RSV scF_SGSGS-bf-pFerr_N19Q_C31S S111C | MELLILKANAITTILTAVTFCFASGQNITEEFYQSTCSAVSKGYLSALRTGWYTSVITIELSNIKEN KCNGTDAKVKLIKQELDKYKNAVTELQLLMGSGNVGLGGAIASGVAVCKVLHLEGEVNKIKSALLST NKAVVSLSNGVSVLTFKVLDLKNYIDKQLLPILNKQSCSISNIETVIEFQQKNNRLLEITREFSVNA GVTTPVSTYMLTNSELLSLINDMPITNDQKKLMSNNVQIVRQQSYSIMCIIKEEVLAYVVQLPLYGV IDTPCWKLHTSPLCTTNTKEGSNICLTRTDRGWYCDNAGSVSFFPQAETCKVQSNRVFCDTMNSRTL PSEVNLCNVDIFNPTYDCKIMTSKTDVSSSVITSLGAIVSCYGKTKCTASNKNRGIIKTFSNGCDYV SNKGVDTVSVGNTLYYVNKQEGKSLYVKGEPIINFYDPLVFPSDEFDASISQVNEKINQSLAFIRKS DELLSGSGSESQVRQQFSKDIEKLLNEQVNKEMQSSNLYMSMSSWSYTHSLDGAGLFLFDHAAEEYE HAKKLIIFLNENNVPVQLTSISAPEHKFEGLTQIFQKAYEHEQHISESINNIVDHAIKCKDHATFNF LQWYVAEQHEEEVLFKDILDKIELIGNENHGLYLADQYVKGIAKSRKS | 5 |
| RF8103: Add a single glycan site S348N to RSVscF_SGSGS-bf-pFerr_N19Q_C31S S111C | MELLILKANAITTILTAVTFCFASGQNITEEFYQSTCSAVSKGYLSALRTGWYTSVITIELSNIKEN AKCNGTDAKVKLIKQELDKYKNVTELQLLMGSGNVGLGGAIASGVAVCKVLHLEGEVNKIKSALLST NKAVVSLSNGVSVLTFKVLDLKNYIDKQLLPILNKQSCSISNIETVIEFQQKNNRLLEITREFSVNA GVTTPVSTYMLTNSELLSLINDMPITNDQKKLMSNNVQIVRQQSYSIMCIIKEEVLAYVVQLPLYGV CIDTPCWKLHTSPLCTTNTKEGSNICLTRTDRGWYCDNAGNVSFFPQAETCKVQSNRVFCDTMNSRT LPSEVNLCNVDIFNPKYDKIMTSKTDVSSSVITSLGAIVSCYGKTKCTASNKNRGIIKTFSNGCDYV SNKGVDTVSVGNTLYYVNKQEGKSLYVKGEPIINFYDPLVFPSDEFDASISQVNEKINQSLAFIRKS DELLSGSGSESQVRQQFSKDIEKLLNEQVNKEMQSSNLYMSMSSWSYTHSLDGAGLFLFDHAAEEYE HAKKLIIFLNENNVPVQLTSISAPEHKFEGLTQIFQKAYEHEQHISESINNIVDHAIKCKDHATFNF LQWYVAEQHEEEVLFKDILDKIELIGNENHGLYLADQYVKGIAKSRKS | 6 |

TABLE 1 -continued (Sequence Table): Description of the Sequences

| Description | Sequence | SEQ ID NO |
|---|---|---|
| RF8104: Add a single glycan site Y478S to RSV scF_SGSGS-bf-pFerr_N19Q_C31S S1 11C | MELLILKANAITTILTAVTFCFASGQNITEEFYQSTCSAVSKGYLSALRTGWYTSVITIELSNIKEN KCNGTDAKVKLIKQELDKYKNAVTELQLLMGSGNVGLGGAIASGVAVCKVLHLEGEVNKIKSALLST NKAVVSLSNGVSVLTFKVLDLKNYIDKQLLPILNKQSCSISNIETVIEFQQKNNRLLEITREFSVNA GVTTPVSTYMLTNSELLSLINDMPITNDQKKLMSNNVQIVRQQSYSIMCIIKEEVLAYVVQLPLYGV IDTPCWKLHTSPLCTTNTKEGSNICLTRTDRGWYCDNAGSVSFFPQAETCKVQSNRVFCDTMNSRTL PSEVNLCNVDIFNPKYDCKIMTSKTDVSSSVITSLGAIVSCYGKTKCTASNKNRGIIKTFSNGCDYV SNKGVDTVSVGNTLYYVNKQEGKSLYVKGEPIINFSDPLVFPSDEFDASISQVNEKINQSLAFIRKS DELLSGSGSESQVRQQFSKDIEKLLNEQVNKEMQSSNLYMSMSSWSYTHSLDGAGLFLFDHAAEEYE HAKKLIIFLNENNVPVQLTSISAPEHKFEGLTQIFQKAYEHEQHISESINNIVDHAIKCKDHATFNF LQWYVAEQHEEEVLFKDILDKIELIGNENHGLYLADQYVKGIAKSRKS | 7 |
| RF8105: Add a single glycan site R507N to RSV scF_SGSGS-bf-pFerr_N19Q_C31S S111C | MELLILKANAITTILTAVTFCFASGQNITEEFYQSTCSAVSKGYLSALRTGWYTSVITIELSNIKEN KCNGTDAKVKLIKQELDKYKNAVTELQLLMGSGNVGLGGAIASGVAVCKVLHLEGEVNKIKSALLST NKAVVSLSNGVSVLTFKVLDLKNYIDKQLLPILNKQSCSISNIETVIEFQQKNNRLLEITREFSVNA GVTTPVSTYMLTNSELLSLINDMPITNDQKKLMSNNVQIVRQQSYSIMCIIKEEVLAYVVQLPLYGV IDTPCWKLHTSPLCTTNTKEGSNICLTRTDRGWYCDNAGSVSFFPQAETCKVQSNRVFCDTMNSRTL PSEVNLCNVDIFNPKYDCKIMTSKTDVSSSVITSLGAIVSCYGKTKCTASNKNRGIIKTFSNGCDYV SNKGVDTVSVGNTLYYVNKQEGKSLYVKGEPIINFSDPLVFPSDEFDASISQVNEKINQSLAFINKS DELLSGSGSESQVRQQFSKDIEKLLNEQVNKEMQSSNLYMSMSSWSYTHSLDGAGLFLFDHAAEEYE HAKKLIIFLNENNVPVQLTSISAPEHKFEGLTQIFQKAYEHEQHISESINNIVDHAIKCKDHATFNF LQWYVAEQHEEEVLFKDILDKIELIGNENHGLYLADQYVKGIAKSRKS | 8 |
| RF8106: RF8108 with I217P that increases expression, and removal of disulfide bond (DS) of DS-CAV1 removed, resulting in even higher expression relative to RF8085 (or RF8090) | mellilkanaittiltavtfcfasgqniteefyqstcsayskgylsalrtgwytsvitielsniken kongtdakvklikqeldkyknavtelqllmgsgnvglggaiasgvayskvlhlegevnkiksallst nkavvslsngvsvltfkvldlknyidkqllpilnkqscsisnpetviefqqknnrlleitrefsvna gvttpvstymltnsellslindmpitndqkklmsnnvqivrqqsysimsiikeevlayvvqlplygv idtpcwklhtsplottntkegsnicltrtdrgwycdnagsysffpqaetckvqsnrvfcdtmnsrtl psevnlonvdifnpkydckimtsktdvsssvitslgaivscygktkotasnknrgiiktfsngodyv snkgvdtvsvgntlyyvnkqegkslyvkgepiinfydplvfpsdefdasisqvnekingslafirks dellsgsgsesqvrqqfskdiekllneqvnkemqssnlymsmsswsythsldgaglflfdhaaeeye hakkliiflnennvpvqltsisapehkfegltqifqkayeheqhisesinnivdhaikckdhatfnf lqwyvaeqheeevlfkdildkielignenhglyladqyvkgiaksrks | 9 |
| RF8107: Proline substitution (I217P) of RF8108 and hydrophobic cavity filling substitution of RF8111 (N228L) together with removal of disulfide bond of DS-CAV1 | mellilkanaittiltavtfcfasgqniteefyqstcsayskgylsalrtgwytsvitielsniken kongtdakvklikqeldkyknavtelqllmgsgnvglggaiasgvayskvlhlegevnkiksallst nkavvslsngvsvltfkvldlknyidkqllpilnkqscsisnpetviefqqknlrlleitrefsvna gvttpvstymltnsellslindmpitndqkklmsnnvqivrqqsysimsiikeevlayvvqlplygv idtpcwklhtsplottntkegsnicltrtdrgwycdnagsysffpqaetckvqsnrvfcdtmnsrtl psevnlonvdifnpkydckimtsktdvsssvitslgaivscygktkotasnknrgiiktfsngodyv snkgvdtvsvgntlyyvnkqegkslyvkgepiinfydplvfpsdefdasisqvnekingslafirks dellsgsgsesqvrqqfskdiekllneqvnkemqssnlymsmsswsythsldgaglflfdhaaeeye hakkliiflnennvpvqltsisapehkfegltqifqkayeheqhisesinnivdhaikckdhatfnf lqwyvaeqheeevlfkdildkielignenhglyladqyvkgiaksrks | 10 |
| RF8108: Proline substitution I217P to stabilize pre-fusion central helix (while DS of DS-CAV1 present) and increase expression | MELLILKANAITTILTAVTFCFASGQNITEEFYQSTCSAVSKGYLSALRTGWYTSVITIELSNIKEN KCNGTDAKVKLIKQELDKYKNAVTELQLLMGSGNVGLGGAIASGVAVCKVLHLEGEVNKIKSALLST NKAVVSLSNGVSVLTFKVLDLKNYIDKQLLPILNKQSCSISNPETVIEFQQKNNRLLEITREFSVNA GVTTPVSTYMLTNSELLSLINDMPITNDQKKLMSNNVQIVRQQSYSIMCIIKEEVLAYVVQLPLYGV IDTPCWKLHTSPLCTTNTKEGSNICLTRTDRGWYCDNAGSVSFFPQAETCKVQSNRVFCDTMNSRTL PSEVNLCNVDIFNPKYDCKIMTSKTDVSSSVITSLGAIVSCYGKTKCTASNKNRGIIKTFSNGCDYV SNKGVDTVSVGNTLYYVNKQEGKSLYVKGEPIINFYDPLVFPSDEFDASISQVNEKINQSLAFIRKS DELLSGSGSESQVRQQFSKDIEKLLNEQVNKEMQSSNLYMSMSSWSYTHSLDGAGLFLFDHAAEEYE HAKKLIIFLNENNVPVQLTSISAPEHKFEGLTQIFQKAYEHEQHISESINNIVDHAIKCKDHATFNF LQWYVAEQHEEEVLFKDILDKIELIGNENHGLYLADQYVKGIAKSRKS | 11 |
| RF8109: Hydrophobic cavity filling Q224L on RSV scF_SGSGS-bf-pFerr_N19Q_C31S S111C | MELLILKANAITTILTAVTFCFASGQNITEEFYQSTCSAVSKGYLSALRTGWYTSVITIELSNIKEN KCNGTDAKVKLIKQELDKYKNAVTELQLLMGSGNVGLGGAIASGVAVCKVLHLEGEVNKIKSALLST NKAVVSLSNGVSVLTFKVLDLKNYIDKQLLPILNKQSCSISNIETVIEFLQKNNRLLEITREFSVNA GVTTPVSTYMLTNSELLSLINDMPITNDQKKLMSNNVQIVRQQSYSIMCIIKEEVLAYVVQLPLYGV IDTPCWKLHTSPLCTTNTKEGSNICLTRTDRGWYCDNAGSVSFFPQAETCKVQSNRVFCDTMNSRTL PSEVNLCNVDIFNPKYDCKIMTSKTDVSSSVITSLGAIVSCYGKTKCTASNKNRGIIKTFSNGCDYV SNKGVDTVSVGNTLYYVNKQEGKSLYVKGEPIINFYDPLVFPSDEFDASISQVNEKINQSLAFIRKS DELLSGSGSESQVRQQFSKDIEKLLNEQVNKEMQSSNLYMSMSSWSYTHSLDGAGLFLFDHAAEEYE HAKKLIIFLNENNVPVQLTSISAPEHKFEGLTQIFQKAYEHEQHISESINNIVDHAIKCKDHATFNF LQWYVAEQHEEEVLFKDILDKIELIGNENHGLYLADQYVKGIAKSRKS | 12 |

TABLE 1 -continued (Sequence Table): Description of the Sequences

| Description | Sequence | SEQ ID NO |
|---|---|---|
| RF8110: Hydrophobic cavity filling substitutions Q224L and Q225V on RSV scF_SGSGS-bf-pFerr_N19Q_C31S S111C | MELLILKANAITTILTAVTFCFASGQNITEEFYQSTCSAVSKGYLSALRTGWYTSVITIELSNIKEN KCNGTDAKVKLIKQELDKYKNAVTELQLLMGSGNVGLGGAIASGVAVCKVLHLEGEVNKIKSALLST NKAVVSLSNGVSVLTFKVLDLKNYIDKQLLPILNKQSCSISNIETVIEFLVKNNRLLEITREFSVNA GVTTPVSTYMLTNSELLSLINDMPITNDQKKLMSNNVQIVRQQSYSIMCIIKEEVLAYVVQLPLYGV IDTPCWKLHTSPLCTTNTKEGSNICLTRTDRGWYCDNAGSVSFFPQAETCKVQSNRVFCDTMNSRTL PSEVNLCNVDIFNPKYDCKIMTSKTDVSSSVITSLGAIVSCYGKTKCTASNKNRGIIKTFSNGCDYV SNKGVDTVSVGNTLYYVNKQEGKSLYVKGEPIINFYDPLVFPSDEFDASISQVNEKINQSLAFIRKS DELLSGSGSESQVRQQFSKDIEKLLNEQVNKEMQSSNLYMSMSSWSYTHSLDGAGLFLFDHAAEEYE HAKKLIIFLNENNVPVQLTSISAPEHKFEGLTQIFQKAYEHEQHISESINNIVDHAIKCKDHATFNF LQWYVAEQHEEEVLFKDILDKIELIGNENHGLYLADQYVKGIAKSRKS | 13 |
| RF8111: Hydrophobic cavity filling substitution N228L on RSV scF_SGSGS-bf-pFerr_N19Q_C31S S111C | MELLILKANAITTILTAVTFCFASGQNITEEFYQSTCSAVSKGYLSALRTGWYTSVITIELSNIKEN KCNGTDAKVKLIKQELDKYKNAVTELQLLMGSGNVGLGGAIASGVAVCKVLHLEGEVNKIKSALLST NKAVVSLSNGVSVLTFKVLDLKNYIDKQLLPILNKQSCSISNIETVIEFQQKNLRLLEITREFSVNA GVTTPVSTYMLTNSELLSLINDMPITNDQKKLMSNNVQIVRQQSYSIMCIIKEEVLAYVVQLPLYGV IDTPCWKLHTSPLCTTNTKEGSNICLTRTDRGWYCDNAGSVSFFPQAETCKVQSNRVFCDTMNSRTL PSEVNLCNVDIFNPKYDCKIMTSKTDVSSSVITSLGAIVSCYGKTKCTASNKNRGIIKTFSNGCDYV SNKGVDTVSVGNTLYYVNKQEGKSLYVKGEPIINFYDPLVFPSDEFDASISQVNEKINQSLAFIRKS DELLSGSGSESQVRQQFSKDIEKLLNEQVNKEMQSSNLYMSMSSWSYTHSLDGAGLFLFDHAAEEYE HAKKLIIFLNENNVPVQLTSISAPEHKFEGLTQIFQKAYEHEQHISESINNIVDHAIKCKDHATFNF LQWYVAEQHEEEVLFKDILDKIELIGNENHGLYLADQYVKGIAKSRKS | 14 |
| RF8112 hydrophobic filling substitution N228F on RSV scF_SGSGS-bf-pFerr_N19Q_C31S S111C | MELLILKANAITTILTAVTFCFASGQNITEEFYQSTCSAVSKGYLSALRTGWYTSVITIELSNIKENK CNGTDAKVKLIKQELDKYKNAVTELQLLMGSGNVGLGGAIASGVAVCKVLHLEGEVNKIKSALLSTNK AVVSLSNGVSVLTFKVLDLKNYIDEQLLPILNKQSCSISNIETVIEFQQKNFRLLEITREFSVNAGVT TPVSTYMLTNSELLSLINDMPITNDQKKLMSNNVQIVRQQSYSIMCIIKEEVLAYVVQLPLYGVIDTP CWELHTSPLCTTNTKEGSNICLTRTDRGWYCDNAGSVSFFPQAETCKVQSNRVFCDTMNSRTLPSEVN LCNVDIFNPKYDCKIMTSKTDVSSSVITSLGAIVSCYGETECTASNENRGIIKTFSNGCDYVSNEGVD TVSVGNTLYYVNKQEGKSLYVKGEPIINFYDPLVFPSDEFDASISQVNEKINQSLAFIRKSDELLSGS GSESQVRQQFSEDIEKLLNEQVNKEMQSSNLYMSMSSWSYTHSLDGAGLFLFDHAAEEYEHAKKLIIF LNENNVPVQLTSISAPEHEFEGLTQIFQKAYEHEQHISESINNIVDHAIKCEDHATFNFLQWYVAEQH EEEVLFEDILDKIELIGNENHGLYLADQYVEGIAKSRKS | 15 |
| RF8113 (I217P mutation of RF8106 while removing DS of DS-CAV1 and with ferritin Wt ser111 and engineered CYS of K79C for conjugation) | mellilkanaittiltavtfcfasgqniteefyqstcsayskgylsalrtgwytsvitielsnikenk ongtdakvklikqeldkyknavtelqllmgsgnvglggaiasgvayskvlhlegevnkiksallstnk pavvslsngvsvltfkvldlknyidkqllpilnkqscsisnetviefqqknnrlleitrefsvnagvt tpvstymltnsellslindmpitndqkklmsnnvqivrqqsysimsiikeevlayvvqlplygvidtp cwklhtsplottntkegsnicltrtdrgwycdnagsysffpqaetckvqsnrvfcdtmnsrtlpsevn lonvdifnpkydckimtsktdvsssvitslgaivscygktkotasnknrgiiktfsngodyvsnkgvd tvsvgntlyyvnkqegkslyvkgepiinfydplvfpsdefdasisqvnekingslafirksdellsgs gsesqvrqqfskdiekllneqvnkemqssnlymsmsswsythsldgaglflfdhaaeeyehakkliif lnennvpvqltsisapehcfegltqifqkayeheqhisesinnivdhaiksdhatfnflqwyvaeqh eeevlfkdildkielignenhglyladqyvkgiaksrks | 16 |
| RF8117 (Combinations of above successful improved expression/ secretion mutations above (FIG. 2): No DS, I217P, E328N, S348N, R507N, ferritinK79C) | mellilkanaittiltavtfcfasgqniteefyqstcsayskgylsalrtgwytsvitielsnikenk ongtdakvklikqeldkyknavtelqllmgsgnvglggaiasgvayskvlhlegevnkiksallstnk avvslsngvsvltfkvldlknyidkqllpilnkqscsisnpetviefqqknnrlleitrefsvnagvt tpvstymltnsellslindmpitndqkklmsnnvqivrqqsysimsiikeevlayvvqlplygvidtp cwklhtsplottntkngsnicltrtdrgwycdnagnvsffpqaetckvqsnrvfcdtmnsrtlpsevn lonvdifnpkydckimtsktdvsssvitslgaivscygktkotasnknrgiiktfsngodyvsnkgvd tvsvgntlyyvnkqegkslyvkgepiinfydplvfpsdefdasisqvnekingslafinksdellsgs lgsesqvrqqfskdiekllneqvnkemqssnlymsmsswsythsldgaglflfdhaaeeyehakkli flnennvpvqltsisapehCfegltqifqkayeheqhisesinnivdhaiksdhatfnflqwyvaeq heeevlfkdildkielignenhglyladqyvkgiaksrks | 17 |
| RF8122 (RF8117 above with additional K498L and K508Q for removing protease (LYS-based) cleavage and increased stability/ expression) | mellilkanaittiltavtfcfasgqniteefyqstcsayskgylsalrtgwytsvitielsnikenk ongtdakvklikqeldkyknavtelqllmgsgnvglggaiasgvayskvlhlegevnkiksallstnk avvslsngvsvltfkvldlknyidkqllpilnkqscsisnpetviefqqknnrlleitrefsvnagvt tpvstymltnsellslindmpitndqkklmsnnvqivrqqsysimsiikeevlayvvqlplygvidtp cwklhtsplottntkngsnicltrtdrgwycdnagnvsffpqaetckvqsnrvfcdtmnsrtlpsevn lonvdifnpkydckimtsktdvsssvitslgaivscygktkotasnknrgiiktfsngodyvsnkgvd tvsvgntlyyvnkqegkslyvkgepiinfydplvfpsdefdasisqvnelingslafingsdellsgs gsesqvrqqfskdiekllneqvnkemqssnlymsmsswsythsldgaglflfdhaaeeyehakkliif lnennvpvqltsisapehcfegltqifqkayeheqhisesinnivdhaiksdhatfnflqwyvaeqh eeevlfkdildkielignenhglyladqyvkgiaksrks | 18 |
| RF8123 (RF8117 with C's at 69 and 212 knocked out for specific conjugation to ferritin CYS: | mellilkanaittiltavtfcfasgqniteefyqstcsayskgylsalrtgwytsvitielsnikenk vngtdakvklikqeldkyknavtelqllmgsgnvglggaiasgvayskvlhlegevnkiksallstnk avvslsngvsvltfkvldlknyidkqllpilnkqsysisnpetviefqqknnrlleitrefsvnagvt tpvstymltnsellslindmpitndqkklmsnnvqivrqqsysimsiikeevlayvvqlplygvidtp cwklhtsplottntkngsnicltrtdrgwycdnagnvsffpqaetckvqsnrvfcdtmnsrtlpsevn lonvdifnpkydckimtsktdvsssvitslgaivscygktkotasnknrgiiktfsngodyvsnkgvd | 19 |

TABLE 1 -continued (Sequence Table): Description of the Sequences

| Description | Sequence | SEQ ID NO |
|---|---|---|
| C69V, C212V) | tvsvgntlyyvnkqegkslyvkgepiinfydplvfpsdefdasisqvnekingslafinksdellsgs gsesqvrqqfskdiekllneqvnkemqssnlymsmsswsythsldgaglflfdhaaeeyehakkliif lnennvpvqltsisapehcfegltqifqkayeheqhisesinnivdhaikskdhatfnflqwyvaeqh eeevlfkdildkielignenhglyladqyvkgiaksrks | |
| RF8134 (RF8122 like with K528N and K532N mutations to limit proteolysis instability | mellilkanaittiltavtfcfasgqniteefyqstcsayskgylsalrtgwytsvitielsnikenk ongtdakvklikqeldkyknavtelqllmgsgnvglggaiasgvayskvlhlegevnkiksallstnk avvslsngvsvltfkvldlknyidkqllpilnkqscsisnpetviefqqknnrlleitrefsvnagvt ltpvstymltnsellslindmpitndqkklmsnnvqivrqqsysimsiikeevlayvvqlplygvidtp cwklhtsplottntkngsnicltrtdrgwycdnagnvsffpqaetckvqsnrvfcdtmnsrtlpsevn lonvdifnpkydckimtsktdvsssvitslgaivscygktkotasnknrgiiktfsngodyvsnkgvd tvsvgntlyyvnkqegkslyvkgepiinfydplvfpsdefdasisqvnelingslafingsdellsgs gsesqvrqqfsndienllneqvnkemqssnlymsmsswsythsldgaglflfdhaaeeyehakkliif lnennvpvqltsisapehcfegltqifqkayeheqhisesinnivdhaikskdhatfnflqwyvaeqh eeevlfkdildkielignenhglyladqyvkgiaksrks | 20 |
| RF8135: RF8122 like with K465N and K470N mutations to limit proteolysis instability | mellilkanaittiltavtfcfasgqniteefyqstcsayskgylsalrtgwytsvitielsnikenk ongtdakvklikqeldkyknavtelqllmgsgnvglggaiasgvayskvlhlegevnkiksallstnk avvslsngvsvltfkvldlknyidkqllpilnkqscsisnpetviefqqknnrlleitrefsvnagvt tpvstymltnsellslindmpitndqkklmsnnvqivrqqsysimsiikeevlayvvqlplygvidtp cwklhtsplottntkngsnicltrtdrgwycdnagnvsffpqaetckvqsnrvfcdtmnsrtlpsevn lonvdifnpkydckimtsktdvsssvitslgaivscygktkotasnknrgiiktfsngodyvsnkgvd tvsvgntlyyvnkqegnslyvngepiinfydplvfpsdefdasisqvnelingslafingsdellsgs lgsesqvrqqfskdiekllneqvnkemqssnlymsmsswsythsldgaglflfdhaaeeyehakklii flnennvpvqltsisapehcfegltqifqkayeheqhisesinnivdhaikskdhatfnflqwyvaeq heeevlfkdildkielignenhglyladqyvkgiaksrks | 21 |
| RF8136: RF8122 like with K465N, K470N, K528N and K532N mutations to limit proteolysis instability | mellilkanaittiltavtfcfasgqniteefyqstcsayskgylsalrtgwytsvitielsnikenk ongtdakvklikqeldkyknavtelqllmgsgnvglggaiasgvayskvlhlegevnkiksallstnk avvslsngvsvltfkvldlknyidkqllpilnkqscsisnpetviefqqknnrlleitrefsvnagvt tpvstymltnsellslindmpitndqkklmsnnvqivrqqsysimsiikeevlayvvqlplygvidtp cwklhtsplottntkngsnicltrtdrgwycdnagnvsffpqaetckvqsnrvfcdtmnsrtlpsevn lonvdifnpkydckimtsktdvsssvitslgaivscygktkotasnknrgiiktfsngodyvsnkgvd tvsvgntlyyvnkqegnslyvngepiinfydplvfpsdefdasisqvnelingslafingsdellsgs gsesqvrqqfsndienllneqvnkemqssnlymsmsswsythsldgaglflfdhaaeeyehakkliif lnennvpvqltsisapehcfegltqifqkayeheqhisesinnivdhaikskdhatfnflqwyvaeqh eeevlfkdildkielignenhglyladqyvkgiaksrks | 22 |
| RF8140: RF8122 with R523Q in the bull frog linker mutated to prevent potential proteolysis in CHO cells | MELLILKANAITTILTAVTFCFASGQNITEEFYQSTCSAVSKGYLSALRTGWYTSVITIELSNIKENK CNGTDAKVKLIKQELDKYKNAVTELQLLMGSGNVGLGGAIASGVAYSKVLHLEGEVNKIKSALLSTNK AVVSLSNGVSVLTFKVLDLKNYIDKQLLPILNKQSCSISNPETVIEFQQKNNRLLEITREFSVNAGVT TPVSTYMLTNSELLSLINDMPITNDQKKLMSNNVQIVRQQSYSIMSIIKEEVLAYVVQLPLYGVIDTP CWKLHTSPLCTTNTKNGSNICLTRTDRGWYCDNAGNVSFFPQAETCKVQSNRVFCDTMNSRTLPSEVN LCNVDIFNPKYDCKIMTSKTDVSSSVITSLGAIVSCYGKTKCDYVSNKGVD TVSVGNTLYYVNKQEGKSLYVKGEPIINFYDPLVFPSDEFDASISQVNELINQSLAFINQSDELLSGS GSESQVQQQFSKDIEKLLNEQVNKEMQSSNLYMSMSSWSYTHSLDGAGLFLFDHAAEEYEHAKKLIIF LNENNVPVQLTSISAPEHCFEGLTQIFQKAYEHEQHISESINNIVDHAIKSKDHATFNFLQWYVAEQH EEEVLFKDILDKIELIGNENHGLYLADQYVKGIAKSRKS | 23 |
| Post-F, benchmark control molecule | MELLILKANAITTILTAVTFCFASGQNITEEFYQSTCSAVSKGYLSALRTGWYTSVITIELSNIKENK CNGTDAKVKLIKQELDKYKNAVTELQLLMQSTPATNNRARRELPRFMNYTLNNAKKTNVTLSKKRKRR AIASGVAVSKVLHLEGEVNKIKSALLSTNKAVVSLSNGVSVLTSKVLDLKNYIDKQLLPIVNKQSCSI SNIETVIEFQQKNNRLLEITREFSVNAGVTTPVSTYMLTNSELLSLINDMPITNDQKKLMSNNVQIVR QQSYSIMSIIKEEVLAYVVQLPLYGVIDTPCWKLHTSPLCTTNTKEGSNICLTRTDRGWYCDNAGSVS FFPQAETCKVQSNRVFCDTMNSLTLPSEVNLCNVDIFNPKYDCKIMTSKTDVSSSVITSLGAIVSCYG KTKCTASNKNRGIIKTFSNGCDYVSNKGVDTVSVGNTLYYVNKQEGKSLYVKGEPIINFYDPLVFPSD EFDASISQVNEKINQSLAFIRKSDELLGLEVLFQGPHHHHHHHHSAWSHPQFEK | 24 |
| DS-CAV1, positive control molecule | mellilkanaittiltavtfcfasgqiniteefyqstcsayskgylsalrtgwytsvitielsniken kongtdakvklikqeldkyknavtelqllmqstpatnnrarrelprfmnytlnnakktnvtlskkrkr rflgfllgvgsaiasgvavckvlhlegevnkiksallstnkavvslsngvsvltfkvldlknyidkql lpilnkqscsisnietviefqqknnrlleitrefsvnagvttpvstymltnsellslindmpitndqk klmsnnvqivrqqsysimciikeevlayvvqlplygvidtpcwklhtsplottntkegsnicltrtdr gwycdnagsysffpqaetckvqsnrvfcdtmnsltlpsevnlonvdifnpkydckimtsktdvssssvi tslgaivscygktkotasnknrgiiktfsngcdyvsnkgvdtvsvgntlyyvnkqegkslyvkgepii nfydplvfpsdefdasisqvnekingslafirksdellsggssgssggsdiikllneqvnkemqssnl ymsmsswcythsldgaglflfdhaaeeyehakkliiflnennvpvqltsisapehkfegltqifqkay eheqhisesinnivdhaikskdhatfnflqwyvaegheeevlfkdildkielignenhglyladqyvk giaksrksgs | 25 |
| Wild-type, Native RSV F (A2 strain) | MELLILKANAITTILTAVTFCFASGQNITEEFYQSTCSAVSKGYLSALRTGWYTSVITIELSNIKENK CNGTDAKVKLIKQELDKYKNAVTELQLLMQSTPPTNNRARRELPRFMNYTLNNAKKTNVTLSKKRKRR FLGFLLGVGSAIASGVAVSKVLHLEGEVNKIKSALLSTNKAVVSLSNGVSVLTSKVLDLKNYIDKQLL PIVNKQSCSISNIETVIEFQQKNNRLLEITREFSVNAGVTTPVSTYMLTNSELLSLINDMPITNDQKK | 26 |

TABLE 1 -continued (Sequence Table): Description of the Sequences

| Description | Sequence | SEQ ID NO |
|---|---|---|
| | LMSNNVQIVRQQSYSIMSIIKEEVLAYVVQLPLYGVIDTPCWKLHTSPLCTTNTKEGSNICLTRTDRG WYCDNAGSVSFFPQAETCKVQSNRVFCDTMNSLTLPSEINLCNVDIFNPKYDCKIMTSKTDVSSSVIT SLGAIVSCYGKTKCTASNKNRGIIKTFSNGCDYVSNKGMDTVSVGNTLYYVNKQEGKSLYVKGEPIIN FYDPLVFPSDEFDASISQVNEKINQSLAFIRKSDELLHNVNAGKSTTNIMITTIIIVIIVILLSLIAV GLLLYCKARSTPVTLSKDQLSGINNIAFSN | |
| RSV G A strain Native UniProtKB/Swiss-Prot: P27022.1 | MSKNKDQRTAKTLERTWDTLNHLLFISSCLYKLNLKSVAQITLSILAMIISTSLIIVAIIFIASANHK ITSTTTIIQDATNQIKNTTPTYLTQNPQLGISPSNPSDITSLITTILDSTTPGVKSTLQSTTVGTKNT TTTQAQPNKPTTKQRQNKPPSKPNNDFHFEVFNFVPCSICSNNPTCWAICKRIPNKKPGKRTTTKPTK KPTPKTTKKGPKPQTTKSKEAPTTKPTEEPTINTTKTNIITTLLTSNTTRNPELTSQMETFHSTSSEG NPSPSQVSITSEYPSQPSSPPNTPR | 27 |
| RSV G ectodomain, residues 66-297 | NHKVTLTTAIIQDATSQIKNTTPTYLTQDPQLGISFSNLSEITSQTTTILASTTPGVKSNLQPTTVKT KNTTTTQTQPSKPTTKQRQNKPPNKPNNDFHFEVFNFVPCSICSNNPTCWAICKRIPNKKPGKKTTTK PTKKPTFKTTKKDHKPQTTKPKEVPTTKPTEEPTINTTKTNIITTLLTNNTTGNPKLTSQMETFHSTS SEGNLSPSQVSTTSEHPSQPSSPPNTTRQ | 28 |
| RSV G peptide A2 for conjugation with N-terminal Azido linker and flanking glutamates (aa 151-193) | Azido-PEG4-SGGSSGSSEEEGGSRQNKPPNKPNNDFHFEVFNFVPCSICSNNPTCWAICKRIPNKKEEE | 29 |
| CpG oligodeoxy-nucleotide (asterisks indicate phosphorothioate linkages) | T*G*A*C*T*G*T*G*A*A*C*G*T*T*C*G*A*G*A*T*G*A | 30 |
| Replacement sequence in RF8117 substituted for positions 98-144 of SEQ ID NO: 26 (wild-type RSV F) | GSGNVGL | 31 |
| RSV Gcc (central conserved region) A2 strain res 151-193 | RQNKPPNKPNNDFHFEVFNFVPCSICSNNPTCWAICKRIPNKK | 32 |
| RSV Gcc (central conserved region) B1 strain | RKNPPKKPKDDYHFEVFNFVPCSICGNNQLCKSICKTIPNKK | 33 |
| Not Used | | 34-200 |
| bfpFerritin-N19Q/C31S/526C | ESQVRQQFSKDIEKLLNEQVNKEMQSSNLYMCMSSWSYTHSLDGAGLFLFDHAAEEYEHAKKLIIFLN ENNVPVQLTSISAPEHKFEGLTQIFQKAYEHEQHISESINNIVDHAIKSKDHATFNFLQWYVAEQHEE EVLFKDILDKIELIGNENHGLYLADQYVKGIAKSRKS | 201 |
| bfpFerritin-N19Q/C31S/572C | ESQVRQQFSKDIEKLLNEQVNKEMQSSNLYMSMSSWSYTHSLDGAGLFLFDHAAEEYEHAKKLIIFLN ENNVPVQLTCISAPEHKFEGLTQIFQKAYEHEQHISESINNIVDHAIKSKDHATFNFLQWYVAEQHEE EVLFKDILDKIELIGNENHGLYLADQYVKGIAKSRKS | 202 |
| bfpFerritin-N19Q/C31S/A75C | ESQVRQQFSKDIEKLLNEQVNKEMQSSNLYMSMSSWSYTHSLDGAGLFLFDHAAEEYEHAKKLIIFLN ENNVPVQLTSISCPEHKFEGLTQIFQKAYEHEQHISESINNIVDHAIKSKDHATFNFLQWYVAEQHEE EVLFKDILDKIELIGNENHGLYLADQYVKGIAKSRKS | 203 |
| bfpFerritin-N19Q/C31S/K79C | ESQVRQQFSKDIEKLLNEQVNKEMQSSNLYMSMSSWSYTHSLDGAGLFLFDHAAEEYEHAKKLIIFLN ENNVPVQLTSISAPEHCFEGLTQIFQKAYEHEQHISESINNIVDHAIKSKDHATFNFLQWYVAEQHEE EVLFKDILDKIELIGNENHGLYLADQYVKGIAKSRKS | 204 |
| bfpFerritin-N19Q/C31S/S100C | ESQVRQQFSKDIEKLLNEQVNKEMQSSNLYMSMSSWSYTHSLDGAGLFLFDHAAEEYEHAKKLIIFLN ENNVPVQLTSISAPEHKFEGLTQIFQKAYEHEQHISECINNIVDHAIKSKDHATFNFLQWYVAEQHEE EVLFKDILDKIELIGNENHGLYLADQYVKGIAKSRKS | 205 |

TABLE 1 -continued (Sequence Table): Description of the Sequences

| Description | Sequence | SEQ ID NO |
|---|---|---|
| bfpFerritin-N19Q/C31S/S111C | ESQVRQQFSKDIEKLLNEQVNKEMQSSNLYMSMSSWSYTHSLDGAGLFLFDHAAEEYEHAKKLIIFLN ENNVPVQLTSISAPEHKFEGLTQIFQKAYEHEQHISESINNIVDHAIKCKDHATFNFLQWYVAEQHEE EVLFKDILDKIELIGNENHGLYLADQYVKGIAKSRKS | 206 |
| bfpFerritin-N19Q/C31S/E12C | ESQVRQQFSKDIEKLLNCQVNKEMQSSNLYMSMSSWSYTHSLDGAGLFLFDHAAEEYEHAKKLIIFLN ENNVPVQLTSISAPEHKFEGLTQIFQKAYEHEQHISESINNIVDHAIKSKDHATFNFLQWYVAEQHEE EVLFKDILDKIELIGNENHGLYLADQYVKGIAKSRKS | 207 |
| Exemplary H. pylori Ferritin with bullfrog linker | ESQVRQQFSKDIEKLLNEQVNKEMNSSNLYMSMSSWCYTHSLDGAGLFLFDHAAEEYEHAKKLIIFLN ENNVPVQLTSISAPEHKFEGLTQIFQKAYEHEQHISESINNIVDHAIKSKDHATFNFLQWYVAEQHEE EVLFKDILDKIELIGNENHGLYLADQYVKGIAKSRKS | 208 |
| Exemplary wild-type H. pylori ferritin (GenBank Accession AAD06160.1) (without bullfrog linker or N-terminal Met) | LSKDIIKLLNEQVNKEMNSSNLYMSMSSWCYTHSLDGAGLFLFDHAAEEYEHAKKLIIFLNENNVPVQ LTSISAPEHKFEGLTQIFQKAYEHEQHISESINNIVDHAIKSKDHATFNFLQWYVAEQHEEEVLFKDI LDKIELIGNENHGLYLADQYVKGIAKSRKS | 209 |
| CpG (ISS-1018) | TGACTGTGAACGTTCGAGATGA | 210 |
| Trichoplusia ni heavy chain ferritin | TQCNVNPVQIPKDWITMHRSCRNSMRQQIQMEVGASLQYLAMGAHFSKDVVNRPGFAQLFFDAASEE REHAMKLIEYLLMRGELTNDVSSLLQVRPPTRSSWKGGVEALEHALSMESDVTKSIRNVIKACEDDS EFNDYHLVDYLTGDFLEEQYKGQRDLAGKASTLKKLMDRHEALGEF IFDKKLLGIDV | 211 |
| Trichoplusia ni light chain ferritin | ADTCYNDVALDCGITSNSLALPRCNAVYGEYGSHGNVATELQAYAKLHLERSYDYLLSAAYFNNYQT NRAGFSKLFKKLSDEAWSKTIDIIKHVTKRGDFMNFDQHSTMKTERKNYTAENHELEALAKALDTQK ELAERAFYIHREATRNSQHLHDPEIAQYLEEEFIEDHAEKIRTLAGHTSDLKKFITANNGHDLSLAL YVFDEYLQKTV | 212 |
| Pyrococcus furiosus ferritin | MLSERMLKALNDQLNRELYSAYLYFAMAAYFEDLGLEGFANWMKAQABEEIGHALRFYNY IYDRNGRVELDEIPKPPKEWESPLKAFEAAYEHEKFISKSIYELAALABEEKDYSTRAFL EWFINEQVEEEASVKKILDKLKFAKDSPQILFMLDKELSARAPKLPGLLMQGGE | 213 |
| human heavy chain ferritin | MTTASTSQVRQNYHQDSEAAINRQINLELYASYVYLSMSYYFDRDDVALKNFAKYFLHQSHEEREHA EKLMKLQNQRGGRIFLQDIKKPDCDDWESGLNAMECALHLEKNVQQSLLELHKLATDKNDPHLCDFI ETHYLNEQVKAIKELGDHVTNLRKMGAPESGLAEYLFDKHTLGDSDQES | 214 |
| human light chain ferritin (signal peptide is underlined) | <u>MDSKGSSQKGSRLLLLLVVSNLLLPQGVLASS</u>QIRQNYSTDVEAAVNSLVNLYLQASYTYLSLGFYF DRDDVALEGVSHFFRELAEEKREGYERLLKMQNQRGGRALFQDIKKPAEDEWGKTPDAMKAAMALEK KLNQALLDLHALGSARTDPHLCDFLETHFLDEEVKLIKKMGDHLTNLHRLGGPEAGLGEYLFERLTL KHD | 215 |
| lumazine synthase from Aquifex aeolicus | MQIYEGKLTAEGLRFGIVASRFNHALVDRLVEGAIDCIVRHGGREEDITLVRVPGSWEIPVAAGELA RKEDIDAVIAIGVLIRGATPHFDYIASEVSKGLANLSLELRKPITFGVITADTLEQAIERAGTKHGN KGWEAALSAIEMANLFKSLR | 216 |
| bullfrog linker | ESQVRQQF | 217 |
| Cysteine-Thrombin-His Linker (cysteine is double underlined) | <u><u>C</u></u>LVPRGSLEHHHHHH | 218 |
| E. coli 6,7-dimethyl-8-ribityllumazine synthase | MNIIEANVATPDARVAITIARFNNFINDSLLEGAIDALKRIGQVKDENITVVWVPGAYELPLAAGAL AKTGKYDAVIALGTVIRGGTAHFEYVAGGASNGLAHVAQDSEIPVAFGVLTTESIEQAIERAGTKAG NKGAEAALTALEMINVLKAIKA | 219 |
| 16 amino acid linker | GGGGSGGGGSGGGGSG | 220 |
| 28 amino acid linker | GGSGSGSNSSASSGASSGGASGGSGGSG | 221 |
| 46 amino acid linker | GGSGSASSGASASGSSNGSGSGSGSNSSASSGASSGGASGGSGGSG | 222 |

TABLE 1 -continued (Sequence Table): Description of the Sequences

| Description | Sequence | SEQ ID NO |
|---|---|---|
| FR1 | GGSGSASAEAAAKEAAAKAGGSGGSG | 223 |
| FR2 | GGSGSASAEAAAKEAAAKEAAAKASGGSGGSG | 224 |
| 47 amino acid linker comprising a C for conjugation | SGGGSGSASSGASASGSSCSGSGSGSSSASSGASSGGASGGGSGGSG | 225 |

This description and exemplary embodiments should not be taken as limiting. For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. "About" indicates a degree of variation that does not substantially affect the properties of the described subject matter, e.g., within 10%, 5%, 2%, or 1%. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

EXAMPLES

The following examples are provided to illustrate certain disclosed embodiments and are not to be construed as limiting the scope of this disclosure in any way.
1. Design and Characterization of Modifications to RSV F Polypeptides Like other paramyxovirus F proteins, RSV F is expressed as a precursor protein with an N-terminal signal peptide and a C-terminal transmembrane region that anchors the protein to the viral surface. RSV F undergoes intracellular cleavage by the protease furin to release a hydrophobic fusion peptide ("FP" in FIG. 1A), whose role is to attach to the target cell during infection. Adjacent to the fusion peptide is the heptad repeat region A (HRA) while the heptad repeat region B (HRB) is adjacent to transmembrane domain.

Crystal structures of RSV F ectodomain trimers in their pre-fusion and post-fusion conformations demonstrate how the HRA and HRB regions undergo significant rearrangement to drive the cellular fusion event (FIG. 1B) (see Swanson, K. A., et al., Proc Natl Acad Sci USA 108(23): p. 9619-24 (2011); McLellan, J. S., et al., Science 342(6158): 592-598 (2013); McLellan, J. S., et al., J Virol 85(15):7788-96 (2011); and McLellan, J. S., et al., Science 342(6158): p. 592-8 (2013)). In the pre-fusion conformation, the heptad repeat A (HRA) region is associated with the globular head, and the tip of the fusion peptide is mostly buried in the center of the protein. The pre-fusion conformation contains a number of helices and involves certain contacts between protomers to form a pre-fusion trimer.

A series of amino acid substitutions were designed to be inter-protomer stabilizing. Exemplary substitutions include V207L; N228F; I217V and E218F; I221L and E222M; or Q224A and Q225L. All RSV F amino acid sequence numbering in the examples uses the numbering of SEQ ID NO: 26.

Amino acid substitutions were designed to be helix stabilizing. As such, these substitutions are predicted to stabilize the helical domain of RSV F. Exemplary substitutions include N216P or I217P.

Amino acid substitutions were designed to be intra-protomer stabilizing. Exemplary substitutions include V220I; or A74L and Q81L.

Amino acid substitutions were designed to be helix capping. Exemplary substitutions include N216P or I217P.

Amino acid substitutions were designed to decrease aggregation. Exemplary substitutions include V192E and L61Q.

Other amino acid substitutions were designed to be cavity-filling by introducing hydrophobic amino acids such as N228F Amino acid substitutions E328N, S348N, and R507N were designed to add glycosylation sites by replacing non-asparagine residues with asparagine. It was hypothesized that addition of non-native glycans could be used to block epitopes that are exposed in the post-fusion RSV F (FIG. 1B) on the pre-fusion F protein surface.

Figure 1B:
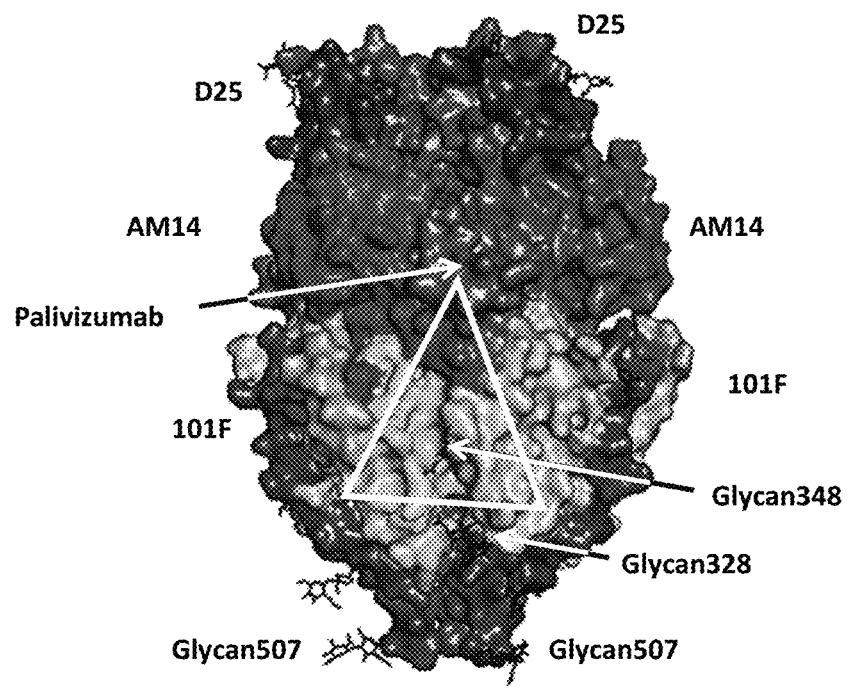
Figure 1C:
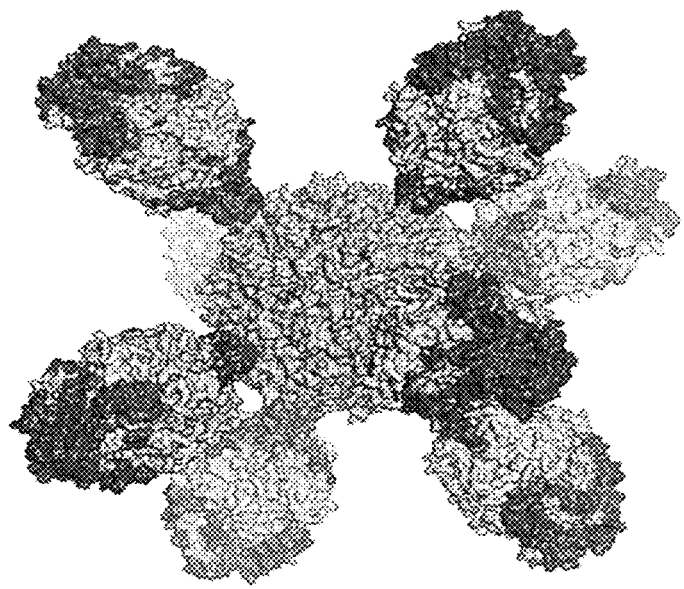

RSV F constructs of interest were generated as single chain (scF) fusion proteins with a hybrid ferritin comprising an N-terminal bullfrog ferritin linker and H. pylori ferritin (pFerr) (FIG. 1A). The ferritin comprised a surface-exposed cysteine resulting from a K79C or S111C mutation (ferritin sequence numbering corresponds to SEQ ID NO: 208).

Generation of the various RSV Pre-F-NP and ferritin coding sequences was performed using standard cloning practices known in the field. Generally speaking, DNA for RSV F constructs with the described substitutions was synthesized and cloned into a mammalian expression vector by Genscript. RSV F DS-CAV1 and post-fusion F trimers were generated similarly to the protocols previously published (see McLellan, J. S., et al., Science 342(6158):592-598 (2013)). The DS-CAV1 construct retained the C terminal trimerization domain of RSV F and combined it with cavity-filling hydrophobic substitutions. The RSV F DS-CAV1 comprises a S155C-S290C disulfide multination (DS) and a 5190F-V207L (CAV1).

Vectors encoding RSV F-ferritin nanoparticles, naked ferritin (i.e., not coupled to RSV F), and RSV F trimers were transfected into 293EXPI cells, and expression products were harvested from the conditioned media after 4 days. RSV F nanoparticles were purified by a series of anionic Q column purifications (GE Healthcare, Cat #17-1154-01) at pH 7.0 and 8.5 followed by Superose 6 SEC purification in PBS (GE Healthcare Cat #90-1000-42) using conventional chromatography methods. DS-CAV1 pre-fusion trimers and post-fusion trimers were stored at −80° C. and RSV F nanoparticles were stored at 4° C.

Figure 1D:
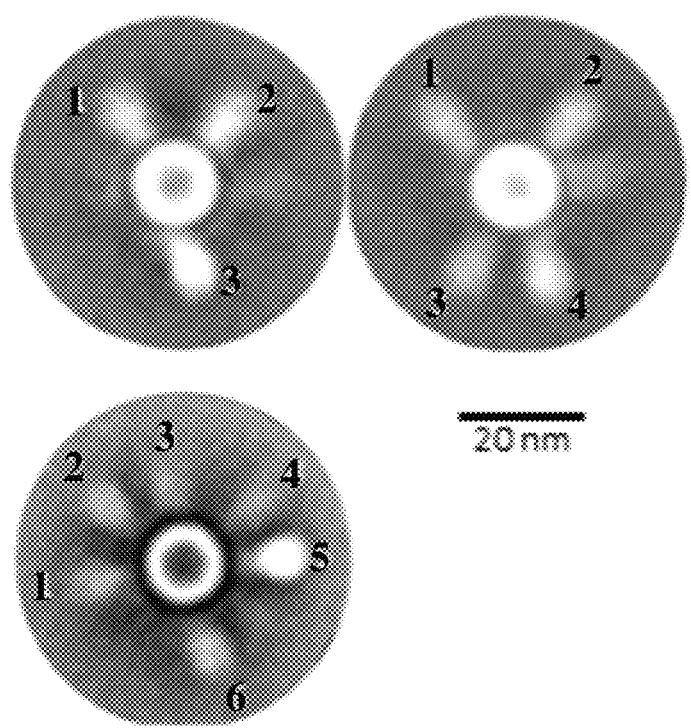

To determine the conformation of RSV F nanoparticles, electron microscopy was performed. RSV F nanoparticle preparations (30m/mL in 25 mM Tris, 50 mM NaCl) were absorbed onto a 400-mesh carbon-coated grid (Electron Microscopy Sciences) and stained with 0.75% uranyl formate. A JEOL 1200EX microscope, operated at 80 kV, was used to analyze the samples. Micrographs were taken at 65,000× magnification and 2D class averages were prepared using conventional methods in the field by the EM company Nanoimaging Services, INC (San Diego, CA) (FIG. 1D).

Expression and secretion of polypeptides comprising these RSV F polypeptides and ferritin (SEQ ID NOs: 1-8 and 11-15) by transiently transfected 293 EXPI cells (Invitrogen) were evaluated by anti-RSV F Western blot. All anti-RSV F Western blots used the site 0-specific D25 antibody described in McLellan et al., *Science* 340(6136): 1113-1117 (2013) and U.S. Pat. No. 8,562,996. As shown in FIG. 2, many constructs were successfully expressed and secreted.

The RF8085 polypeptide (SEQ ID NO: 1) represents a single chain mutant of the published DS-CAV1 RSV F (see McLellan, J. S., et al., *Science* 342(6158):592-598 (2013)) fused N-terminally to ferritin nanoparticle. This construct comprises a S155C-S290C double mutant (DS) of RSV F that retains antigenic site 0.

Figure 3:
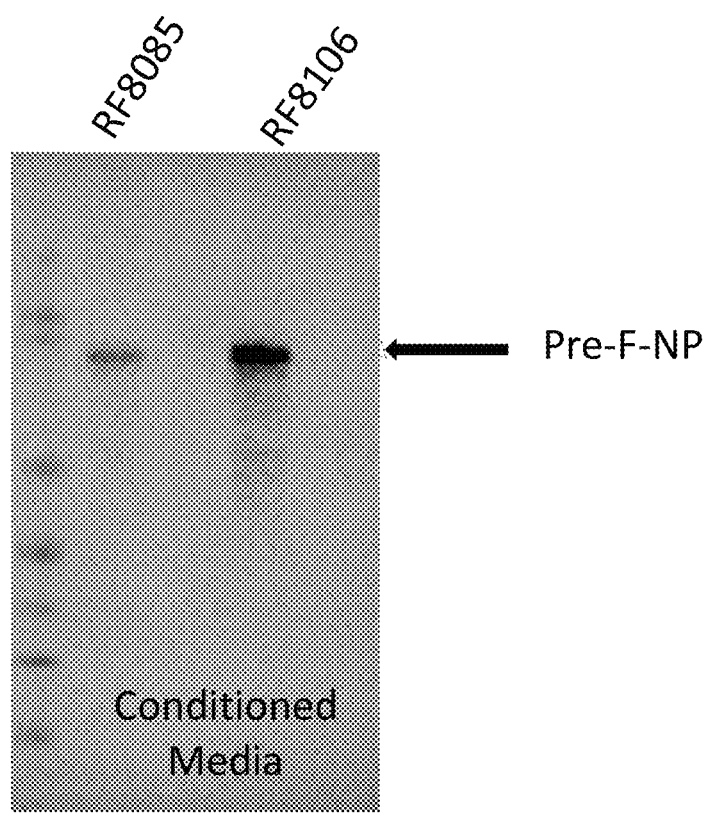
FIG. 3 shows expression of RF8085 (SEQ ID NO: 1; control construct) and RF8106 (SEQ ID NO: 9; comprising a I217P mutation as in RF8108 and lacking the disulfide (DS) mutation of DS-CAV1) as measured by the Western blot analysis of conditioned media from 293 expression. Replacing the DS with the central helix capping mutation I217P increased expression significantly. Replacing the DS with the central helix capping mutation does not affect binding of the construct to pre-fusion-specific antibodies D25 and AM14.

The RF8106 polypeptide (SEQ ID NO: 9) has an I217P substitution instead of the 2 cysteines substituted into DS-CAV1. As shown in FIG. 3, the RF8106 construct had significantly better expression in transiently transfected 293 EXPI cells as assessed from conditioned media after 4 days by anti-RSV F Western blot.

Figure 4:
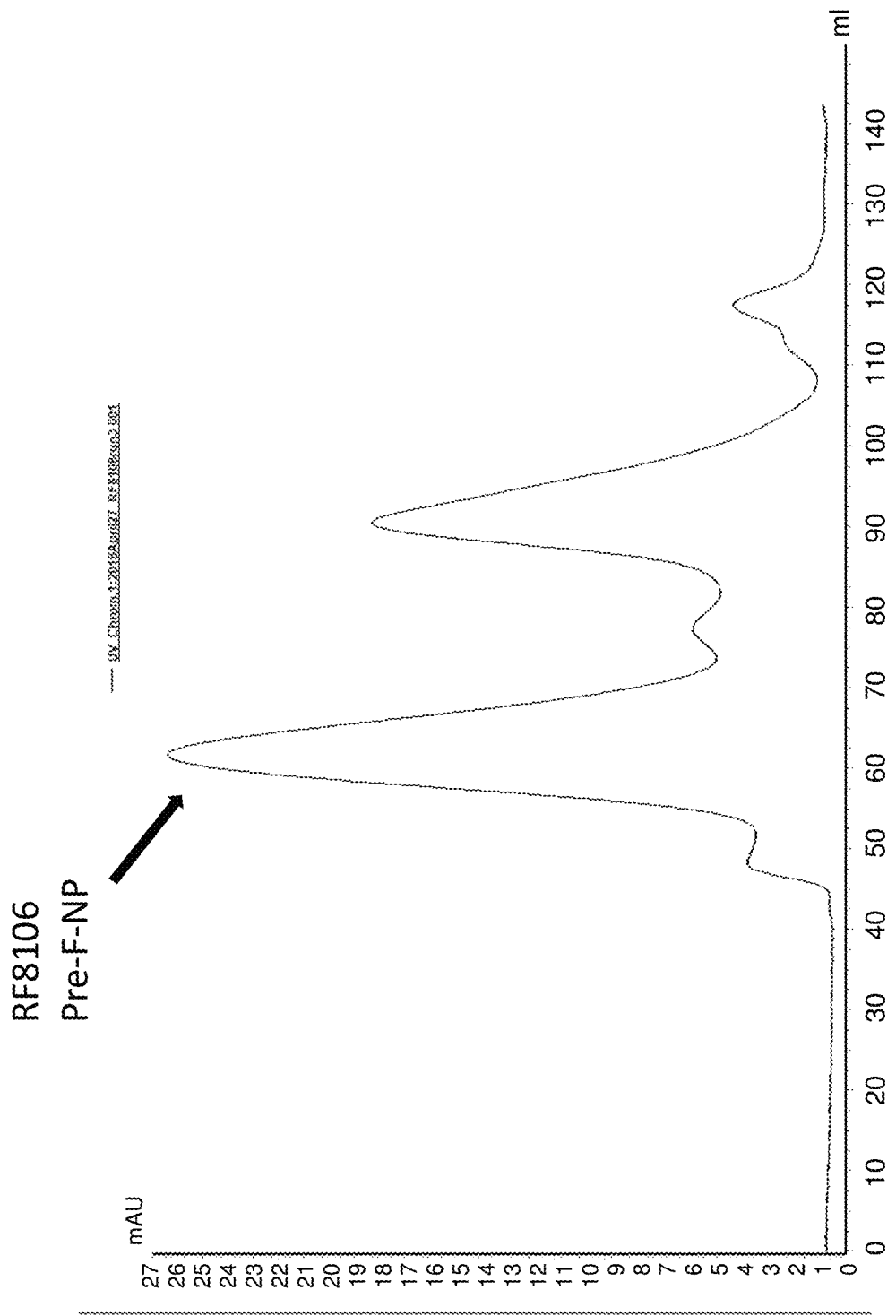
FIG. 4 shows results of size exclusion chromatography purification of the RF8106 construct (SEQ ID NO: 9). The retention volume of the RF8106 nanoparticle of approximately 65 ml on the Superose 6 preparatory SEC column is consistent with a folded 24-mer nanoparticle, suggesting the mutations in RF8106 did not hinder nanoparticle formation.
Figure 5A:
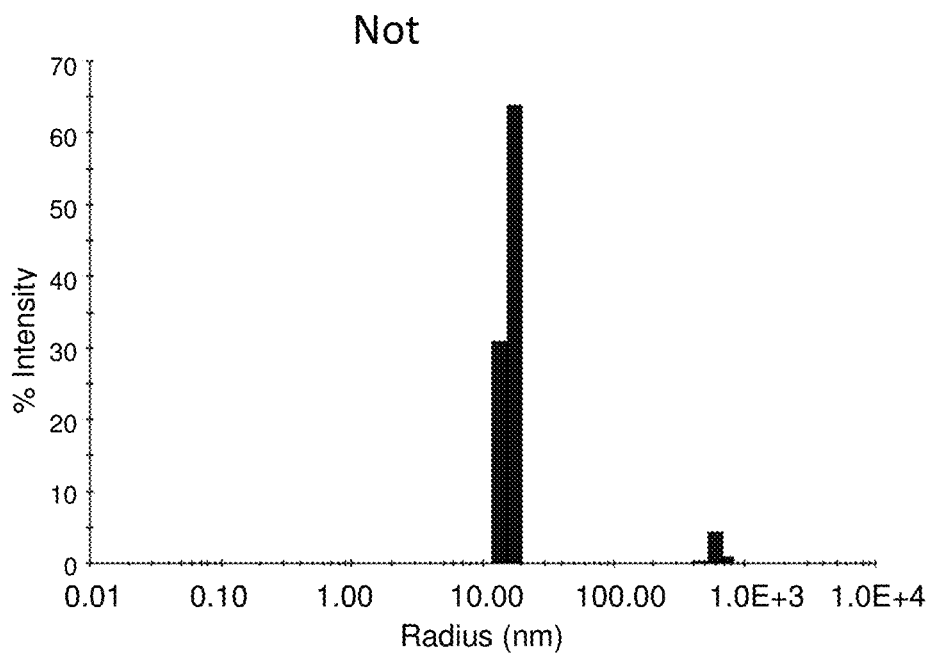
FIGS. 5A-5B show dynamic light scattering (DLS) analysis of nonreduced (5A) and reduced (5B) RF8106. Like the SEC analysis, the DLS demonstrates that the RSV Pre-F-NP formed the expected, folded nanoparticle. The reduced data further show that the particle was not disrupted by reduction, which was performed before adjuvant conjugation to the surface-exposed cysteine introduced on ferritin by a mutation (see FIG. 6).
Figure 5B:
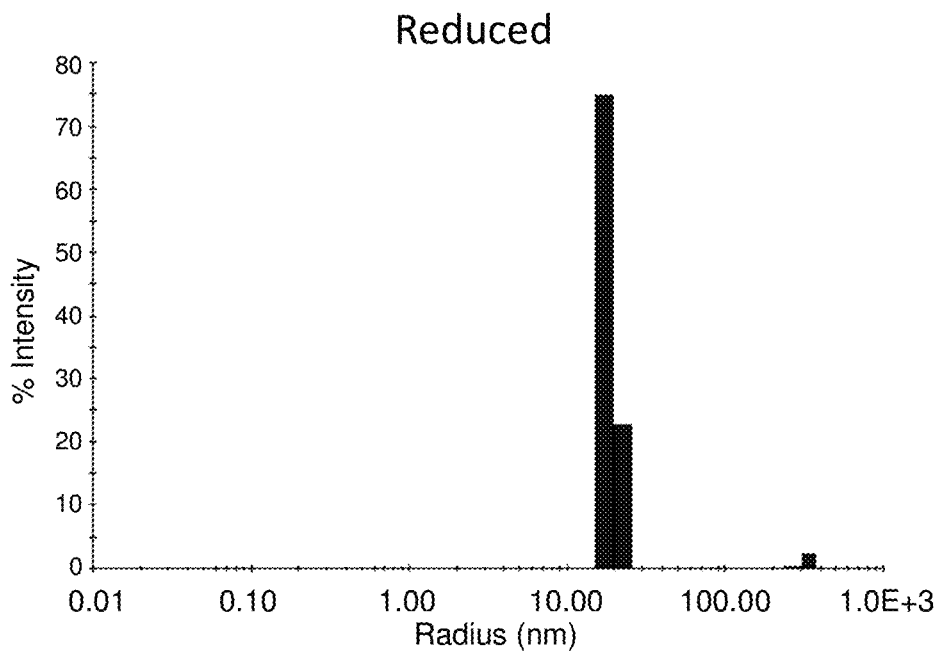

Size exclusion chromatography (SEC) of RF8106 showed elution of a main peak at a retention time consistent with an assembled ferritin particle fused to the RSV antigen consistent with a fusion protein nanoparticle (Pre-F-NP, FIG. 4). Dynamic light scattering (DLS) analysis of RF8106 was done in the reduced (FIG. 5B) and non-reduced states (FIG. 5A). Reduction was by treatment with 2 mM TCEP. RF8106 had a radius of approximately 15 nm, which is consistent with incorporation into a nanoparticle (24-mer) in both the reduced and nonreduced states. Stability of the fusion protein to reducing agents facilitates conjugation of adjuvants to the fusion proteins to form self-adjuvanting nanoparticles, as described below.

Figure 6:
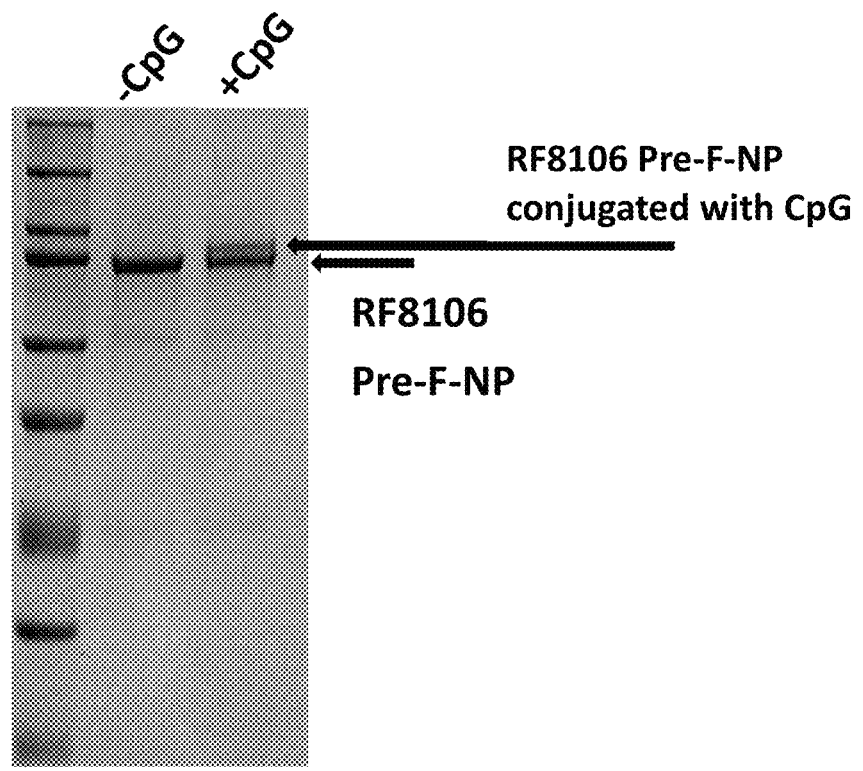
FIG. 6 shows a coomassie-stained SDS-PAGE gel analysis of RF8106 with and without conjugation to the TLR9 agonist CpG. The increased gel shift of the CpG-treated nanoparticle demonstrated that the CpG adjuvant can be added to the RSV F nanoparticle to approximately 40-50% completion. Conjugation of CpG or other immune-stimulatory moieties such as TLR7/8 agonist SM7/8 did not inhibit the particle's ability to bind pre-fusion specific antibodies D25 and AM14.

Next, conjugation of an adjuvant to the fusion protein of RSV F polypeptide and ferritin (Pre-F-NP) was assessed. It was found that the free surface cysteine on the ferritin can be used to attach an additional moiety to the scF-pFerr fusion protein. FIG. 6 shows successful conjugation of a CpG oligodeoxynucleotide (ODN) with the sequence T*G*A*C*T*G*T*G*A*A*C*G*T*T*C*G*A*G*A*T*G*A (SEQ ID NO: 30; asterisks indicate phosphorothio- ate linkages) to RF8106, as evidenced by an increase in the molecular weight as assessed by Coomassie-stained SDS-PAGE gel.

Figure 7:
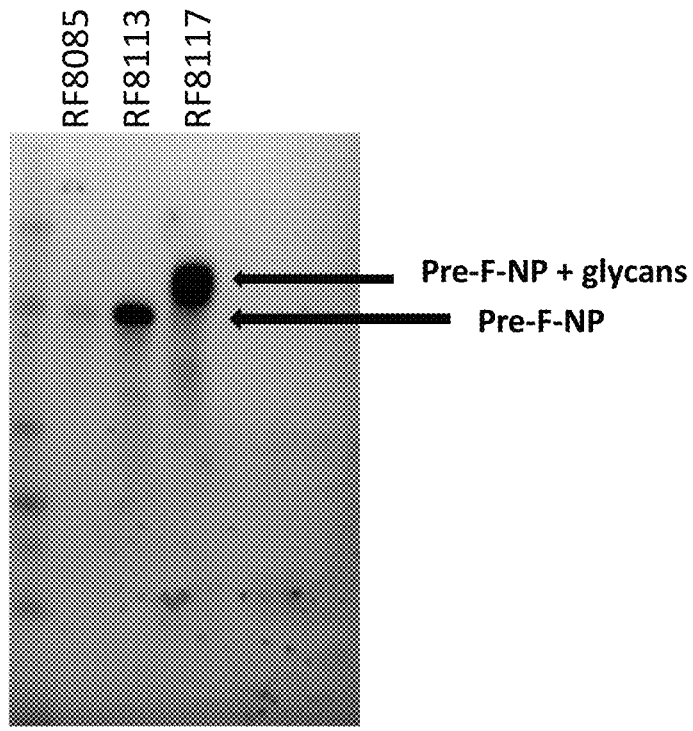
FIG. 7 shows Western blot of nanoparticles comprising RSV F with (RF8117, SEQ ID NO: 17) and without additional glycans (RF8085, SEQ ID NO: 1; and RF8113, SEQ ID NO: 16). RF8113 is like RF8106, but the S111C surface-exposed cysteine (using ferritin residue numbering, i.e., corresponding to positions in the ferritin sequence of SEQ ID NO: 208) from RF8106 has been replaced with a K79C surface-exposed cysteine (also using ferritin residue numbering) to place the conjugation site further from the Pre-F moiety. Like RF8106, RF8113 retains improved expression over the benchmark molecule RF8085. RF8117 is like RF8113 but further comprises the three glycosylation mutations identified in FIG. 2, i.e. E328N, S348N and R507N, to further improve expression and block the non-neutralizing epitopes shared between the Pre-fusion F and Post-fusion F conformations as described in FIG. 1B.

The effect of adding glycosylation sites using E328N, S348N, and R507N substitutions (RF8117, SEQ ID NO: 17) was assessed in 293EXPI cells transiently transfected with this construct as a fusion protein with ferritin (i.e., as Pre-F-NP constructs). RF8117 also contains an I217P substitution, as in RF8113. As shown in FIG. 7, increased expression was seen for RF8117 as compared with both the RF8085 control construct and the RF8113 construct (SEQ ID NO: 16, which comprises a proline substitution of I217P but not the E328N, S348N, and R507N substitutions). RF8113 is similar to RF8106 described previously except the engineered ferritin cysteine is on ferritin residue K79C rather than S111C. The RF8117 construct also showed an increase in the molecular weight of the RF8113 and RF8117, indicating the successful addition of glycans.

Figure 8:
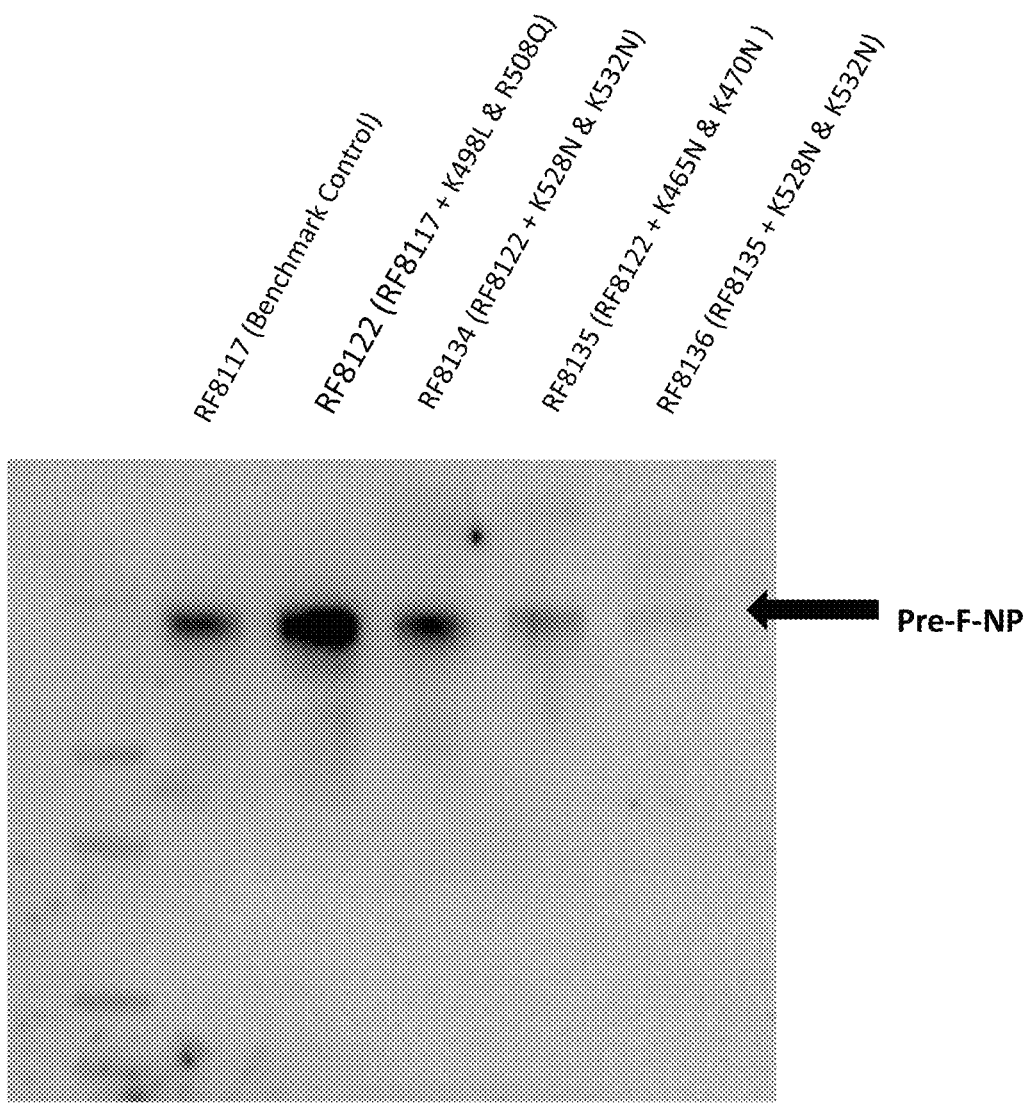
FIG. 8 shows expression of RSV F constructs with different substitutions at potential trypsin-like protease cleavage sites. It was observed in CHO cell line expression of RF8090 (same protein sequence as RF8085 with a different DNA sequence adapted to the CHO expression vector) that the polypeptide was clipped between the F and ferritin moiety, resulting in reduced expression. By the resulting masses of the F moiety, it was estimated that proteolysis could be taking place near the HRB, bull-frog linker region of the Pre-F-NP construct. Mutations of lysine and arginine residues within this region (residues ~450-550) were explored to eliminate potential trypsin-like proteolysis of the construct. The mutations in RF8122 (SEQ ID NO: 18) relative to RF8117 (K498L and K508Q) provided improved expression in 293 cells and may reduce or eliminate proteolysis in CHO cells. Alternative mutations limited expression.

FIG. 8 summarizes modifications to RSV F nanoparticles that increased the proteolytic stability of the Pre-F-NP. The starting construct was RF8117 (above). When the earlier construct RF8085 was cloned into CHO vector as RF8090 and transfected into CHO cells, it was observed that some material was clipped between the F and ferritin moiety. It was suspected that arginine or lysine residues in the HRB region or the linker between the F and ferritin moiety were being cut by trypsin-like proteases. Mutations to lysine and arginine residues within the region were tested with respect to expression in 293 cells. FIG. 8 identifies mutations K498L and R508Q (in RF8122, SEQ ID NO: 18) as not affecting or increasing expression relative to RF8117. These mutations, with R523Q, were combined with the herein mentioned mutations of RF8117 to form construct RF8140 (SEQ ID NO: 23).

Greater improvements in expression (approximately 5-fold) were seen with the combination of single chain and proline (I217P) modifications in 293 cell expression (exemplary constructs with these substitutions include RF8106 (SEQ ID NO: 9) and RF8113 (SEQ ID NO: 16)) with further improvement in expression and solubility resulting from added glycosylation site modifications of RSV F (exemplary constructs RF8117 (SEQ ID NO: 17) and RF8140 (SEQ ID NO: 23). These constructs all have the fusion peptide and p27 peptide regions (amino acids 98-144 of SEQ ID NO: 26) replaced with the sequence GSGNVGL (SEQ ID NO: 31). However, when RF8090 was expressed in CHO manufacturing cell lines, additional RSV F bands in Western blots were observed, suggesting the construct was susceptible to proteolysis, perhaps trypsin-like cleavage at an arginine or lysine residue.

Figure 9A:
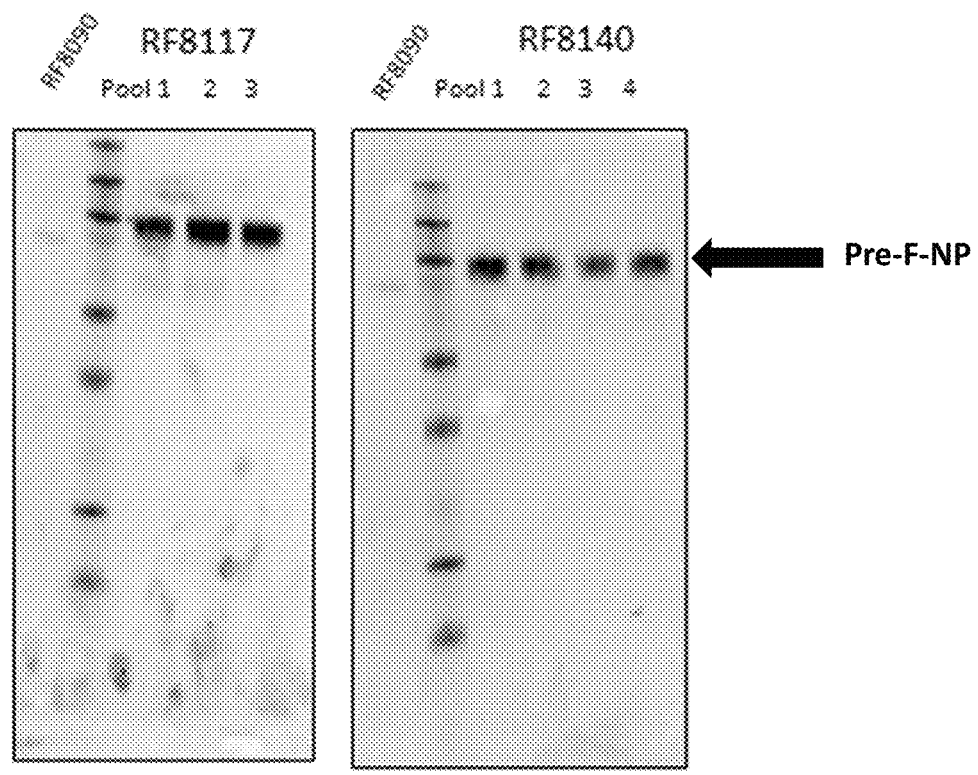
FIGS. 9A-B. Expression of RF8090, RF8117 and RF8140 in stably transfected CHO cells. Expression yield of RF8090 (SEQ ID NO: 2) was observed at low levels. Mutations to replace the disulfide of DS-CAV1 and mutations to the linker between the F moiety and ferritin moiety to eliminate potential typsin cleavage sites were introduced as described above to constructs RF8117 (SEQ ID NO: 17) and RF8140 (SEQ ID NO: 23), which were cloned into stably expressing CHO cells.
Figure 9B:
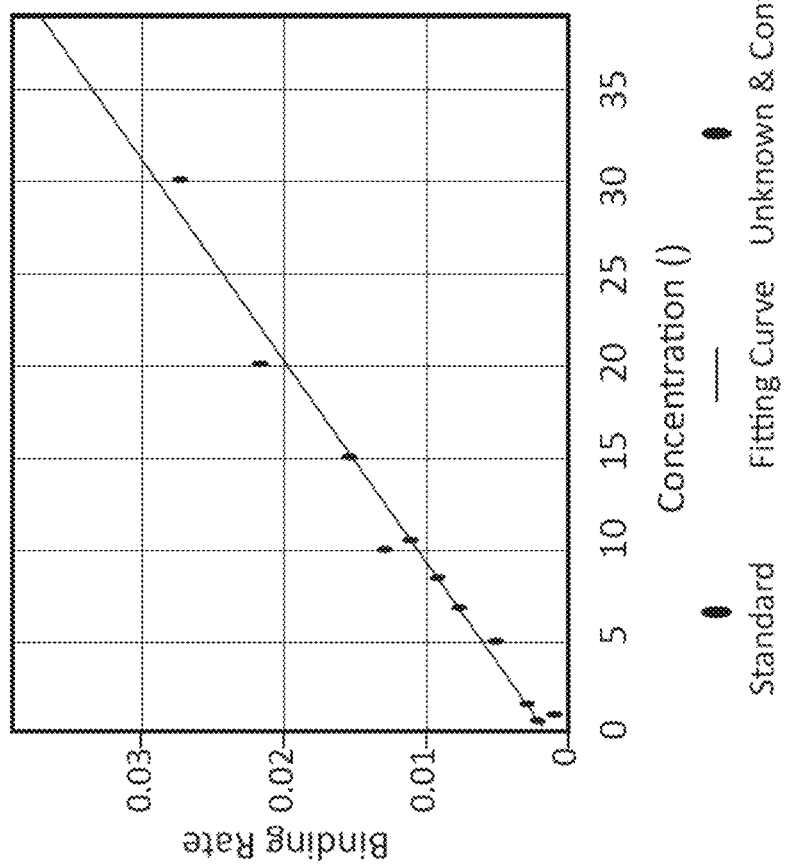

The potential role of protease susceptibility was also investigated. Substitution of K residues (knockout or KO) in the HRB region and in the linker between F moiety and ferritin moiety were made, as they were predicted to be possible sites of K-mediated cleavage initially observed in the CHO manufacturing cell line. As shown in FIGS. 9A and 9B, RF8117 and RF8140 both express to high levels relative to RF8090 in the CHO manufacturing cell line as measured by D25 Western blot or D25 and AM14 Octet analysis.

These data indicate that single chain constructs and amino acid modifications for helix capping, increasing glycosylation, and elimination of lysines or arginines susceptible to protease cleavage can improve expression of RSV F polypeptides, including RSV Pre-F-NP antigens.

2. Characterization of Fusion Proteins of RSV F and Ferritin Nanoparticles

Prior to animal studies, the concentration of DS-CAV1 and RSV F nanoparticles were analyzed by binding using Octet. The binding of the pre-fusion antigens to pre-fusion specific antibodies D25 and AM14 was also measured using a FortéBio Octet instrument. All assays were performed in PBS at 30° C. Antibodies were loaded onto Protein A (ProA) sensor tips (fortéBio #18-5013) for 400 seconds to allow capture to reach near saturation. Biosensor tips were then equilibrated for 90 seconds in PBS, followed by antigen association at known concentrations in PBS for 300 seconds, followed by dissociation of the antigen in PBS. Data analysis and curve fitting, assuming a 1:1 interaction, were carried out with Octet Data Analysis HT10.0 software using an external standard curve of binding of a purified Pre-F-NP at known concentration. An exemplary assay result to determine Pre-F-NP concentration in CHO conditioned media is shown in FIG. 9B.

3. In Vivo Characterization of Immune Response to RSV F Polypeptides

To assess the in vivo response to RSV antigens in mice, female BALBc mice were intramuscularly immunized with RSV antigens at specified doses at week 0, 3 and 6. Unless otherwise noted, RSV antigens (e.g., in the experiments of FIGS. 10A-B and 12A-B, among others) were adjuvanted with AF03 with a bedside mixing strategy. That is, 50 μl of the relevant protein solution were mixed with 50 μl of Sanofi adjuvant AF03 (a squalene-based emulsion; see Klucker et al., J Pharm Sci. 2012 December; 101(12):4490-500) just prior to injection of 50 μl into each hind leg. For unadjuvanted groups, antigens were mixed as above, but the AF03 was replaced with an equivalent volume of PBS. For antigens mixed with SPA09 or Alum, the above procedure was performed replacing the AF03 with an equivalent volume of SPA09 or Alum, respectively. No adverse effects from immunization were observed for any formulation. Blood was collected 1 day prior to first immunization and at least 2 weeks after each injection (i.e. weeks 2, 5 and 8). Unless otherwise specified, data shown was for 2 weeks post third injection (week 8, also denoted as 2wp3). Typically, sera were analyzed from pre-immunized animals (denoted as naïve), two weeks post second injection (post-2 or 2wp2) or two weeks post third injection (post-$3^{rd}$ or 2wp3).

For the Vero cell neutralizing assay, serum was heat-inactivated for 30 minutes at 56° C. A four-fold serial dilution series of the inactivated serum was made in Dulbecco's Modified Eagle Medium (DMEM) supplemented with 2% Fetal Bovine Serum (FBS), 1% GlutaMAX, and 1% antibiotic-antimitotic. RSV viral stocks were combined 1:1 with the serum dilutions and incubated for 1.5 hours at 37° C. The virus-serum mixture was then added to 24 well plates containing confluent Vero cell monolayers at 100 μL per well and incubated for 1.5 hours at 37° C., 5% CO2. The inoculum was then overlaid with 1 mL per well of 0.75% Methyl cellulose in DMEM supplemented with 2% FBS and 2% GlutaMAX and 2% antibiotic-antimitotic. Following 5 days of incubation at 37° C., 5% CO2, the overlay was removed and the monolayers were fixed with ice-cold methanol for 20 minutes.

The plates were then washed once in water and blocked with 5% non-fat dry milk in Phosphate Buffered Saline (PBS) for 30 minutes at room temperature with gentle agitation. The blocking solution was then replaced with 200 μL per well of 2% dry milk in PBS containing a 1:2000 dilution of anti-RSV antibody conjugated to horse radish peroxidase (Abcam AB20686). Following 3 hours of incubation at room temperature, the plates were washed 2 times with water, developed with TrueBlue HRP substrate, washed twice more in water and air-dried.

The stained plaques were counted using a dissecting microscope. The neutralizing antibody titers were determined at the 60% reduction end-point of mock neutralized virus controls using the formula: 60% plaque reduction titer=(C/V×0.4−Low)/(High−Low)×(HSD−LSD)+LSD, where C/V=average of RSV plaques in mock neutralized virus control wells, Low and High are the average number of RSV plaques in the two dilutions which bracket the C/V×0.4 value for a serum sample, and the HSD and LSD are the Higher and Lower Serum Dilutions.

For the HAE neutralizing assay, serum was heat-inactivated for 30 minutes at 56° C. A fourfold serial dilution series of the inactivated serum was made in PneumaCult™-ALI Basal Medium (Stem Cell Technologies; 05002) supplemented with PneumaCult™-ALI 10× Supplement (Stem Cell Technologies; 05003) and 1% Antibiotic/Antimycotic (hence media). RSV viral stocks were combined 1:1 with the serum dilutions and incubated for 1.5 hours at 37° C. The virus-serum mixture was then added to 24 well plates containing fully differentiated HAE cells at 50 μL, per well and incubated for 1.5 hours at 37° C., 5% $CO_2$. Following incubation, the inoculum was removed, the wells were washed twice with media to remove unbound virus and incubated a further 20 hours at 37° C., 5% $CO_2$. Infection events in cultures infected with RSV expressing the mKate (TagFP635) reporter were counted on a fluorescent microscope.

To detect infection with RSV not expressing the mKate reporter, the pseudostratified epithelia were washed extensively with media to remove mucus then fixed with 4% paraformaldehyde for 30 minutes at room temperature, permeabilized with 0.25% Triton X-100 for 30 minutes, and blocked with DMEM supplemented with 2% FBS for 1 hour at 37° C. The blocking solution was replaced with 100 μL per well of Mouse Anti-RSV monoclonal Ab mixture (Millipore; MAB 858-4) diluted 1:200 in DMEM supplemented with 2% FBS, and the plates were incubated at 37° C. for 2 hours. The plates were then washed 3 times with PBS supplemented with 0.05% Tween 20. 100 μL of Goat anti-mouse IgG (H+L) (Invitrogen; A11001) diluted 1:200 in DMEM supplemented with 2% FBS was added per well, and the plates were incubated overnight at 4° C. Next morning, the plates were washed 3 times with PBS supplemented with 0.05% Tween 20, the florescent signal was stabilized with ProLong Gold AntiFade with DAPI (Thermo Fisher Scientific; P36935) and counted on a fluorescent microscope. The neutralizing antibody titers were determined at the 60% reduction end-point as above.

For anti-F binding, either pre-fusion F (DS-CAV1) or post-fusion F were bound to anti-HIS antibody tips on the Octet. Unless specified, all anti-F binding refers to anti-pre-fusion F trimer (DS-CAV1) binding. His6-tagged (SEQ ID NO: 230) RSV F trimer (DS-CAV1 or Post-fusion F were pre-loaded onto Anti-Penta-HIS (HIS1K) sensor tips (FortéBio #18-5122) for 400 seconds to allow capture to reach near saturation. Biosensor tips were then equilibrated for 90 seconds in Octet Wash Buffer, followed by diluted sera association for 300 seconds. Association curve final responses were measured using Octet Data Analysis HT10.0 software, and the response was multiplied by the dilution factor (100 or 300) to obtain the final reported response.

For anti-Gcc binding, a trimerized dimer of Gcc peptide with a C-terminal HIS tag was used on an Octet tip similar to above. His6-tagged (SEQ ID NO: 230) Gcc (A2 strain)

hexamer was pre-loaded onto Anti-Penta-HIS (HIS1K) sensor tips (ForteBio #18-5122) for 400 seconds to allow capture to reach near saturation. Biosensor tips were then equilibrated for 90 seconds in Octet Wash Buffer, followed by diluted sera association for 300 seconds. Association curve final responses were measured using Octet Data Analysis HT10.0 software, and the response was multiplied by the dilution factor (100 or 300) to obtain the final reported response.

For non-human primate (NHP) studies, NHPs were pre-screened for RSV response (baselines were found to be below detection limits for all assays). NHPs were immunized with 50 µg of RF8140 with denoted adjuvant similar to the mouse protocol above but with larger volume of adjuvant (FIG. 11C-D and FIG. 18).

For non-human primate study, VERO neutralization assays were performed as described above. Pre-F-binding was assessed by ELISA assay below.

The NHP serum samples were serially diluted 2-fold (initial dilution 1:100) and incubated on blocked RSV soluble F (Sinobiological #11049-V08B) coated plates (1 µg/mL, 100 µL/well) for 1h at 37° C. RSV F-specific IgGs were detected using horseradish peroxidase-conjugated anti-monkey IgG (BioRad AAI42P, 1:10,000 dilution) for 90 minutes at 37° C. Plates were developed using 3, 3',5, 5'-tetramethylbenzidine (TMB Tebu-Bio) and stopped with 1 N hydrochloric acid (Prolabo #30024290). The optical density (OD) was measured at 450 nm-650 nm with a microplate reader (SpectraMax). RSV sF-specific IgG titers were calculated using the SoftmaxPro software, for the OD value range of 0.2 to 3.0, from the titration curve (standard mouse hyper-immune serum put on each plate).

The IgG titers of this reference, expressed in arbitrary ELISA units (EU), corresponded to the log 10 of the reciprocal dilution giving an OD of 1.0. The threshold of antibody detection was 20 (1.3 log 10) EU. All final titers were expressed in log 10 for graphing. To each titer <1.3 log 10, an arbitrary titer of 1.0 log 10 was assigned.

To assess the cell mediated immunity in the NHP study, IFNγ/IL-2 FluoroSpot kit (FS-2122-10, Mabtech) was used following manufacturer's instructions. Briefly, membrane of the IPFL plates were pre-wet with 35% ethanol and the capture antibodies (anti-IFNγ and anti-IL-2) were coated overnight at 4° C.

Plates were then blocked for 2 hours at 37° C. with 200 µL/well of cell incubation medium containing 10% fetal calf serum (FCS). The medium was removed and the stimuli added in the wells: full-length F antigen (antigen-specific stimulation), anti-CD3 (positive control) or cell culture medium (unstimulated control). Macaque Peripheral Blood Mononuclear Cells (PBMCs) were thawed and numerated. 400,000 cells were added per well and incubated for 24 h at 37° C. in a humidified incubator with 5% CO2.

For detection the cells were removed and the detection antibodies (conjugated anti-IFNγ and anti-IL-2) were added and incubated 2h at room temperature. The fluorophore-conjugated reagents were then added and incubated 1h at RT. Plates were empty, dried and stored in the dark at RT until analysis. Anti-CD3 mAb was used as positive control and responses of >500 Spot Forming Counts (SFC)/million PBMCs were found in all samples, verifying acceptable sample quality. Spots detected in the non-stimulated wells (cell culture medium) were subtracted to F-antigen stimulated cells.

For the human cell (or B-cell) analysis, experiments were performed similar to referenced experiment Dauner, et al. Vaccine 2017 Oct. 4; 35(41):5487-5494 (FIG. 20). Cells were either not treated (treated with PBS) or treated with RSV F or RSV G polypeptides as denoted at 100 ng doses. F-binding and G-binding responses were performed using the luminex assay described in the literature with beads coated with pre-F-trimer (DS-CAV1) or G ectodomain, respectively.

Figure 10A:
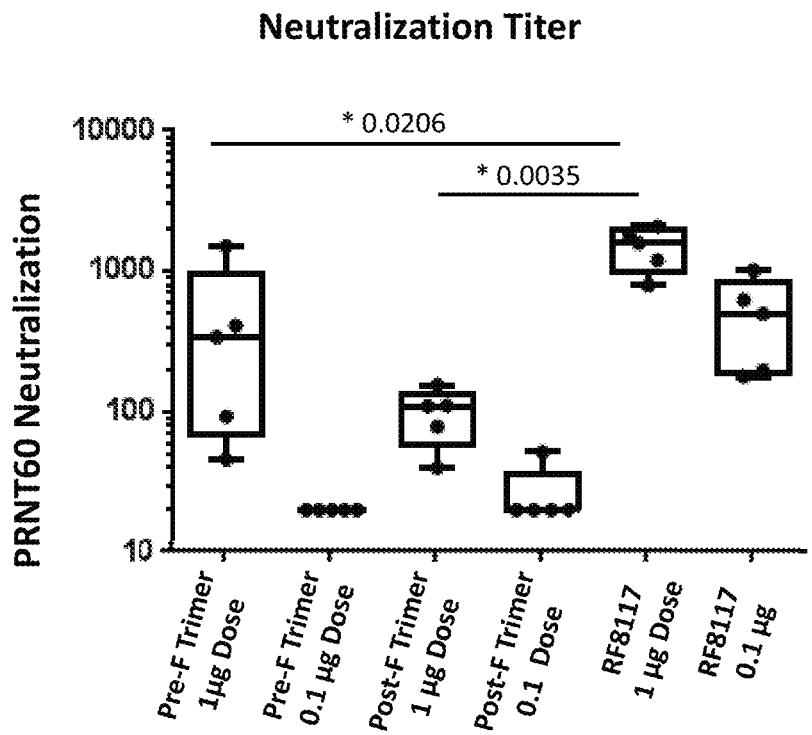
FIGS. 10A-B. Neutralizing antibody response to Pre-F-NP RF8117.

RF8117 (SEQ ID NO: 17) comprises engineered glycosylation sites at E328N, S348N and R507N, which as mentioned above do not prevent D25 or AM14 binding. To demonstrate this pre-fusion nanoparticle elicits a similar immune response to other pre-fusion antigens (DS-CAV1) we immunized mice in groups of 5 with either pre-F trimer (DS-CAV1), post-fusion F or RF8117 at 1 µg or 0.1 µg doses, all adjuvanted with AF03, three times with three weeks between injections. Sera was tested for neutralizing titer two weeks after the third immunization using the VERO cell assay. RF8117 at the higher dose elicited a neutralizing titer similar to the pre-fusion control, and superior to the post-fusion control. At the lower dose, RF8117 elicited a higher neutralizing titer than both pre-fusion control and post-fusion control (FIG. 10A).

Figure 10B:
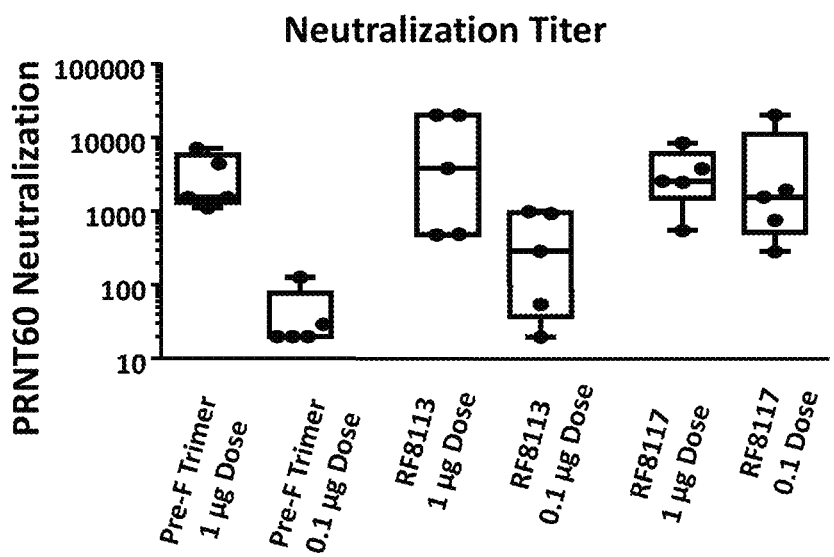

The RSV Pre-F-NP harbors glycosylation sites engineered to block epitopes shared between the pre-fusion and post-fusion confirmation. Whether these glycans were inhibiting the neutralizing response was evaluated. RF8117, with engineered glycans (SEQ ID NO: 17), was compared to RF8113 (similar to RF8117 but lacking the engineered glycans; SEQ ID NO: 16) and pre-fusion trimer control (DS-CAV1). Mice in groups of 5 were immunized with 1 µg or 0.1 µg doses, all adjuvanted with AF03, three times with three weeks between injections. Sera was tested for neutralizing titer two weeks after the third immunization using the VERO cell assay. There was no significant difference at either dose between the RF8113 and RF8117 constructs as judged by neutralizing titer (FIG. 10B).

Figure 11A:
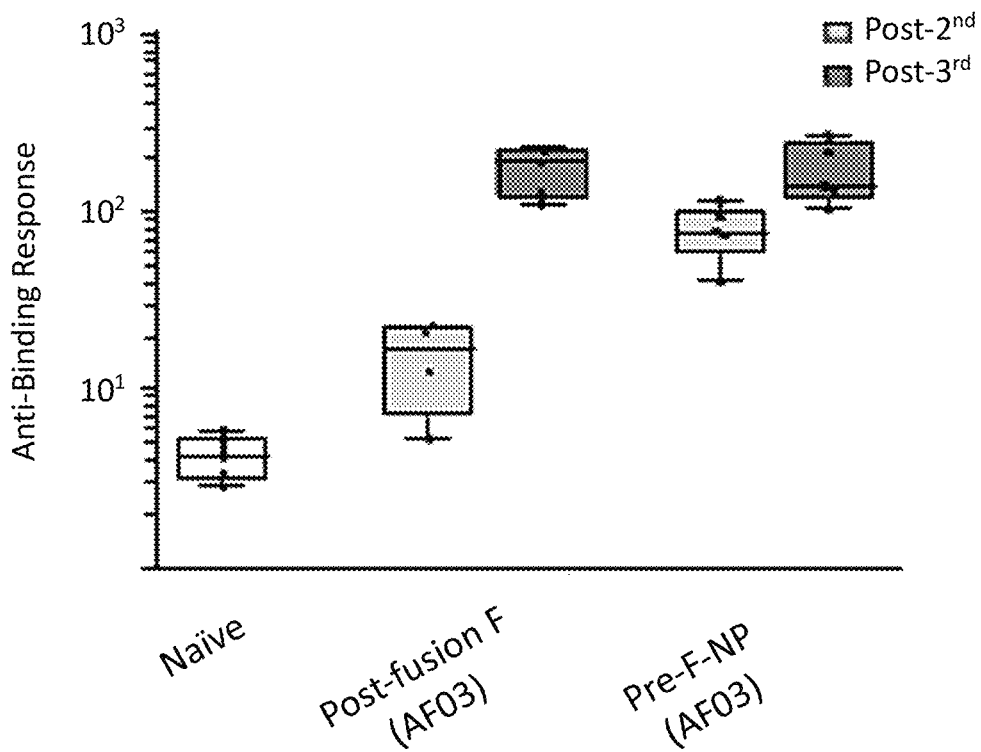
FIG. 11A-D. Comparison of RSV pre-fusion F trimer (DS-CAV1) binding antibody and RSV neutralizing antibodies elicited by immunization with post-fusion F trimer (SEQ ID NO: 24) or Pre-F-NP (RF8140 SEQ ID NO: 23) in mouse or non-human primate models.
Figure 11B:
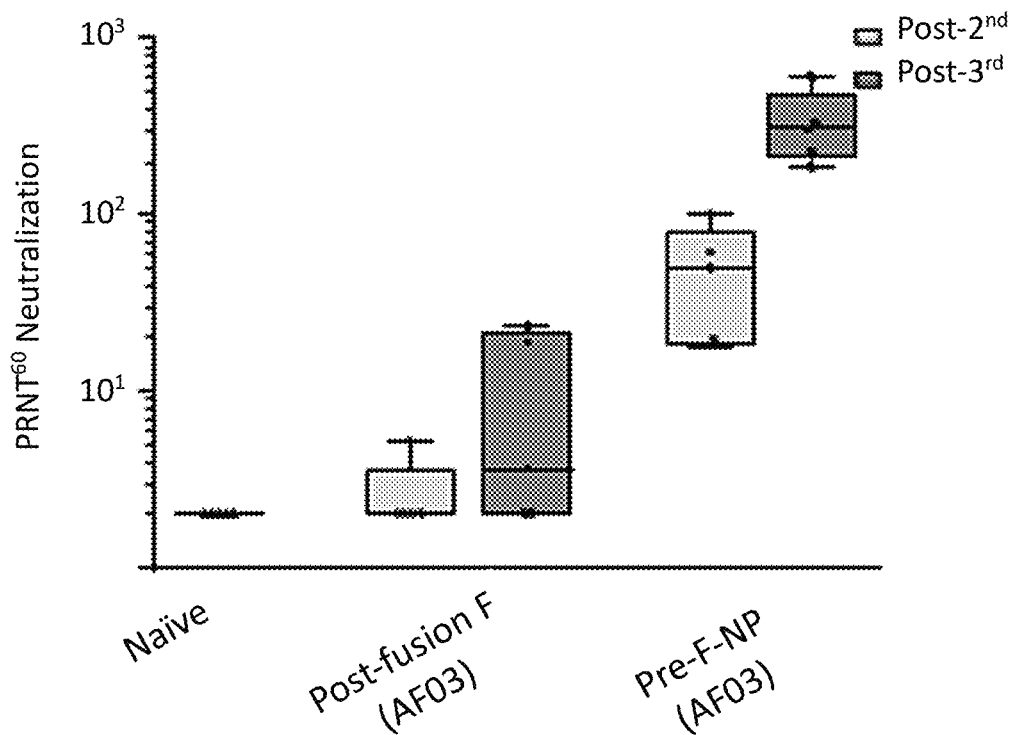
Figure 11C:
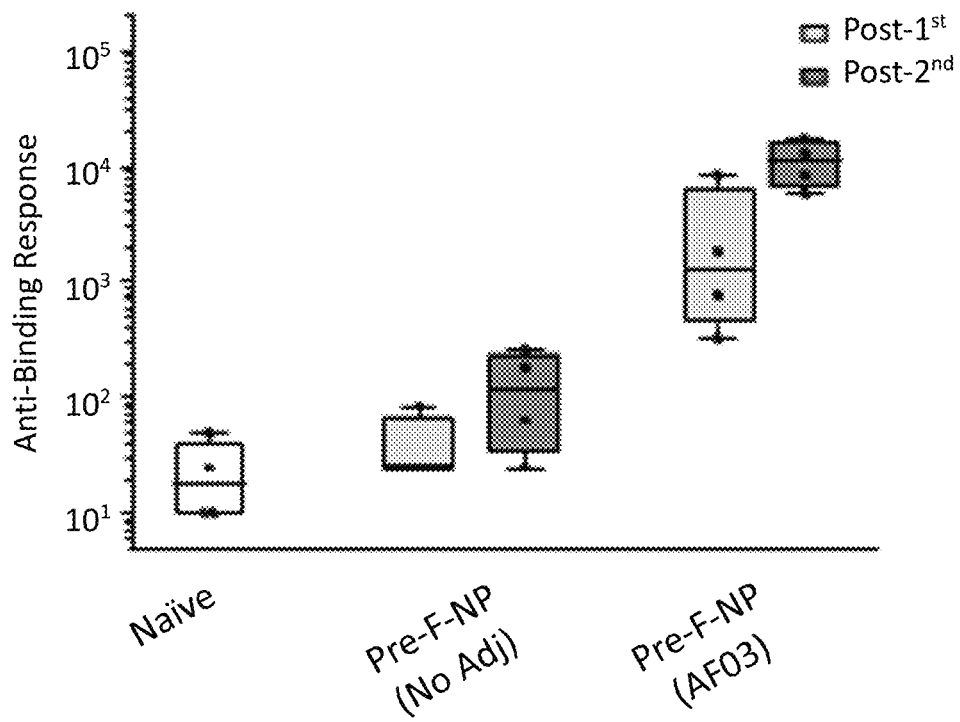
Figure 11D:
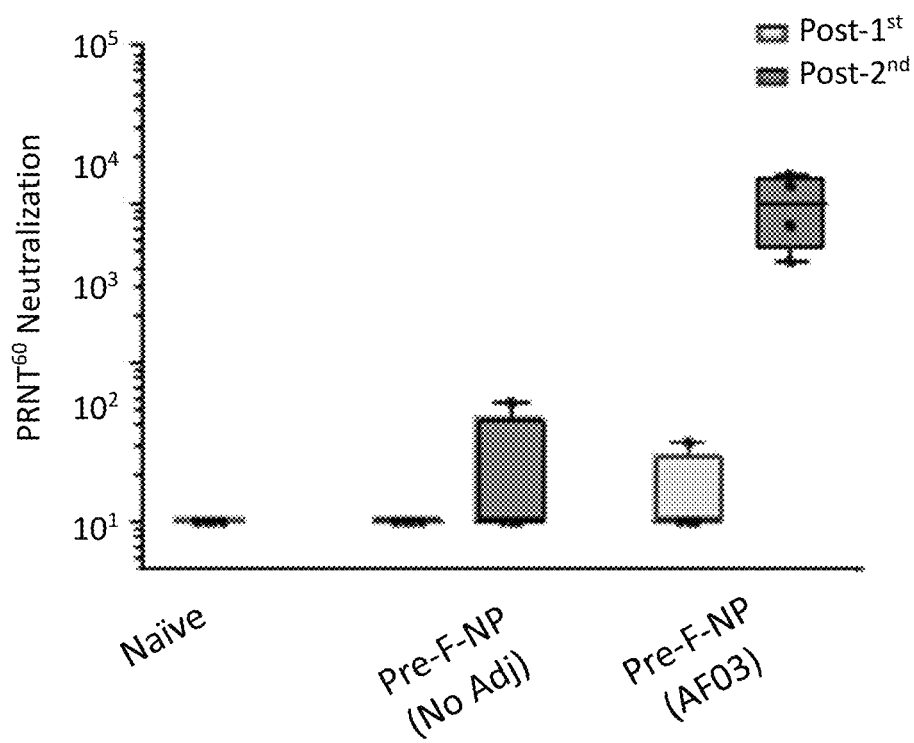

To demonstrate that the herein mentioned lysine and arginine knockouts of RF8140 (SEQ ID NO: 23) do not upset the ability of the antigen to elicit a neutralizing response, we compared the immunogenicity of RF8140 (SEQ ID NO: 25) to that of post-fusion F trimer (SEQ ID NO: 24) in mice (FIGS. 11A&B). At low dose (0.1 µg) RF8140 (SEQ ID NO: 25) elicits a superior neutralizing titer to post-fusion trimer (SEQ ID NO: 24). To demonstrate RF8140 (SEQ ID NO: 23) elicits an immune response in NHPs, we immunized NHPs with RF8140 (SEQ ID NO: 25) with or without adjuvant (AF03). FIG. 11C shows the RSV F-binding response (ELISA titer) while FIG. 11D compares RSV neutralizing titers elicited by immunization with Pre-F-NP (RF8140, SEQ ID NO: 23). Both unadjuvanted and adjuvanted RF8140 (SEQ ID NO: 25) elicit an immune response in NHPs.

Having shown the engineered glycosylation sites of RF8117 (SEQ ID NO: 17) and RF8140 (SEQ ID NO: 23) do not prevent these antigens from eliciting a neutralizing response, we wanted to demonstrate they do block non- or poorly neutralizing epitopes shared between the pre-fusion and post-fusion conformation (FIG. 12). Antibody response to Pre-fusion F (DS-CAV1, SEQ ID NO: 25) elicited by immunization with Pre-F-NP without engineered glycosylation (RF8113, SEQ ID NO: 16) or Pre-F-NP with engineered glycosylation (Engineered Gly Particle, RF8117 SEQ ID NO: 17) at high (1 µg) and low (0.1 µg) dose as measured by Octet (FIG. 12A). Responses elicited by either Pre-F-NP were similar. Antibody response to post-fusion trimer elicited by immunization with Pre-F-NP without engineered glycosylation (RF8113, SEQ ID NO: 16) or Pre-F-NP with engineered glycosylation (RF8117, SEQ ID NO: 17) at high (1 μg) and low (0.1 μg) dose as measured by Octet (FIG. 12B). The post-fusion F-binding responses elicited by RF8117 (SEQ ID NO:17) were significantly lower than those elicited by RF8113 (SEQ ID NO: 16). Therefore, while both RF8113 and RF8117 elicit robust antibody responses to pre-fusion F, the post-fusion F antibody response elicited by RF8117 is greatly repressed. This is due to the engineered glycans mapping to the shared pre-fusion and post-fusion epitopes (FIG. 2B).

Figure 13A:
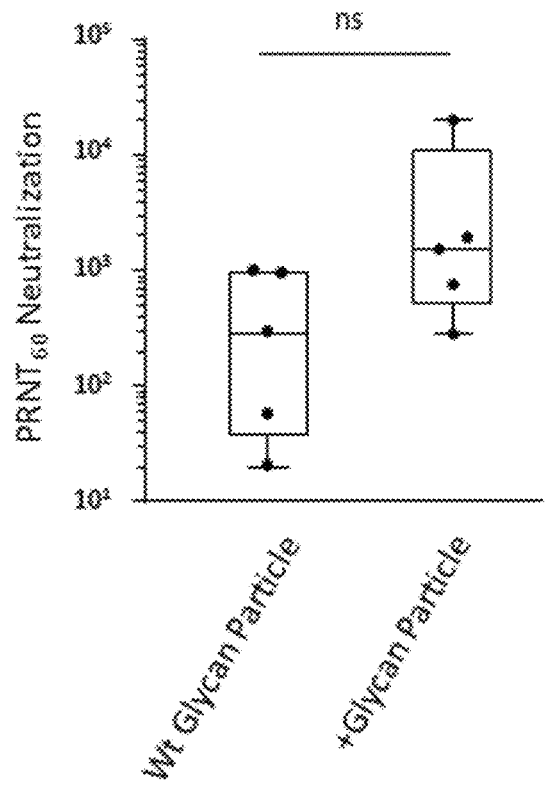
Figure 13B:
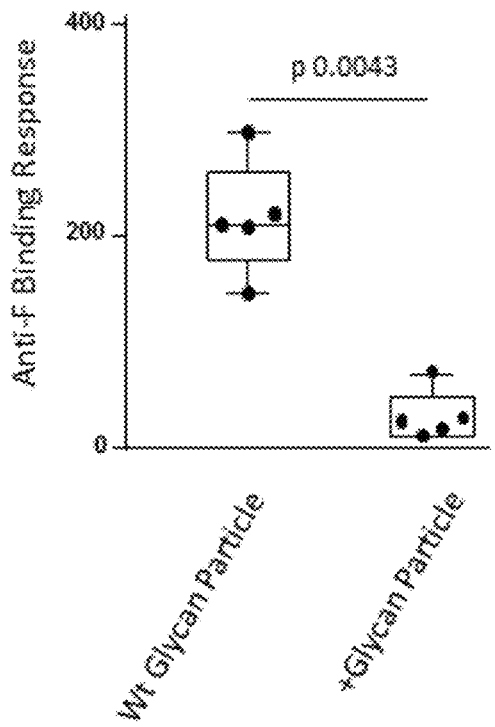
Figure 13C:
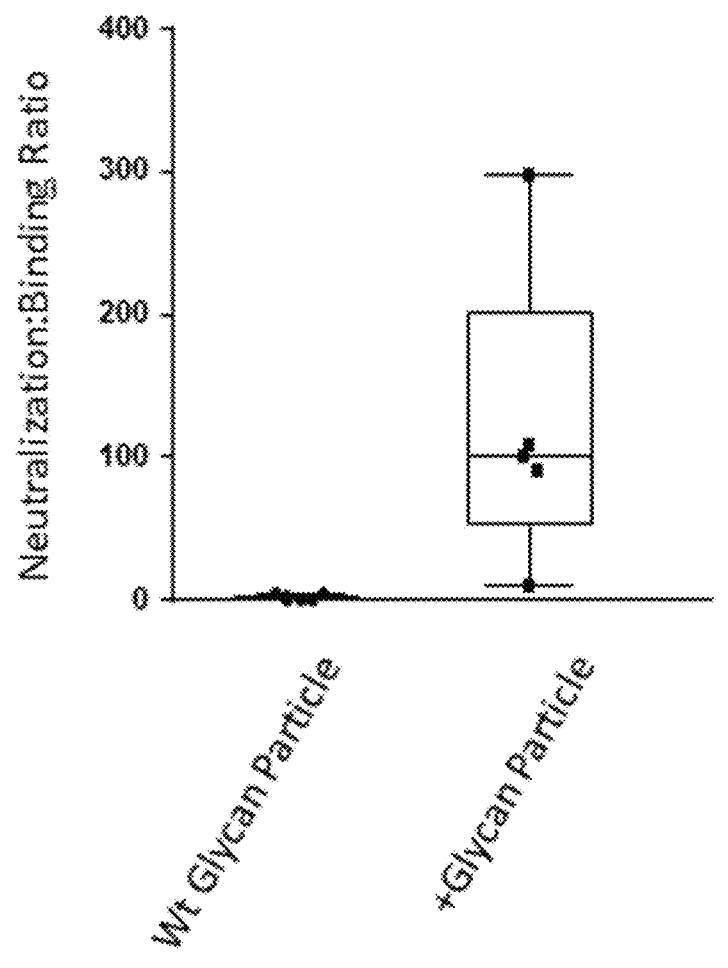

To further demonstrate that the engineered glycosylation sites block non-neutralizing epitopes but bias the neutralizing to non-neutralizing antibody titer, we analyzed the above data in a different way (FIG. 13). Comparison of RSV neutralizing titers as measured by VERO cell assay elicited by immunization with Pre-F NP with wild-type glycosylation sites (Wt Glycan Particle; RF8113, SEQ ID NO: 16) versus Pre-F NP with additional engineered glycosylation sites (+Glycan Particle; RF8117, SEQ ID NO: 17) in mouse studies were measured and showed no significant difference (FIG. 13A). Comparison of RSV Post-fusion F trimer-binding antibody responses elicited by immunization with Wt Glycan Particle (RF8113, SEQ ID NO: 16) versus +Glycan Particle (RF8117, SEQ ID NO: 17) in mouse studies showed a repressed post-fusion F-binding response for the Pre-F-NP with engineered glycans (FIG. 13B). To demonstrate that engineered glycans do not reduce the functional, neutralizing antibody response but decrease the non-neutralizing antibodies elicited to the shared pre-fusion/post-fusion epitopes, thus improving the neutralizing to total antibody ratio elicited by the engineered glycan constructs, the ratio of neutralizing titer to F-binding response was plotted (FIG. 13C). Therefore, the Pre-F-NPs with the engineered glycans elicit a superior neutralizing to binding antibody profile in mouse studies.

To demonstrate the ferritin nanoparticle can be used to improve the immunogenicity of the RSV G central domain antigen we developed a method of chemically conjugating the Gcc peptide (SEQ ID NO: 29) to the ferritin nanoparticle. Ferritin harboring the S111C mutation described herein can be conjugated with the Gcc peptide (SEQ ID NO: 29) synthesized with a maleimide group on a PEG4 linker attached to the N-terminus via a NHS group. Gcc peptide with an N-terminal maleimide was synthesized and HPLC purified by Peptides International (Louisville, KY, USA). When the maleimide-Gcc antigen is added to the ferritin S111C particle, the maleimide conjugates to the free cysteine and forms a Gcc-NP that can be observed by Coomassie-stained SDS-PAGE gel (FIG. 14A). While the conjugation is typically 50% to 90% efficient, a model of a Gcc peptide ferritin nanoparticle (100% conjugated) is shown in FIG. 14B.

Figure 14C:
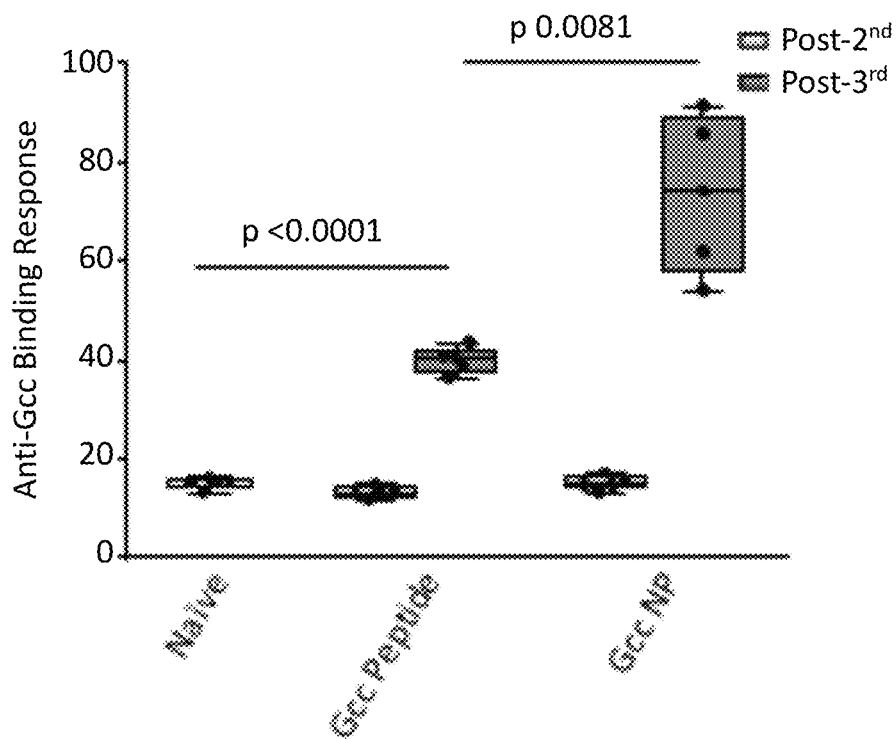
Figure 14D:
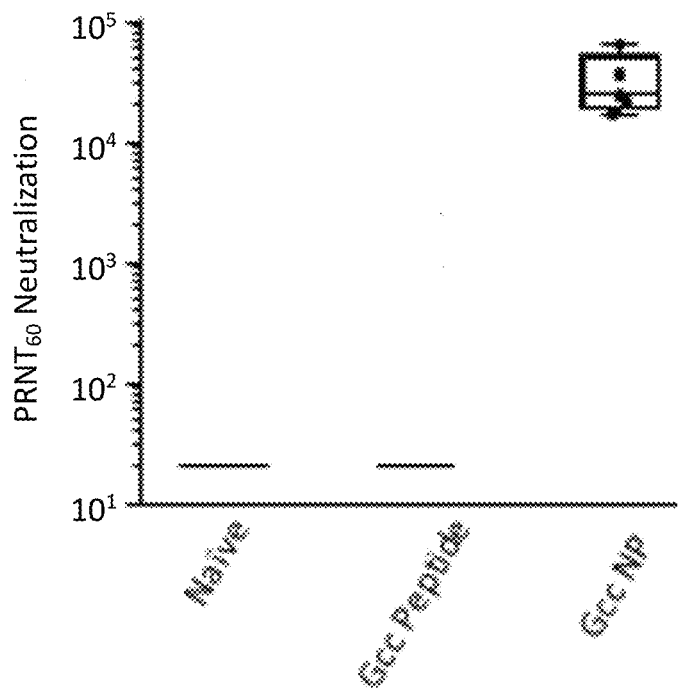

To determine if the Gcc-NP elicits an immune response superior to the Gcc peptide (SEQ ID NO: 29), 5 mice per group were immunized with either Gcc peptide or Gcc-NP (1.3 μg dose mixed 1:1 with RIBI for each immunization). The Gcc-binding response (Octet) at two weeks post-second and two weeks post-third immunizations was compared to a representative group of naïve mice sera (FIG. 14C). The neutralizing response elicited by immunization with Gcc peptide (SEQ ID NO. 29) versus Gcc-NP in mouse studies post-third injection was also compared in HAE neutralizing assays (FIG. 14D). Gcc-NP elicits a superior immune response than Gcc peptide alone as judged by both Gcc-binding response and neutralizing response.

Figure 15A:
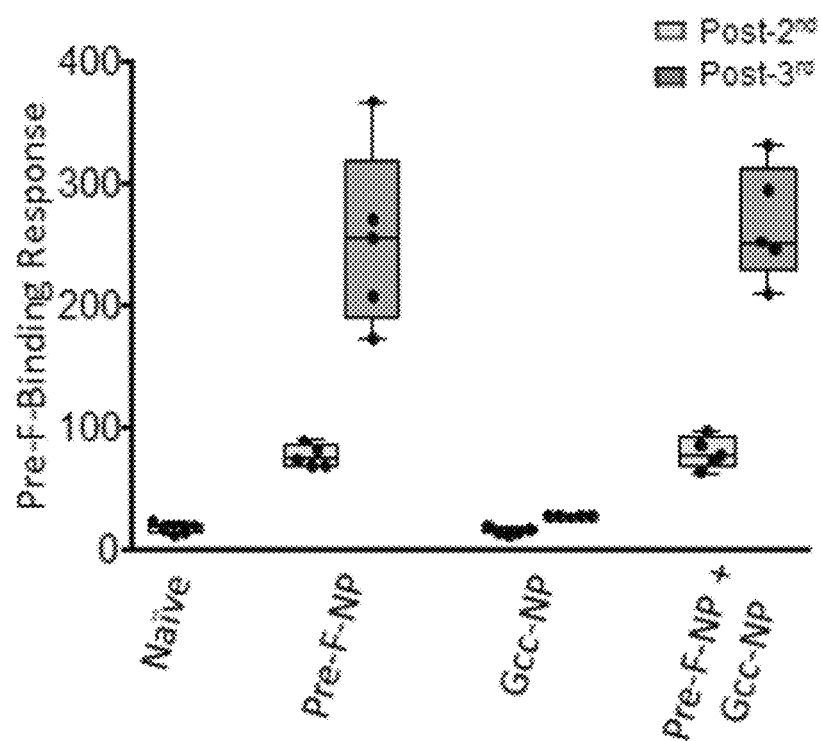
FIGS. 15A-C. Co-administration of RSV Pre-F-NP (RF8140) and Gcc-NP elicit a neutralizing response. Mice were immunized with Pre-F-NP (RF8140) alone, Gcc-NP alone, or Pre-F-NP and Gcc-NP combined at 1 µg dose per antigen. All immunizations were adjuvanted with AF03 as above.
Figure 15B:
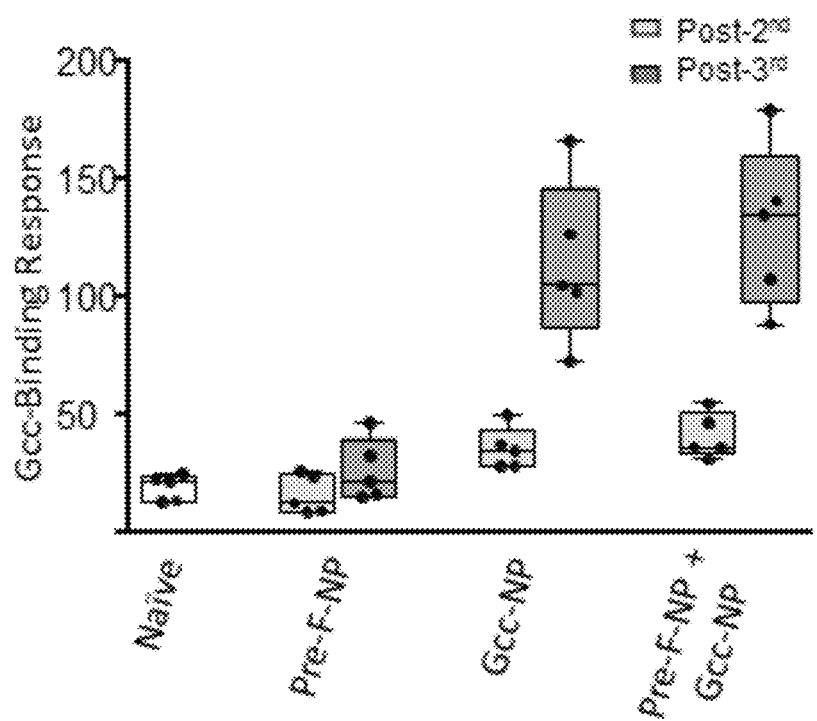
Figure 15C:
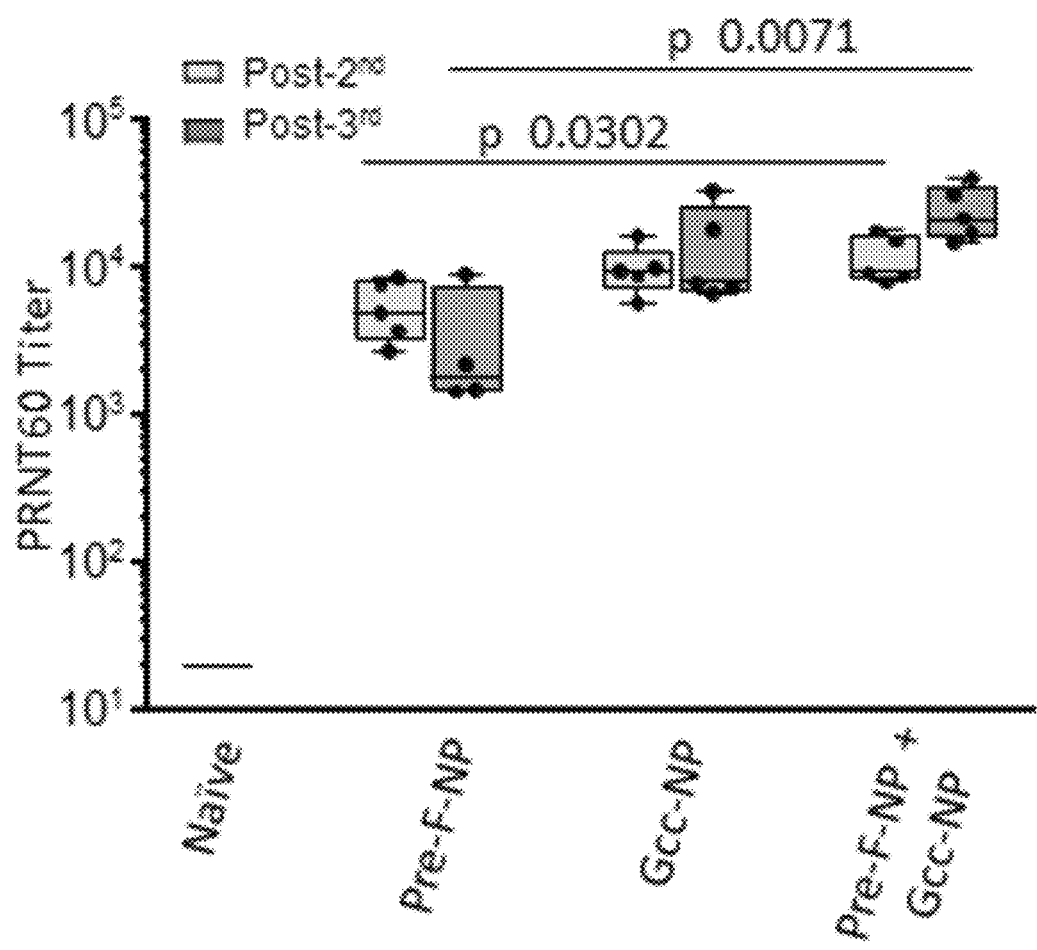

To demonstrate that co-administration of RSV Pre-F-NP (RF8140) and Gcc-NP does not interfere with either antigen's ability to elicit an immune response, mice were immunized with either Pre-F-NP alone (RF8140, SEQ ID NO: 23), Gcc-NP (ferritin conjugated with Gcc peptide SEQ ID NO: 29), or Pre-F-NP (RF8140, SEQ ID NO: 23) combined with Gcc-NP (FIG. 15A-C). All immunizations were adjuvanted with AF03. Mice immunized with RF8140 alone (Pre-F-NP) or RF8140 and Gcc-NP (Pre-F-NP+Gcc-NP) developed antibodies that bind pre-fusion F trimer (DS-CAV1, SEQ ID: 25) while mice immunized with Gcc-NP did not. Mice immunized with Gcc-NP alone (Gcc-NP) or RF8140 and Gcc-NP developed antibodies that bind Gcc peptide, while mice immunized with just RF8140 did not. Animals immunized with either Pre-F-NP alone, Gcc-NP alone, or the co-administration of Pre-F-NP and Gcc-NP all developed a neutralizing response post-second and post-third immunization as measured by HAE neutralizing assay.

Figure 16B:
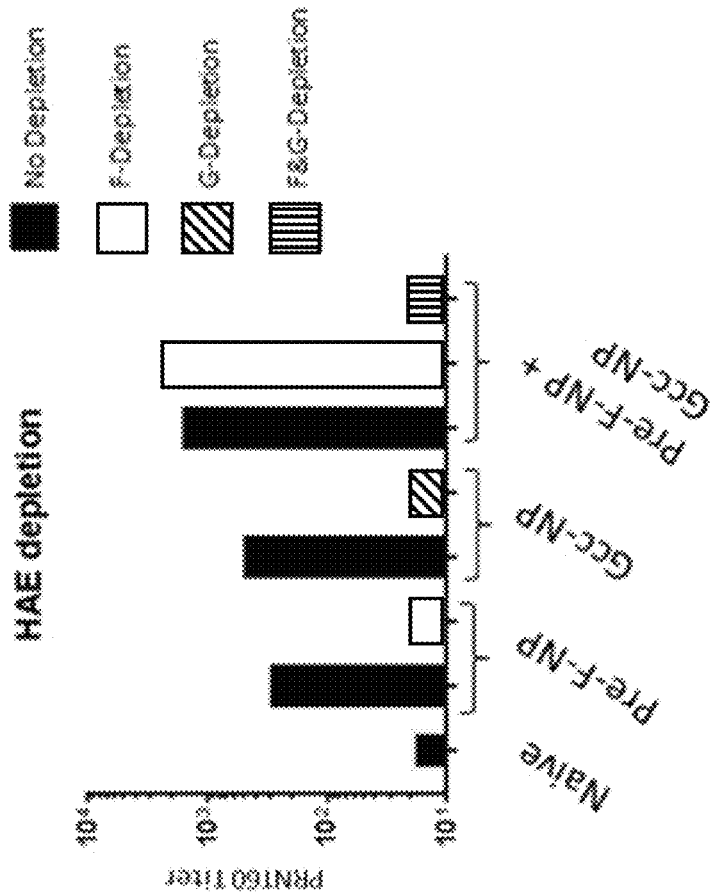
FIG. 16A-B. Co-administration of Pre-F-NP and Gcc-NP does not interfere with elicitation of antibodies that bind Pre-fusion F trimer or Gcc-nanoparticle. Neutralizing titers measured by the F-sensitive VERO cell assay are on the left in FIG. 16A, while neutralizing titers measured by the F- and G-sensitive HAE assay are shown on the right in FIG. 16B. Animal immunizations were as in FIG. 15. RSV polypeptides used in the immunization are below the horizontal axis. The black bars represent sera pooled from the immunization groups described in FIG. 15 and are similarly labeled. Sera from naïve animals are also shown as black bars and labeled for comparison. Sera depleted with pre-fusion F trimer are in white, just to the right of the corresponding black bar. Sera depleted with G ectodomain are in diagonally striped bars, just to the right of the corresponding black bar. Sera depleted with pre-fusion F trimer followed by depletion with G ectodomain is in a vertically striped bar.
Figure 16A:
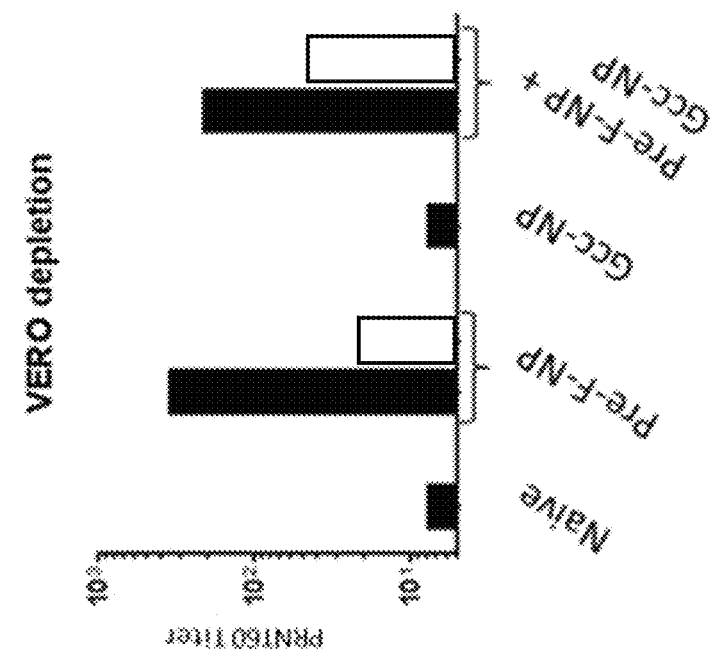

To determine if co-administration of RSV Pre-F-NP and Gcc-NP interfered with either antigen's ability to elicit neutralizing antibodies, neutralizing antibodies to both F and G were studied in a depletion assay (FIG. 16A-B). To demonstrate that the addition of Gcc-NP does not interfere with Pre-F-NP's ability to elicit a neutralizing response, the neutralizing titers were measured by the F-sensitive VERO cell assay for the groups mentioned above (FIG. 16A). Sera from naïve animals were also tested to judge the quality of the antigen depletions. In the VERO assay, sera from mice immunized with either RF8140 (SEQ ID NO: 23) alone or RF8140 mixed with Gcc-NP elicited similar neutralizing responses, while Gcc-NP did not appear to elicit neutralizing response in the F-antibody sensitive VERO assay. When antibodies that bind pre-fusion trimer (DS-CAV1, SEQ ID: 25) were depleted from pooled sera from animals immunized with RF8140 (SEQ ID NO: 23) alone or immunized with RF8140 (SEQ ID: 23) and Gcc-NP, a reduction in the measurable neutralizing titers was observed in the VERO assay. When the above groups were measured for neutralizing titer in the HAE cell assay, all immunization groups were observed to develop a neutralizing response in the F- and G-sensitive assay (FIG. 16B). Pooled sera from animals immunized with RF8140 (SEQ ID NO: 23) alone elicited a neutralizing response in the HAE assay that could be depleted out with pre-fusion F trimer (DS-CAV1, SEQ ID NO: 25). Pooled sera from animal immunized with Gcc-NP alone elicited a neutralizing response in the HAE assay that could be depleted out with G ectodomain (SEQ ID NO: 28). Pooled sera from animals immunized with both Pre-F-NP (RF8140, SEQ ID NO: 23) and Gcc-NP elicited a neutralizing response in the HAE assay that was not fully depleted by DS-CAV1 (SEQ ID NO: 25) but was fully depleted by subsequent depletions with DS-CAV1 then G ectodomain (SEQ ID NO: 28). Together, these data suggest co-administration with the Pre-F-NP and Gcc-NP does not interfere with either antigen's ability to elicit neutralizing antibodies to pre-fusion F or G, respectively.

Figure 17B:
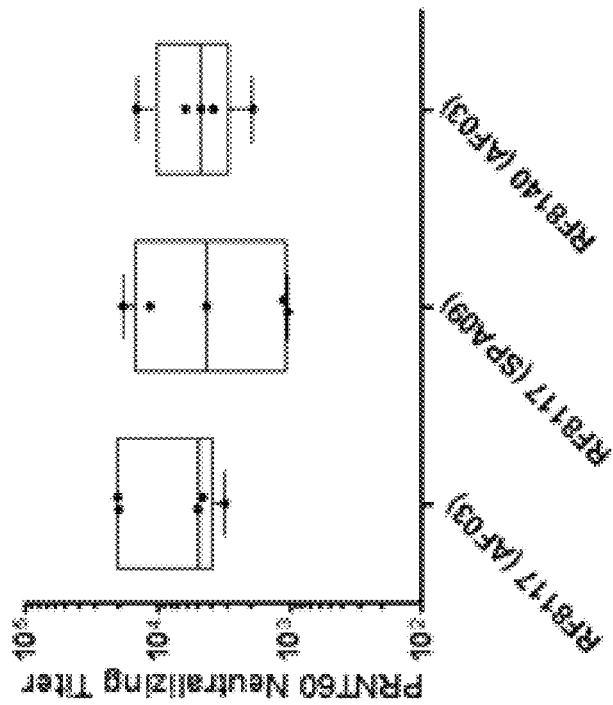
FIGS. 17A-B. Adjuvanting RF8117 or RF8140 with AF03, SPA09 or Alum elicits a superior neutralizing response in mice relative to unadjuvanted RF8117.
Figure 17A:
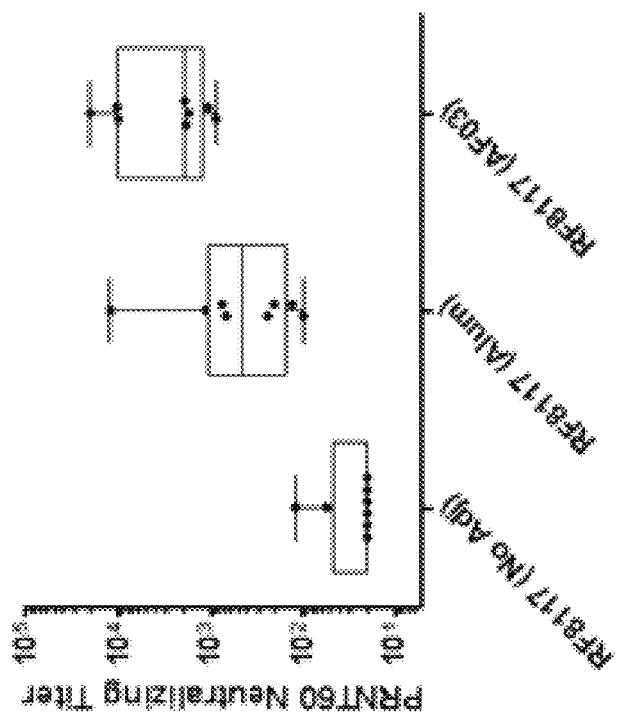

To demonstrate the effect of adjuvanting RF8117 (SEQ ID NO: 17) or RF8140 (SEQ ID NO: 23), mice were dosed with these constructs mixed with AF03, SPA09 or Alum. In FIG. 17A, mice were immunized with 10 μg antigen mixed with adjuvant, while in FIG. 17B, mice were immunized with 1 μg antigen mixed with adjuvant. In FIG. 17A, neutralizing titers measured by VERO cell assay at the two week post-third immunization timepoint. Sera from mice immunized with RF8117 (SEQ ID NO: 17) either unadjuvanted (No Adj), adjuvanted with Alum, or adjuvanted with AF03 are shown. In FIG. 17B, neutralizing titers were measured by VERO cell assay for sera from mice immunized with RF8117 (SEQ ID NO: 17) adjuvanted with AF03, RF8117 (SEQ ID NO: 17) adjuvanted with SPA09, or RF8140 adjuvanted with AF03. In all cases for either RF8117 (SEQ ID NO: 17) or RF8140 (SEQ ID NO: 23), in naïve mice adjuvanted groups elicit a higher neutralizing titer than non-adjuvanted groups. Mice immunized with RF8117 (SEQ ID NO: 17) or RF8140 (SEQ ID NO: 23) mixed with AF03 elicited a similar neutralizing response, suggesting the added lysine and arginine mutations of RF8140 (SEQ ID NO: 23) do not interfere with the Pre-F-NP's ability to elicit a neutralizing response.

Figure 18A:
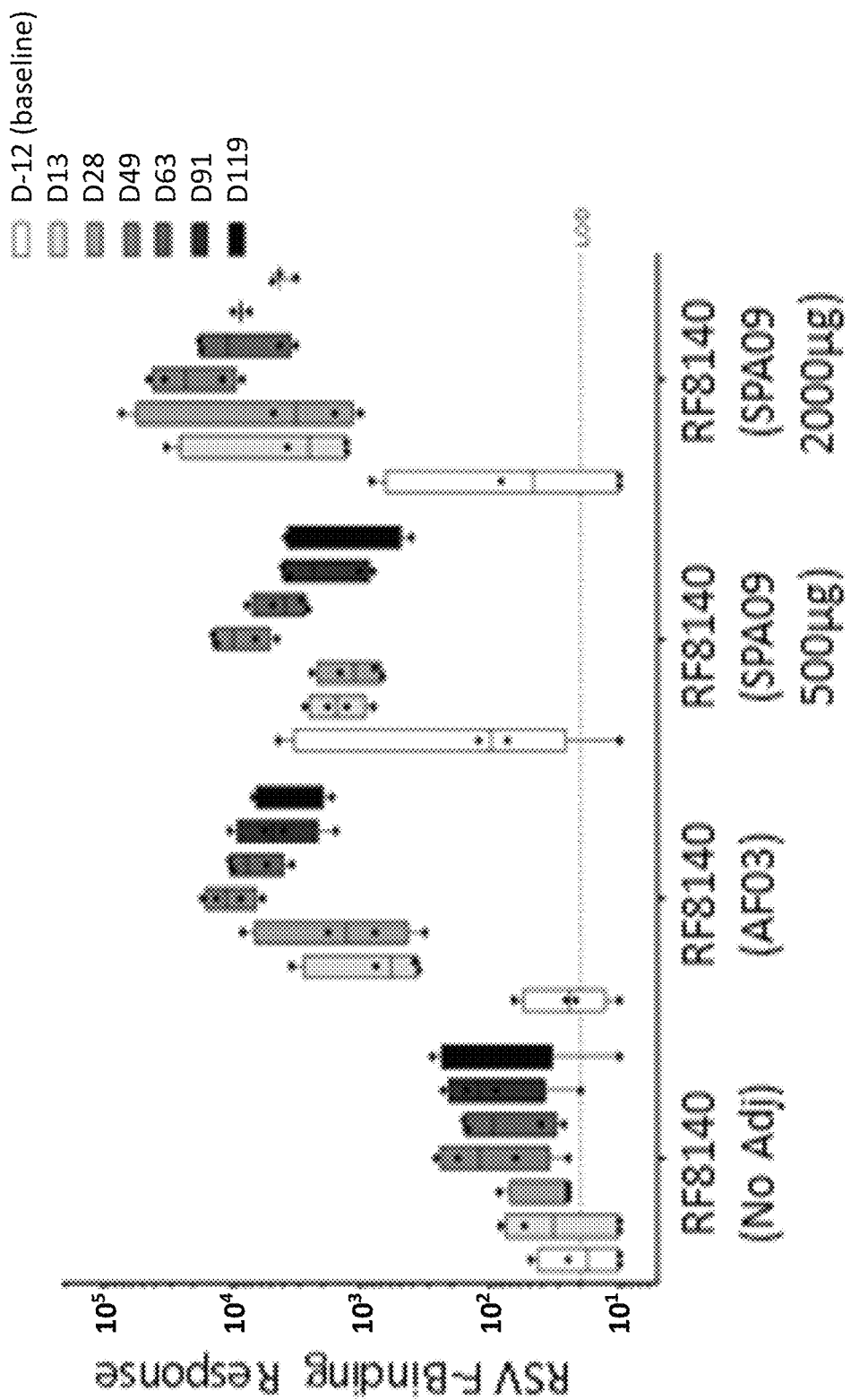
FIGS. 18A-B. Adjuvanting RF8140 with AF03 or SPA09 elicits a superior neutralizing response in non-human primates (NHPs) relative to unadjuvanted RF8140 immunizations.
Figure 18B:
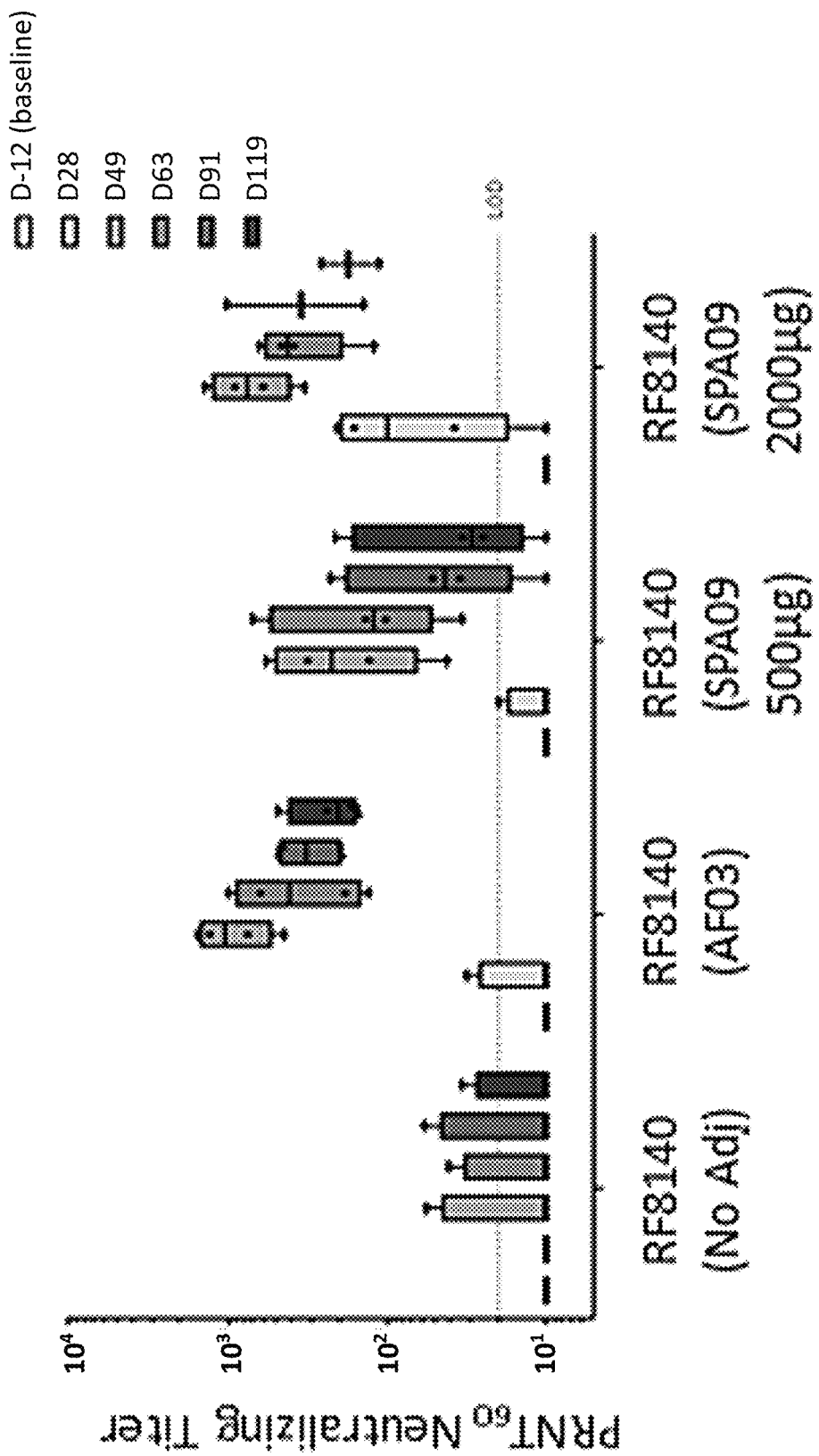

To further explore the adjuvanting effect of AF03 and SPA09, non-human primates (NHPs) were immunized with RF8140 unadjuvanted, adjuvanted with AF03, or adjuvanted with two doses of SPA09 (FIG. 18A). NHPs were immunized with 50 µg of antigen mixed with indicated adjuvant at days 0 and 29 and immune response was measured by ELISA or VERO neutralizing response at indicated time points. Pre-fusion F trimer ELISA responses were measured in NHP sera after immunization with RF8140 either unadjuvanted (No Adj), adjuvanted with AF03, or adjuvanted with SPA09 (500 µg and 2000 µg doses of SPA09 were used). At all timepoints, adjuvanting with AF03 or SPA09 elicits a superior neutralizing response. Neutralizing titers of sera for the above NHP groups were also measured by VERO cell assay (FIG. 18B). In all cases immunization with RF8140 with adjuvant elicits a higher neutralizing titer than non-adjuvanted groups at all timepoints.

The effect of direct conjugation of RF8140 (SEQ ID NO: 23) to TLR7/8 agonist SM7/8 or TLR9 agonist CpG was tested. The antigen was conjugated with the small molecules SM7/8 or CpG and mice were dosed with 10 µg dose. RF8140 contains a mutation in its ferritin sequence replacing a surface exposed amino acid with a cysteine (K79C), which can be used for conjugation by click chemistry. For comparison, mice were dosed with RF8140 either unadjuvanted (No-adj), or adjuvanted by mixing with the small molecule at a high or low dose (not conjugated) as indicated in FIG. 19. Sera from animals post-second and post-third immunization was tested for Pre-fusion F trimer-binding.

Figures 19A, 19B:
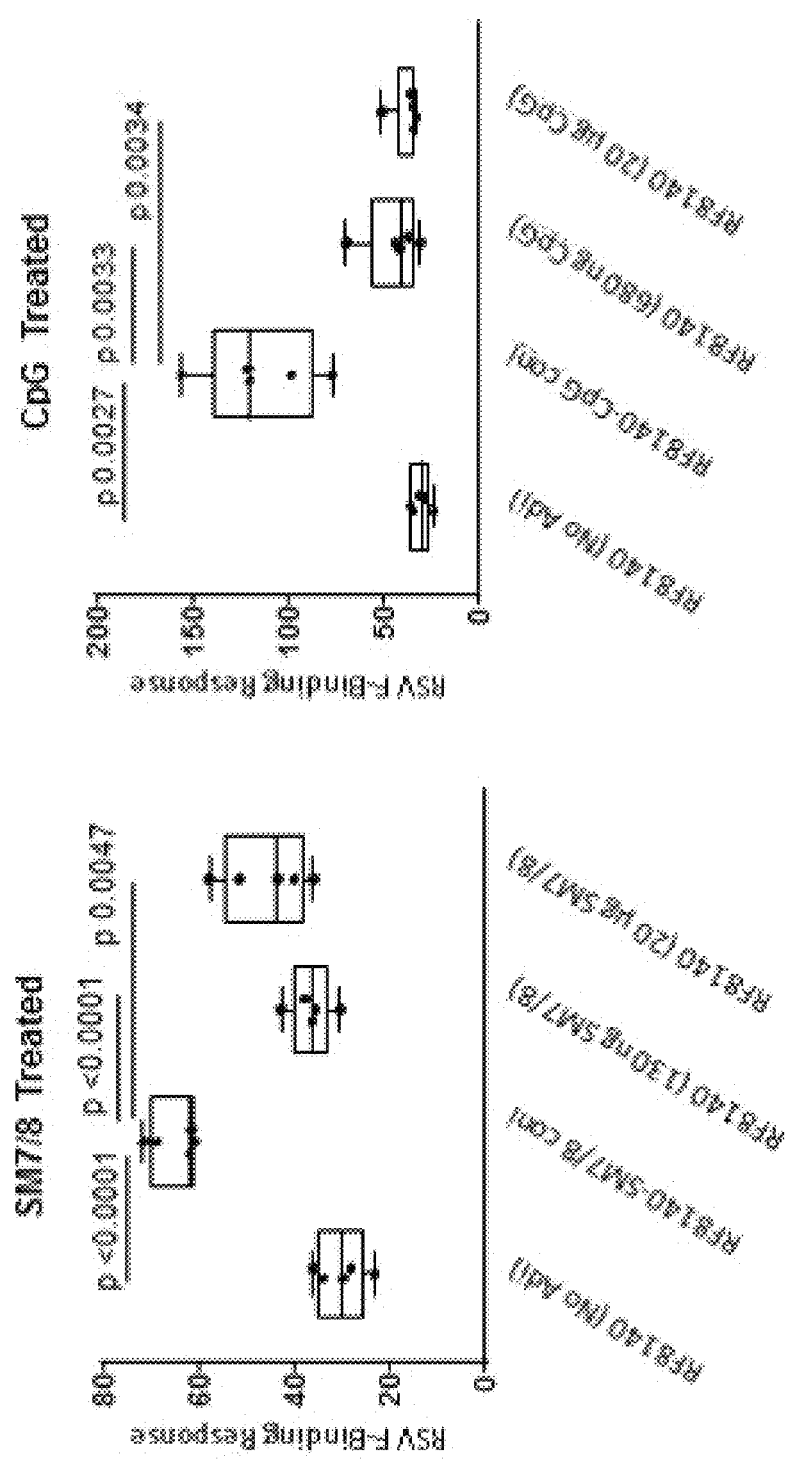

In FIG. 19A, pre-fusion F trimer-binding response was measured in sera from either naïve mice, mice immunized with unadjuvanted RF8140 (SEQ ID NO: 23), mice immunized with RF8140 (SEQ ID NO: 23) conjugated with SM7/8 adjuvant, RF8140 (SEQ ID NO: 23) adjuvanted with 130 ng of SM7/8, or RF8140 (SEQ ID NO: 23) adjuvanted with 20 µg SM7/8. RF8140 (SEQ ID NO: 23) conjugated to SM7/8 elicits a higher pre-fusion F trimer-binding titer than unadjuvanted or SM7/8 adjuvanted groups.

In FIG. 19B, pre-fusion F trimer-binding response was also measured in sera from either naïve mice, mice immunized with unadjuvanted RF8140 (SEQ ID NO: 23), mice immunized with RF8140 (SEQ ID NO: 23) conjugated with CpG adjuvant, RF8140 (SEQ ID NO: 23) adjuvanted with 680 ng of CpG, or RF8140 (SEQ ID NO: 23) adjuvanted with 20 µg CpG. RF8140 (SEQ ID NO: 23) conjugated to SM7/8 elicits a higher pre-fusion F trimer-binding titer than unadjuvanted or SM7/8 adjuvanted groups.

Figure 20D:
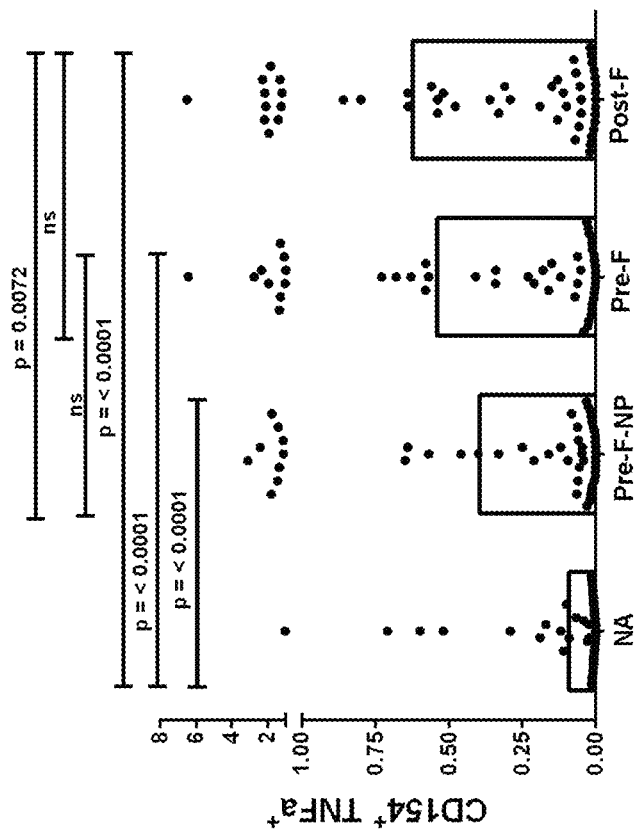
Figure 20C:
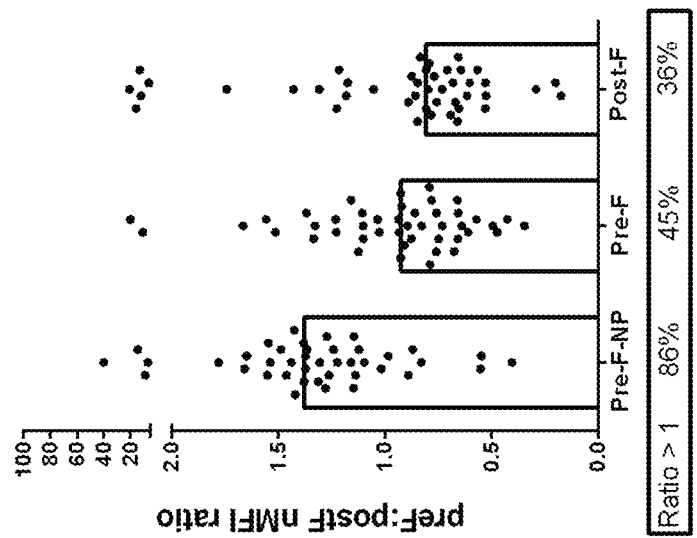

To demonstrate the ability of the Pre-F-NP antigen and the Gcc-NP antigen to elicit a response in human cells, experiments were performed with the MIMIC platform (FIGS. 20A-D). The MIMIC platform is comprised solely of autologous human immune cells capable of quickly and reproducibly generating antigen-specific innate and adaptive responses upon challenge. Previous work has demonstrated the ability of the MIMIC system to recapitulate in vivo immune profiles against such diverse targets as HBV, tetanus toxoid, monoclonal antibodies, YF-VAX, and influenza B-cell responses. RSV Pre-fusion F trimer-binding antibody responses elicited by treatment with Pre-F-NP RF8140 (SEQ ID NO: 23) versus post-fusion F trimer (SEQ ID NO: 24) were compared in human B-cells, and a representative baseline response is shown for comparison (No Treatment) (FIG. 20A). Ratios of measured binding responses to pre-fusion F trimer (DS-CAV1, SEQ ID NO: 25) versus post-fusion F trimer (SEQ ID NO: 24) elicited by treatment with Pre-F-NP (RF8140, SEQ ID NO: 23) versus Post-fusion F (SEQ ID NO: 24) in human B-cells are shown in FIG. 20C. Antibodies from MIMIC elicited by treatment with different F antigens were measured using the VERO cell assay (FIG. 20B). Neutralizing titers elicited by treatment with Pre-F NP (RF8140, SEQ ID NO: 23) versus Post-fusion F trimer (SEQ ID NO: 24) in human B-cells were compared to a no treatment group showing RF8140 (SEQ ID NO: 23) elicited a superior neutralizing response in human cells.

Figure 20F:
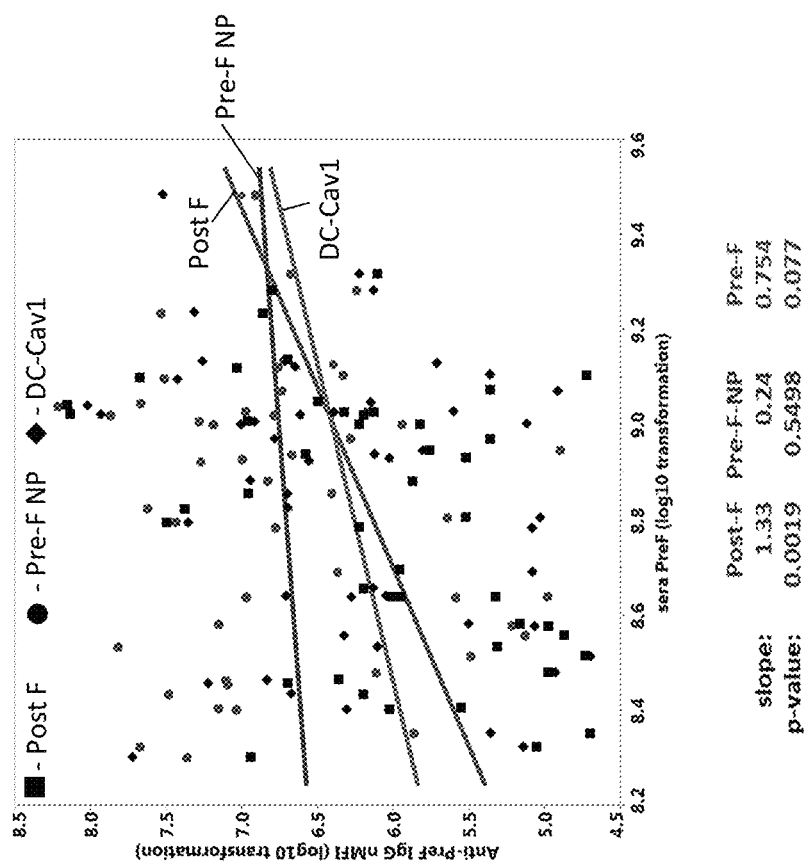
Figure 20E:
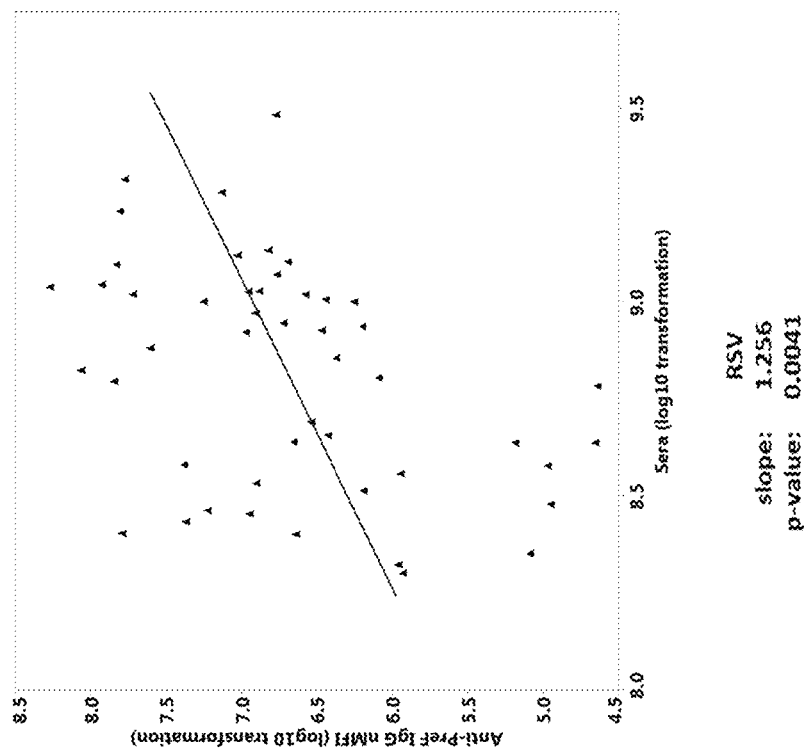

The magnitude of Ab response to RSV infection or to F subunit vaccine candidates was determined based on the sero-status of the human subjects investigated in MIMIC studies, which was assessed by linear regression analysis. Donors with higher pre-existing circulating titers of anti-pre-F IgG produced significantly more anti-pre-F IgG after RSV treatment (FIG. 20E, p=0.0041) and after post-F priming (FIG. 20F, p=0.0019). Although the correlation did not reach statistical significance, pre-F also showed a relationship between the level of Ab induced and the level of pre-existing Ab. It is noteworthy that unlike other treatments, pre-F-NP induced comparably high level of anti-pre-F IgG from donors with low pre-existing anti-pre-F IgG as from donors with high pre-existing Ab (FIG. 20F). This indicates that pre-F-NP is capable of rescuing (or enhancing) Ab response even from donors with low pre-existing IgG level effectively.

Figure 20G:
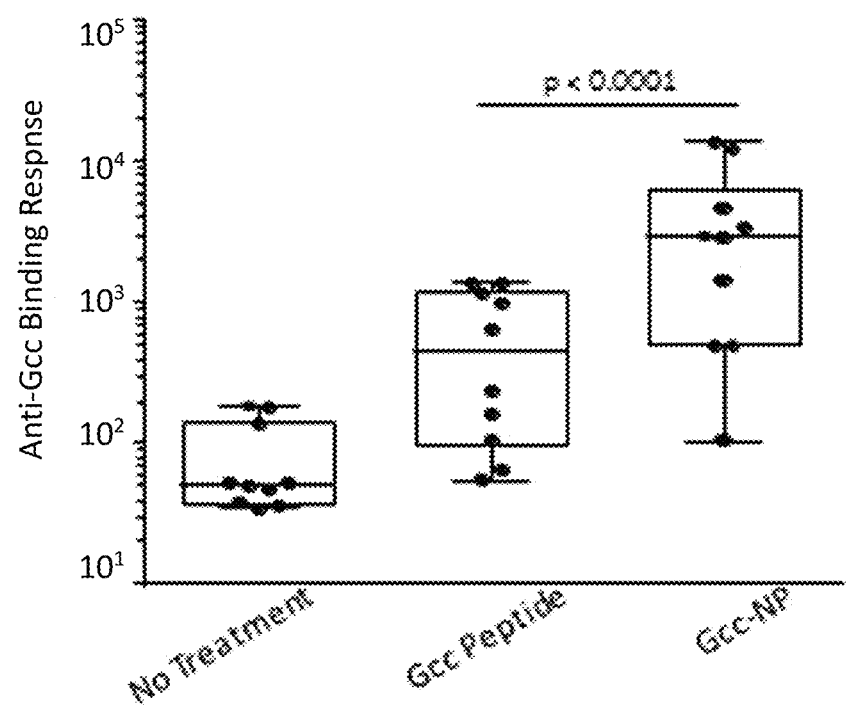
Figure 21A:
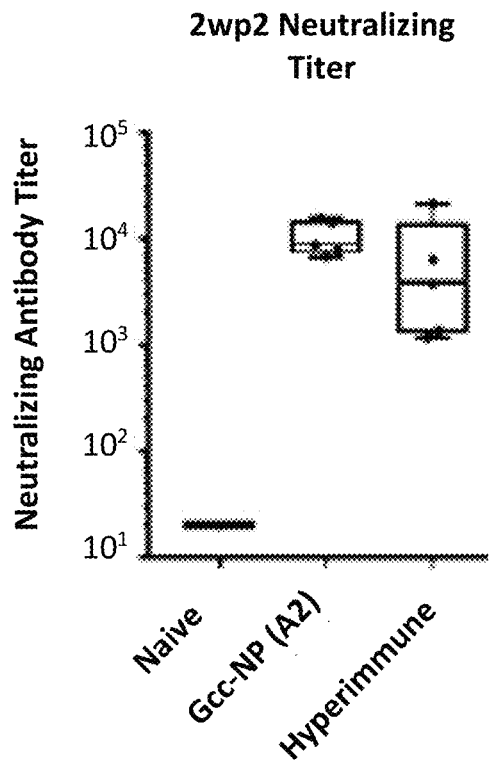
FIGS. 21A-C. Neutralizing antibody titers elicited by a low dose (0.5 µg) of RSV Gcc-ferritin nanoparticles ("Gcc-NP"). Shown are RSV A strain HAE neutralizing titers elicited from immunization with RSV Gcc-NP containing the RSV A2 Gcc sequence (formulated with AF03), from sera taken two weeks post the second immunization (2wp2) (FIG. 21A) or two weeks post the third immunization (2wp3) (FIG. 21B), with naïve and hyperimmune sera as negative and positive controls. Also shown is an RSV B strain HAE neutralizing titer elicited from immunization with RSV Gcc-NP containing the RSV A2 Gcc sequence (formulated with AF03), from sera taken two weeks post the third immunization (2wp3) (FIG. 21C).
Figure 21B:
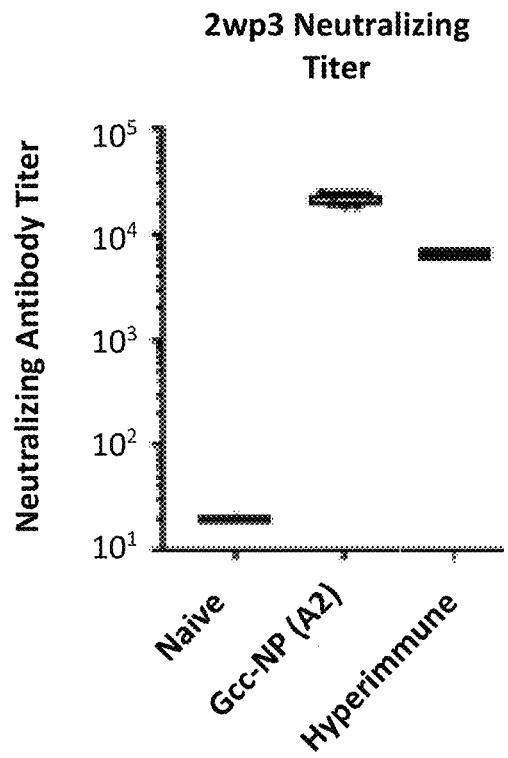
Figure 21C:
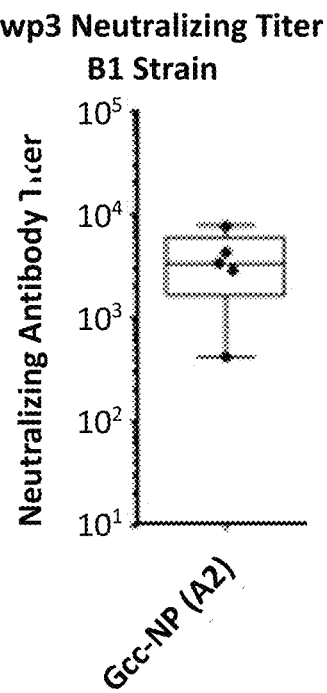
Figure 22A:
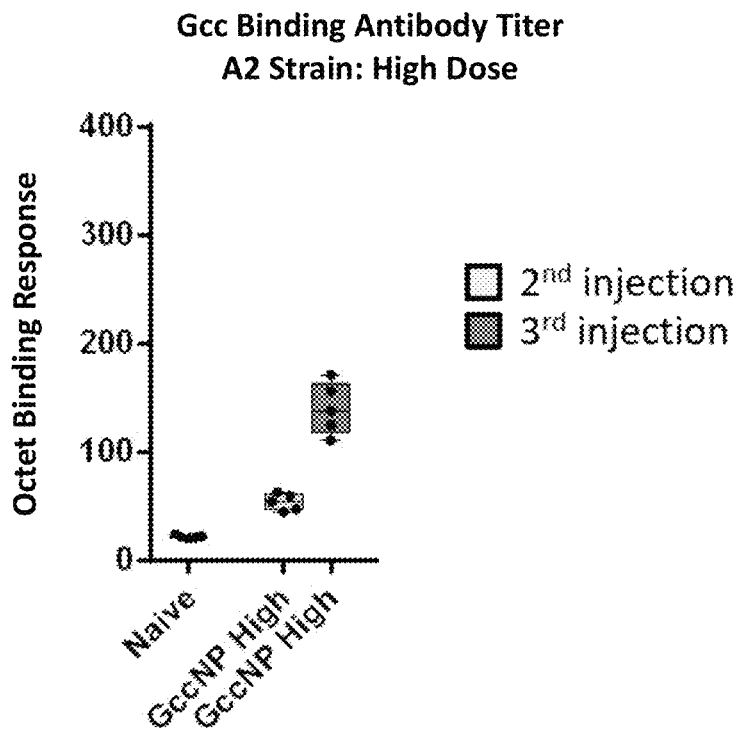
FIGS. 22A-B. RSV A2 strain antigen-binding antibody responses elicited by RSV Gcc-NP.
Figure 22B:
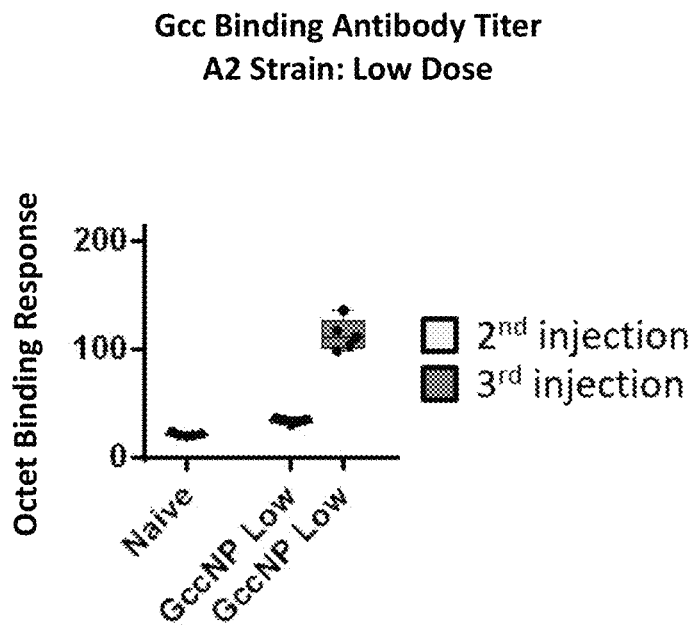
Figure 23A:
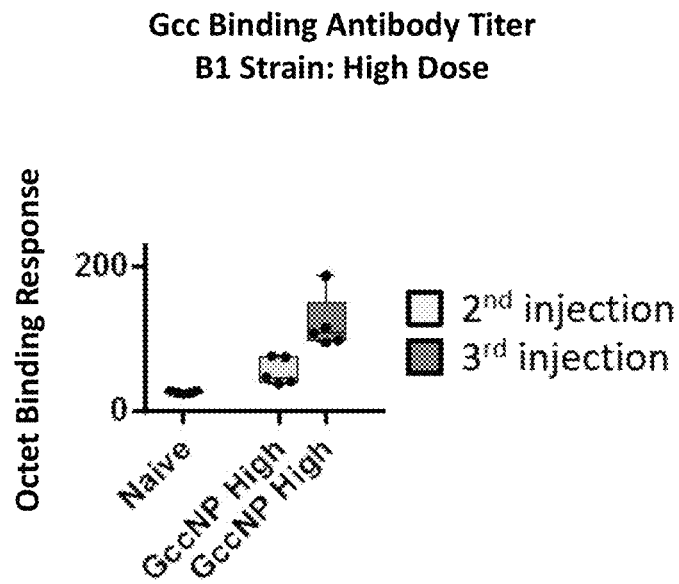
FIGS. 23A-B. RSV B1 strain antigen-binding antibody responses elicited by RSV Gcc-NP.
Figure 23B:
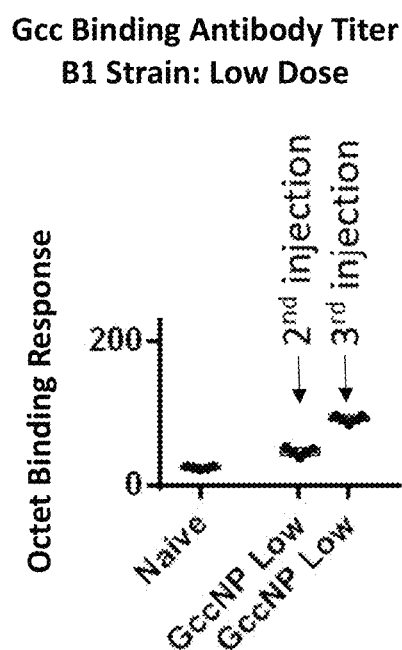

To demonstrate Gcc-NP elicits a superior G antibody response than Gcc peptide (SEQ ID NO: 29) alone, human cells were treated with Gcc peptide alone (SEQ ID NO: 29) or Gcc peptide conjugated to nanoparticle (Gcc-NP) in human B-cells. Gcc-NP elicited a superior G-binding antibody response (FIG. 20G). Combined, these data suggest the Pre-F-NP and Gcc-NP will elicit immune responses in human immunization.

4. In Vivo Characterization of Immune Response to RSV Gcc-Ferritin Nanoparticles RSV Gcc-NP was prepared as described above. To assess the in vivo response to RSV Gcc-NP in mice, female BALBc mice were intramuscularly immunized with RSV antigens at specified doses at week 0, 3 and 6 with either a high dose (5 µg) or low dose (0.5 µg) of antigen. Unless otherwise noted, RSV Gcc-NP was adjuvanted with AF03 with a bedside mixing strategy. That is, 50 µl of the protein solution was mixed with 50 µl of Sanofi adjuvant AF03 (a squalene-based emulsion; see Klucker et al., J Pharm Sci. 2012 December; 101(12):4490-500) just prior to injection of 50 µl into each hind leg. No adverse effects from immunization were observed. Blood was collected 1 day prior to first immunization and at least 2 weeks after each injection (i.e. weeks 2, 5 and 8). Unless otherwise specified, data shown was for 2 weeks post third injection (week 8, also denoted as 2wp3). Typically, sera were analyzed from pre-immunized animals (denoted as naïve), two weeks post second injection (post-2 or 2wp2) or two weeks post third injection (post-$3^{rd}$ or 2wp3).

For the HAE neutralizing assay, serum was heat-inactivated for 30 minutes at 56° C. A fourfold serial dilution series of the inactivated serum was made in PneumaCult™-ALI Basal Medium (Stem Cell Technologies; 05002) supplemented with PneumaCult™-ALI 10× Supplement (Stem Cell Technologies; 05003) and 1% Antibiotic/Antimycotic (hence media). RSV viral stocks were combined 1:1 with the serum dilutions and incubated for 1.5 hours at 37° C. The virus-serum mixture was then added to 24 well plates containing fully differentiated HAE cells at 50 µL per well and incubated for 1 hour at 37° C., 5% $CO_2$. Following incubation, the inoculum was removed, the wells were washed twice with media to remove unbound virus and incubated a further 20 hours at 37° C., 5% $CO_2$. Infection events in cultures infected with RSV expressing the mKate (TagFP635) reporter were counted on a fluorescent microscope.

To detect infection with RSV not expressing the mKate reporter (RSV B strain neutralization), the pseudostratified epithelia were washed extensively with media to remove mucus then fixed with 4% paraformaldehyde for 30 minutes at room temperature, permeabilized with 0.25% Triton X-100 for 30 minutes, and blocked with DMEM supplemented with 2% FBS for 1 hour at 37° C. The blocking solution was replaced with 100 µL per well of Mouse Anti-RSV monoclonal Ab mixture (Millipore; MAB 858-4) diluted 1:200 in DMEM supplemented with 2% FBS, and the plates were incubated at 37° C. for 2 hours. The plates were then washed 3 times with PBS supplemented with 0.05% Tween 20. 100 µL of Goat anti-mouse IgG (H+L) (Invitrogen; A11001) diluted 1:200 in DMEM supplemented with 2% FBS was added per well, and the plates were incubated overnight at 4° C. Next morning, the plates were washed 3 times with PBS supplemented with 0.05% Tween 20, the florescent signal was stabilized with ProLong Gold AntiFade with DAPI (Thermo Fisher Scientific; P36935) and counted on a fluorescent microscope. The neutralizing antibody titers were determined at the 60% reduction endpoint.

To demonstrate that higher multivalency improves elicitation of neutralizing response by RSV G antigens, mice were immunized with RSV F antigens. All immunizations were adjuvanted with AF03. Mice immunized with RSV Gcc-NP formulated with AF03 and neutralizing titers were measured at 2 weeks post second and 2 weeks post third injections (FIG. 21A-C). RSV Gcc-NP elicited a neutralizing response relative to naïve mouse sera. At both 2 weeks post second (FIG. 21A) and 2 weeks post third (FIG. 21B) immunization mice immunized with Gcc-NP, containing Gcc from the A2 strain showed neutralizing responses for RSV A strain. At 2 weeks post third injection, Gcc-NP also elicited a neutralizing response for the RSV B1 strain (FIG. 21C).

For anti-Gcc binding, a trimerized dimer of Gcc peptide with a C-terminal HIS tag was used on an Octet tip. A His6-tagged Gcc (A2 strain) hexamer or His6-tagged Gcc (B1 strain) hexamer was pre-loaded onto Anti-Penta-HIS (HIS1K) sensor tips (ForteBio #18-5122) for 400 seconds to allow capture to reach near saturation. Biosensor tips were then equilibrated for 90 seconds in Octet Wash Buffer, followed by diluted sera association for 300 seconds. Association curve final responses were measured using Octet Data Analysis HT10.0 software, and the response was multiplied by the dilution factor (100 or 300) to obtain the final reported response.

To determine if the RSV Gcc-NP elicits a Gcc-binding immune response, the sera from the immunizations described above were tested for their ability to bind Gcc A2 hexamer or Gcc B1 hexamer. The Gcc-binding response at high dose (FIG. 22A and FIG. 23A) and low dose (FIG. 22B and FIG. 23B) were tested at 2 weeks post-second and 2 weeks post-third immunizations. For both A2 strain (FIG. 22A-B) and B1 strain (FIG. 23A-B), RSV Gcc-NP elicited a binding response relative to naïve mice sera.

5. Response to Pre-F-NP and Gcc-NP in Human Cells

To demonstrate the ability of Pre-F-NP and Gcc-NP to elicit a response in human cells, experiments are performed with the MIMIC platform. The MIMIC platform is comprised solely of autologous human immune cells capable of quickly and reproducibly generating antigen-specific innate and adaptive responses upon challenge. Previous work has demonstrated the ability of the MIMIC system to recapitulate in vivo immune profiles against such diverse targets as HBV, tetanus toxoid, monoclonal antibodies, YF-VAX, and influenza B-cell responses. RSV Pre-fusion F trimer-binding antibody responses elicited by treatment with Pre-F-NP RF8140 (SEQ ID NO: 23) versus post-fusion F trimer (SEQ ID NO: 24) are compared in human B-cells, and are compared to a representative baseline response. Ratios of measured binding responses to pre-fusion F trimer (DS-CAV1, SEQ ID NO: 25) versus post-fusion F trimer (SEQ ID NO: 24) elicited by treatment with Pre-F-NP (RF8140, SEQ ID NO: 23) versus Post-fusion F (SEQ ID NO: 24) in human B-cells are determined. Antibodies from MIMIC elicited by treatment with different F antigens are measured using the VERO cell assay. Neutralizing titers elicited by treatment with Pre-F NP (RF8140, SEQ ID NO: 23) versus Post-fusion F trimer (SEQ ID NO: 24) in human B-cells are compared to a no treatment group, showing RF8140 (SEQ ID NO: 23) elicit a superior neutralizing response in human cells. To demonstrate Gcc-NP elicits a superior G antibody response than Gcc peptide (SEQ ID NO: 29) alone, human cells are treated with Gcc peptide alone (SEQ ID NO: 29) or Gcc peptide conjugated to nanoparticle (Gcc-NP) in human B-cells. Gcc-NP elicits a superior G-binding antibody response. Thus, Pre-F-NP and Gcc-NP will elicit immune responses in human immunization.

We claim:

1. An antigenic respiratory syncytial virus (RSV) polypeptide comprising an RSV F polypeptide, wherein an asparagine of the RSV F polypeptide is glycosylated, thereby blocking an epitope of the RSV F polypeptide that is shared between pre-fusion RSV F and post-fusion RSV F, wherein the RSV F polypeptide comprises a sequence having at least 90% identity to amino acids 1-478 of SEQ ID NO: 23, and wherein the asparagine corresponds to position 288, 308, or 467 of SEQ ID NO: 23.

2. An antigenic RSV polypeptide comprising an RSV F polypeptide, wherein the RSV F polypeptide comprises amino acid residues 62-69 and 196-209 of SEQ ID NO: 26, wherein an asparagine of the RSV F polypeptide is glycosylated, thereby blocking an epitope of the RSV F polypeptide that is shared between pre-fusion RSV F and post-fusion RSV F, and wherein the asparagine corresponds to position 328, 348, or 507 of SEQ ID NO: 26.

3. The antigenic RSV polypeptide of claim 1, wherein the RSV F polypeptide is a pre-fusion RSV F.

4. The antigenic RSV polypeptide of claim 1, wherein the RSV F polypeptide is recognized by a pre-fusion RSV F-specific antibody selected from D25 or AM14.

5. The antigenic RSV polypeptide of claim 3, wherein the pre-fusion RSV F comprises an epitope not found on post-fusion RSV F.

6. The antigenic RSV polypeptide of claim 1, wherein the RSV F polypeptide is a post-fusion RSV F.

7. The antigenic RSV polypeptide of claim 1, wherein the asparagine corresponds to a non-asparagine residue in a wild-type RSV F sequence (SEQ ID NO: 26), wherein the non-asparagine residue corresponds to position 328, 348, or 507 of SEQ ID NO: 26.

8. The antigenic RSV polypeptide of claim 1, further comprising a ferritin protein.

9. An antigenic RSV polypeptide comprising an RSV F polypeptide and a ferritin protein, wherein the ferritin protein comprises a mutation replacing a surface exposed amino acid with a cysteine, and wherein the RSV F polypeptide comprises a sequence having at least 90% identity to amino acids 1-478 of SEQ ID NO: 23.

10. The antigenic RSV polypeptide of claim 9, wherein the ferritin comprises one or more of E11C, S25C, S71C, A74C, K78C, S99C, and S110C mutations corresponding to the *H. pylori* ferritin sequence of SEQ ID NO: 209 as determined by pair-wise or structural alignment, or one or more corresponding mutations in a non-*H. pylori* ferritin as determined by pairwise or structural alignment.

11. The antigenic RSV polypeptide of claim 8, comprising one or more immune-stimulatory moieties linked to the ferritin via a surface-exposed amino acid of the ferritin, wherein the surface-exposed amino acid is a cysteine resulting from a mutation.

12. The antigenic RSV polypeptide of claim 8, wherein the ferritin comprises a mutation replacing a surface-exposed asparagine with a non-asparagine amino acid, wherein the asparagine is at a position corresponding to position 18 of *H. pylori* ferritin sequence of SEQ ID NO: 209 as determined by pair-wise or structural alignment, or is at an analogous position in a non-*H. pylori* ferritin as determined by pairwise or structural alignment.

13. The antigenic RSV polypeptide of claim 8, wherein the ferritin comprises a mutation replacing an internal cysteine with a non-cysteine amino acid, wherein the internal cysteine is at position 30 of the *H. pylori* ferritin sequence of SEQ ID NO: 209, or is at a position that corresponds to position 30 of the *H. pylori* ferritin sequence of SEQ ID NO: 209 as determined by pair-wise or structural alignment.

14. The antigenic RSV polypeptide of claim 8, wherein the RSV F polypeptide comprises an epitope not found on post-fusion RSV F which is a site 0 epitope, wherein the site 0 epitope comprises amino acid residues 62-69 and 196-209 of SEQ ID NO: 26.

15. The antigenic RSV polypeptide of claim 2, wherein the RSV F polypeptide comprises a) an asparagine at a position corresponding to position 328, 348, or 507 of SEQ ID NO: 26; b) a leucine at a position corresponding to position lysine 498 of SEQ ID NO: 26; c) a proline at a position corresponding to position isoleucine 217 of SEQ ID NO: 26; d) or comprising a serine at a position corresponding to position 155 of SEQ ID NO: 26; e) a serine at a position corresponding to position 290 of SEQ ID NO: 26; f) an amino acid other than cysteine at a position corresponding to position 155 of SEQ ID NO: 26; and/or g) an amino acid other than cysteine at position corresponding to position 290 of SEQ ID NO: 26.

16. The antigenic RSV polypeptide of claim 1, wherein the RSV F polypeptide lacks a furin cleavage site, wherein a linker is present in place of the furin cleavage site.

17. The antigenic RSV polypeptide of claim 1, comprising the sequence of any one of SEQ ID NOs: 3-23.

18. A ferritin particle comprising the antigenic RSV polypeptide of claim 8.

19. A composition comprising the antigenic RSV polypeptide of claim 1 and an RSV G polypeptide.

20. A method of eliciting an immune response to RSV or protecting a subject against RSV infection comprising administering the antigenic RSV polypeptide of claim 1 to a human subject.

21. A nucleic acid encoding the antigenic RSV polypeptide of claim 1, wherein the nucleic acid is an mRNA or DNA.

\* \* \* \* \*